(12) United States Patent
Andrews et al.

(10) Patent No.: US 12,305,157 B2
(45) Date of Patent: May 20, 2025

(54) SYSTEM AND METHOD FOR CENTRALIZED FLUID MANAGEMENT AND CULTURE CONTROL

(71) Applicant: DEKA Products Limited Partnership, Manchester, NH (US)

(72) Inventors: Richard E. Andrews, Manchester, NH (US); Dave D. B. Cannan, Manchester, NH (US); Alekhya Akkapeddi, Manchester, NH (US); Andrew G. Remec, Manchester, NH (US); Bryan A. Finseth, Newbury, NH (US); Kevin Kim, Hookset, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1058 days.

(21) Appl. No.: 17/243,324

(22) Filed: Apr. 28, 2021

(65) Prior Publication Data

US 2021/0340486 A1 Nov. 4, 2021

Related U.S. Application Data

(60) Provisional application No. 63/019,260, filed on May 1, 2020.

(51) Int. Cl.
*C12M 1/36* (2006.01)
*C12M 1/00* (2006.01)
(Continued)

(52) U.S. Cl.
CPC ............ *C12M 41/48* (2013.01); *C12M 23/28* (2013.01); *C12M 23/42* (2013.01); *C12M 23/44* (2013.01);
(Continued)

(58) Field of Classification Search
CPC ...... C12M 41/48; C12M 23/28; C12M 23/42; C12M 23/44; C12M 27/18; C12M 29/00;
(Continued)

(56) References Cited

U.S. PATENT DOCUMENTS

| 4,673,400 A | 6/1987 | Martin |
| 8,507,266 B2 | 8/2013 | Welter et al. |

(Continued)

FOREIGN PATENT DOCUMENTS

| AU | 2009/202146 | 6/2009 |
| JP | 2019/092515 | 6/2019 |

OTHER PUBLICATIONS

Demirelli et al., Polymer Degradation and Stability, 72:80, 2001.
(Continued)

*Primary Examiner* — John McGuirk
(74) *Attorney, Agent, or Firm* — Mark E. Tetreault

(57) ABSTRACT

System and method for providing biocompatible, nutrient filled media to the Human Cells, Tissues, and cellular and tissue-based Products (HCT/P) while removing wastes. The present teachings provide for sensing the characteristics of the media, and modifying the characteristics when necessary. The present teachings can also provide components that can provide fluid pumping integrated with fluid gas exchange, and sensing of fluid characteristics at consistent times during the fluid flow cycle. System and method control multiple bioreactors from a centralized media reservoir, while fluidically isolating the bioreactors from cross-contamination.

10 Claims, 158 Drawing Sheets

(51) Int. Cl.
*C12M 1/34* (2006.01)
*C12M 3/00* (2006.01)
(52) U.S. Cl.
CPC ............ *C12M 27/18* (2013.01); *C12M 29/00* (2013.01); *C12M 29/20* (2013.01); *C12M 41/12* (2013.01); *C12M 41/16* (2013.01); *C12M 41/32* (2013.01); *C12M 41/34* (2013.01)
(58) Field of Classification Search
CPC ...... C12M 29/20; C12M 41/12; C12M 41/16; C12M 41/32; C12M 41/34; C12M 23/58; C12M 41/14
See application file for complete search history.

(56) References Cited

U.S. PATENT DOCUMENTS

| | | | |
|---|---|---|---|
| 2009/0311778 A1 | 12/2009 | Luning et al. | |
| 2013/0171679 A1* | 7/2013 | Lee | C12M 41/34 |
| | | | 435/303.1 |
| 2013/0210130 A1 | 8/2013 | Larcher et al. | |
| 2018/0057783 A1* | 3/2018 | Paldus | C12M 23/40 |
| 2018/0298319 A1 | 10/2018 | Wikswo et al. | |
| 2019/0352589 A1* | 11/2019 | Jing | C12M 41/36 |

OTHER PUBLICATIONS

Esmonde-White et al., Raman spectroscopy as a process analytical technology for pharmaceutical manufacturing and bioprocessing, Anal Bioanal Chem, 409:637-649, Aug. 4, 2016.

Invitation to Pay Additional Fees, App. # PCT/US2021/029706, Aug. 26, 2021.

Joshi et al., Flexible Lactate and Glucose Sensors using Electrolyte-Gated Carbon Nanotube Foe;d Effect Transistor for Non-invasive Real-time Monitoring, IEEE Sensors Journal, 1530-437X DOI 10.1109/jSEN.2017/2707521.

Kropff et al., Accuracy and Longevity of an Implantable Continuous Glucose Sensor in the PRECISE Study: A 180-Day Prospective, Multicenter, Pivotal Trial, Diabetes Care, vol. 40:Jan. 1-6, 2017.

McNichols et al., Optical glucose sensing in biolocal fluids: an overview, Journal of Biomedical Optics 5(1), Jan. 5-16, 2000.

Pandey et al., Noninvasive Monitoring of Blood Glucose with Raman Spectroscopy, Accounts of Chemcial Research, DOI: 10.1021/acs.accounts.6b00472, Jan. 2017.

Poscia et al., A novel continuous subcutaneous lactate monitoring system, Biosensors and Bioelectronics 20:2244-2250, 2005.

Resolution Spectra Systems, Procellics In-Line $ Real-Time Bioprocess Raman Analyser Multi-Channel Unit option, http://web.archive.org/web/20210328115955/https://resolutionspectra.com/products/procellics-raman-analyzer/, Nov. 2018.

Resolution Spectra Systems, ProCellics In-Line & Real-Time Bioprocess Raman Analyzer, http://web.archive.org/web/20210328115955/https://resolutionspectra.com/products/procellics-raman-analyzer/, Nov. 2018.

Singh et al.,, Evaluation of accuracy dependence of Raman spectroscopic models on the ratio of calibration and validation points for non-invasive glucose sensing, Analytical and Bioanalytical Chemistry, springer—Verlag GmbH Germany, part of Springer Nature, https://doi.org/10.1007/s00216/018-1244-y, Jul. 25, 2018.

Wrobel, Non-invasive blood glucose monitoring with Raman spectroscopy: prospects for device miniaturization, IOP Conf. Ser,: Mater. Sci. Eng. 104 012036, doi:10.1088/1757-899X/104/0120362016.

* cited by examiner

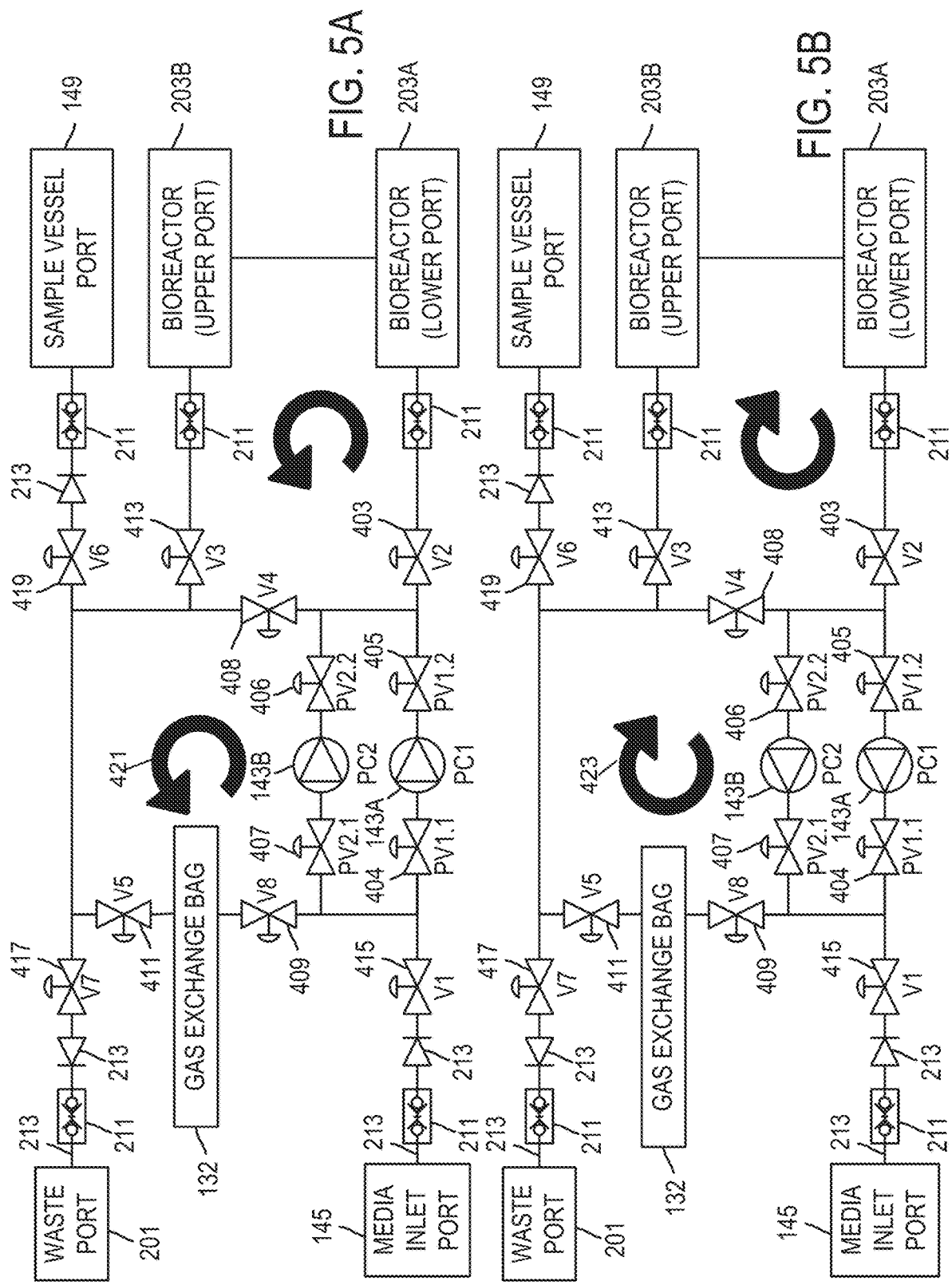

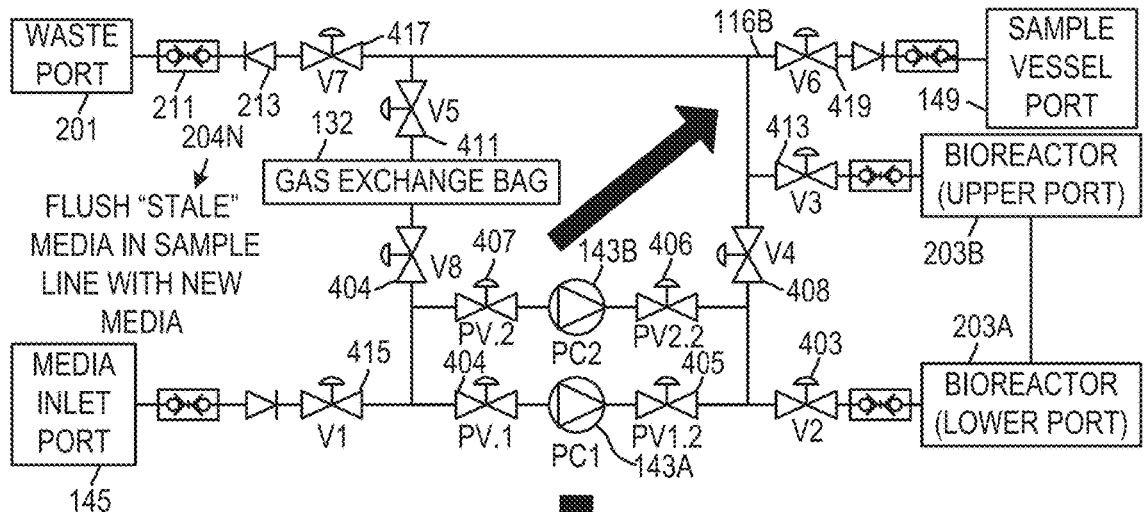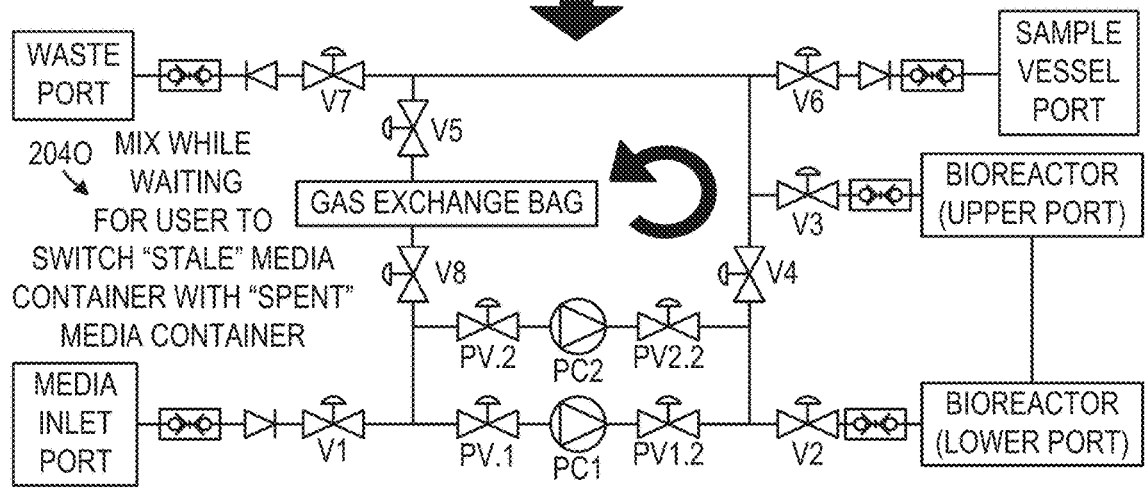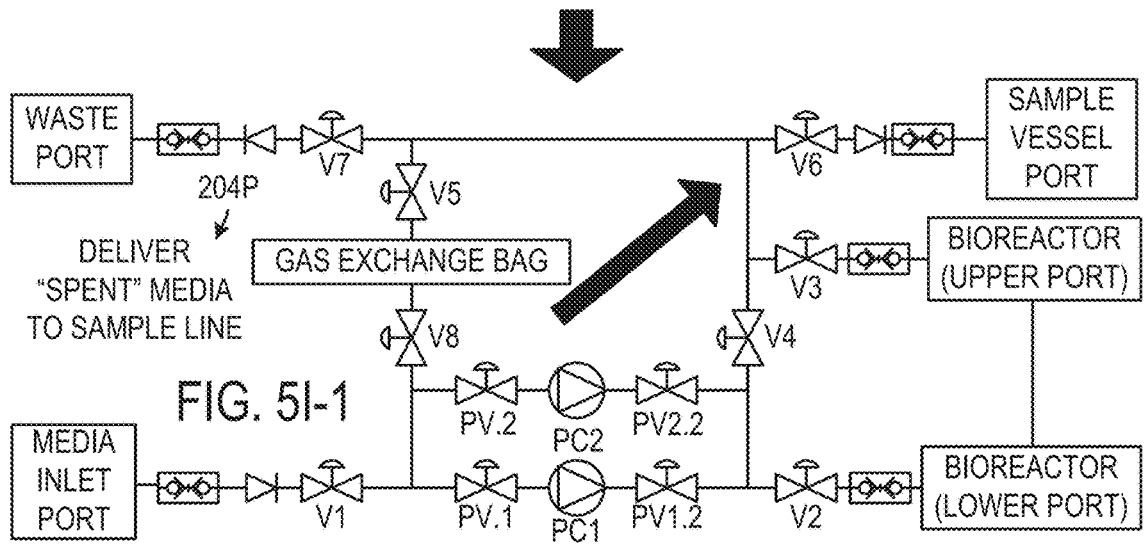
FIG. 5I-1

FIG. 12AB

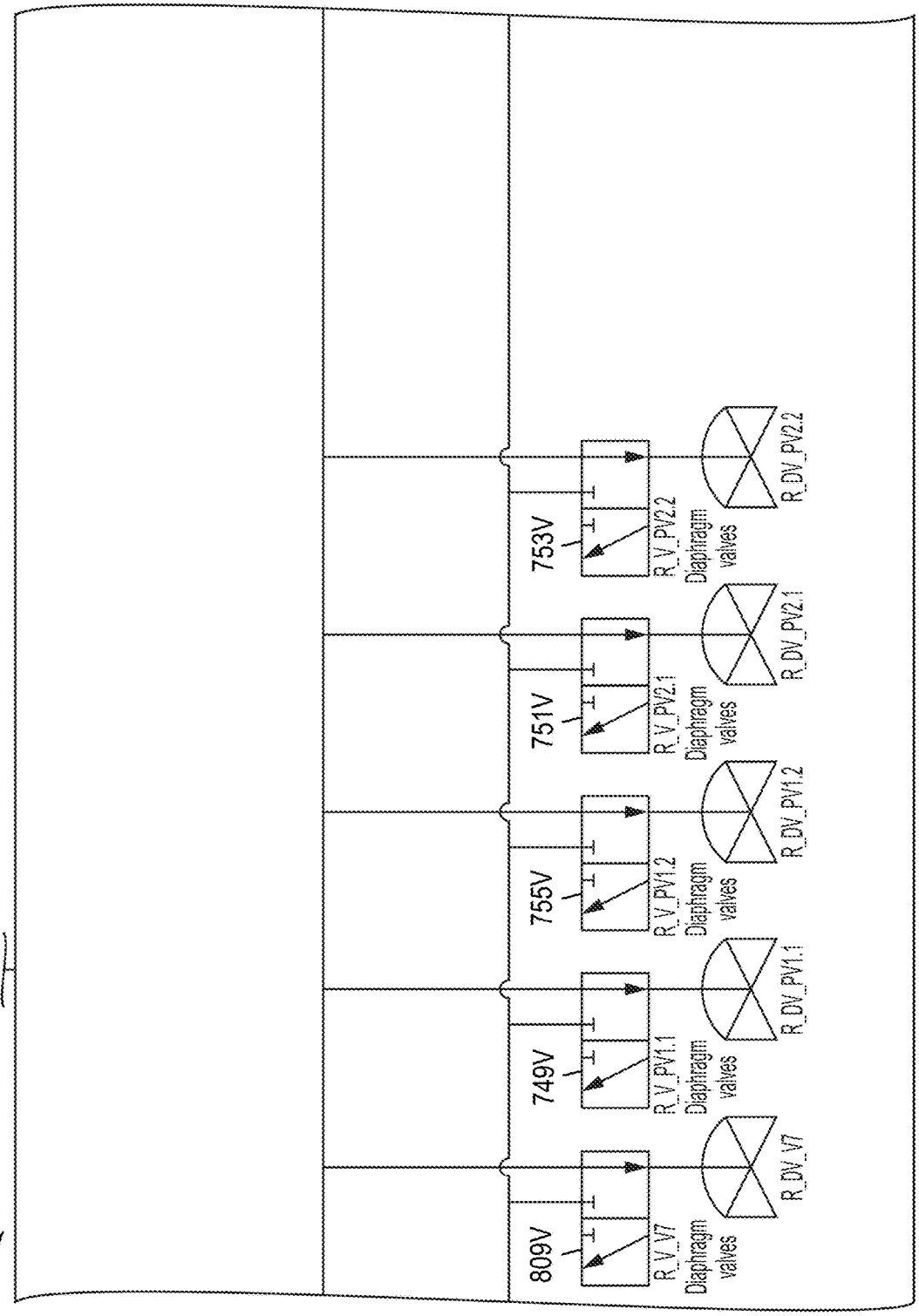

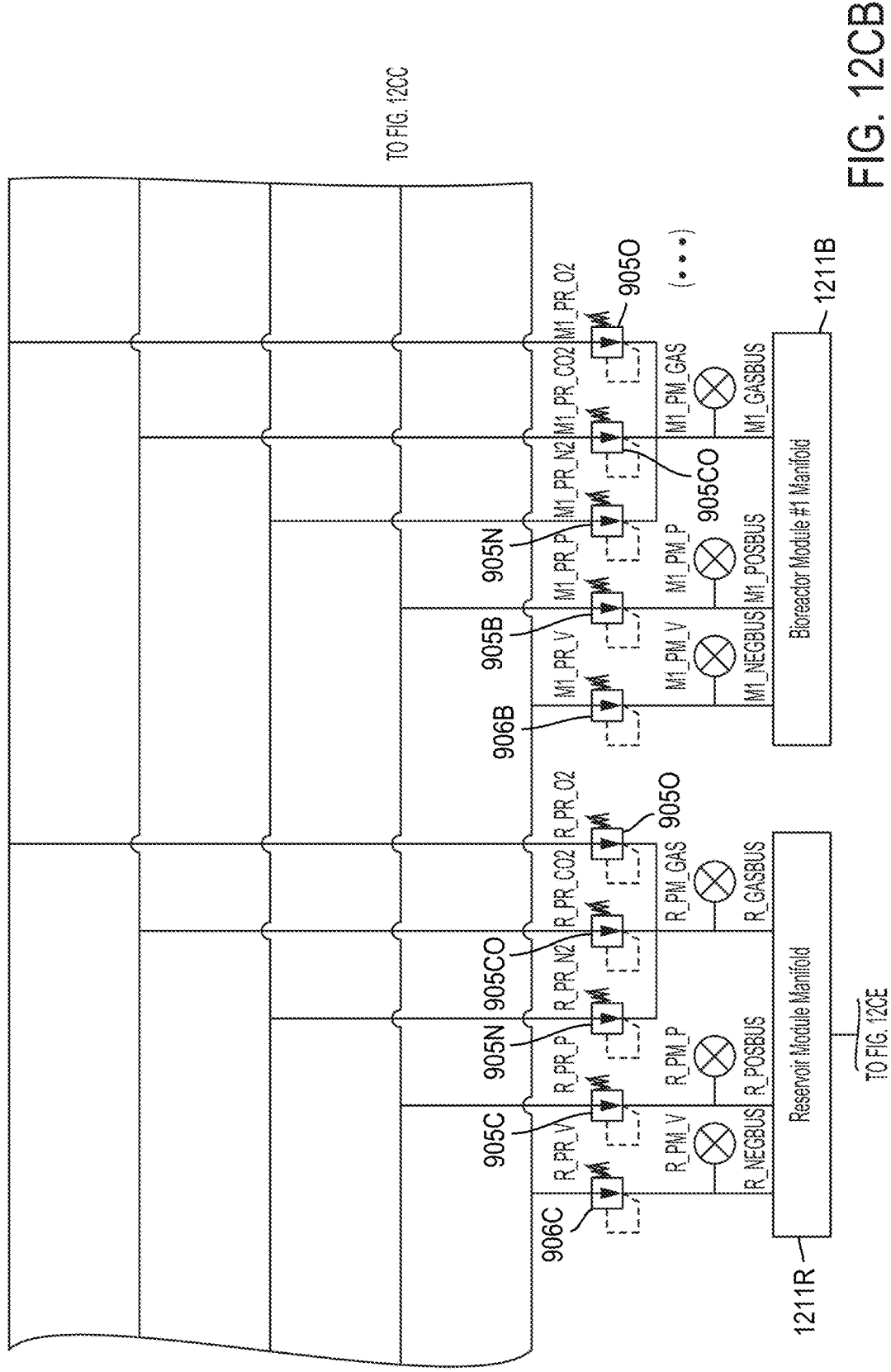

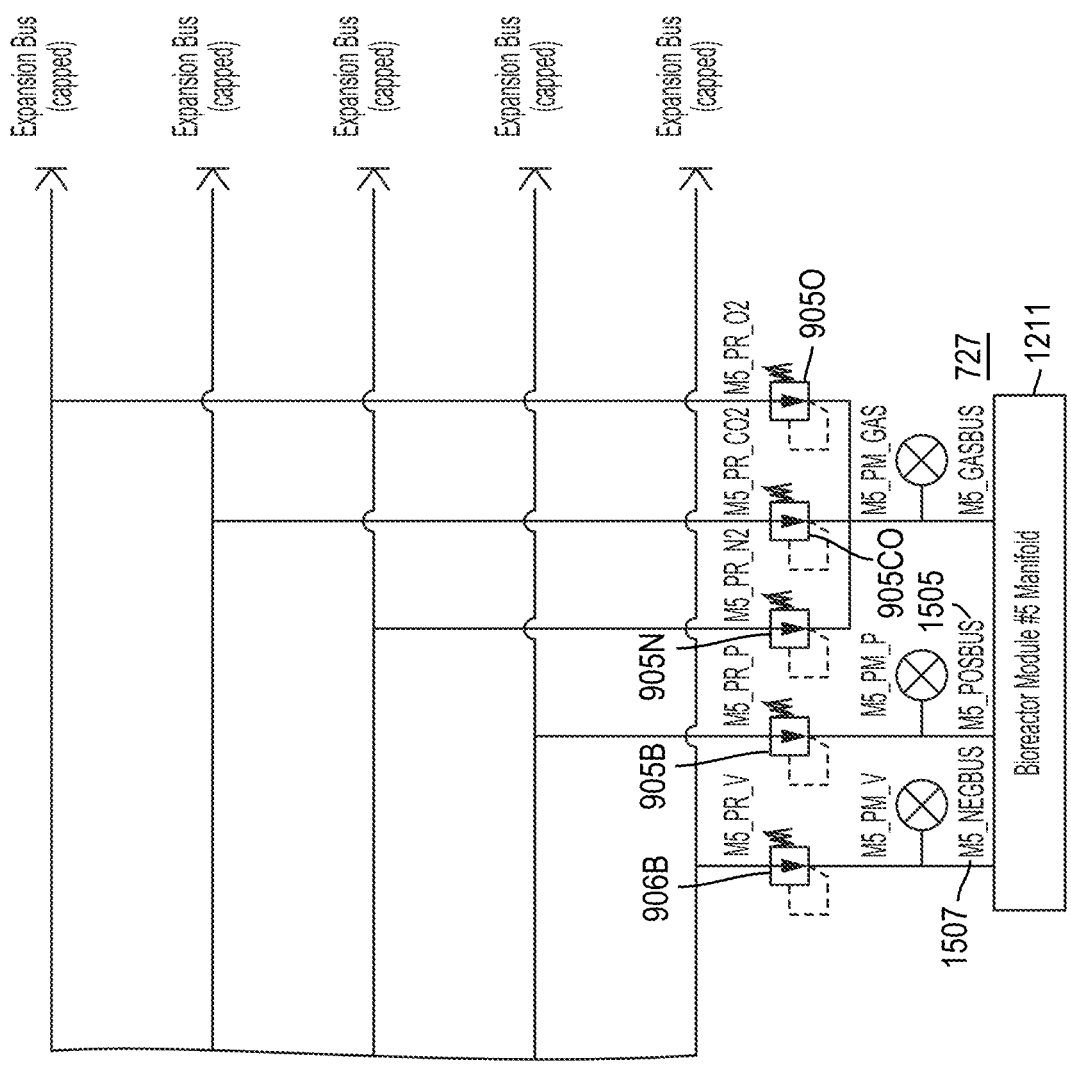

FIG. 12CE

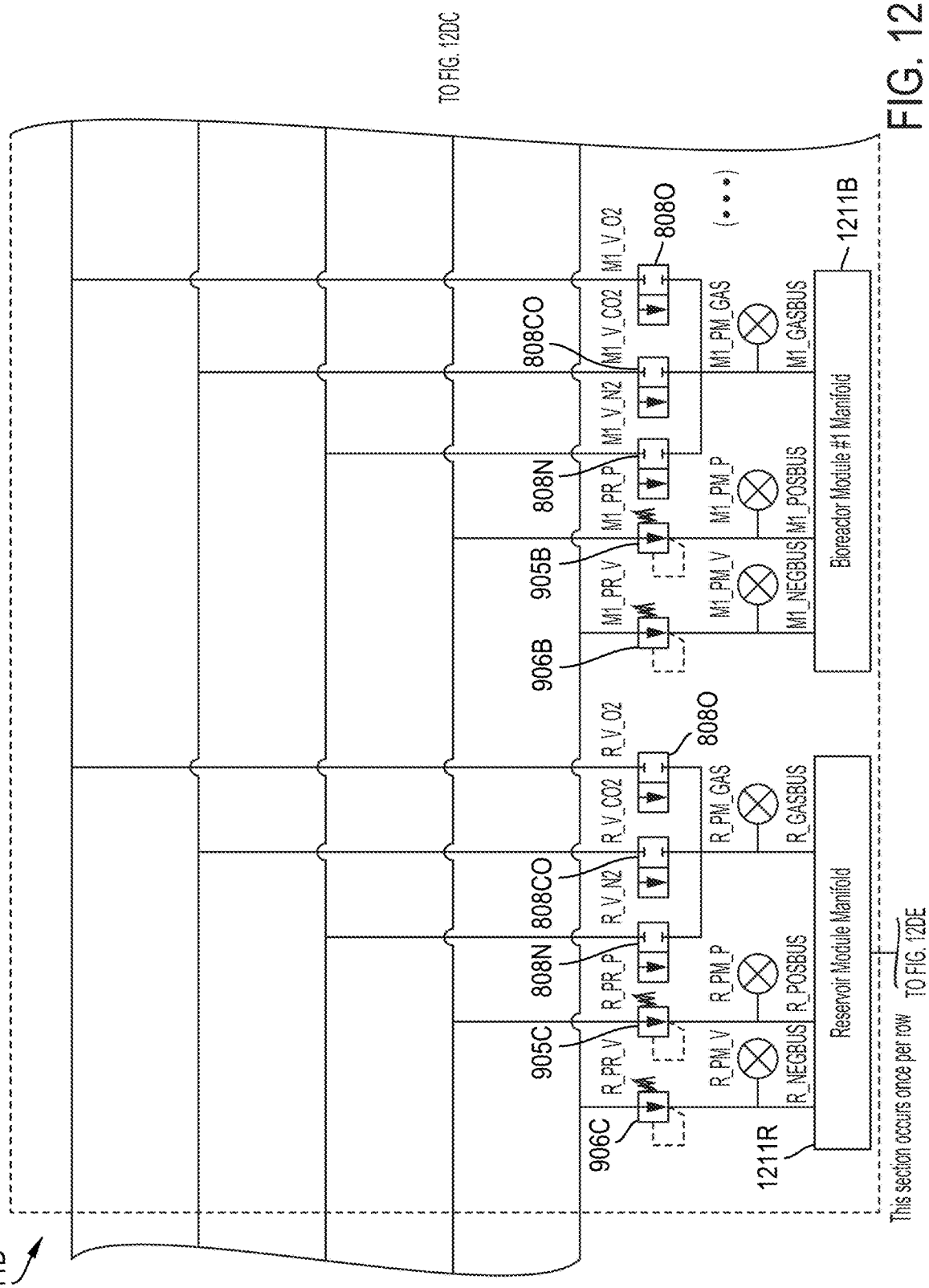

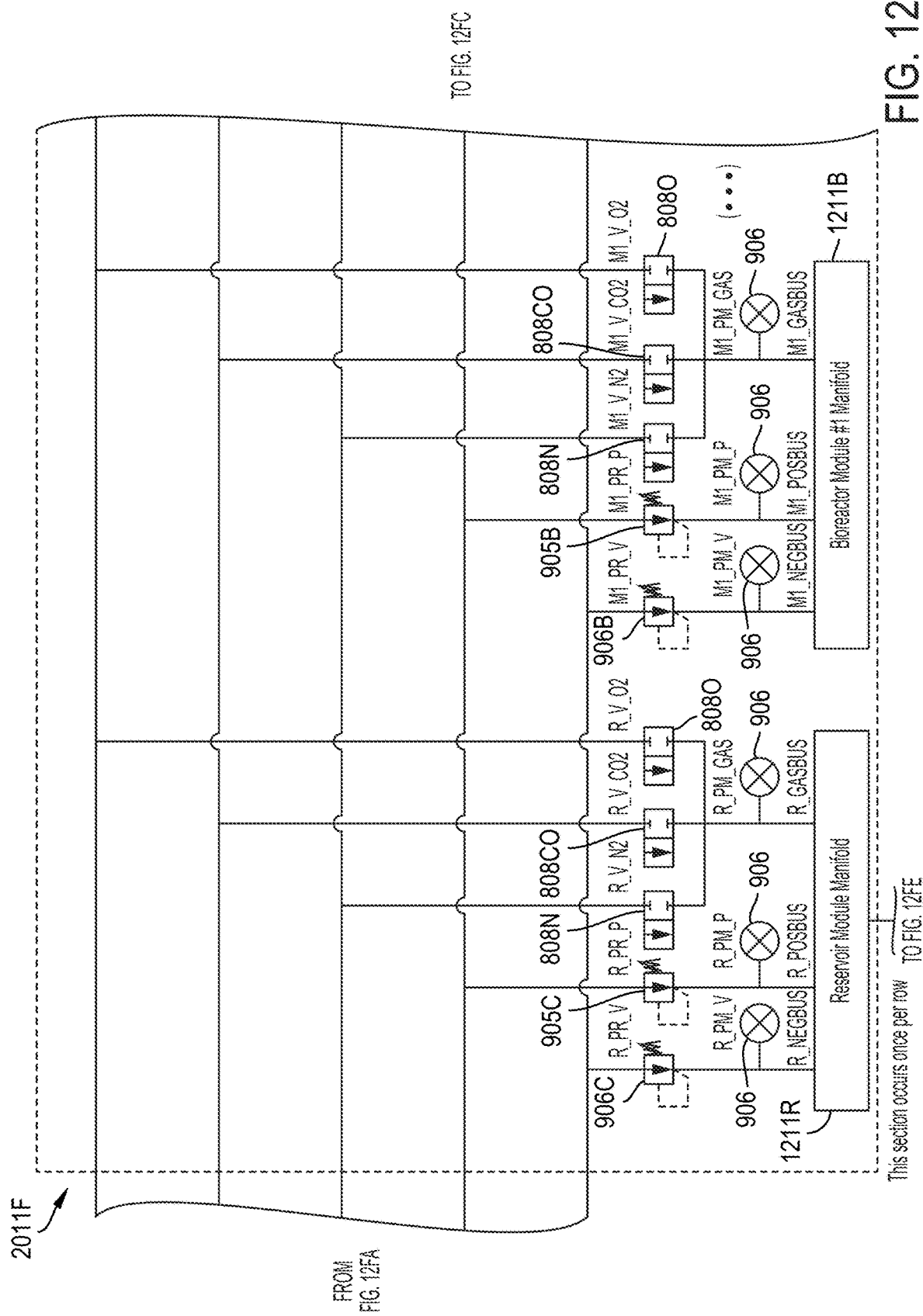

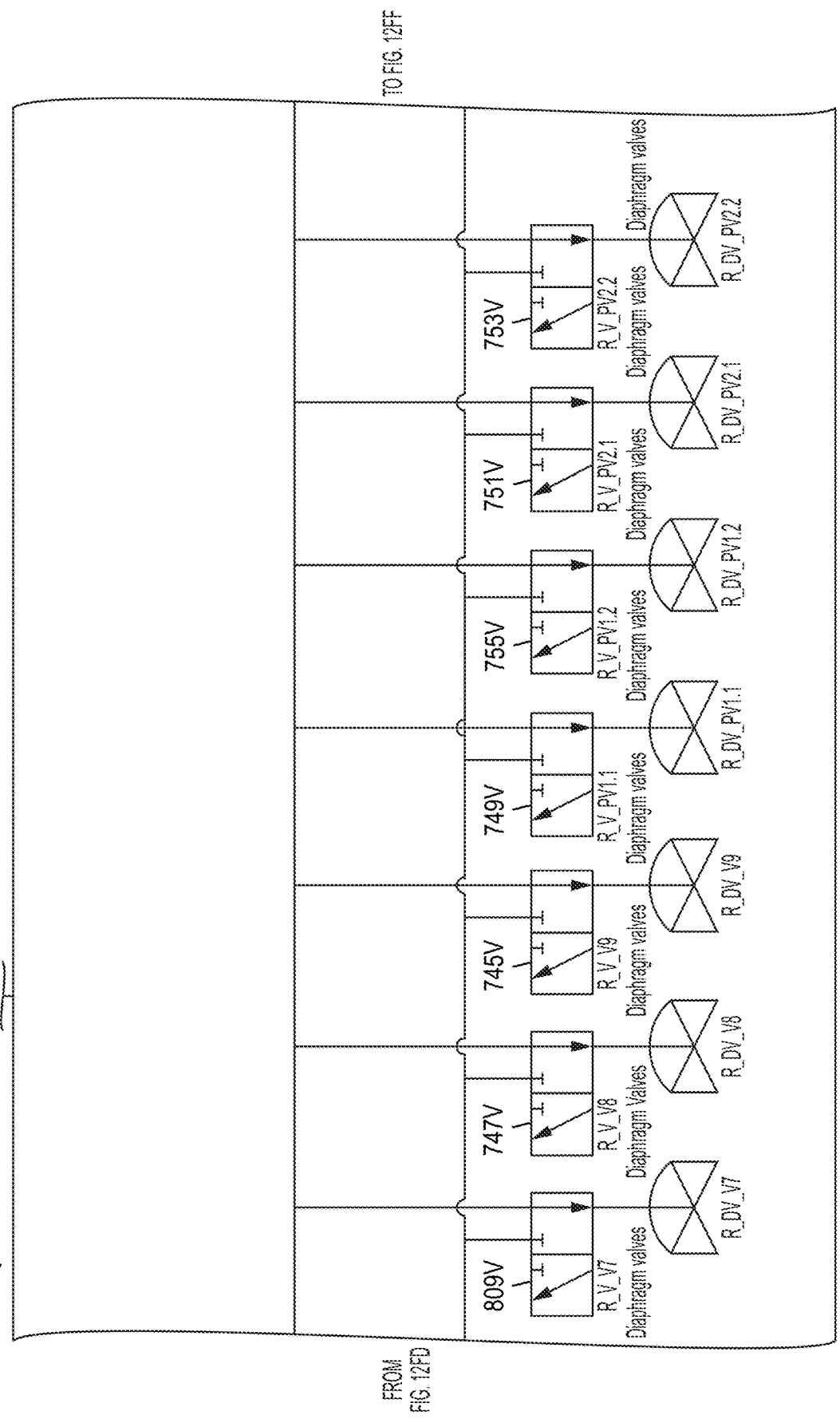

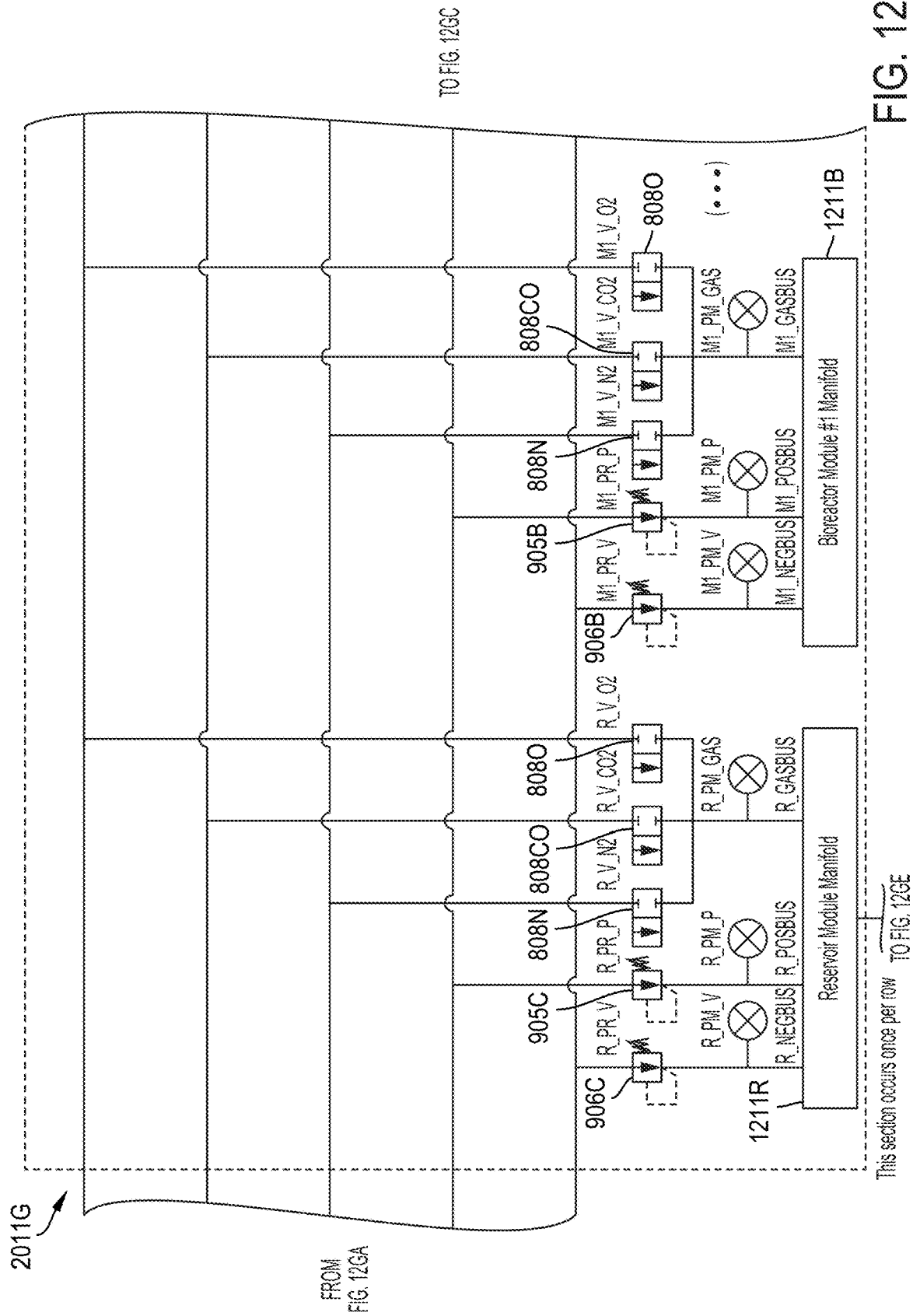

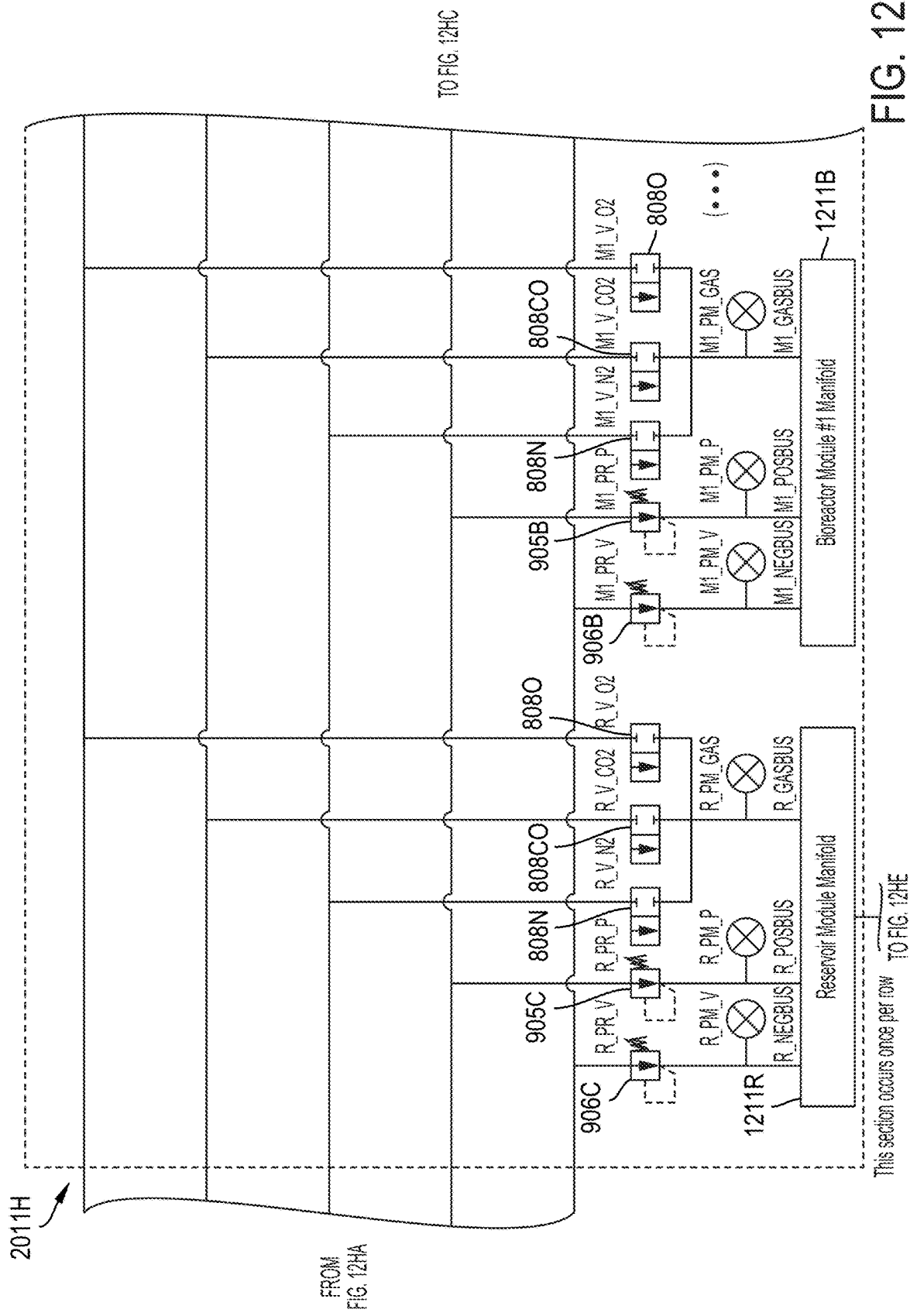

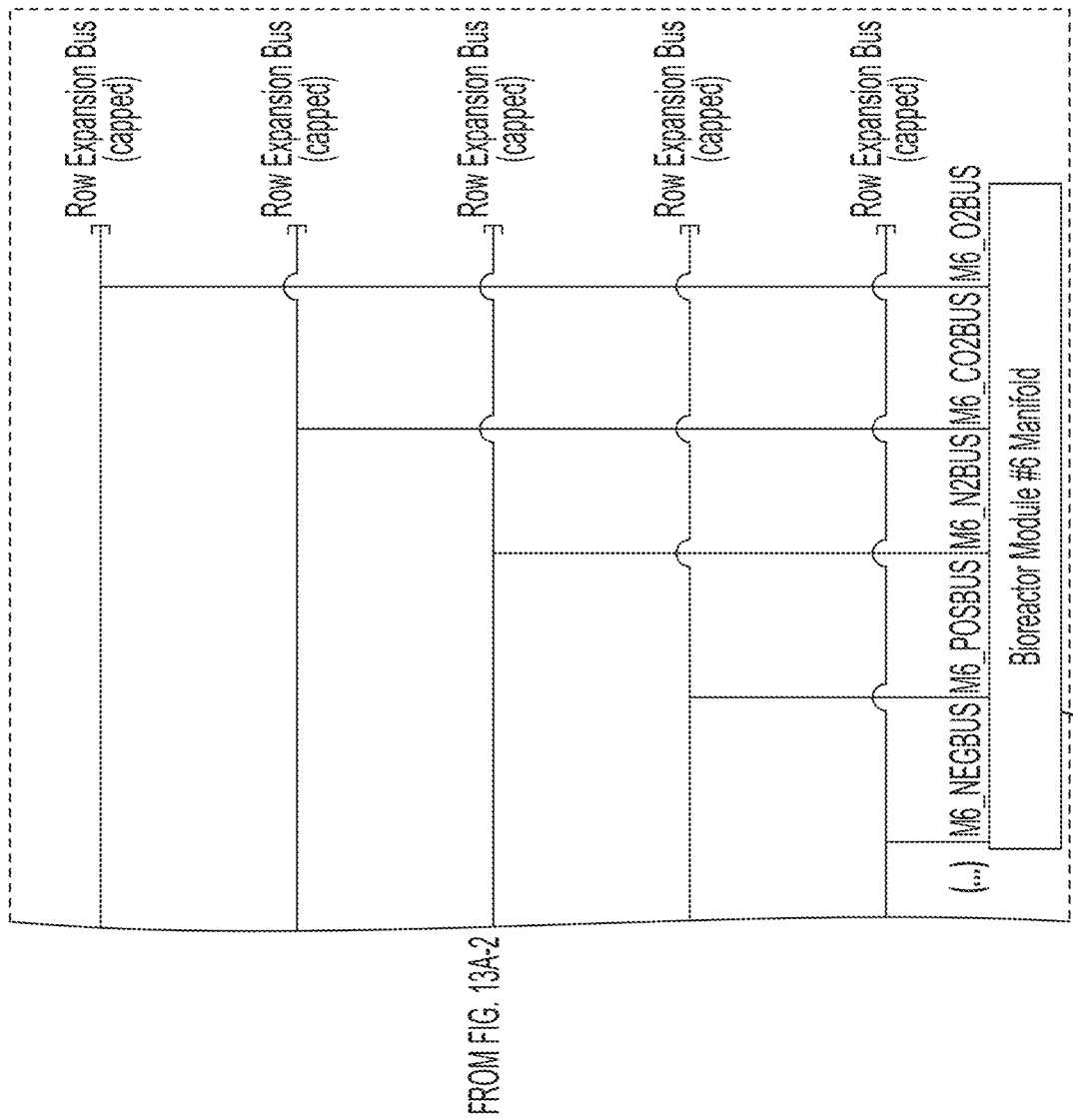

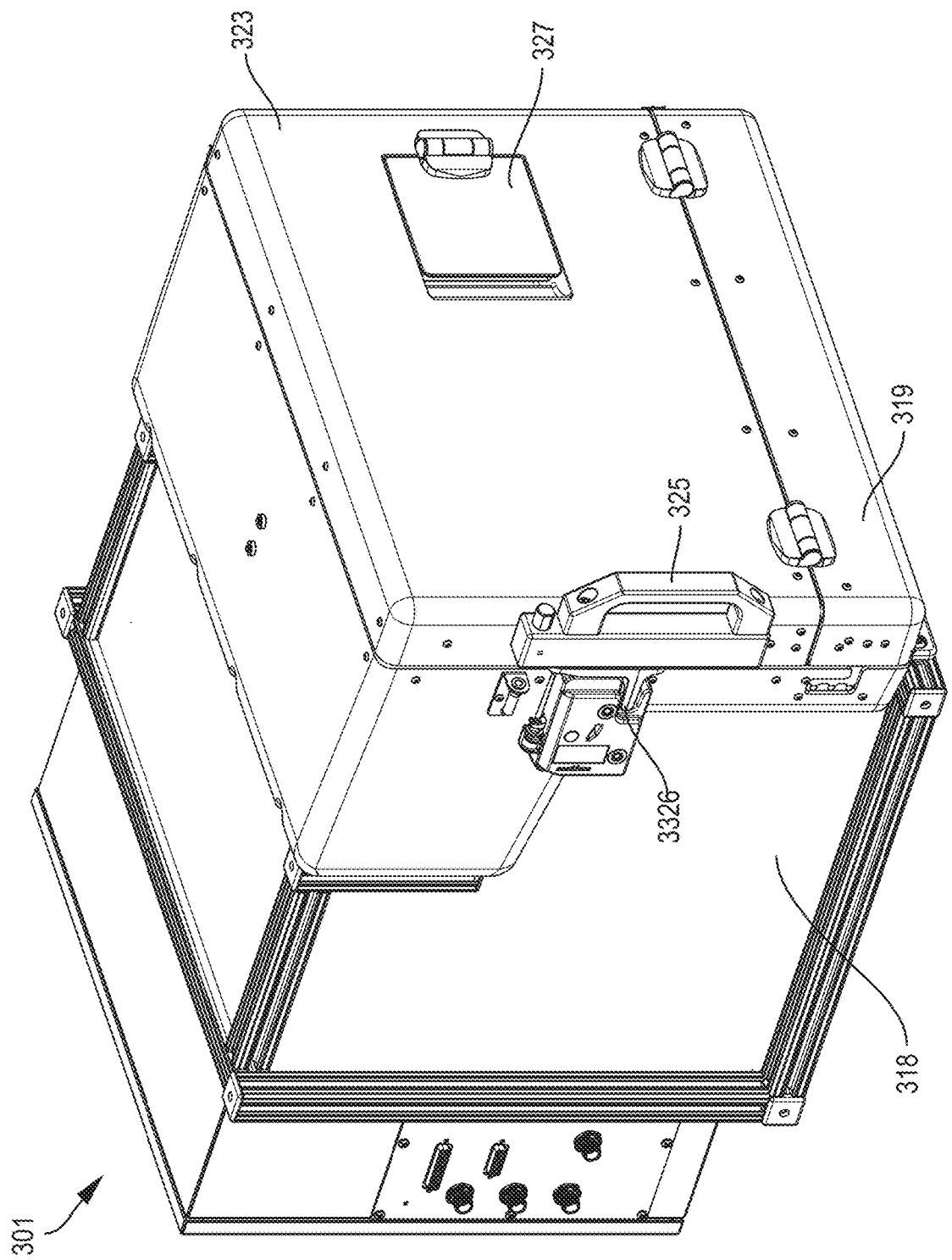

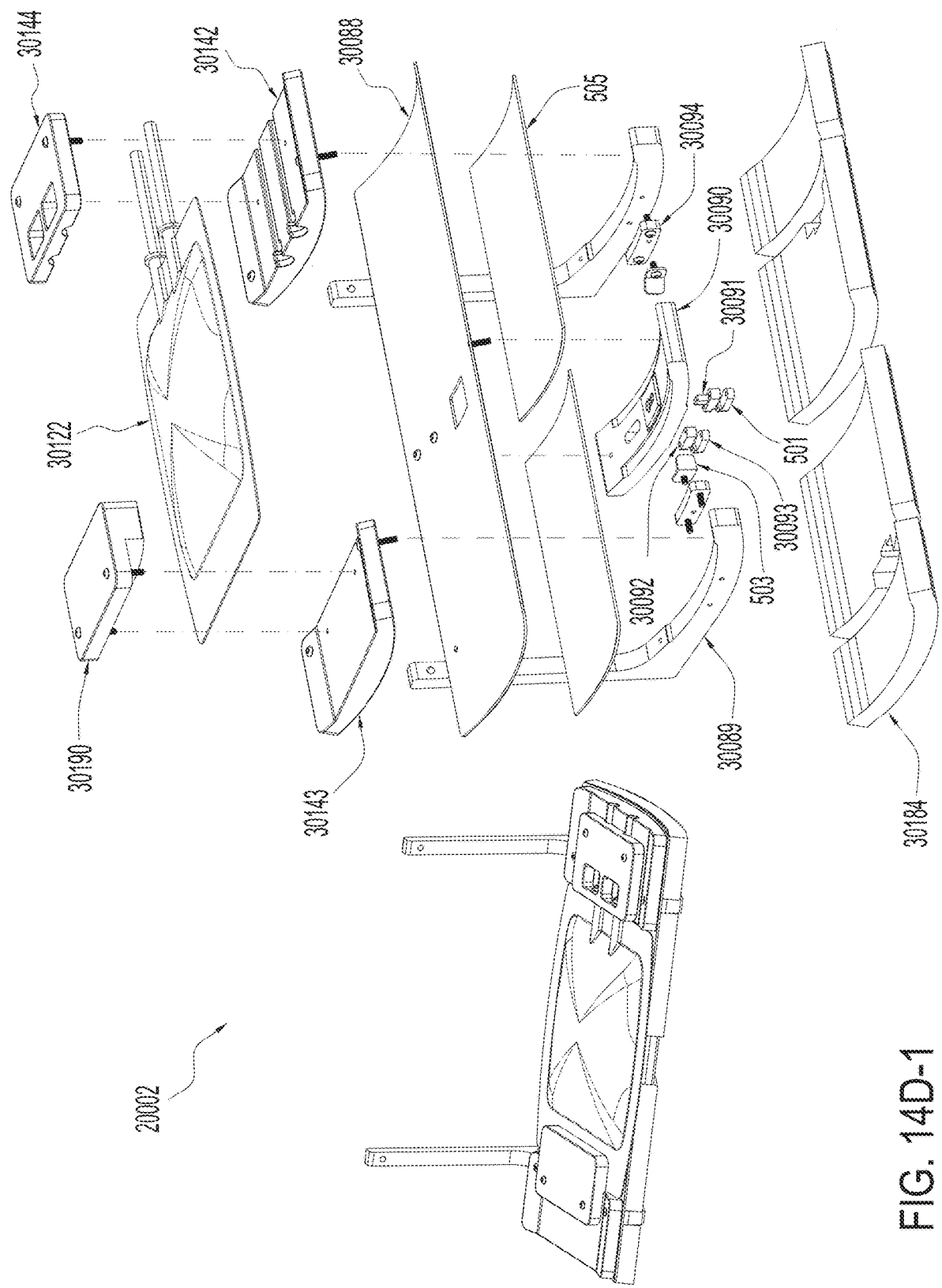

SYSTEM AND METHOD FOR CENTRALIZED FLUID MANAGEMENT AND CULTURE CONTROL

CROSS REFERENCE TO RELATED APPLICATIONS

This application claims the benefit of U.S. Provisional Application Ser. No. 63/019,260, filed May 1, 2020, entitled SYSTEM AND METHOD FOR CENTRALIZED FLUID MANAGEMENT AND CULTURE CONTROL, which is incorporated herein by reference in its entirety.

GOVERNMENT LICENSE RIGHTS

This invention was made with government support under W911NF-17-3-0003, subaward T0064-A, awarded by Advanced Regenerative Manufacturing Institute. The government has certain rights in the invention.

BACKGROUND

The present disclosure pertains to growing and maintaining tissue in a bioreactor, and more specifically to the flow of media in a thermally-controlled environment in which the characteristics of the media can be dynamically adjusted.

Systems have been described that include bioreactors in chambers where the bioreactors include detectors capable of detecting a change in metabolites associated with the growth of cells or tissue cultures. When changes are detected, the bioreactor is opened in a clean room or a biosafety cabinet and some or all of the media is manually replaced with fresh media. Still other systems change the media out completely or rotate the media based on a time schedule, regardless of the characteristics of the media. Systems have been described that include bioreactor controllers for supporting the development of a single unit of tissue. When multiple tissues are desired, the full bioreactor controller must be replicated, resulting in a substantial cost for scaling up the process.

There is an unmet need for scalable systems that dynamically change media based on characteristics of the media, and pump the media into and out of a bioreactor containing growing tissue. There is an unmet need for such a system to be closed to limit the potential for contamination without the cost required for maintaining clean space. There is an unmet need for a scalable multi-bioreactor control system that can draw from a shared media reservoir to reduce operating costs and that is flexible to support a broad range of bioreactor designs.

SUMMARY

In accordance with some configurations, the present teachings include a system and method for providing biocompatible, nutrient filled media to the Human Cells, Tissues, and cellular and tissue-based Products (HCT/P) while removing wastes. The present teachings provide for sensing the characteristics of the media, and modifying the characteristics when necessary. The present teachings can also provide components that are capable of fluid pumping integrated with fluid gas exchange, and sensing of fluid characteristics at consistent times during the fluid flow cycle.

The method of the present teachings for producing a plurality of independent tissue constructs simultaneously in a bioreactor system, can include, but is not limited to including, fluidically isolating each of the plurality of bioreactors from each other and from other components of the bioreactor system. Each of the plurality of bioreactors can produce one of the plurality of independent tissue constructs. The bioreactor system can include a plurality of bioreactors, and at least one waste line can conduct waste from the plurality of bioreactors. At least one media line can conduct a media towards the plurality of bioreactors. The at least one media line, the at least one waste line, and the plurality of bioreactors can be coupled by a fluid path. The method can include feeding the plurality of independent tissue constructs with the media conducted from a central media reservoir through the at least one media line to the plurality of independent tissue constructs. Fluidically isolating each of the plurality of bioreactors can optionally include preventing waste line backflow from the at least one waste line to the plurality of bioreactors using a first of an at least one check valve, preventing bioreactor backflow from the plurality of bioreactors to the at least one media line using a second of the at least one check valve, preventing sample backflow from the plurality of sample lines to the plurality of bioreactors using a third of the at least one check valve, and fluidically isolating a chiller media enclosure from the bioreactor system using a fourth of the at least one check valve. The at least one check valve can optionally include at least one valve completely sealing the fluid path when the at least one valve is exposed to neutral pressure or backflow, and/or at least one spring style check valve, and/or non-corrosive, non-leaching, autoclavable, gamma radiation resistant materials.

The method of the present teachings for alternating a direction of a fluid flow of a fluid through a cassette without changing the direction of the fluid flow past at least one on-cassette inline sensor can include, but is not limited to including, pumping the fluid in a first flow path past the at least one on-cassette inline sensor if a first valve is open, a gas exchange zone if a second valve is open, and a sample line if a third valve is open by applying pneumatic pressure to the pumping chamber cassette membrane, the corresponding pumping valve being open. The cassette can include a pumping chamber, and the pumping chamber can include a pumping chamber cassette membrane. The pumping chamber can be associated with a corresponding pumping valve. The method can include isolating the pumping chamber by closing a valve corresponding to a second flow path. The second flow path can traveling in an opposite direction to the first flow path, by blocking the pumped fluid in the second flow path. The method can include routing the fluid to the pumping chamber using a fourth valve or a fifth valve, and tying the first valve and the fourth valve together, and the second valve and the fifth valve together.

The method of the present teachings for achieving consistent and/or tightly controlled flow rates and flow continuity of a fluid flow traversing a cassette can include, but is not limited to including, metering the fluid flow of gas into the pneumatic side of the pumping chamber using a single q-port/s-position valve. The cassette can include a pumping chamber, and the pumping chamber can include a pneumatic side. The value for q can optionally equal 3, and the value for s can optionally equal 2. The value for q can optionally equal 2, and the value for s can optionally equal 2.

Another method of the present teachings for achieving consistent and/or tightly controlled flow rates and flow continuity of a fluid flow traversing a cassette can include, but is not limited to including, directly controlling the fluid flow of gas to the pneumatic side of the pumping chamber using variable or pulse width modulated current and a proportional valve, and providing a parallel q-port/s-position valve. The parallel q-port/s-position valve can allow increased of the flow rates. The method can include providing a series q-port/s-position valve. The series q-port/s-position valve can prevent leaking when the proportional valve is in a closed position. The cassette can include a pumping chamber, and the pumping chamber can include a pneumatic side. The value for q can optionally equal 3, and the value for s can optionally equal 2. The value for q can optionally equal 2, and the value for s can optionally equal 2.

Another method of the present teachings for achieving consistent and/or tightly controlled fluid flow rates and flow continuity of a fluid flow traversing a cassette can include, but is not limited to including, using a plurality of orifices as part of the pneumatic flow path. Each of the plurality of orifices can include a q-port/s-position valve, and the q-port/s-position valve can control a fluid flow rate through the plurality of orifices. The method can include sizing the plurality of orifices based on at least on a desired of the fluid flow rate, and adjusting the fluid flow rate to the desired fluid flow rate by pulsing the q-port/s-position valve. The cassette can include a pumping chamber, and the pumping chamber can include a pneumatic side. The value for q can optionally equal 3, and the value for s can optionally equal 2. The value for q can optionally equal 2, and the value for s can optionally equal 2.

The method of the present teachings for thermally isolating each of a plurality of bioreactors and at least one reservoir from each other can include, but is not limited to including, providing a horizontally hinged door enclosing the tubing in the thermal enclosure, providing an analysis door storing the sample tubing, providing a left or right hinged door enabling access to at least one of the plurality of pumping cassettes and the plurality of bioreactors, and providing at least one slot in the thermal enclosure for inserting the at least one of the plurality of pumping cassettes into a manifold gasket slot. The plurality of bioreactors and the at least one reservoir can be enclosed in a thermal enclosure, and the plurality of bioreactors and the at least one reservoir can be fluidically coupled with tubing and a plurality of pumping cassettes. The thermal enclosure can include a sample area, and the sample area can be fluidically coupled with the plurality of bioreactors with sample tubing.

The method of the present teachings for managing at least one process parameter in media prior to exposing tissue to the media can include, but is not limited to including, placing at least one sensor on the pumping cassette, and pumping the media in a loop. The tissue can be enclosed in a bioreactor, and the media can be pumped into the bioreactor by a pumping cassette. The loop can be isolated from the tissue, and the loop can include the at least one sensor, which could be a spot sensor. The method can include applying, by the at least one sensor, at least one test of the at least one process parameter of the media. When the at least one test indicates the at least one process parameter to be within pre-selected limits, the method can include including the tissue in the loop, where the loop moves the media to the tissue. The method can include applying, by the at least one sensor, the at least one test of the at least one process parameter of the media.

The system of the present teachings can alternate a direction of a fluid flow of a fluid entering, exiting, or both entering and exiting the pumping cassette without changing the direction of the fluid flow past at least one on-cassette inline sensor. The system can include, but is not limited to including, a pumping chamber including a pumping chamber cassette membrane. The pumping chamber can be associated with a corresponding pumping valve. The system can include a fluidic pathway analogous to an h-bridge enabling applying pneumatic pressure to the pumping chamber cassette membrane. The corresponding pumping valve can be open. The pneumatic pressure can enable pumping the fluid in a first flow path past the at least one on-cassette inline sensor if a first valve is open, can enable pumping the fluid into a gas exchange zone if a second valve is open, and can enable pumping the fluid into a sample line if a third valve is open. The fluidic pathway can enable isolating the pumping chamber by closing a valve corresponding to a second flow path by blocking the pumped fluid in the second flow path. The second flow path can travel in an opposite direction to the first flow path, the fluidic pathway enabling routing the fluid to the pumping chamber using a fourth valve or a fifth valve. The fluidic pathway can enable tying the first valve and the fourth valve together, and the second valve and the fifth valve together.

The system of the present teachings can achieve consistent and/or tightly controlled flow rates and flow continuity of a fluid flow traversing a cassette. The system can include, but is not limited to including, a single q-port/s-position valve metering the flow of gas into the pneumatic side of the pumping chamber. The system can include a pumping chamber, and the pumping chamber can include a pneumatic side. The value for q can optionally equal 3, and the value for s can optionally equal 2. The value for q can optionally equal 2, and the value for s can optionally equal 2.

In another configuration, the system of the present teachings for achieving consistent and/or tightly controlled flow rates and flow continuity of a fluid flow traversing a cassette can include, but is not limited to including, a variable or pulse width modulated current and a proportional valve directly controlling the flow of gas to the pneumatic side of the pumping chamber, a parallel q-port/s-position valve enabling increased of the flow rates, and a series q-port/s-position valve preventing leaking when the proportional valve is in a closed position. The value for q can optionally equal 3, and the value for s can optionally equal 2. The value for q can optionally equal 2, and the value for s can optionally equal 2.

In another configuration, the system of the present teachings for achieving consistent and/or tightly controlled fluid flow rate and flow continuity of a fluid flow traversing the pumping cassette can include, but is not limited to including, a plurality of orifices as part of the pneumatic flow path. Each of the plurality of orifices can include a q-port/s-position valve. The q-port/s-position valve can control the fluid flow rate through the plurality of orifices. The plurality of orifices can be sized based at least on a desired of the fluid flow rate, and the fluid flow rate can be adjusted to the desired fluid flow rate by pulsing the q-port/s-position valve. The value for q can optionally equal 3, and the value for s can optionally equal 2. The value for q can optionally equal 2, and the value for s can optionally equal 2.

The thermal enclosure of the present teachings for growing tissue can include, but is not limited to including, a plurality of bioreactors isolated from each other, and a plurality of pumping cassettes fluidically coupled with the plurality of bioreactors. The plurality of bioreactors can be prevented from providing backflow into the plurality of pumping cassettes by a first of an at least one check valve. The thermal enclosure can include at least one media reservoir fluidically coupled with the plurality of pumping cassettes. The at least one media reservoir can provide media to the plurality of pumping cassettes, and the plurality of pumping cassettes can pump the media to the plurality of bioreactors. The thermal enclosure can include a waste line that can be fluidically coupled with the plurality of bioreactors. The waste line can be prevented from providing backflow into the plurality of bioreactors by a second of the at least one check valve. The media reservoir fluidic coupling, the plurality of pumping cassettes, and the plurality of bioreactors can form a fluid path. The first of the at least one check valve can optionally include at least one valve completely sealing the fluid path when the first of the at least one valve is exposed to neutral pressure or backflow. The thermal enclosure can optionally include a chilled media enclosure that can provide chilled media to the at least one media reservoir. The chilled media enclosure can prevent sample backflow from the plurality of sample lines to the plurality of bioreactors using a third of the at least on check valve. The chilled media can be fluidically isolated from the at least one media reservoir by a fourth of the at least one check valve. The at least one check valve can include at least one spring style check valve.

The method of the present teachings for automatic centralized fluid management and culture control can include, but is not limited to including, (a) automatically, by a system controller, monitoring temperature and dissolved gas concentrations of a cell or tissue culture media, (b) automatically, by the system controller, maintaining the temperature of the cell or tissue culture media in a media reservoir at a first pre-selected value, (c) automatically, by the system controller, adjusting the temperature and the dissolved gas concentrations of the cell or tissue culture media to second pre-selected values prior to delivery to a user-supplied device, (d) automatically, by the system controller, delivering the temperature and dissolved gas concentration-adjusted cell or tissue culture media to the user-supplied device, (e) automatically, by the system controller, recirculating the temperature and dissolved gas concentration-adjusted cell or tissue culture media through the user-supplied device, (f) automatically, by the system controller, adjusting the temperature and the dissolved gas concentrations of the cell or tissue culture media to the second pre-selected values prior to the delivery to the user-supplied device, and (g) automatically, by the system controller, monitoring the temperature-adjusted cell or tissue culture media through the user-supplied device. If the temperature or the dissolved gas concentrations of the cell or tissue culture media meet the second pre-selected values, the method can include (h) automatically, by the system controller, repeating steps (e)-(g). If the temperature or the dissolved gas concentrations of the cell or tissue culture media do not meet the second pre-selected values, the method can include (i) automatically, by the system controller, delivering the recirculated temperature-adjusted cell or tissue culture media to a waste vessel or a sample vessel. The user-supplied device can optionally include a bioreactor. The automatic delivering of the temperature and dissolved gas concentration-adjusted cell or tissue culture media can optionally include delivery through a sterile flow path including disposable hardware. The first pre-selected temperature value can optionally include a range of 0-8° C. The second pre-selected temperature value can optionally include a range of 32-40° C. Automatically maintaining the temperature can optionally include enabling heating elements in a pumping manifold and a holding container. Recirculating can optionally include a flow path including the media reservoir, a reservoir line, a reservoir module cassette, the holding container, a module line, a waste line to the waste vessel, and a bioreactor module cassette. Recirculating can optionally include a sterile flow path including the media reservoir, a reservoir line, a reservoir module cassette, the holding container, a module line, a waste line to the waste vessel, a bioreactor module cassette, and the user-supplied device. The disposable hardware can optionally include gamma sterilizable hardware, and the gamma sterilizable hardware can optionally be resistant to leaching and particulate generation. Monitoring can optionally include using disposable sensors and non-invasive sensors. Disposable sensors can optionally include integration into the bioreactor module cassette and the reservoir module cassette. Adjusting can optionally include temperature control using the heating elements, gas diffusion through semipermeable plastics, and replacement of the cell or tissue culture media. In some configurations, the system can automatically perform a partial media exchange to the bioreactor recirculation loop. The partial media exchange can maintain selected nutrients in the media at a pre-selected threshold, for example, a minimum concentration. Selected nutrients can include glucose, for example.

BRIEF DESCRIPTION OF THE DRAWINGS

The foregoing features of the disclosure will be more readily understood by reference to the following description, taken with reference to the accompanying drawings, in which:

FIGS. 5A and 5B are fluid flow paths for bioreactor input and output flows in the cassette of FIG. 5;

FIGS. 5F-1 and 5F-2 are fluid flow paths for a priming sequence for the cassette of FIG. 5D;

FIGS. 5I-1 and 5I-2 are fluid flow paths for providing a media sample and flushing stale media for the cassette of FIG. 5D;

FIGS. 11A-1 through 11A-3 are fluid flow diagrams of initial configuration of the cassette of FIGS. 6A-6D;

FIGS. 11B-1 and 11B-2 are fluid flow diagrams of partial media replenishment of the cassette of FIGS. 6A-6D;

FIGS. 11D-1 through 11D-3 are fluid flow diagrams of circulation scenarios of the cassette of FIGS. 6A-6D;

FIGS. 12AA-12AF, 12BA-12BF, 12CA-12CF, 12DA-12DF, 12EA-12EF, 12FA-12FF, 12GA-12GF, 12HA-12HF, and 13A-1 through 13A-6 are pneumatic diagrams for various configurations of the pneumatic system of the present teachings;

FIGS. 14A-14D, 14D-1 through 14D-12, and 14E-14G are perspective diagrams of the system enclosure of the present teachings;

DETAILED DESCRIPTION

The system and method for providing biocompatible, nutrient filled media to the HCT/P while removing wastes can include a reservoir system to store and condition the media, a bioreactor system to house the HCT/P while it is being exposed to the conditioned media, and the control and pumping systems to maintain the conditioned media and the flow of media.

Figure 1:
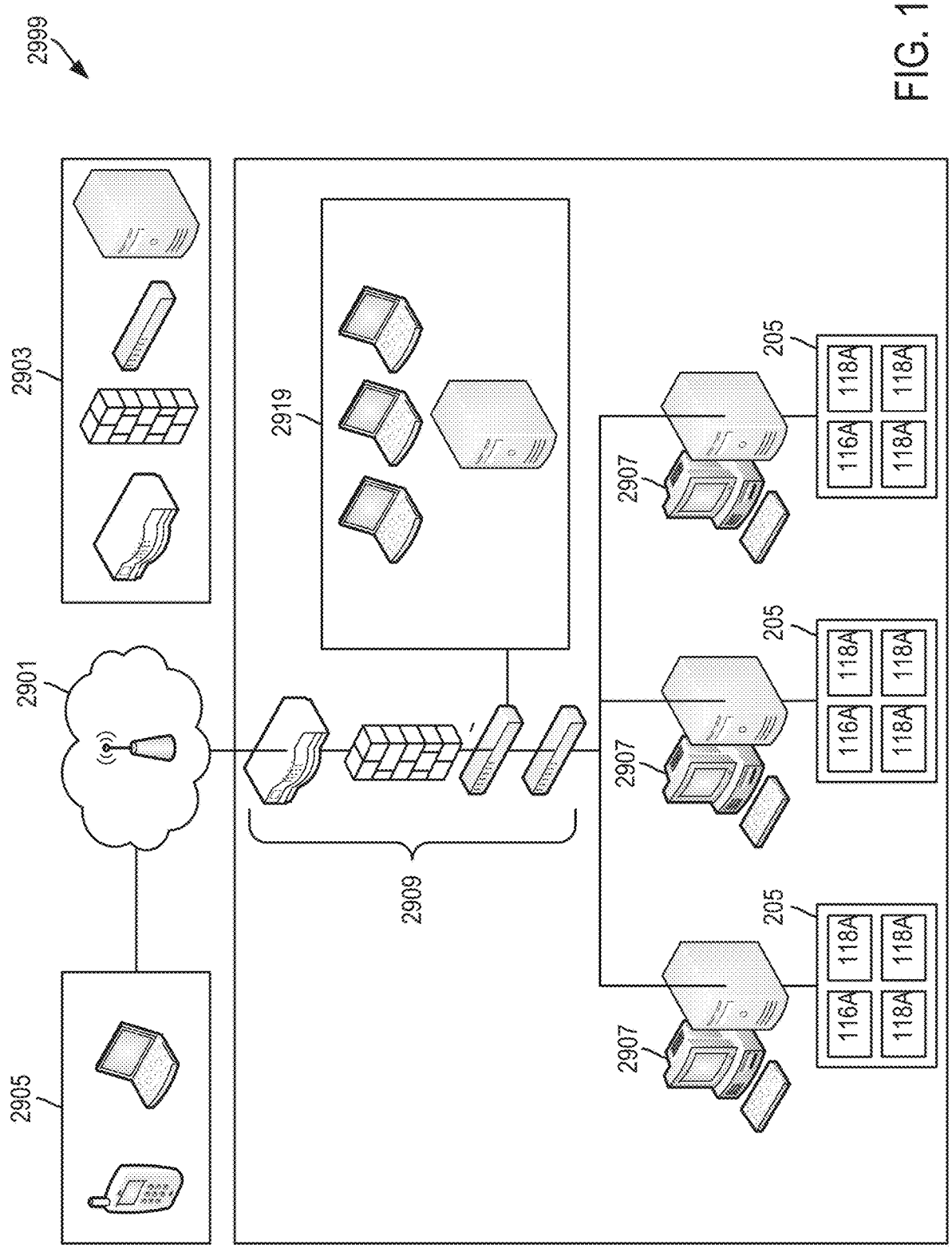
FIG. 1 is a pictorial representation of the system of the present teachings.

Referring now to FIG. 1, system 2999 that can house the HCT/P and provide media to the HCT/P can include control, storage, and fluid components that can be communicatively coupled by electronic connections among the components. Control of the components can be accomplished locally and/or remotely through remote control means 2905 and/or local control means server PC 2919 which can communicate with each other through electronic communications means 2901 and local communications means 2909. Remote control means 2905 can include conventional means to enable, for example, but not limited to, remote data access, remote control of system 2999, and remote event notification. Server PC 2919 can include conventional means to enable, for example, but not limited to, local data access, local control of system 2999, and local event notification. Electronic communications 2901 can include, but are not limited to including, conventional means such as, but not limited to, cellular means. Local communication means 2909 can include, but are not limited to including, local area network(s), conventional router(s), firewall(s), and switch(es) that can enable communications among fluid component controls 2907 and server PC/remote control means 2919/2905. Storage means 2903 can enable data retention for system control and operational analysis, and can include cloud storage and/or local storage by conventional means. The fluid system can include, for example, but not limited to, fluid component controls 2907, racks 205, reservoir systems 116A, and bioreactor systems 118A, all of which are described herein. In some configurations, the fluid system can include a pneumatic system, a manifold system, a control system, a source of media, a bioreactor, and sensors that can enable bi-directional flow through the bioreactor, recirculation to sensors in a fluid path that does not include the bioreactor, recirculation to the bioreactor in a fluid path that does not include the media source, and smooth and/or pulsatile fluid flow capability.

Figure 1A:
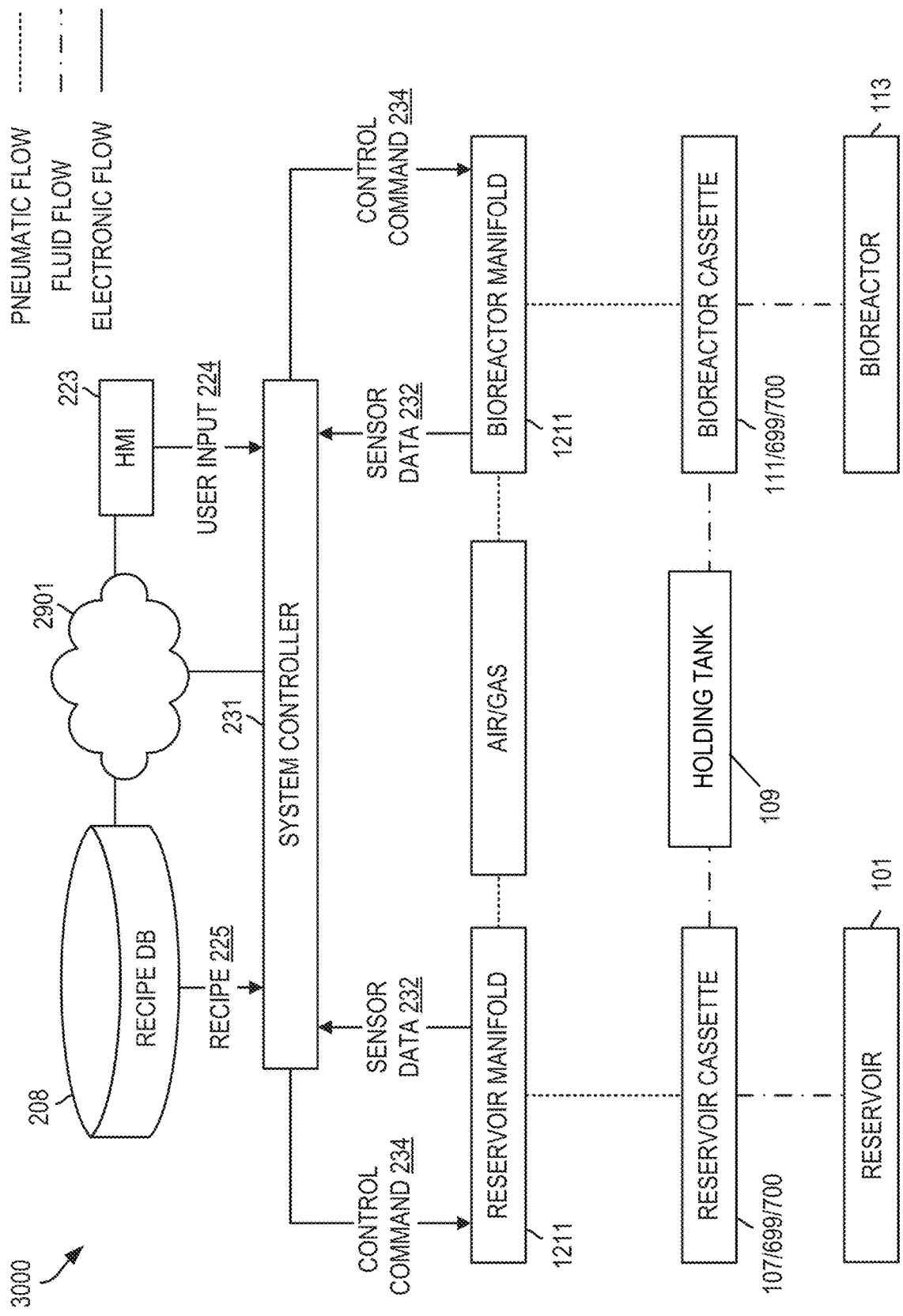
FIG. 1A is a schematic block diagram of the system of the present teachings.

Referring now to FIG. 1A, system 3000 of the present teachings can supply nutrients and remove waste from multiple user-supplied devices 113 containing HCT/P. System 3000 can provide the structure for controlled HCT/P growth and management. The purpose of system 3000 is to provide consistently accurate, repeatable, and timely results during HCT/P generation. System 3000 can include automated controls that can ensure repeatability, as well as manual controls that can override the automatic controls when required. In some configurations, system 3000 can include, but is not limited to including, electronic, pneumatic, and fluid flow paths. System controller 231 can enable electronic control of system 3000, according to user-selected and pre-selected processes. System controller 231 can control, monitor, and adjust the speed, direction, and physical properties of the media in fluid flow path, and can enable circulation of the media to enable the addition and mixing of media while the physical properties are adjusted. The monitoring and adjustment of the physical properties of the media can enable HCT/P to live and grow. System controller 231 can enable waste removal and sampling from the fluid path. System controller 231 can receive sensor data 232 through bioreactor/reservoir manifolds 1211 from sensors located on reservoir/bioreactor cassettes 107/111/699/700, and can formulate control commands 234. Control commands 234 can be issued to bioreactor/reservoir manifolds 1211 which can use control commands 234 to manage fluid flow. System controller 231 can receive information such as, for example, but not limited to, recipes 225 from recipe database 208 and user input 224 from human/machine interface (HMI) 223. In some configurations, recipe database 208 can be stored remotely from system 3000, and can be accessed through a communications network or any other remote means. In some configurations, user input 224 can be provided through a remote HMI 223 that can be accessed through a communications network or any other remote means. System controller 231 can enable opening and closing of valves in reservoir/bioreactor manifolds 1211 that can enable drawing in various gasses that can be used to, for example, but not limited to, (1) pressurize a pumping system in the fluid path to push the fluid in desired directions through the fluid path, and (2) condition the fluid to achieve various fluid characteristics that promote tissue viability and growth. Reservoir/bioreactor manifolds 1211 can issue commands that can control fluid flow. In some configurations, a single reservoir manifold 1211 can control the fluid flow path from a single reservoir cassette 107/699/700 to a plurality of bioreactor cassettes 111/699/700.

Continuing to refer to FIG. 1A, in some configurations, recipes 225 can provide automated control of the HCT/P engineering process by indicating, for each type of activity required to keep the HCT/P thriving, a series of steps system 3000 should take. HMI 223 can provide a mechanism for user control of the HCT/P engineering process. In some configurations, at least some of the directions received from human-machine interface 223 can override directions received from recipes 225. Through HMI 223, the user can create, load, or modify production recipes 225, initiate user actions such as loading or removing a user-supplied device, monitor the status of in-progress production runs, or access logs from previous production runs. System 3000 can maintain logs of relevant production information for each HCT/P production run. Maintenance, calibration, and user access logs can be recorded. Logs can be locally stored, and can be stored remotely. In some configurations, redundant log copies can be mirrored on a cloud-connected data management system. Access to the cloud-connected data management system and local device record can be limited to authorized users, and log data can be write protected.

Continuing to refer to FIG. 1A, exemplary pumping actions are described herein. Each pumping action can be performed until a specific endpoint is reached. Pumping actions like priming or sampling can require a certain volume delivered to a specific location, while recirculation pumping actions can require fluid to circulate in a desired fluid path for a specific duration of time. Endpoint triggers can be created based on output from devices such as HCT/P-specific sensors. While pumping actions are being performed, system 3000 can monitor and control, for example, but not limited to, temperature, pH, dissolved oxygen concentration, and glucose concentration to approach setpoints indicated in recipe 225. During a production run, the user can access, but is not limited to accessing, production identifiers, device identifiers, alarm/alert details, bioreactor status, sensor values, power status, and production run details, and time elapsed since the last partial replenishment of media. Sampling scheduling can be based at least on the last partial replenishment of media.

Continuing to refer to FIG. 1A, with respect to the pneumatic flow path, gas can be received and distributed through a network of pneumatic valves. Some of the gas can provide positive and negative pressure to components of the fluid path, and some of the gas can provide a means to adjust the physical properties of the fluid. Pneumatic valves can supply pressure from gas sources 903 to the enable movement of fluid in the fluid flow path. Additionally, system controller 231 can gather sensor data 232, and can enable the fluid in the fluid path to be mixed through a membrane with gas from gas sources 903 to achieve desired physical properties of the fluid. The gas exchange membrane characteristics can include high permeability and resistance to tearing. In some configurations, high purity silicone can be used as the gas exchange membrane. In some configurations, the silicone membrane can be bonded to the cassette with an RTV adhesive (Nusil MED-4013). In some configurations where the cassette is made out of a material that does not accept adhesives well, the silicone membrane can be bonded to the cassette with a combination of a primer (Nusil MED-162) and the RTC adhesive. In some configurations, system controller 231 can control coordinated and/or independent activity among multiple reservoir/bioreactor manifolds 1211. In some configurations, a fluid path connecting reservoir cassette 107/699/700 with multiple bioreactor cassettes 111/699/700 can include multiple fluid flow paths controlled by system controller 231 in a coordinated, but independent, way. In some configurations, system controller 231 can manage multiple reservoir manifolds 1211 while maintaining their fluid isolation from one another and from their associated bioreactor manifolds 1211, reservoir cassettes 107/699/700, and bioreactor cassettes 111/699/700. System controller 231 can enable fluid flow from media reservoir 101, past mechanisms that can monitor the status of the tissue by monitoring the fluid in media reservoir 101 and the circulating fluid, past and through the tissue in bioreactor 113, and into waste 117 (FIG. 1C), for example.

Continuing to refer to FIG. 1A, system 3000 can include technology that can ensure the security of system 3000, control critical process parameters, and maintain run-time information. Ensuring the security of system 3000 can include, but is not limited to including, limiting which users can access which features based on, for example, but not limited to authorization level. Security breaches that can affect remote control, remote data access, and remote data storage, such as in-flight modification of remote messages, eavesdropping on communications lines, and malicious applications tampering with system 3000, can also be protected against. Controlling critical process parameters can protect the tissues incubated by system 3000 from succumbing to system malfunctions. Critical process parameters can be controlled by real-time closed loop control. Cloud-connected data management, on-board or removable storage systems, and real or virtual memory, for example, can be used for access to run-time information such as, for example, historic and real-time sensor data.

Figure 1B:
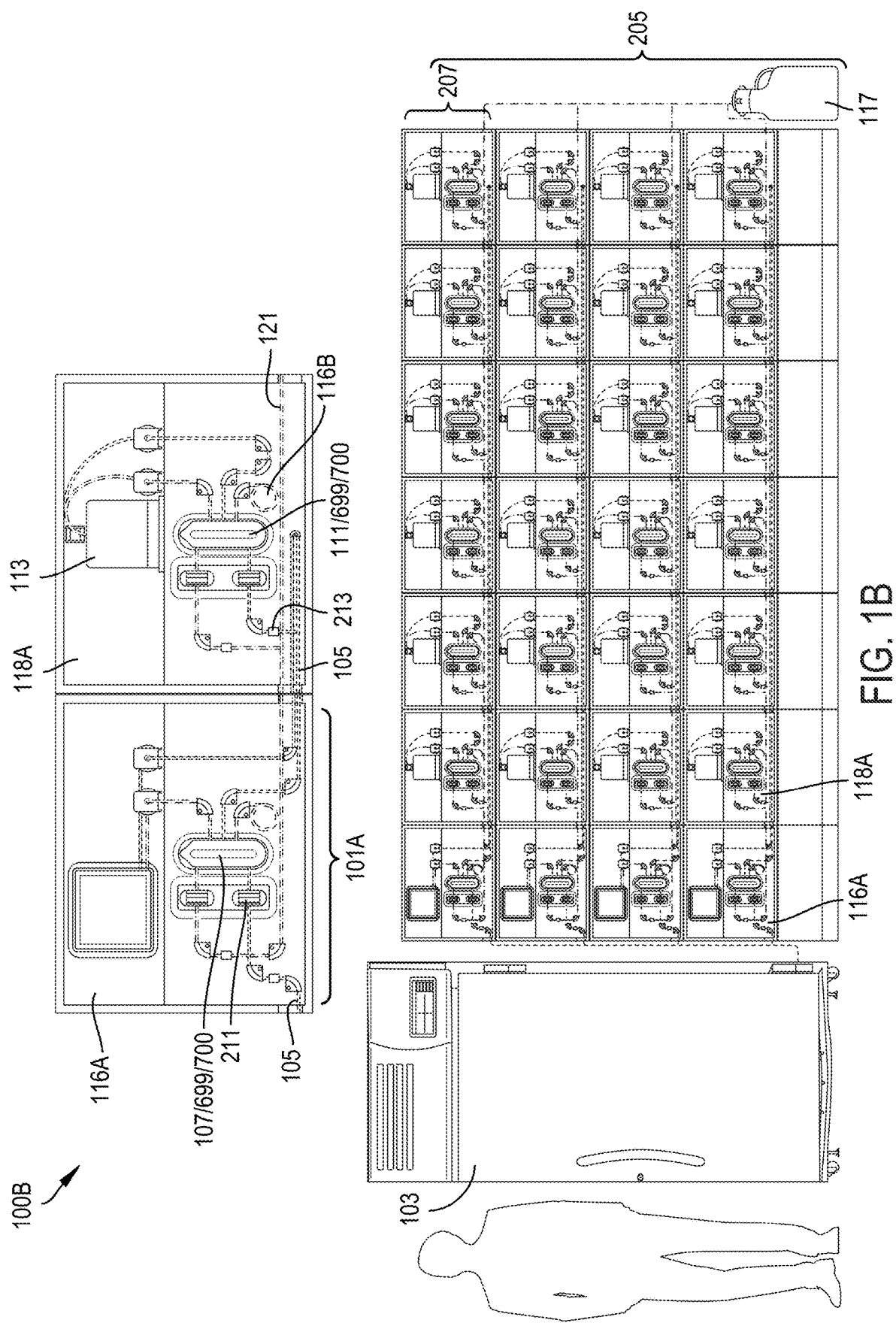
FIG. 1B is a pictorial representation of a configuration of the reservoir and bioreactor systems of the present teachings.

Referring now to FIG. 1B, system 3000 (FIG. 1A) can include subsystem 100B that can include, but is not limited to including, reservoir module 116A that can receive the fluid/media from temperature regulator 103, and adjust the dissolved gas concentrations in the fluid prior to delivery to user-supplied device 113 (also referred to herein as bioreactor 113). Subsystem 100B can include bioreactor module 118A that can receive the fluid/media from reservoir module 116A, and monitor and circulate the fluid/media through user-supplied device 113 prior to delivery to waste container 117 and/or sample vessel 115 (FIGS. 2A/2B), for example. To enable temperature control of the tissue process, each component of subsystem 100B can include thermal enclosure 101A that can enclose and thermally manage the components therein.

Continuing to refer to FIG. 1B, the condition of the media within the flow path can be monitored through the use of disposable and/or non-invasive sensors. The media quality can be adjusted through a combination of temperature regulation means, gas diffusion through semi-permeable membranes, and full or partial replacements with fresh media. The media can be delivered from holding container 109 (FIG. 1A) to user-supplied device 113 through a sterile, disposable flow path that can include, but is not limited to including, disposable reservoir line 105, disposable reservoir module cassette 107/699/700, disposable module line 119 (FIGS. 2A/2B), disposable waste line 121, and disposable bioreactor module cassette 111. The disposable hardware can, for example, be gamma sterilizable, and resistant to leaching and particulate generation. Disposable sensors can be integrated into cassette types 699, 700, and 107/111. To prevent cross-contamination among media reservoir 101 (FIG. 1A), reservoir module 116A and bioreactor module 118A, the fluid path can include backflow protection measures 213. To connect different components that are installed at different times, subsystem 100B can include, for example, but not limited to, connectors 211 and/or or tubing welding. In some configurations, connectors 211 can include, for example, but not limited to, CPC® AseptiQuik S Connector https://www.cpcworldwide.com/Product-List/Series/108/Category/40/Product/6488.

Continuing to refer to FIG. 1B, in some configurations, system 3000 (FIG. 1A) can be mounted in rack 205 that can include a support structure that can hold the durable hardware of system 3000 (FIG. 1A). Rack 205 can include functional blocks, referred to herein as rows 207, that can provide mounting for at least one reservoir module 116A, and at least one bioreactor module 118A. The main function of rack 205 is to provide common rails for pneumatic, electrical, and control communication connections. Rack 205 can provide pneumatic inlets to enable downstream gas mixing. Rack 205 can include programmable logic controllers (PLC) that can be controlled by system controller 231 (FIG. 1A). HMI 223 (FIG. 1A) can be located locally to rack 205, or through a cloud-based remote access system, for example. In order to reduce the user interactions necessary to set up a large number of simultaneous production runs, media reservoir 101 (FIG. 1A) can feed each row 207 of reservoir modules 116A. In some configurations, temperature manager 103 can be housed outside of rack 205. Within rack 205 are functional blocks, rows 207. Each of rows 207 can include a single reservoir module 116A fluid handling system that can support at least one bioreactor module 118A fluid handling system. In some configurations, row 207 can include a single reservoir module 116A fluid and a plurality of bioreactor modules 118A. Temperature manager 103 can maintain cell or tissue culture media in centralized media reservoir 101 (FIG. 1A) at temperatures designed to extend the life of the media. In some configurations, the fluid pathways from media reservoir 101 (FIG. 1A) to reservoir modules 116A can be fluidically isolated between rows 207.

Continuing to refer to FIG. 1B, reservoir module 116A can supply media to bioreactor modules 118A. Each of bioreactor modules 118A can incubate tissue in isolation from other bioreactor modules 118A, but media flow and monitoring can be centrally controlled. One reason to maintain isolation between modules is to enable growth and maintenance of both autologous and allogeneic tissue constructs. Autologous HCT/P, made using individual patient's cells, must be isolated from each other and from allogeneic HCT/P to prevent potential immune rejection issues. Allogeneic HCT/P, made using non-patient cells, can contaminate autologous HCT/P, possibly requiring immunosuppression to prevent rejection of the HCT/P. In some configurations, temperature manager 103 can, under the control of system controller (FIG. 1A), maintain the temperature of the media at a desired level. In some configurations, temperature management system 103, which can be durable, can maintain the temperature and gas concentrations of the media as it enters the fluid flow path. Accurate temperature control can slow the degradation of the media, and can decrease the time needed to prepare the media for delivery to user-supplied device 113. Each of bioreactor modules 118A can accommodate a variety of user-supplied devices 113, such as various different kinds of bioreactors. Any number of reservoir modules 116A and bioreactor modules 118A can be included in rack 205, depending upon the physical size of rack 205. Any row 207 can include any number of reservoir modules 116A and bioreactor modules 118A.

Figure 1C:
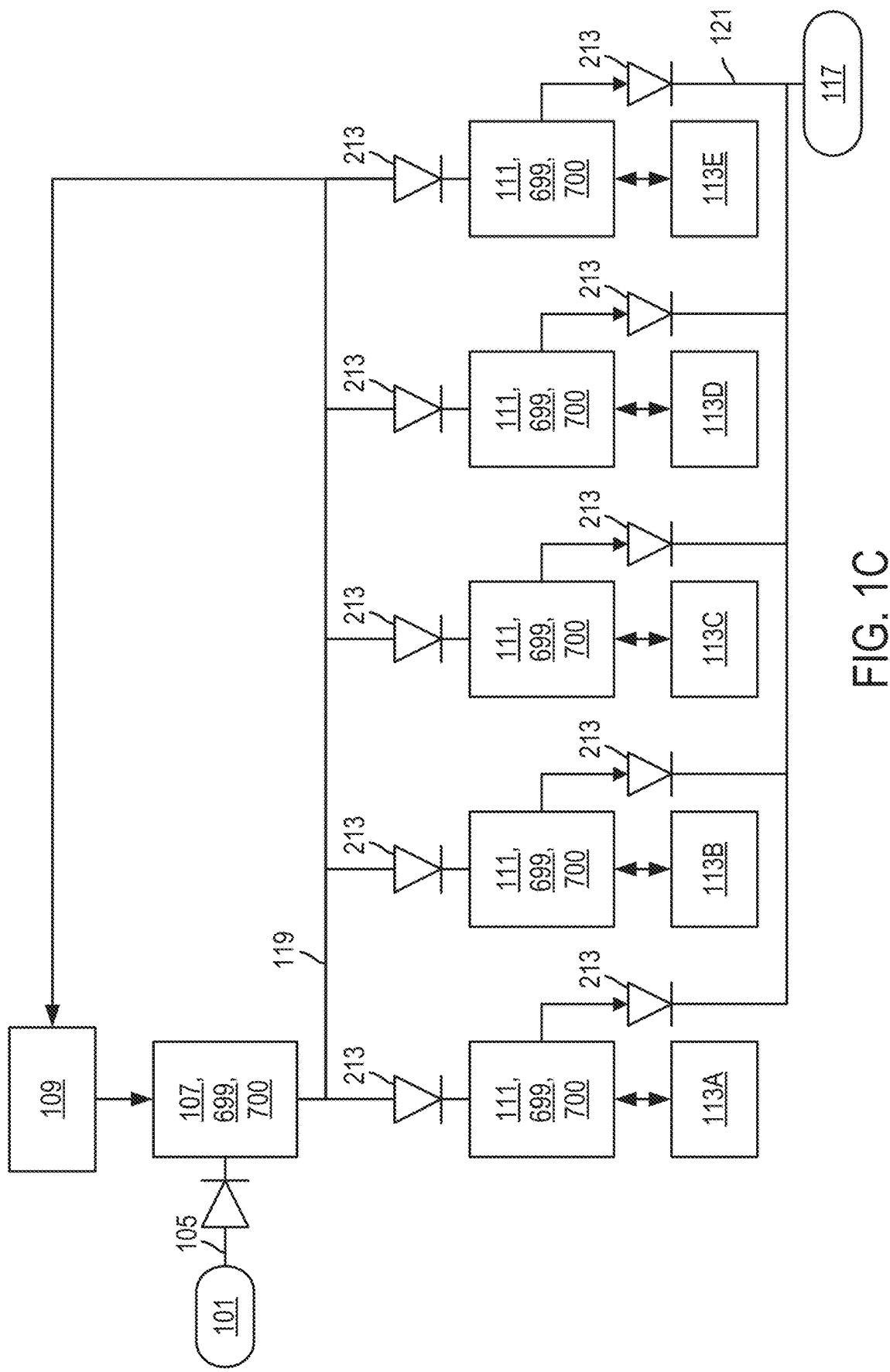
FIG. 1C is a schematic block diagram of the configuration of FIG. 1B.
Figure 4:
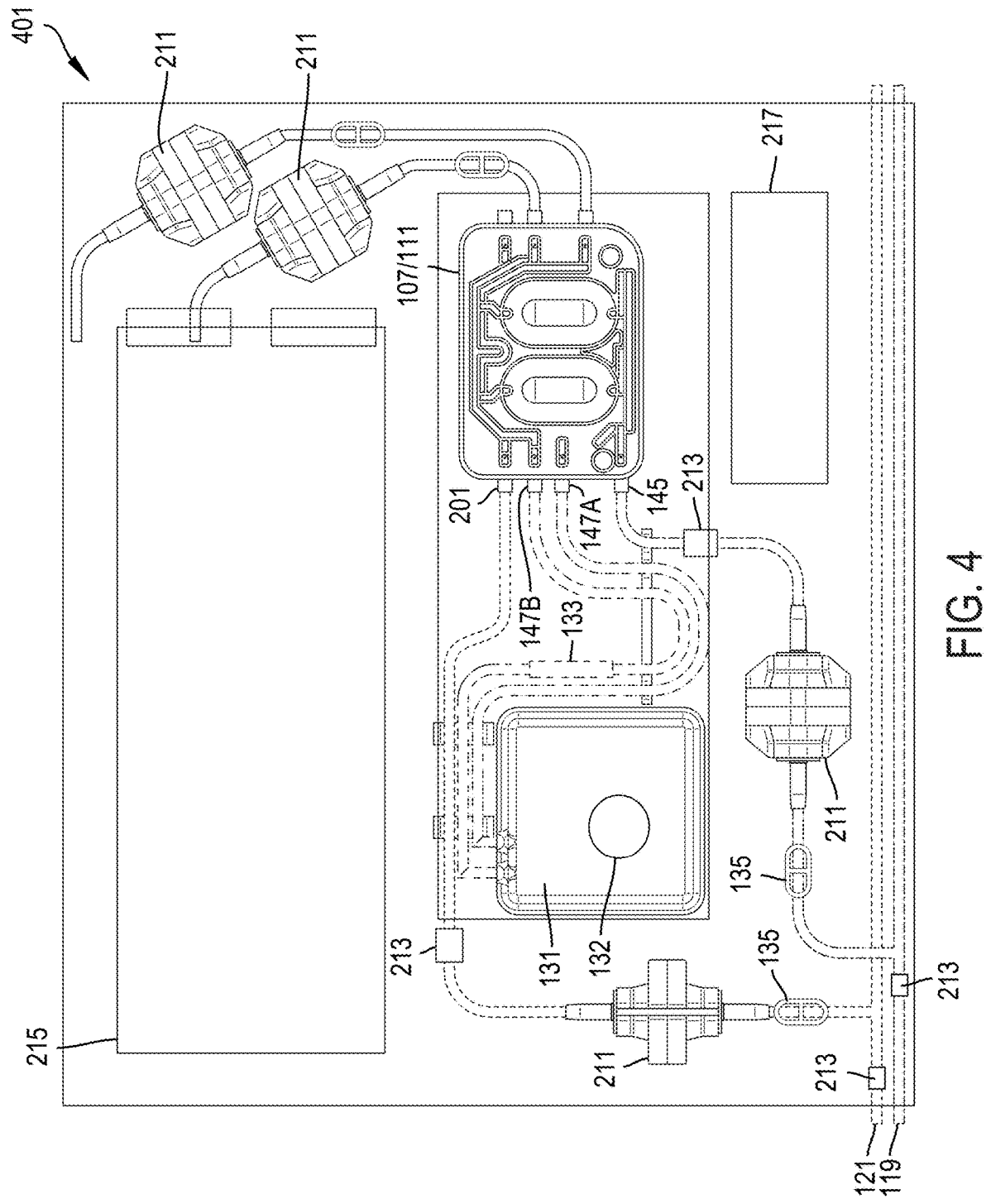
FIG. 4 is a pictorial representation of a configuration of a pumping cassette in line with a gas exchange chamber.

Referring now to FIG. 1C, in some configurations, HCT/P grown in each user-supplied device 113A/B/ . . . can include patient-specific HCT/P. Isolating each user-supplied device 113A/B/ . . . from the other user-supplied devices 113A/B . . . can prevent cross talk among the HCT/P cultures that could lead to immunogenic events or inconstant maturation. Isolation of user-supplied devices 113A/B/ . . . from each other can be enabled by preventing backflow from various tubing to/from user-supplied devices 113A/B/ . . . by using one-way check valves 213, for example. In some configurations, tubing can include waste line 121, reservoir line 105, module line 119, and sample line 116B (FIG. 1B). Media reservoir 101 can be isolated from reservoir module cassette 107/699/700 to prevent mixing of warm or partially degraded media, or media with materials that might result in immunogenic events, with the fresh media, limiting the potential delay of treatment and financial losses associated with the spread of contaminated materials. In some configurations, media flow path isolation can be enabled by check valves 213. In some configurations, spring style check valves can be used to completely seal the flow path when exposed to neutral pressure, insufficient pressure, or backflow. In some configurations, media isolation valves can include on/off valves such as rocker and diaphragm. In some configurations media isolation means can include pinch valves 135 (FIG. 4).

Continuing to refer to FIG. 1C, the reservoir fluid handling system is an intermediate step between temperature management system 103 and the bioreactor module fluid handling system. The intermediate step can prevent the HCT/P from being exposed to cold media of unknown pH and dissolved oxygen concentration. The reservoir module fluid handling system can support the following pumping actions: filling of holding container 109, circulating through holding container 109, and purging media to waste container 117. With respect to filling of holding container 109 a volume of media from media reservoir 101 can be withdrawn, and the media can be delivered to holding container 109. The media can be delivered to holding container 109 in anticipation of priming second/third configuration cassette 699/700 and user-supplied device 113A/B/C . . . when starting a new tissue production run, or when partially replacing the media within second/third configuration cassette 699/700 and user-supplied device 113A/B/C . . . during an existing tissue production run. Media can be pumped from the outlet of holding container 109 back to the inlet of holding container 109 in order to continually mix the media within reservoir cassette 699/700. This function can be performed while adjusting the physical properties of the media to comply with tolerances for temperature, dissolved oxygen, and pH. The tolerances can be set by default values, user-defined values, and/or dynamically-determined values. The mixing action can pass the media over cassette sensing elements in reservoir cassette 699/700 so that accurate measurements may be taken. The media in reservoir cassette 699/700 or holding container 109 can be disposed of by withdrawing all the media from holding container 109 and delivering the media to waste container 117. The old media can be purged after adding a new media reservoir or for purging unneeded media to prevent dilution of future media with thermally degraded media. If additional confidence in the quality of the media in holding container 109 is required, the current fluid can be purged to waste container 117, and a full or partial fill can be performed, fluid can be purged to waste container 117, and another full or partial fill can be performed in anticipation of priming or replenishment activities.

Figure 2A:
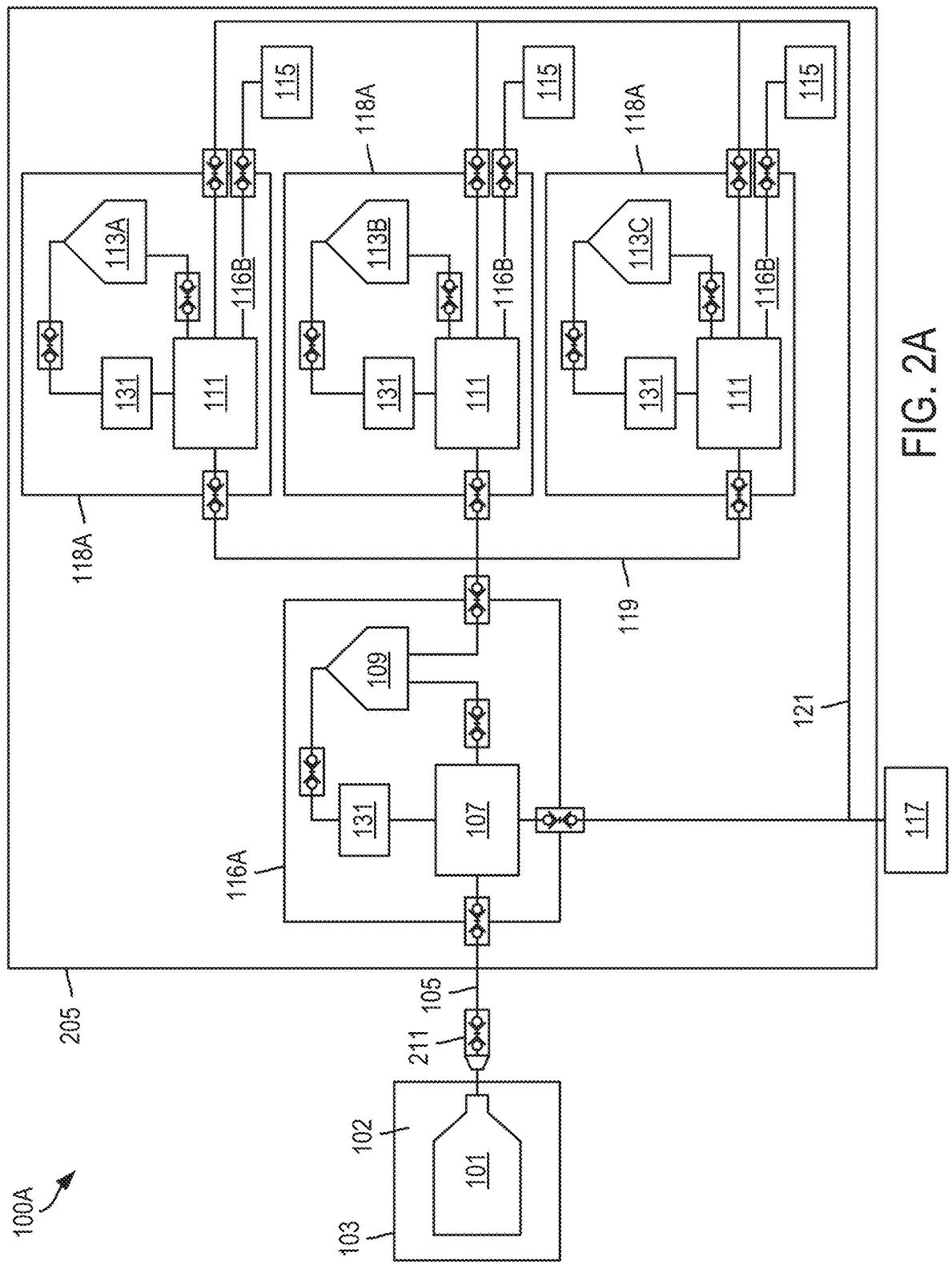
FIGS. 2A and 2B are schematic block diagrams of configurations of bioreactor and reservoir flow.
Figure 2B:
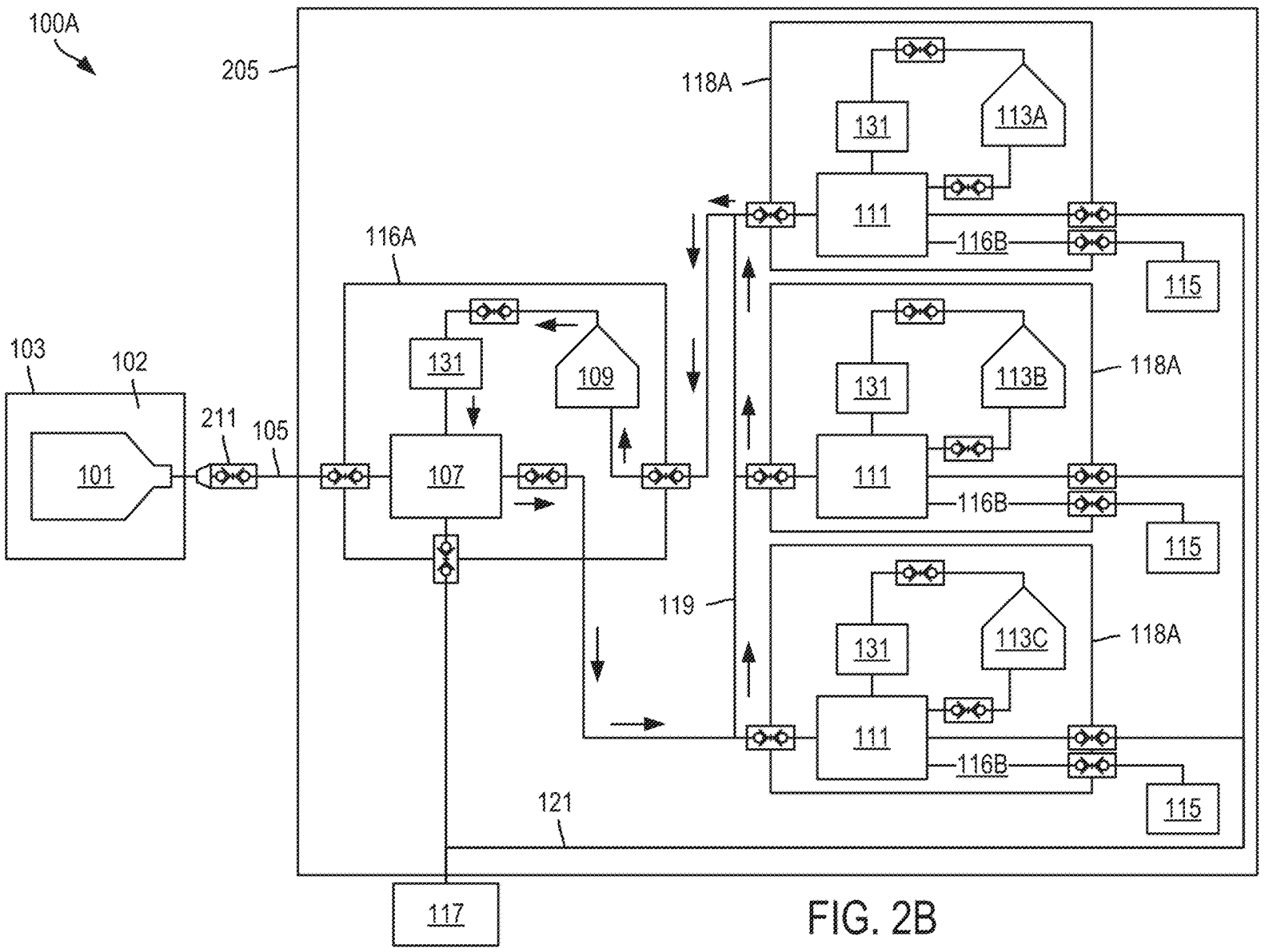

Referring now to FIGS. 2A and 2B, system 100A illustrates a first configuration of reservoir module 116A, bioreactor module 118A, and temperature manager 103. The components of system 100A can include disposable hardware and durable hardware. Disposable hardware components can function together to provide a sterile flow path from media reservoir 101 to bioreactor module 118A to waste vessel 117, for example. All disposable components of the sensing system can be integrated into reservoir and bioreactor cassettes 107/111. The disposable hardware can be gamma sterilizable, resistant to leaching and particulate generation, and pre-packaged to minimize accumulation of contaminants on the surfaces of reservoir and bioreactor cassettes 107/111. Disposable hardware can include, but is not limited to including, media reservoir 101, reservoir line 105, reservoir cassette 107, holding container 109, module line 119, waste line 121, and bioreactor cassette 111.

Continuing to refer to FIGS. 2A and 2B, media reservoir 101 can hold fresh media at a pre-selected temperature in the range of about 2-6° C. Media reservoir 101 can be replaceable or refillable during the operation of system 100A, while fluid circulates through system 100A. In some configurations, media reservoir 101 can hold a sufficient amount of fluid to support continual operation. In some configurations, the minimum amount of fluid that can be held by media reservoir 101 can include at least, for example, 10 liters. Media reservoir 101 can include gas permeable shell 102 that can enable the diffusion of gases in temperature manager 103 through gas permeable shell 102 into media reservoir 101. The diffused gases can acclimate the media within media reservoir 101, which can decrease the amount of time it takes to adjust, for example, but not limited to, the pH and the dissolved oxygen in the media to desired values, and can decrease outgassing. Media reservoir 101 can be of any shape and size. Reservoir line 105 can include a fluid pathway from media reservoir 101 to reservoir cassette 107. Reservoir line 105 can be integrated with reservoir cassette 107, or can include an extension line that is separate from reservoir cassette 107. In some configurations, the same disposable hardware can be used for reservoir cassette 107 and bioreactor cassette 111. In some configurations, reservoir cassette 107 can be physically identical to bioreactor cassette 111. In some configurations, both cassettes 107/111 can include, but are not limited to including, two pumping chambers, a gas exchange port connecting the cassette to gas exchange area 131, and ports for the media, sample line 116B, waste line 121, and a recirculation loop. The tubing leading to and membrane covering the fluid pathways of reservoir cassette 107 and bioreactor cassette 111 can be relatively gas-impermeable, and can have high flexibility and low fatigue. In some configurations, the pumping membrane can be constructed of Renolit 8300, for example. The membrane can be attached to the cassette creating a clean tight seal, for example, ultrasonically welding the membrane to the cassette. Cassettes 107/111 can include features to prevent misloading into, for example, a manifold structure.

Continuing to refer to FIGS. 2A and 2B, holding container 109 can hold media while the material properties are adjusted as the media are circulated in the reservoir cassette recirculation loop. Holding container 109 can include inlet and outlet ports to/from reservoir cassette 107, possibly to/from gas exchange zone 131, and an outlet port to module line 119. Holding container 109 can be manufactured from relatively gas impermeable materials. Module Line 119 can provide a sterile fluid pathway from the outlet port from holding container 109 to each of bioreactor cassettes 111. Module line 119 can be placed in rack 205 when setting up reservoir cassette 111, and can be left in place until the last HCT/P in row 207 (FIG. 1B) is finished. Pinch valves 135 (FIG. 4) can be used to prevent the flow of media to ports until they are connected to bioreactor cassette(s) 111, to possibly protect sterile fitting membranes from exposure to fluids. The membranes can be removed when making the sterile connection. Pinch valves 135 (FIG. 4) can be closed to prevent flow to/from bioreactor cassettes 111, for example, after the HCT/P production run is finished.

Continuing to refer to FIGS. 2A and 2B, waste line 121 can provide a fluid pathway from reservoir cassette 107 and each of bioreactor cassettes 111 to waste container 117. Waste line 121 can be placed in rack 205 when setting up reservoir cassette 107 and left until the last process in row 207 (FIG. 1B) is finished.

Continuing to refer to FIGS. 2A and 2B, bioreactor cassette 111 can pump media from module line 119 to user-supplied device 113A/B/C and then from user-supplied device 113A/B/C to waste line 121 and/or sample lines 116B. Possible flow paths through bioreactor cassette 111 can allow the media within bioreactor cassette 111 to be recirculated through user-supplied device 113A/B/C, and can allow for the direction of recirculation flow to be reversible. The fluid valves in bioreactor cassette 111 can be enabled/disabled in such a way as to allow a desired flow path to user-supplied device 113A/B/C to be isolated from the rest of bioreactor cassette 111 and exchange ports, i.e. the media inlet, waste, and sample vessel ports, or the flow path to the exchange ports to be isolated from the rest of bioreactor cassette 111, or both.

Continuing to refer to FIGS. 2A and 2B, system 100A can include durable hardware. Durable hardware can manipulate and monitor the media within the fluid path circulating through the disposable hardware. Durable hardware can include, but is not limited to including, the bioreactor pneumatics, some bioreactor sensors, an outer door to the bioreactor system, an inner gas exchange door/chamber, a port for sample line 116B, a tray for the fluid pathway lines, i.e. reservoir line 105, module line 119, and waste line 121, ports for the same, ports for connections to user-supplied device 113A/B/C which can be user-defined, temperature manager 103, rack 205, reservoir pneumatics, and some reservoir sensors. The durable hardware can enable monitoring the status of various parameters throughout an HCT/P production run.

Continuing to refer to FIGS. 2A and 2B, rack 205 can include a support structure that can house the durable hardware. In some configurations, temperature manager 103 can reside outside rack 205. Rack 205 can include rows 207 (FIG. 1B) that can include a single reservoir module 116A that can support any number of bioreactor modules 118A. Rack 205 can provide for cooling and common rails for pneumatic, electrical, and software communication connections among components of system 100A. The reservoir line fluid pathways from media reservoir 101 in temperature manager 103 to reservoir cassettes 107 in the reservoir module can be fluidically decoupled between different rows 207 (FIG. 1B).

Continuing to refer to FIGS. 2A and 2B, rack 205 can accommodate an array of situations through a combination of components reacting to system controller 231 (FIG. 1A) executing sequences of commands that can be based, for example, on recipes stored in recipe database 225 (FIG. 1A). For example, reservoir module 116A can receive a specific volume of media from media reservoir 101, and can deliver the media to holding container 109. The media can be used to prime bioreactor module cassette 111 and user-supplied device 113A/B/C when a new production run is started, or can be used to partially replace the media within bioreactor cassette 111 and user-supplied device 113A/B/C during an existing production run. If the media in reservoir cassette 107 or holding container 109 is to be disposed of, the media can be directed to waste vessel 117. Disposing of media can happen when, for example, but not limited to, purging old media after adding a new media reservoir or purging unneeded media to prevent dilution of future media with thermally or otherwise degraded media. If, for example, additional confidence in the quality of the media in holding container 109 is required, whatever fluid is in reservoir module cassette 107 and holding container 109 can be purged to waste vessel 117, a full or partial fill can be performed, and purge/fill process can be repeated until the fluid has reached desired characteristics.

Referring now to FIG. 2B, media can be pumped from an outlet of holding container 109 back to an inlet of holding container 109, enabling continual mixing of the media through reservoir module cassette 107. Continual mixing can be performed while the physical properties of the media are adjusted to comply with desired tolerances for characteristics such as, for example, but not limited to, temperature, dissolved oxygen, and pH. The mixing action can pass the media over the disposable sensing elements in reservoir module cassette 107 so that measurements of characteristics of the media may be taken.

Continuing to refer to FIGS. 2A and 2B, system 100A can include variety of sensing elements to monitor, evaluate, and control critical process parameters (CPP). For CPP within the flow path, disposable sensor elements can be placed within the cassettes prior to sterilization and read during the production run using durable hardware located outside of the cassettes. For CPP outside of the flow path, durable sensors can be positioned within the corresponding subsystem. The values measured by the durable sensors may shift based on the user-supplied media formulation or disposable sensor element manufacturing lot. Calibration of the sensing elements can be performed using cassettes filled with standards for pH, dissolved oxygen, or glucose as necessary. The results can be confirmed using external probes. Empirically-determined calibration factors for a given sensing element can be applied to readings from the calibrated cassettes and others like them. In some configurations, the sensors can be located as shown in Table I.

TABLE I

|  | $O_2$ (Gas) | $CO_2$ (Gas) | °C. | pH | $DO_2$ | Glucose | Volume Delivered | Flow Rate |
|---|---|---|---|---|---|---|---|---|
| Temperature Manager | X | X | X | | | | | |
| Gas Exchange Chambers | X | X | | | | | | |
| Reservoir Module | | | | X | X | X | | X |
| Bioreactor Module | | | | X | X | X | X | X | X |

Temperature manager 103, maintaining the temperature and gas concentrations of the media within media reservoir 101, can include sensors that can monitor, for example, but not limited to, temperature, gaseous oxygen, and gaseous carbon dioxide. Maintaining the temperature of the media can slow the degradation of sensitive supplements in the media and can decrease the time needed to prepare the media for delivery to user-supplied device(s) 113A/B/C. Gas exchange chambers 131, enabling media characteristics to be modified through the introduction of gases, can include sensors that monitor gaseous oxygen and gaseous carbon dioxide. Reservoir module 116A, enabling media withdrawal from media reservoir 101 and media conditioning, can include, but is not limited to including, sensors that monitor temperature, pH, dissolved oxygen, and the volume of media delivered to bioreactor module 118A. Bioreactor module 118A, enabling circulation of media through user-supplied devices 113A/B/C, can include, but is not limited to including, sensors that monitor temperature, pH, dissolved oxygen, glucose, the volume of media delivered to user-supplied devices 113A/B/C, and the flow rate of the media.

Figure 3A:
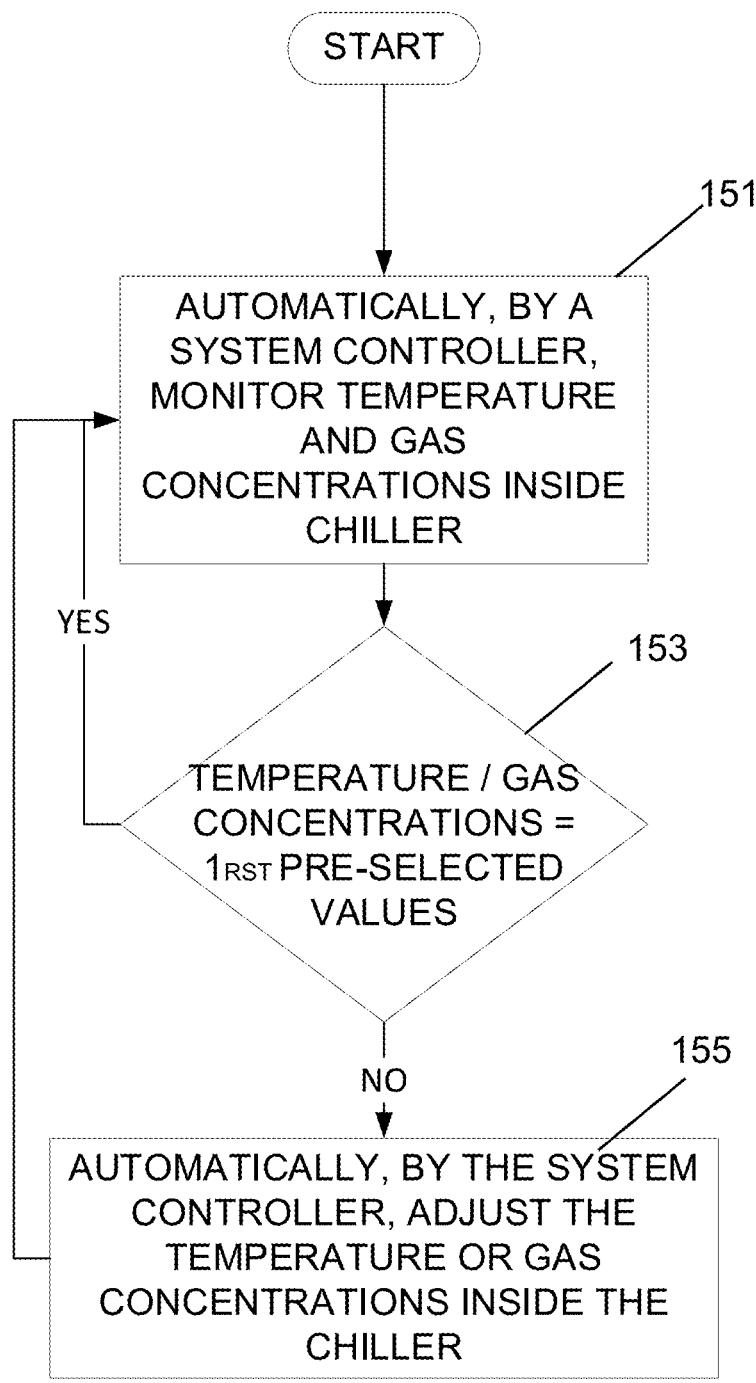
FIGS. 3A, 3B, 3C, and 3D are flowcharts of the method of the present teachings for dynamically adjusting characteristics of media.
Figure 3B:
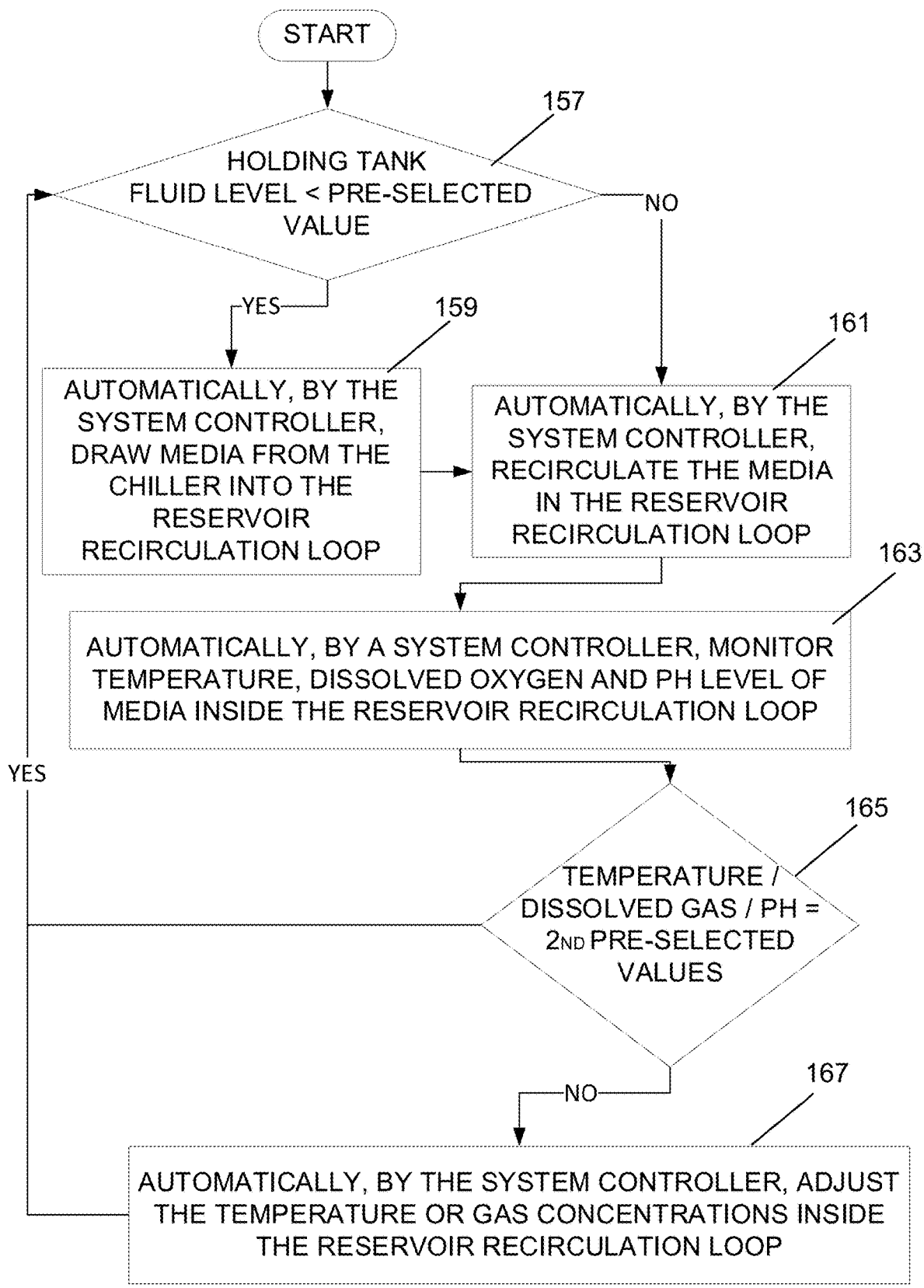
Figure 3C:
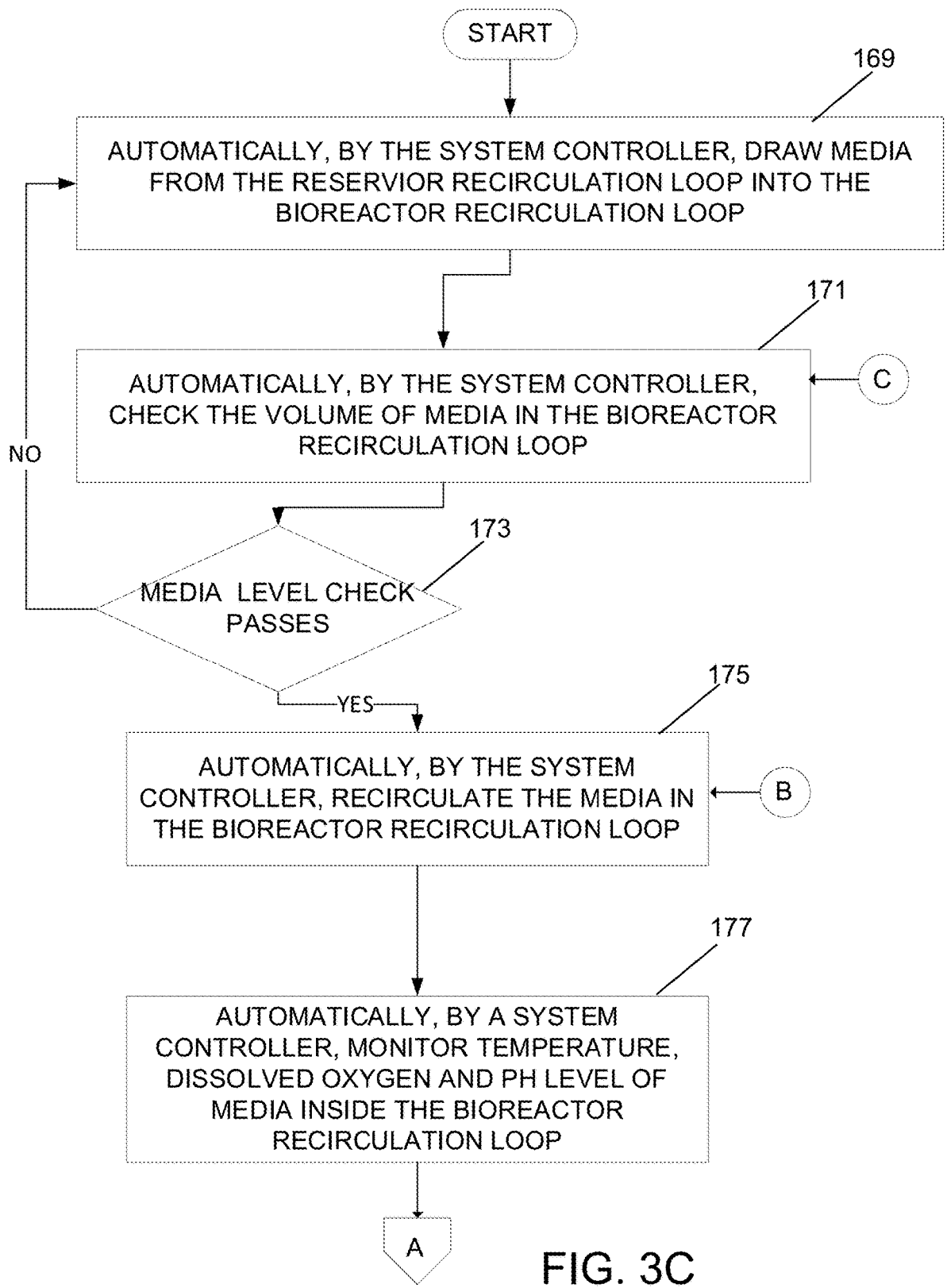
Figure 3D:
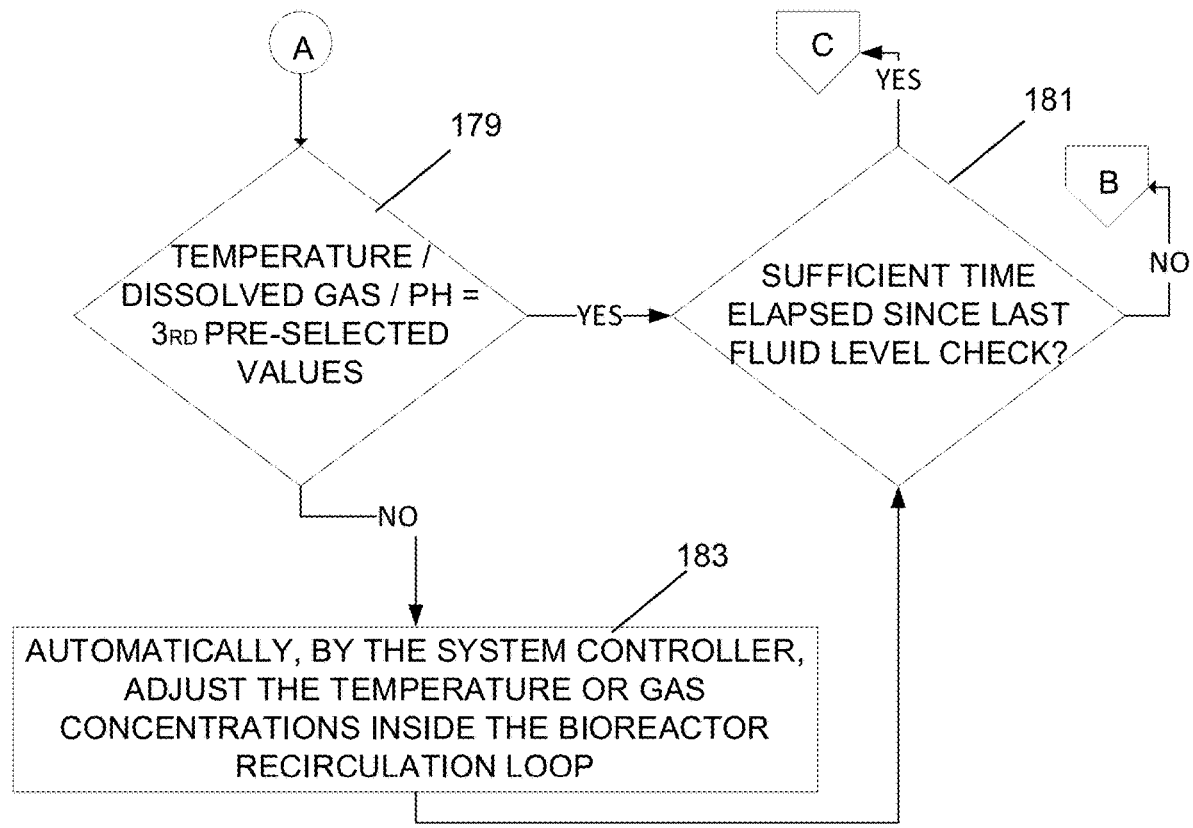

Referring now to FIGS. 3A-3C, methods 150A-150C of the present teachings for centralized fluid management and culture control can include, but are not limited to including, at least one control loop representing steps taken to implement temperature control of the media, circulation of the media in a path including the reservoir, and circulation of the media in a path including the user-supplied device. In some configurations chiller controller (method 150A (FIG. 3A)) can implement the temperature control steps, reservoir module/recirculation controller (method 150B (FIG. 3B)) can implement the reservoir circulation, and bioreactor module(s)/user-supplied device recirculation controller (method 150C (FIG. 3C)) can implement the user-supplied device circulation. In some configurations, these control loops can execute independently from one another. In some configurations, a system controller can execute the control loops automatically.

Referring now to FIG. 3A, method 150A can include, but is not limited to including, automatically monitoring 151 characteristics such as, for example, but not limited to, temperature and gas concentrations of cell or tissue culture media inside a controlled environment such as, for example, but not limited to, a chiller. Gas control in the controlled environment can decrease outgassing upon warming up the media by surrounding the media with a set concentration of primarily lower-solubility gas. Gas control in the controlled environment can improve the speed of adjusting the media to further setpoints in the reservoir recirculation loop shown in FIG. 3B. For some media, for example, relatively low temperatures can extend the life of the media. If 153 the characteristics fail to reach first pre-selected values, method 150A can include automatically adjusting 155 the characteristics inside the controlled environment. If 153 the characteristics reach first pre-selected values, method 150A can include continuing to automatically monitor 151 the characteristics inside the controlled environment, thereby maintaining the characteristics at the desired first pre-selected values.

Referring now to FIG. 3B, method 150B can include, but is not limited to including, if 157 a media holding tank is less than a pre-selected amount, method 150B can include automatically moving 159 media from the controlled environment through the reservoir circulation loop. If 157 a media holding tank greater than or equal to the pre-selected amount, method 150B can include automatically recirculating 161 the media in the reservoir circulation loop, and automatically monitoring 163 the values of characteristics of the media inside the reservoir circulation loop. If 165 the values of the characteristics fail to reach second pre-selected values, method 150B can include automatically adjusting 167 the values of the characteristics inside the reservoir circulation loop. If 165 the values of the characteristics reach second pre-selected values, method 150B can include returning to step 157 to continue the reservoir loop. Characteristics of the contents of the reservoir circulation loop can include, but are not limited to including, temperature, dissolved gas, and pH.

Referring now to FIG. 3C, method 150C can include, but is not limited to including, automatically moving 169 media from the reservoir circulation loop into the user-supplied device circulation loop, and automatically checking 171 the volume of the media in the user-supplied device circulation loop. If 173 the volume of the media in the user-supplied device circulation loop reaches a second pre-selected threshold, method 150C can include automatically recirculating 175 the media in the user-supplied device circulation loop, and automatically monitoring 177 the characteristics of the media inside the user-supplied device circulation loop. If 179 the values of the characteristics reach third pre-selected values, and if 181 a pre-selected amount of time has elapsed since a previous fluid level check, method 150C can include returning to step 171. If 179 the values of the characteristics fail to reach third pre-selected values, method 150C can include automatically adjusting 183 the values of the characteristics inside the user-supplied device circulation loop, and returning to step 181. With respect to the values of characteristics, in some configurations, a relatively low temperature value can include a range of 0-8° C., and a relatively high temperature value can include a range of 32-40° C. In some configurations, a desired value of the relatively low temperature is 4° C. In some configurations, a desired value of the relatively high temperature is 37° C.

In some configurations, the media can be warmed from 4° C. to 37° C. in holding container 109 (FIGS. 2A/2B), recirculating from holding tank 109 (FIGS. 2A/2B) to cassette 107/111 (FIGS. 2A/2B) and gas exchange 131 (FIGS. 2A/2B) area and back. In some configurations, the media can be warmed from 4° C. to 37° C. in media reservoir 101 (FIG. 1B), and can circulate through reservoir/bioreactor cassettes 699/700 (FIGS. 6A-6D) and across integrated gas exchange area 701A/701 (FIGS. 6A-6D). The media can be maintained at about 37°, for example, in the user-supplied device. In some configurations, the ranges of other characteristics can include, but are not limited to including,

| Characteristic | Range |
| --- | --- |
| Gaseous $CO_2$ | 0-100% |
| Gaseous $O_2$ | 0-25% |
| Dissolved $O_2$ | .65-6.75 mg/L |
| pH | 6.8-7.8 |
| Glucose (dissolved $CO_2$) | 0.2-4.5 g/L |

Referring now to FIG. 4, in some configurations, enclosure 401 can be used to house reservoir module 116A (FIGS. 2A/2B) or bioreactor module 118A (FIGS. 2A/2B). A plurality of enclosures 401 can be grouped to form row 207 (FIG. 1B) of rack 205 (FIG. 1B). Within enclosure 401 can be mounted, for example, but not limited to, cassette 107/111, gas exchange chamber 131/zone 132, connectors 211, check valves 213, pinch valves 135, and tubing, for example, but not limited to, module line 119, sample line 116B (FIGS. 2A/2B), and waste line 121. Enclosure 401 can include cavity 215 that can be used for mounting, for example, one of user-supplied devices 113A/B/C (FIGS. 2A/2B). User-supplied devices 113A/B/C (FIGS. 2A/2B) can be operably coupled with cassette 111 to enable pumping fluid between cassette 111 and user-supplied devices 113/A/B/C (FIGS. 2A/2B). In some configurations, user-supplied devices 113A/B/C (FIGS. 2A/2B) can include a bioreactor housing growing HCT/P, and cassette 111 can pump media through user-supplied devices 113A/B/C (FIGS. 2A/2B) to ensure the viability of the HCT/P.

Figure 5:
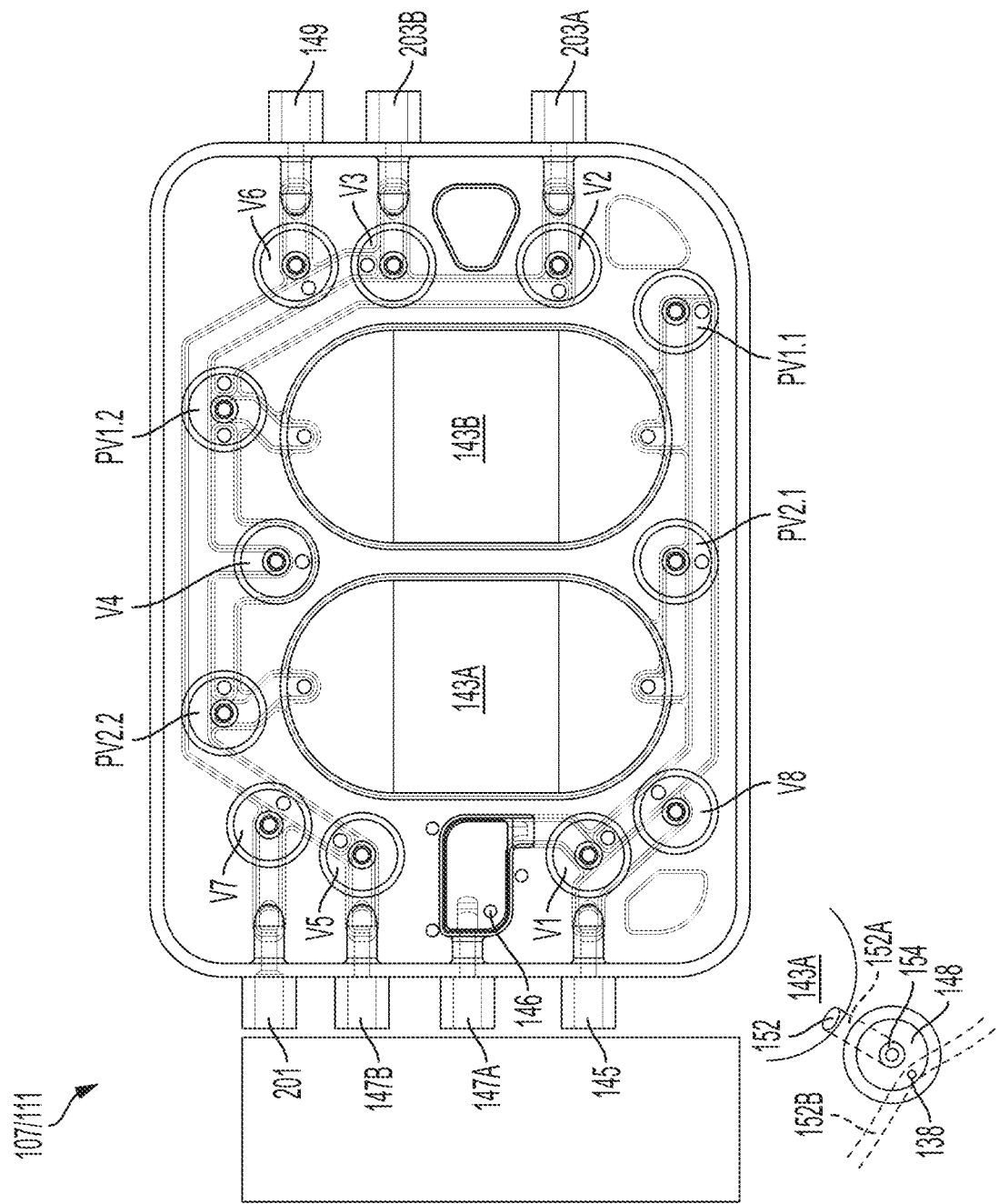
FIG. 5 is a pictorial representation of a configuration of the pumping cassette of FIG. 4.

Referring now to FIG. 5, fluid that enters first configuration cassette 107/111 from bioreactor lower port 203A can flow past sensors 146 before passing into gas exchange zone 132 (FIG. 4), and then eventually can flow back into user-supplied device 113A/B/C (FIGS. 2A/2B) through bioreactor upper port 203B. In this case, fluid can flow from bioreactor lower port 203A to fluid valve V2 402, through pumping valve V2.2 406, into pump chamber 2 143B. While pump chamber 2 143B is delivering media, pump chamber 1 143A can pull fluid from gas exchange zone 132, through pumping valve V1.2 405, in order to be prepared to start pumping once pumping chamber 2 143B is depleted. Pump chamber 2 143B can become depleted by pumping fluid, through pumping valve V2.1 407, into gas exchange zone 132 (FIG. 4) through valve V8 409. The general order of operations can include the following repeatable steps.

TABLE I

| | Arbitrary time units | | | | | |
| --- | --- | --- | --- | --- | --- | --- |
| | 0 | 1 | 2 | 3 | 4 | 5 |
| Pumping Chamber 1 | Start delivering fluid | Keep delivering | Keep delivering | Keep delivering | Keep delivering | Keep delivering/ End-of-stroke detection |

TABLE I-continued

| Pumping Chamber 2 | Stop delivering fluid | Measure volume | Fill chamber | Measure volume | Wait | Wait |

| Arbitrary time units | | | | | | |
| --- | --- | --- | --- | --- | --- |
| 6 | 7 | 8 | 9 | 10 | 11 |

| Pumping Chamber 1 | Stop delivering fluid | Measure volume | Fill chamber | Measure volume | Wait | Wait |
| Pumping Chamber 2 | Start delivering fluid | Keep delivering | Keep delivering | Keep delivering | Keep delivering | Keep delivering/ End-of-stroke detection |

Continuing to refer to FIG. 5, pump chamber 2 143B can know that pump chamber 1 143A is depleted based on an end-of-stroke detection. In addition to another method described herein the end-of-stroke can be determined by, for example, but not limited to, rate of pulse width modulation pressure decay, gas mass flow, or time, if using constant pressure. Assuming that the end-of-stroke detection can determine that pump chamber 1 143A is close to empty before it is actually empty, and the switch from pumping from pump chamber 1 143A to pump chamber 2 143B is smooth (time points 0 and 5 in Table I), the flow can be continuous. Achieving continuous flow can depend upon a configuration that can include multiple pumping chambers, fine measurement/control of the pumping pressure, a "circular" fluid pathway, and sufficient compliant space so that the filling of an empty pumping chamber does not substantially affect the flow from a full pumping chamber. Sufficient compliant space can include, but is not limited to including, more space than one pumping chamber can accommodate. The size of each pumping chamber 143A/B can depend upon the desired time to complete each volume measurement. When pump chamber 1 143A is near the end-of-stroke, valves PV2.1/PV1.2 407/405 can close, valves PV1.1/PV2.2 404/406 can open, pump chamber 1 143A can switch to filling (vacuum on membrane), and pump chamber 2 143B can switch to delivering (pressure on membrane).

Referring again to FIG. 4, fluid characteristics can be modified in gas exchange zone 132 by the gas in gas exchange chamber 131. The composition of the gas in gas exchange chamber 131 can be based at least on the data gathered by sensors 146. Fluid can remain in gas exchange zone 132 a desired amount of time, and can be pumped out of gas exchange zone 132 by pumping action of pumping chambers 143A/B. After the fluid exits gas exchange zone 132, it can pass through valve V5 411 (FIG. 5), past closed valves V7 417 (FIG. 5), V4 418 (FIG. 5), and V6 419 (FIG. 5), through valve V3 413 (FIG. 5), and into bioreactor upper port 203B (FIG. 5). Fluid flowing in the opposite direction can travel from user-supplied device 113 (FIG. 1B) through bioreactor upper port 203B (FIG. 5), and follow the same path outlined herein, but in the reverse direction. In this case, spot sensors 146 can be encountered by the fluid after the fluid has passed through gas exchange zone 132.

Continuing to refer to FIG. 4, sensors can together monitor the media entering user-supplied devices 113A/B/C (FIGS. 2A/2B) and can examine the characteristics of the media after its contact with the HCT/P. In order to prevent cross-contamination, one-way valves 213 in the flow path can enable backflow protection to prevent materials from traveling from cassettes 107/111 to module line 119 or from waste/sample lines 121/116B (FIGS. 2A/2B) back to cassettes 107/111. In some configurations, one-way valves 213 can be positioned as part of waste line 121 and module line 119. This positioning can prevent backflow during normal use, and if cassette 107/111 is connected incorrectly. In some configurations, one-way valves can be positioned in the flow path surrounding cassettes 107/111, which can enable further backflow protection.

Continuing to refer to FIG. 4, cassettes 107/111 can be operably coupled with gas exchange chamber 131/zone 132. Gas exchange zone 132 can house media that can arrive from holding container 109, and can include a membrane surrounding the media that can be relatively gas permeable. The concentrations of gasses within gas exchange chamber 131 can be adjusted according to the needs of the media as informed, at least in part, by sensors. Sensors can be mounted within and around gas exchange chamber 131/zone 132. In some configurations, sensors can include, but are not limited to including, gaseous oxygen sensors, gaseous carbon dioxide sensors, dissolved oxygen sensors, dissolved carbon dioxide sensors, pH sensors, and state detection for, for example, enclosure latches.

Continuing to refer to FIG. 4, the characteristics of the media can be monitored by, for example, but not limited to, placing disposable sensor elements within cassettes 107/111 prior to sterilization. Sensor data can be received from the disposable sensor elements during a production run using durable hardware located outside of cassettes 107/111. Characteristics of the media that can be monitored and adjusted can include, but are not limited to including, glucose, pH, temperature, conductivity, turbidity, spectrophotometric characteristics, flow rate, viscosity, color, dielectric properties, acoustic impedance, dissolved gas content (e.g. dissolved oxygen), fluorescence, dissolved organic matter, and flow cytometrics. On- or off-board sensors may be, but are not limited to being, thermocouples, thermistors, resistance thermometers, conductivity sensors or probes, turbidity sensors or probes, spectrophotometers, flow sensors, flow meters, velocimeters, viscosity sensors, optical sensors, capacitance probes or sensors, ultrasonic sensors, dissolved oxygen sensors, fluorescence sensors, colored dissolved organic matter sensors (CDOM), fluorescent dissolved organic matter sensors (fDOM), glucose sensors, pH sensors, and flow cytometers. On- or off-board sensors may also monitor for a particular condition of interest. For example, on- or off-board sensors may monitor for air bubbles. The system can include oxygen sensors to detect gaseous oxygen, dissolved oxygen, and oxygen leaks. Gaseous oxygen detection enables the system to set the oxygen to levels that enable adjusting the values of dissolved oxygen in the circulating fluid. Dissolved oxygen detection enables the system to determine if more gaseous oxygen needs to be introduced to the gas exchange chamber. Sensors can detect oxygen leaks to enable safe operation when using oxygen. In some configurations, gaseous oxygen sensors can include, for example, but not limited to, SST® Sensing LOX-02-S. In some configurations, dissolved oxygen sensors can include, for example, but not limited to, PRESENS® EOM-O2-FOM-PHB50-T4D-AO-v1 sensors and PRESENS® SP-PSt3-NAU-D5-YOP-S spots. In some configurations, external oxygen sensors that can enable safe use of oxygen can include, for example, but not limited to, AMI Model 221R https://www.amio2.com/products/details/Model-221R/. In some configurations, gaseous carbon dioxide sensors can include, for example, but not limited to, Gas Sensing Solutions ExplorIR-M. In some configurations, pH sensors can include, for example, but are not limited to, PRESENS® EOM-pH-mini-90-v3 sensors and PRESENS® SP-HP5-F100-D5-S spots. In some configurations, glucose (/lactate) sensors can include, for example, but not limited to, JOBST® Technologies Barbed B.LV5 Biosensor.

Continuing to refer to FIG. 4, the concentration of dissolved oxygen can be measured through the use of spot sensors 146 (FIG. 5) incorporated into cassettes 107/111, and read by, for example, but not limited to, at least one external (durable) optical meter. If spot sensor 146 (FIG. 5) is excited using, for example, but not limited to, a 505 nm wavelength light in the absence of dissolved oxygen, spot sensor 146 (FIG. 5) can emit light in response. If dissolved oxygen is present, the oxygen molecules can bind to spot sensor 146 (FIG. 5), and the optical excitation energy can be transferred to the oxygen molecule in a non-radiative manner. The transfer can result in a decrease in both the intensity and decay time of the emitted light corresponding to the concentration of dissolved oxygen in the surrounding media. The following Stern-Volmer relationship can be used, for example, to describe the intensity and decay time intensity of the media.

$$\frac{I_{0\%DO}}{I_{Current\%DO}} = \frac{\tau_{0\%DO}}{\tau_{Current\%DO}} = 1 + K_{SV} * \%DO$$

where I is the intensity if the emitted light, τ is the decay time, $K_{SV}$ is the Stern-Volmer constant, and % DO is the concentration of dissolved oxygen in the surrounding media. If the concentration of dissolved oxygen is above or below a setpoint, the concentration of gaseous oxygen in gas exchange chamber 131 can be decreased or increased, respectively. Valves associated with gas exchange chamber 131/zone 132 can be used to control the addition/subtraction of gaseous oxygen, nitrogen, and carbon dioxide that can moderate the presence of dissolved gas, for example, but not limited to, oxygen and carbon dioxide, in the media. The gases in gas exchange chamber 131 can provide pressure against gas permeable zone 132 and to increase the dissolved gas in gas exchange zone 132. Nitrogen, an inert gas, can replace oxygen in gas exchange chamber 131, and can drive the dissolved oxygen concentration in the media down.

Continuing to still further refer to FIG. 4, with respect to pH, the media can be buffered with sodium bicarbonate (NaHCO$_3$), which can increase the pH of the media above a desired level. Controlled addition of carbon dioxide can be used to decrease the pH to a desired level. Nitrogen can be used to replace carbon dioxide and can allow the NaHCO$_3$ to drive the pH up. The pH of the media can be measured through the use of a sensor, for example, but not limited to, spot sensor 146 (FIG. 5) incorporated into the cassette, and read by an external optical meter. Spot sensor 146 (FIG. 5) can be composed of indicator and reference molecules that are excited using, for example, but not limited to, a 470 nm wavelength light. If the pH of the surrounding solution is low, the indicator and reference molecules can emit in nearly the same manner. If the pH of the surrounding solution is high, the difference in emitted fluorescent intensity, decay, and phase shift between the reference and indicator are large, and the indicator can emit at a significantly higher intensity. The ratio between the excitation and emission windows can be calculated and correlated to the pH level. If the pH is above or below a setpoint, the gas mixing system can compensate by, for example, but not limited to, decreasing or increasing (respectively) the concentration of gaseous carbon dioxide in gas exchange chamber 131.

Continuing to refer to FIG. 4, the concentration of glucose in the media can be measured through the use of glucose sensor 133, which can include, for example, but not limited to, a flow-through biosensor array incorporated into the cassette circulation loop. In some configurations, the biosensor array can be composed of, for example, but not limited to, a series of platinum electrodes with enzyme membrane "spots". The enzyme membrane spots can be formed by following a procedure including, but not limited to, placing a mixture of, for example, but not limited to, enzymes and precursor hydrogel on a wafer, photo crosslinking the hydrogel with UV, adding a diffusion limiting pHEMA layer to lower the effects of pH and sample concentration, and top coating with a catalase enzyme membrane to lower the effects of flow rate. See Moser, I., Jobst, G., & Urban, G. A., *Biosensor arrays for simultaneous measurement of glucose, lactate, glutamate, and glutamine*, Biosensors and Bioelectronics, 17(4), 297-302, 2002. In some configurations, a correction factor of 3.8%/° C. for glucose readings taken at temperatures other than 37° C. can be applied. If the concentration of glucose in the media falls below a setpoint, module controllers can, for example, but not limited to, enable a partial replenishment pumping action.

Figure 4A:
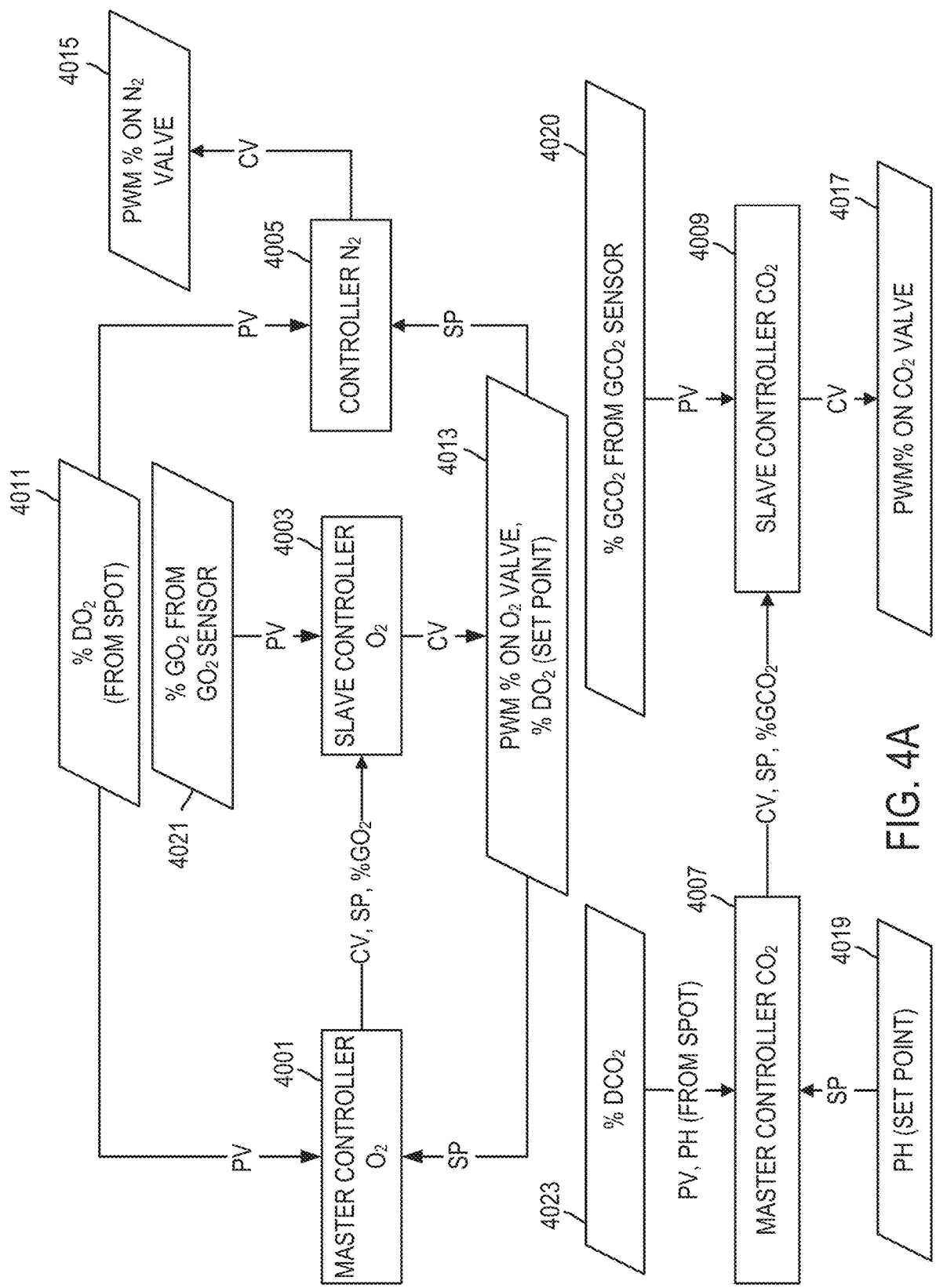
FIGS. 4A and 4B are flowcharts of a first method of the present teachings for adjusting concentrations of various gases exposed to the media.

Referring now to FIG. 4A, one approach to gas exchange management can include cascading controllers where a first PID can determine the gas percentage that is needed and a second PID can control the gas valve to the percent dictated by a master. In this approach, dissolved oxygen (DO$_2$) in the media and pH of the media can be controlled by controlling the gaseous oxygen (GO$_2$) and gaseous carbon dioxide (GCO$_2$) percentages in a gas chamber. The media can be circulated within a gas permeable enclosed area exposed to the gas in the gas chamber. Nitrogen gas can be used to displace excess oxygen and carbon dioxide in the chamber. The percentage of the gases in the gas chamber can be controlled by controlling the cycles and duration of each cycle of gas valves metering gas flow from gas supplies to the gas chamber. In some configurations, a controller can be used. In some configurations, a PID controller that can receive a single input and a single output can be used. The controller can be set to operate in one direction, i.e., the controller can be enabled if input is greater than a set point or if input is less than the set point. Two controllers can be configured for this action, one being enabled if input is below the set point, and the other being enabled if input is above the set point. The controller can calculate the error—the difference between the set point and the input—and can calculate the output of the controller. The controller can be tuned to accurately calculate the output by adjusting the proportional, integral and derivative gains. When the controller is in automatic mode, the controller can automatically calculate the output that would reduce the error. If the controller is in manual mode, the output can be preset, and the controller can follow this output until it is switched back into automatic mode. The effect provides cascading controllers where the first PID can determine the gas percentage needed and the second PID can control the gas valve to the percent dictated by the master.

Continuing to refer to FIG. 4A, oxygen master controller 4001 can receive oxygen sensor readings as process variable (PV) input, and oxygen slave controller 4003 can control the oxygen valve as a control variable (CV) output, pulse width modulation (PWM) % 4013 on the oxygen valve. The goal of the oxygen master/slave controllers 4001/4003 is to maintain dissolved oxygen ($DO_2$) % concentration 4011 at set point (SP) by exposing the media to gaseous oxygen ($GO_2$). The % $GO_2$ from $GO_2$ sensor can be the PV for slave controller $O_2$ 4003. Therefore, the oxygen master/slave controllers 4001/4003 can be enabled when $DO_2$% 4011 (measured in mg/L) is less than the SP or target concentration. If $DO_2$% concentration 4011 overshoots and exceeds the SP, oxygen in the media can be displaced to bring $DO_2$% concentration 4011 back to the SP. Nitrogen controller 4005 can be enabled for this purpose. The PV for nitrogen controller 4005 can be defined as 100%-$GO_2$%-$GCO_2$%. The SP for nitrogen controller 4005 can be defined as 100-$GO_2$ SP-$GCO_2$ SP. Nitrogen controller 4005 can control PWM % 4015 on the nitrogen valve as the CV output. Nitrogen controller 4005 can be configured to perform a PV-SP action. Since the system has sensors to measure $GO_2$% and $GCO_2$% in the gas exchange chamber or portion of the cassette, the remainder of the gas can be assumed to be predominantly nitrogen. The control action of nitrogen controller 4005 can be opposite to the direction of oxygen master/slave controllers 4001/4003. If either of $DO_2$ or $DCO_2$ exceeds the SP, then the nitrogen concentration is too low, triggering nitrogen controller 4005 to open the nitrogen valve. If either or both of $DO_2$ or $DCO_2$ falls below its SP, then the nitrogen concentration exceeds its SP, triggering nitrogen controller 4005 to close the nitrogen valve.

Continuing to refer to FIG. 4A, carbon dioxide ($CO_2$) master controller 4007 can receive pH sensor readings 4019 as PV input, and $CO_2$ slave controller 4009 can control PWM % 4017 on the carbon dioxide valve as CV output. The goal of $CO_2$ master/slave controllers 4007/4009 is to maintain the dissolved $CO_2$ ($DCO_2$) % concentration 4023 (pH level of the media) at SP by pumping in more $CO_2$. Therefore, $CO_2$ master/slave controllers 4007/4009 can be enabled when $DCO_2$ is less than the SP (i.e., when the pH value is greater than the set point). $CO_2$ master/slave controllers 4007/4009 can be configured with SP-PV action. If $DCO_2$% concentration 4023 overshoots and exceeds the SP, nitrogen can be introduced in the gas chamber to displace $CO_2$. In order to displace $DCO_2$, nitrogen controller 4005 can be switched to manual mode and tieback can be enabled, and the CV output on the nitrogen valve can be preset. The tieback value can be provided by the user or any other source, and nitrogen PID controller 4005 can adjust its internal values to generate PWM % 4015 of the nitrogen valve at the output. The tieback value can be set at, but is not limited to being set at, 50% of 2 seconds, which serves to turn the nitrogen valve on every second to add nitrogen for as long as needed. The addition of nitrogen can decrease $CO_2$, and oxygen can also decrease. When the pH returns to within 0.1 pH of the set point, nitrogen PID controller 4005 can be taken out of tieback mode, and can return automatic control mode. $CO_2$ stripping is a relatively slow process. Nitrogen can be purged in the gas chamber at a substantially constant rate to reduce the $CO_2$ percentage. When the $DCO_2$% concentration 4023 reaches the SP or goes below the SP, which means that the pH exceeds the SP, nitrogen controller 4005 can be switched back to automatic mode. The $GCO_2$ sensor can provide 4020% $GCO_2$ as the PV to $CO_2$ PID slave controller 4009. The pH can be calculated from the pH reading from a sensor as follows:

$$pH = 6.1 + \log_{10}((51.98 * NaHCO_{3(g/L)} / \% CO_2) - 1)$$

When the pH reading is above the pH set point, $CO_2$ PID slave controller 4009 can increase PWM % 4017 on the $CO_2$ valve, which can increase the $CO_2$ percentage and can decrease the pH value towards the SP. When the pH reading is below the pH SP, nitrogen controller 4005 can be set to manual mode and tieback can be enabled. Nitrogen can be fed at a constant rate in order to displace the $CO_2$ in the gas chamber. During this action, oxygen can become displaced, and oxygen master/slave controllers 4001/4003 can perform closed loop control.

Figure 4B:
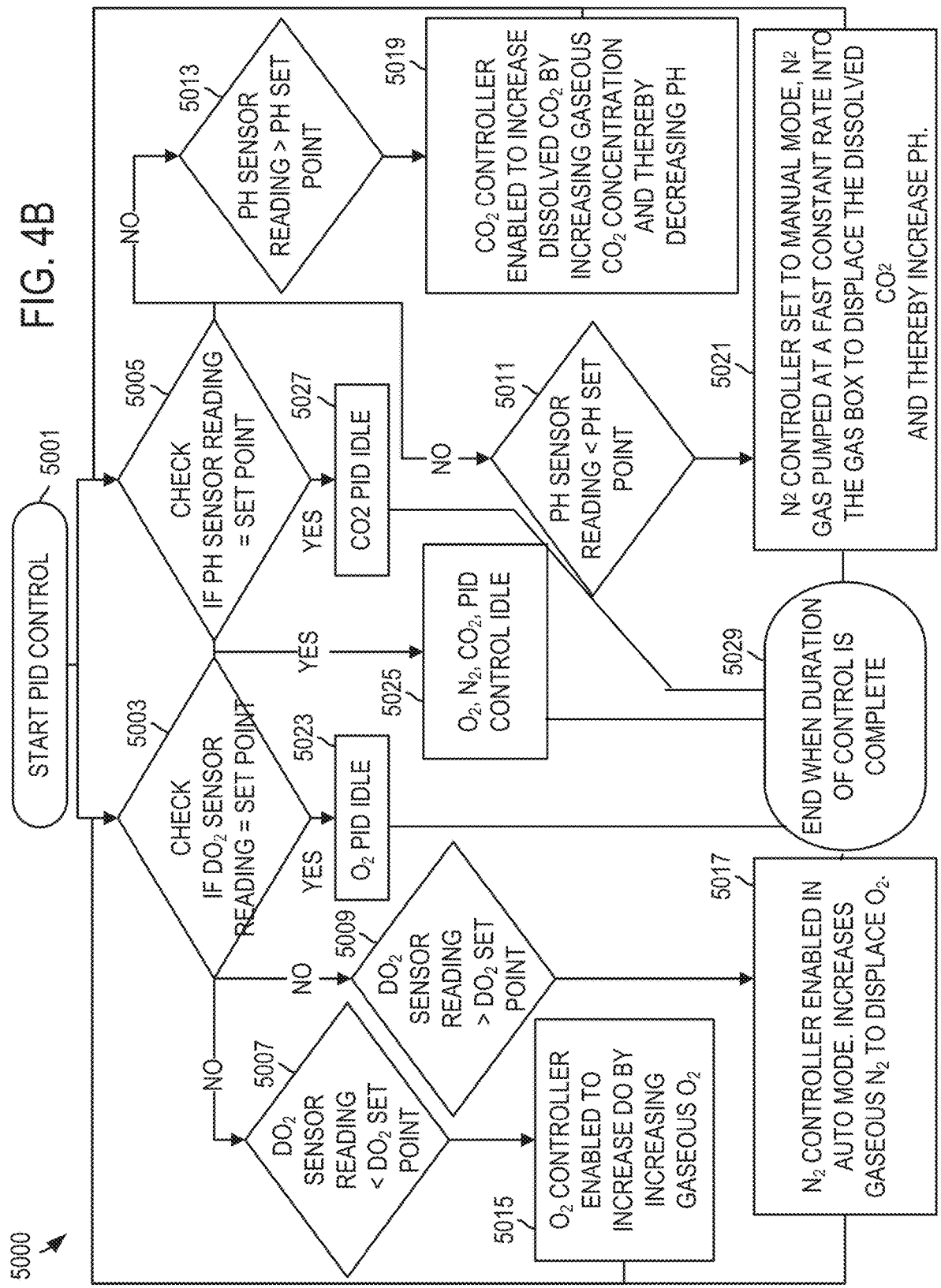

Referring now to FIG. 4B, to control dissolved gaseous percentages by controlling gaseous concentrations, a cascaded control strategy (master-slave) can be used. The slave controller can read the CV of the master controller to use as the SP of the slave controller. Sensor readings of dissolved gas concentrations can be used as the PV to the master controller, and gaseous sensor readings can be used by the slave controller as the PV. The master controller can achieve a target dissolved concentration of the gases in the media and the slave controller can achieve a target gaseous concentration in the gas chamber. The target gaseous concentration in the gas chamber can be based on the CV of the master controller. As the master controller moves the dissolved concentration closer to the target, the SP of the slave controller can decrease. As the master controller moves the dissolved concentration farther from the target, the slave controller can cause the SP to increase. Slave $CO_2$ controller 4009 can control the $GCO_2$ concentration. In some configurations, the $GCO_2$ sensor can sense up to a 20% gaseous concentration. Therefore, when decreasing pH, when the $GCO_2$ sensor reads 20% $CO_2$, the $CO_2$ valve can be closed. Slave $CO_2$ controller 4009 can open the $CO_2$ valve if the system is still trying to decrease pH and the $GCO_2$% drops below 20%. Similar strategy can be used with the $GO_2$ control. In some configurations, the $GO_2$ sensor can sense up to 25%. Therefore, when increasing $O_2$, when the $GO_2$ sensor reads 25% $O_2$, the $O_2$ valve can be closed. Slave $O_2$ controller 4003 can open the $O_2$ valve if the system is still trying to increase $O_2$ and the $GO_2$% drops below 25%. Turning the gases off when the gaseous sensors are railed at their maximum readings can avoid leaking more gas into the gas chamber or gas exchange area and can avoid exceeding SPs.

Continuing to refer to FIG. 4B, method 5000 for controlling the characteristics of the media can include, but is not limited to including, starting 5001 the controller, checking 5003 if the $DO_2$ reading is at the $DO_2$ SP, and checking 5005 if the pH sensor reading is at the pH SP. If 5003 the $DO_2$ sensor reading is at the $DO_2$ set point, method 5000 can include idling 5023 the $DO_2$ controller. If 5003 the $DO_2$ sensor reading is not at the $DO_2$ SP, method 5000 can include if 5007 the $DO_2$ sensor reading is less than the $DO_2$ SP, method 5000 can include enabling 5015 the $DO_2$ controller to increase the $DO_2$ by increasing $GO_2$ and returning to step 5003. If 5009 the $DO_2$ sensor reading is greater than the $DO_2$ SP, method 5000 can include enabling 5017 the nitrogen controller in automatic mode, thus increasing gaseous nitrogen ($GN_2$) to displace $DO_2$. If 5005 the pH sensor reading is at SP, method 5000 can include idling 027 the carbon dioxide controller. If 5003 both the $DO_2$ sensor reading is at the $DO_2$ set point, and the pH sensor reading is at SP, method 5000 can include idling the $O_2$, $N_2$, and $CO_2$ controllers. If 5013 the pH sensor reading is greater than set point, that is, when the dissolved carbon dioxide is lower than SP, method 5000 can include enabling 5019 the carbon dioxide controller to increase dissolved carbon dioxide ($DCO_2$) by increasing gaseous carbon dioxide ($GCO_2$) concentration and thereby decreasing pH. If 5011 the pH sensor reading is greater than SP, that is, when the dissolved carbon dioxide is lower than SP, method 5000 can include setting 5021 the nitrogen controller to manual mode, enabling tieback, and feeding nitrogen at a constant rate into the gas chamber, thus displacing the $DCO_2$, and enabling the $DO_2$ controller to perform closed loop control, thereby increasing the pH. The tieback value is taken as an input and the controller adjusts its internal values to generate the same value at the output. In some configurations, the tieback value can be set to 50% of 2 seconds. Nitrogen flow can be enabled for one second and disabled for one second. The nitrogen controller can return to automatic mode when the pH reading is within 0.1 pH of the SP. Method 5000 can include ending 5029 when the duration of the control is complete.

Figure 4C:
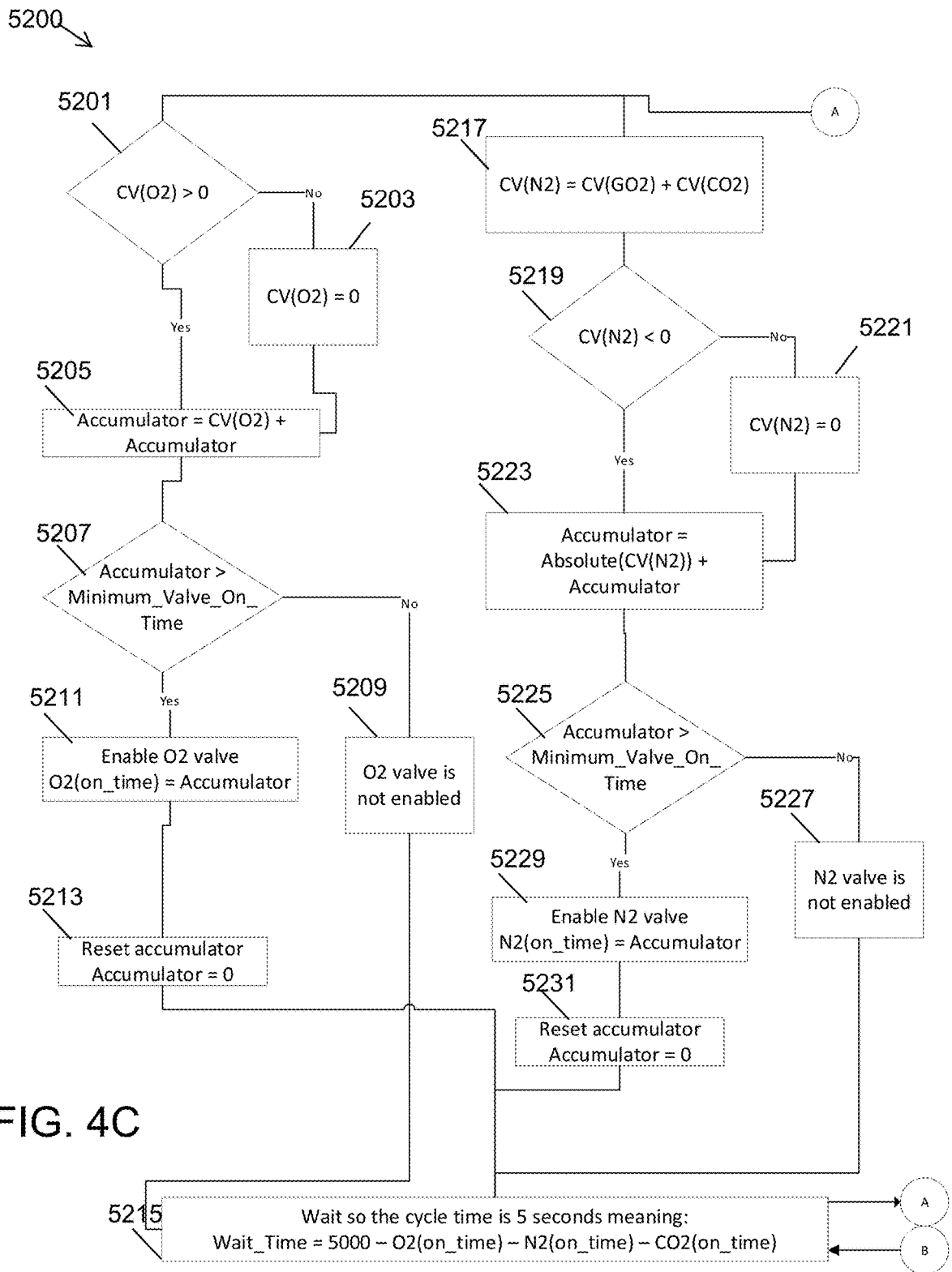
FIGS. 4C, 4D, and 4E are flowcharts of a second method of the present teachings for adjusting concentrations of various gases exposed to the media.

Referring now to FIG. 4C, in another approach to gas exchange management, a $DO_2$ controller and a pH controller can control timers, and those timers can be used to control gas valves. In this approach, if 5201 the $O_2$ control variable (CV) is less than or equal to zero, method 5200 can include setting 5203 the CV for $O_2$ to zero. If 5201 the $O_2$ CV is greater than zero, method 5200 can include incrementing 5205 a first counter by the CV for $O_2$. If 5207 the first counter is less than or equal to a first threshold, method 5200 can include enabling 5211 the $O_2$ valve, noting when the $O_2$ valve was enabled, for example, by setting an on-time value to the value of the first counter, and resetting 5213 the first counter. If 5207 the first counter is greater than the first threshold, method 5200 can include maintaining 5209 the $O_2$ valve in an off state.

Continuing to refer to FIG. 4C, computing 5217 the CV for $N_2$ to the sum of the CV for $GO_2$ and CV for $CO_2$. If 5219 the CV for $N_2$ is greater than or equal to zero, method 5200 can include setting 5221 the CV for $N_2$ to zero. If 5219 the $N_2$ CV is less than zero, method 5200 can include incrementing 5223 a second counter by the value of the CV for $N_2$. If 5225 the second counter is less than or equal to a second threshold, method 5200 can include enabling 5229 the $N_2$ valve, noting when the $N_2$ valve was enabled, for example, by setting an on-time value to the value of the second counter, and resetting 5231 the second counter. If 5225 the second counter is greater than the second threshold, method 5200 can include maintaining 5227 the $N_2$ valve in an off state.

Figure 4D:
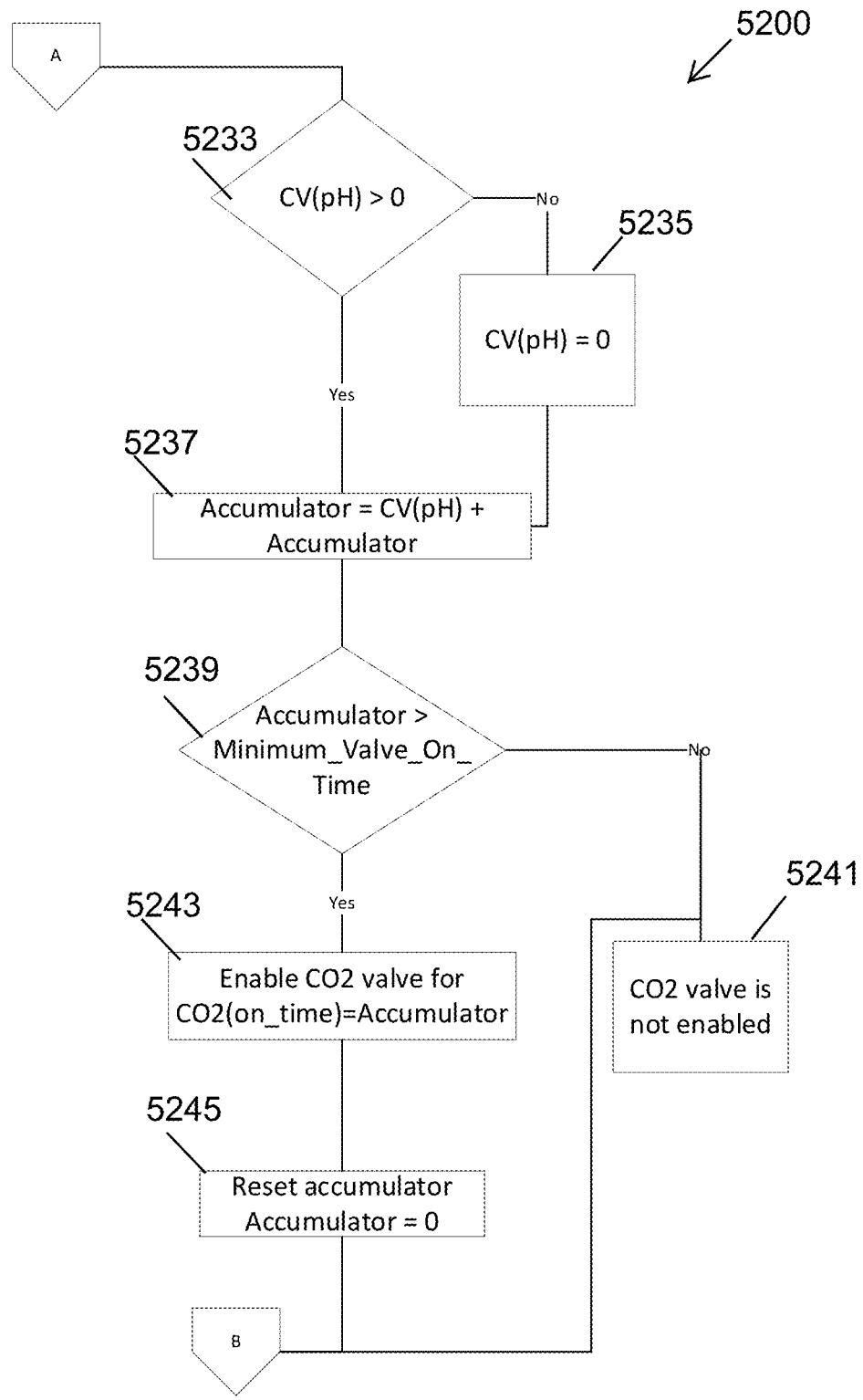

Referring now to FIG. 4D, if 5233 the pH2 control variable (CV) is less than or equal to zero, method 5200 can include setting 5235 the CV for pH to zero. If 5233 the pH control variable (CV) is greater than zero, method 5200 can include incrementing 5237 a third counter by the value of the CV for pH. If 5239 the third counter is less than or equal to a third threshold, method 5200 can include enabling 5243 the $CO_2$ valve, noting when the $CO_2$ valve was enabled, for example, by setting an on-time value to the value of the third counter, and resetting 5245 the third counter. If 5239 the third counter is greater than the third threshold, method 5200 can include can include maintaining 5241 he $CO_2$ valve in an off state.

Referring again to FIG. 4C, method 5200 can include calculating 5215 a wait time. This calculation can include, for example, but not limited to, subtracting the on-time for $O_2$, $N_2$, and $CO_2$, from a pre-selected amount of time, for example, but not limited to 5 seconds. The wait time is used to meter the flow of gas in each cycle, and can be adjusted based on factors such as, for example, but not limited to, sensor response times, characteristics being measured, characteristics of the gas, and characteristics of the circulating media.

Figure 4E:
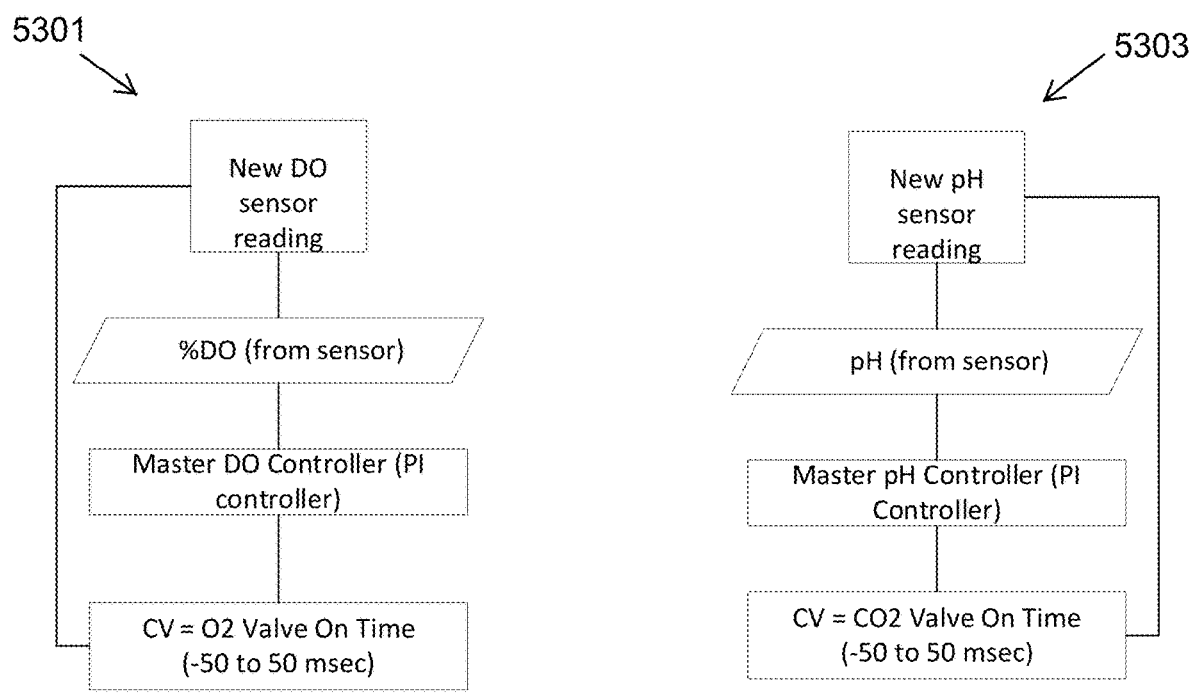

Referring now to FIG. 4E, the value received from each sensor measuring characteristics of the circulating media can be used to adjust the CV through PI processes. For example, if the sensors are sensing $DO_2$ and pH, $DO_2$ PI process 5301 and pH PI process 5303 can be used to adjust the $DO_2$ CV and the pH CV respectively.

There is a pi controller on the spot (ph and do), doing pi controller on set points on spots, gas sensors got moisture, they didn't work well, mechanical layout might change that, but gas sensors were slow, painful to tune.

Spots only read every 3 minutes, get new spot reading, find error between sp and reading. Spots have a life. Shing a spot with light, then measuring properties, runs out of juice quickly. 3 minutes gives a life of 1 month or longer. If need to change the cassette, can isolate the cassette, take out, and reprime, and continue growing. Not a lot of small devices for ph and do.

Referring again to FIG. 4, in some configurations, temperature management 103 can include heaters and coolers for managing the thermal properties of the media. In some configurations, temperature management 103 can, for example, include any of a variety of suitable heating elements such as a resistive heater or a number of resistive heaters. Temperature readings of the media can be obtained by, for example, but not limited to, an on-board temperature sensor and/or an external resistance temperature detector (RTD) probe pressed against the cassette membrane. The temperature of the media in reservoir module 116A (FIGS. 2A/2B) and bioreactor module 118A (FIGS. 2A/2B) can be measured to detect potential gradients that might affect user-supplied devices 113A/B/C (FIGS. 2A/2B). If the temperature of the media deviates by a pre-selected threshold from a pre-selected SP, temperature manager 103 (FIG. 1B) can enable cutting off a heat source, for example, to maintain a safe situation in the enclosure. In some configurations, excess heat can be allowed to passively radiate from the media. In some configurations, heat sinks and cooling fans can be utilized.

Referring again to FIG. 5, reservoir module cassette 107 can be physically identical to bioreactor module cassette 111, each including, but not limited to including, two pumping chambers 143A/B, media inlet port 145, gas exchange zone ports 147A/B, sample line port 149, waste line port 201, and recirculation loop ports 203A/B. Cassettes 107/111 can include bioreactor recirculation loop lines 203A/B and sample out line 149 on one side or portion of cassettes 107/111, and waste out line port 201, gas exchange loop line ports 147A/B, and media inlet port 145 on another side or portion of cassettes 107/111. e.g., an opposite side of cassettes 107/111. Cassettes 107/111 can include a generally planar body having ports stated herein connected to lines that allow fluid flow into/out of cassettes 107/111. The lines can be attached to one or more media containers or other sources of material, one or more waste/sample containers for disposal and sampling purposes, and one or more user-supplied devices for example, but not limited to, bioreactors. Cassettes 107/111 can include a relatively thin form factor whose size can be based, for example, but not limited to, upon the desired depth of pumping chambers 143A/B. and/or based upon a desired pumping rate, and/or manufacturing limitations. In some configurations, cassettes 107/111 can include a wall thickness in the range of 0.5 mm 1.5 mm. Cassettes 107/111 can include a relatively flat member having generally planar shapes, and can include components that are molded, extruded or otherwise formed from a suitable disposable materials. In some configurations, the base member can be molded or otherwise formed from a suitable plastic or other material, such as a polymethyl methacrylate (PMMA) acrylic, or a cyclic olefin copolymer/ultra low density polyethylene (COC/ULDPE), and can be relatively rigid. In some configurations, the ratio of COC to ULDPE can be approximately 85%/15%. Cassettes 107/111 can include a base member that can function as a frame or structural member for cassettes 107/111, and can form, at least in part, various flow channels, ports, valve portions, etc.

Continuing to refer to FIG. 5, both sides of the base member may be covered, at least in part, by a cassette membrane, also referred to herein as a membrane, that can include. for example, but not limited to, a flexible polymer film made from, for example, polyvinyl chloride (PVC), that can be cast, extruded or otherwise formed. In some configurations, the cassette membrane can be formed as a laminate of two or more layers of poly-cyclohexylene dimethylene cyclohexanedicarboxylate (PCCE) and/or ULDPE, held together, for example, by a coextrudable adhesive (CXA). In some configurations, the cassette membrane can include a thickness in the range of approximately 0.002 in-0.020 in. In some configurations, a PVC-based cassette membrane can include a thickness of approximately 0.012 in-0.016 in. In some configurations, laminate in laminate sheets can include a thickness in the range of approximately 0.006 in-0.010 in. The cassette membrane can close or otherwise form a part of flow paths of cassettes 107/111, and can be moved or otherwise manipulated to open/close valve ports and/or to function as part of a pump diaphragm, septum or wall that moves fluid in cassettes 107/111. In some configurations, the cassette membrane can be positioned on the base member and sealed (e.g., by heat, adhesive, ultrasonic welding or other means) to a rim around the periphery of the base member to prevent fluid from leaking from cassettes 107/111. In some configurations, the cassette membrane may also be bonded to other, inner walls of the base member, e.g., those that form various channels, or may be pressed into sealing contact with the walls and other features of the base member. Once placed in a housing, such as, for example, but not limited to, thermal enclosure 101A (FIG. 1B), cassettes 107/111 may be squeezed between opposing gaskets or other members so that the cassette membrane can be pressed into sealing contact with the base member at regions inside of the periphery, thereby suitably sealing channels, valve ports, etc., from each other. In some configurations, the cassette membrane can be formed by a rigid sheet of material that is bonded or otherwise made integral with cassettes 107/111. In some configurations, the cassette membrane can include one or more flexible portions to permit pump and/or valve operation, and one or more rigid portions, e.g., to close flow paths of cassettes 107/111. In some configurations, the cassette membrane can include a pump chamber portion that can be formed to have a shape that closely conforms to the shape of the depressions of pump chambers 143A/B. In some configurations, the cassette membrane can be generally formed as a flat member with thermoformed (or otherwise formed) dome-like shapes that can conform to the depressions of pump chambers 143A/B. The dome-like shape of the preformed pump chamber portions can be constructed, for example, by heating and forming the cassette membrane over a vacuum form mold. In some configurations, the cassette membrane can be constructed to move relative to pump chambers 143A/B to effect pumping action with minimal or no stretching.

Continuing to refer to FIG. 5, in some configurations, cassettes 107/111 can include a pair of pump chambers 143A/B, although one pump chamber or more than two pump chambers are possible. In some configurations, the inner wall of pump chambers 143A/B can include spacer elements (not shown) that can be spaced from each other and extend from the inner walls of pump chambers 143A/B to help prevent portions of the cassette membrane from contacting the inner wall of pump chamber 143A/B. Further details regarding the arrangement and/or function of the spacers are provided in in U.S. Pat. No. 6,302,653, filed Jul. 20, 1999, and entitled METHODS AND SYSTEMS FOR DETECTING THE PRESENCE OF A GAS IN A PUMP AND PREVENTING A GAS FROM BEING PUMPED FROM A PUMP, U.S. Pat. No. 6,382,923, filed Jul. 20, 1999, and entitled PULP CHAMBER HAVING AT LEAST ONE SPACER FOR INHIBITING THE PUMPING OF A GAS, and U.S. Pat. No. 9,078,971, filed Nov. 2, 2012, and entitled MEDICAL TREATMENT SYSTEM AND METHODS USING A PLURALITY OF FLUID LINES, all of which are incorporated herein by reference in their entireties. In some configurations, the cassette membrane can include spacer elements or other features (not shown), such as ribs, bumps, tabs, grooves, channels, etc., in addition to, or in place of the spacer elements.

Continuing to refer to FIG. 5, in some configurations, the base member can define a plurality of fluid valve features, fluid pathways and other structures to guide the movement of fluid in cassette 107/111. Channels from each of the ports can fluidically communicate with a respective valve well. Valve wells can be fluidically isolated from each other by walls surrounding each valve well, and by sealing engagement of the cassette membrane with the walls around valve wells. Fluid in valve wells may flow into a valve port, if the cassette membrane is not pressed into sealing engagement with a valve port. Valves, for example, but not limited to, volcano valves, can be opened and closed by selectively moving a portion of the cassette membrane associated with the valve. Flow through the valve ports leads to the channel side (channels from which are shown in shadow) of the base member. Fluid in valve wells can flow into a respective valve port if the cassette membrane is not in sealing engagement with the port. On the channel sides of cassettes 107/111 are channels 152A that can fluidically communicate with openings 152 of pump chambers 143A/B by way of openings 154 that lead to wells 148. Flow from wells 148 can pass through respective ports 154 if a respective portion of the cassette membrane is not pressed in sealing engagement with port 154. Port 154 can lead to channel 152A that communicates with opening 152. Flow out of pump chambers 143A/B can pass through opening 152 and into channel 152A that communicates with port 146A. Flow from port 146A (if the cassette membrane is not in sealed engagement with port 146A) can pass into well 148 and into opening 138 that can fluidically communicate with channel 152B on the channel side of cassettes 107/111. Cooperating ports can be opened and closed, and the portion of the cassette membrane associated with pump chamber 143A/B can be moved, so as to lower/raise the pressure in pump chamber 143A/B, thereby drawing media in or expelling media from pump chamber 143A/B. Ports can be independently operable, allowing for the option to draw fluid through any one or a combination of lines, in any desired sequence, or simultaneously. When media is in pump chamber 143A/B, and when the cassette membrane is moved toward the base member, the pressure in pump chamber 143A/B can rise, causing fluid in pump chamber 143A/B to move into a channel. Media in the channel can be routed to bioreactor recirculation loop ports 203A/B, sample port 149, and/or waste port 201. In this way, for example, media can be drawn into cassette 107/111, and pumped out of cassette 107/111. The description herein can generally apply to any cassettes described herein, for example, cassettes 699/700 (FIGS. 6A-6I).

Referring now to FIGS. 5A and 5B, bioreactor module cassette 111 can provide a flow path from module line 119 (FIGS. 2A/2B) to user-supplied device 113A/B/C (FIGS. 2A/2B), and from user-supplied device 113A/B/C (FIGS. 2A/2B) to waste line 121 (FIGS. 2A/2B) and/or sample line 116 (FIGS. 2A/2B). The flow path of bioreactor module cassette 111 (FIG. 5) can enable the media within bioreactor module cassette 111 (FIG. 5) to be recirculated through user-supplied device 113A/B/C (FIGS. 2A/2B), and the direction of recirculation flow can be reversible. Reservoir module cassettes 107 (FIG. 5) can provide at least one recirculation loop that can enable the addition and mixing of media in holding container 109 (FIGS. 2A/2B) while physical properties are adjusted. In some configurations and referring now to FIG. 5A, fluid can circulate from bioreactor upper port 203B through gas exchange loop 147A/B (FIG. 5) (through gas-exchange zone 132 (FIG. 5)) past sensors such as, for example, but not limited to, spot sensors 146 (FIG. 5) and back to user-supplied device 113 A/B/C (FIGS. 2A/2B) through bioreactor lower port 203A. In some configurations and referring now to FIG. 5B, circulation 423 (FIG. 5A) can be reversed when flowing from bioreactor lower port 203A rather than to bioreactor lower port 203A. When flowing from bioreactor lower port 203A to bioreactor upper port 203B, for circulation 421 (FIG. 5B), the flow path begins at bioreactor lower port 203A, continues past spot sensors 146 (FIG. 5) and gas exchange loop outlet/inlet 147B/A (FIG. 5), and back to bioreactor upper port 203B. For either circulation 423 (FIG. 5A) or 421 (FIG. 5B), valves V2 403, V8 409, V5 411, and V3 413 are open, while other valves are closed. During the pumping process, PV1.2 405/PV2.1 407 and PV1.1 404/PV2.2 406 alternate being open and closed. In particular, valve V1 415 admitting material from media inlet port 145, valve V7 417 disposing of material through one-way valves 213 through waste port 201 to waste vessel 117 (FIG. 1B), and valve V6 419 allowing material to pass through one-way valve 212 through sample vessel port 149 to sample vessel 115 (FIG. 1B) are closed. Circulation 423 (FIG. 5A) can circulate past spot sensors 146 (FIG. 5) after passing through gas exchange loop outlet/inlet 147A/B (FIG. 5), whereas circulation 421 (FIG. 5B) can circulate past spot sensors 146 before passing through gas exchange loop outlet/inlet 147A/B (FIG. 5).

Figure 5C:
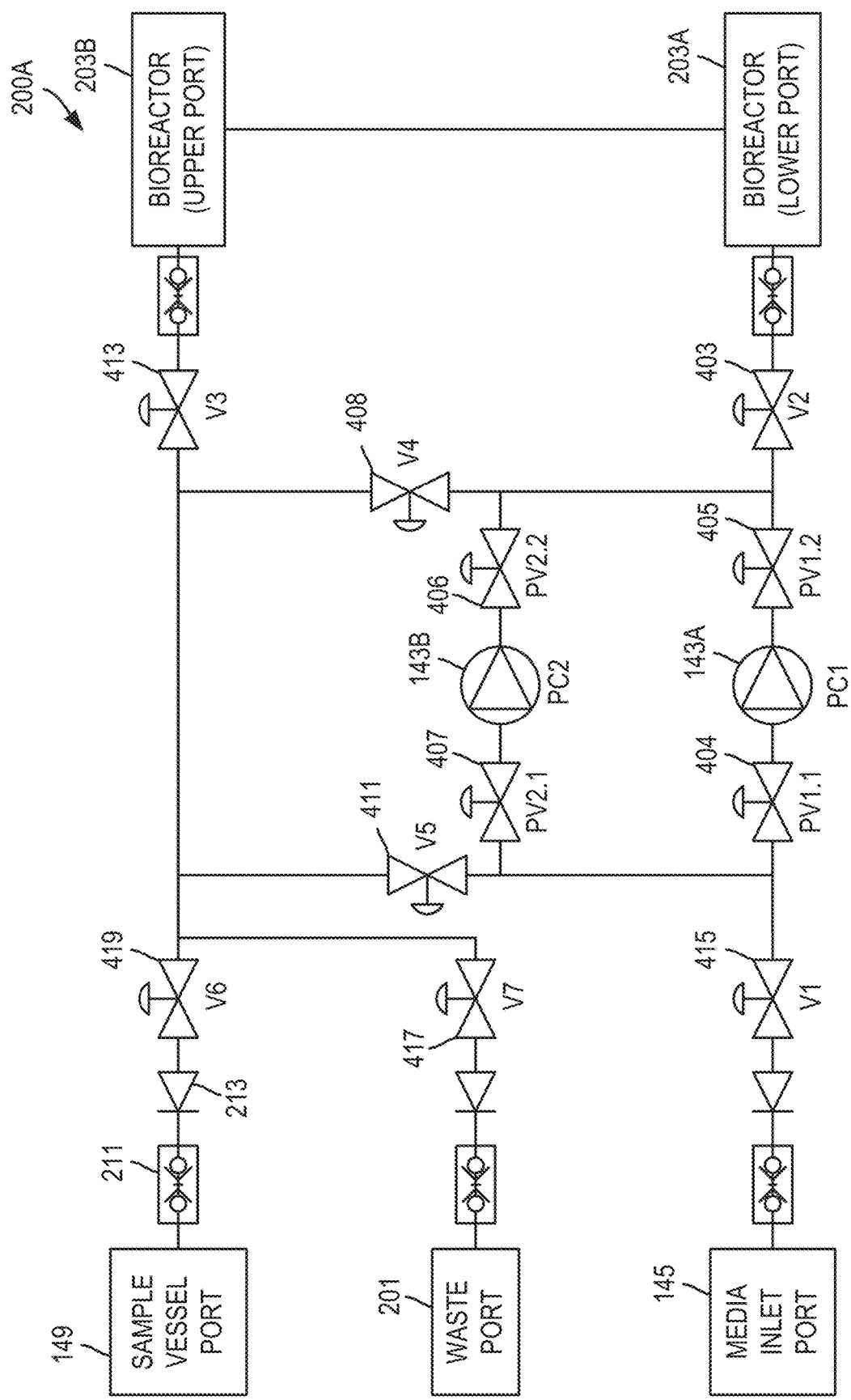
FIG. 5C is a fluid flow path for another configuration of the cassette of FIG. 5.
Figure 5D:
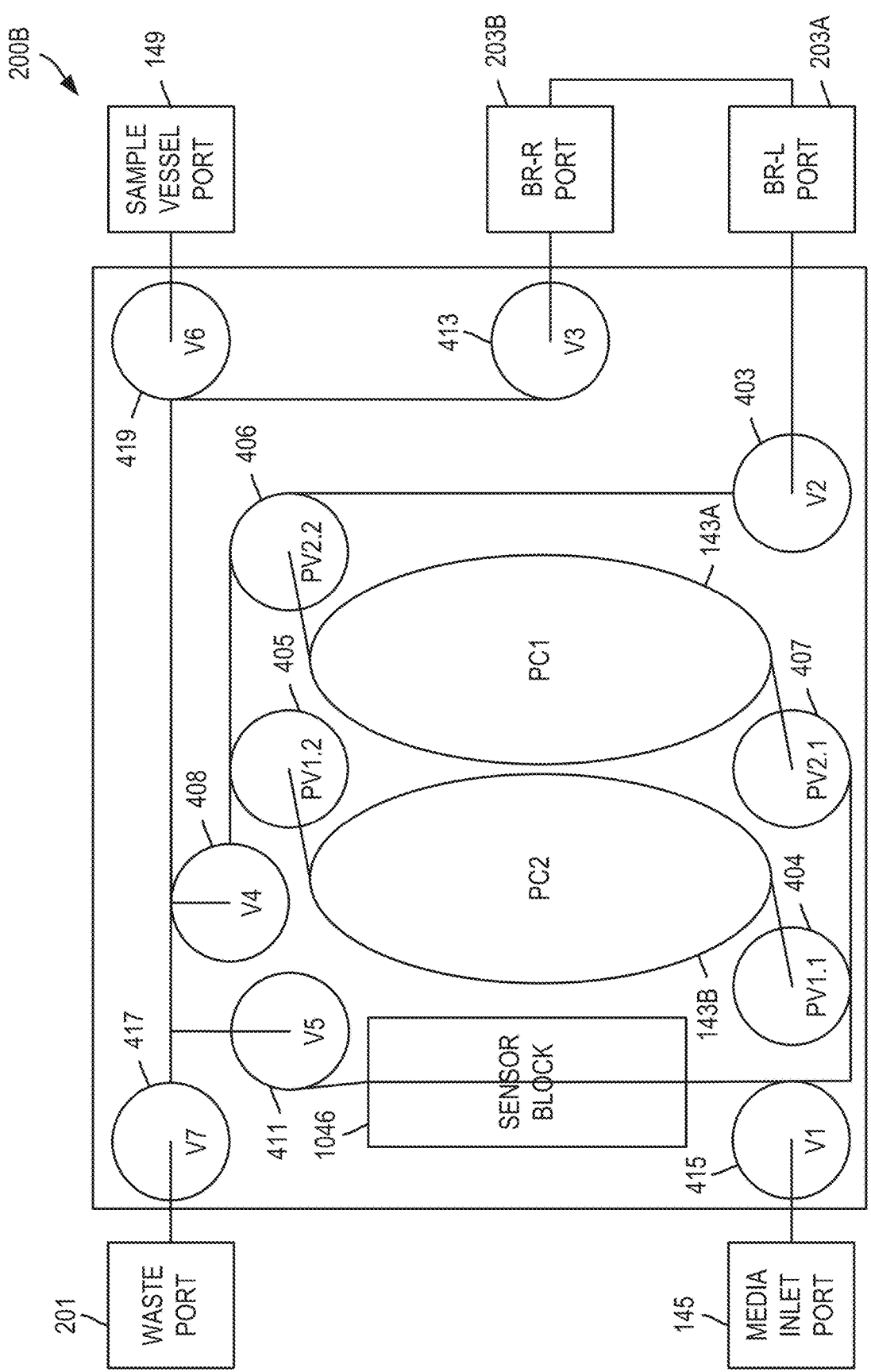
FIG. 5D is a cassette layout for another configuration of the cassette of FIG. 5.
Figure 5E:
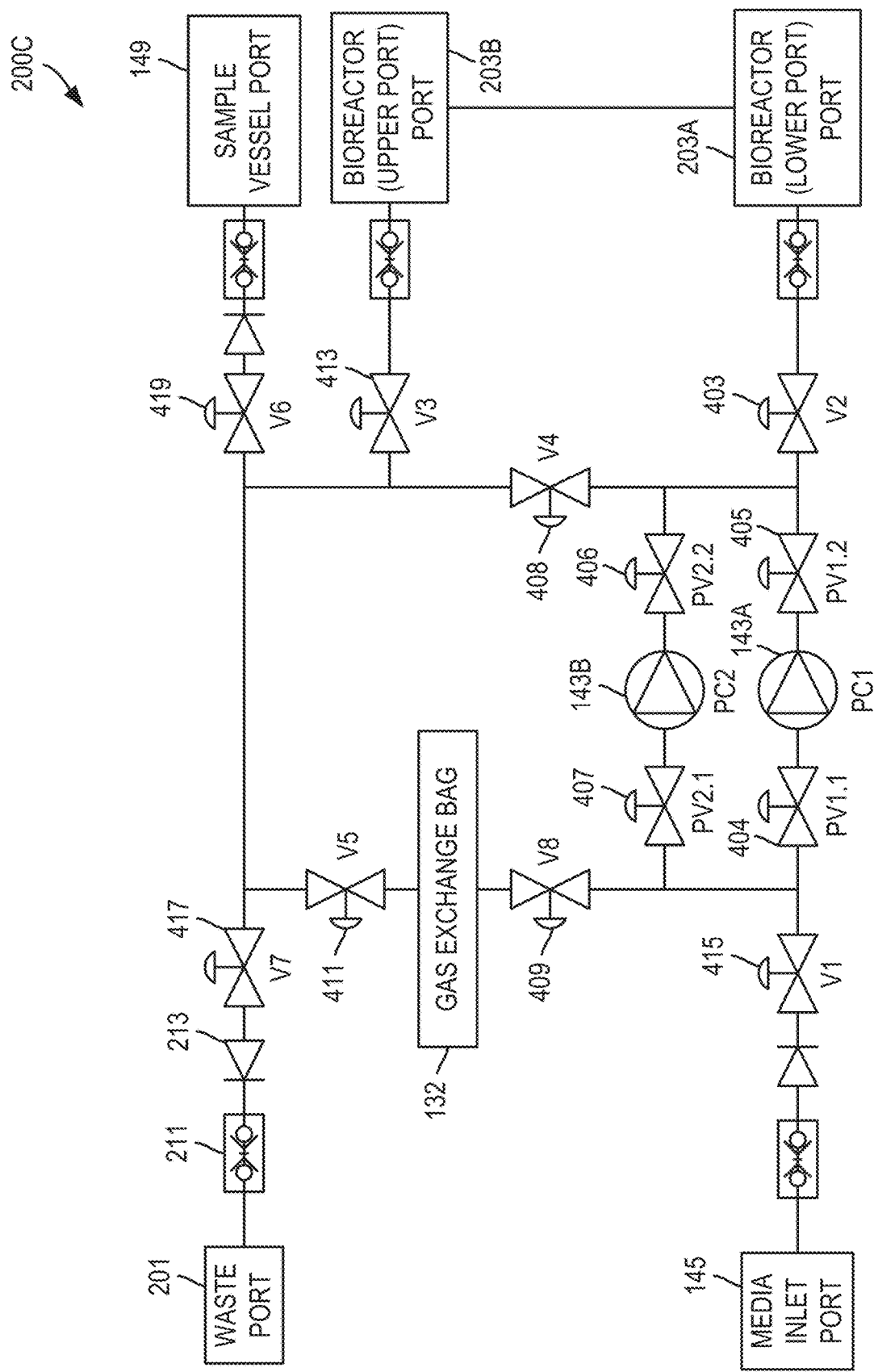
FIG. 5E is a fluid flow path for the cassette of FIG. 5D.
Figures 1, 5F:
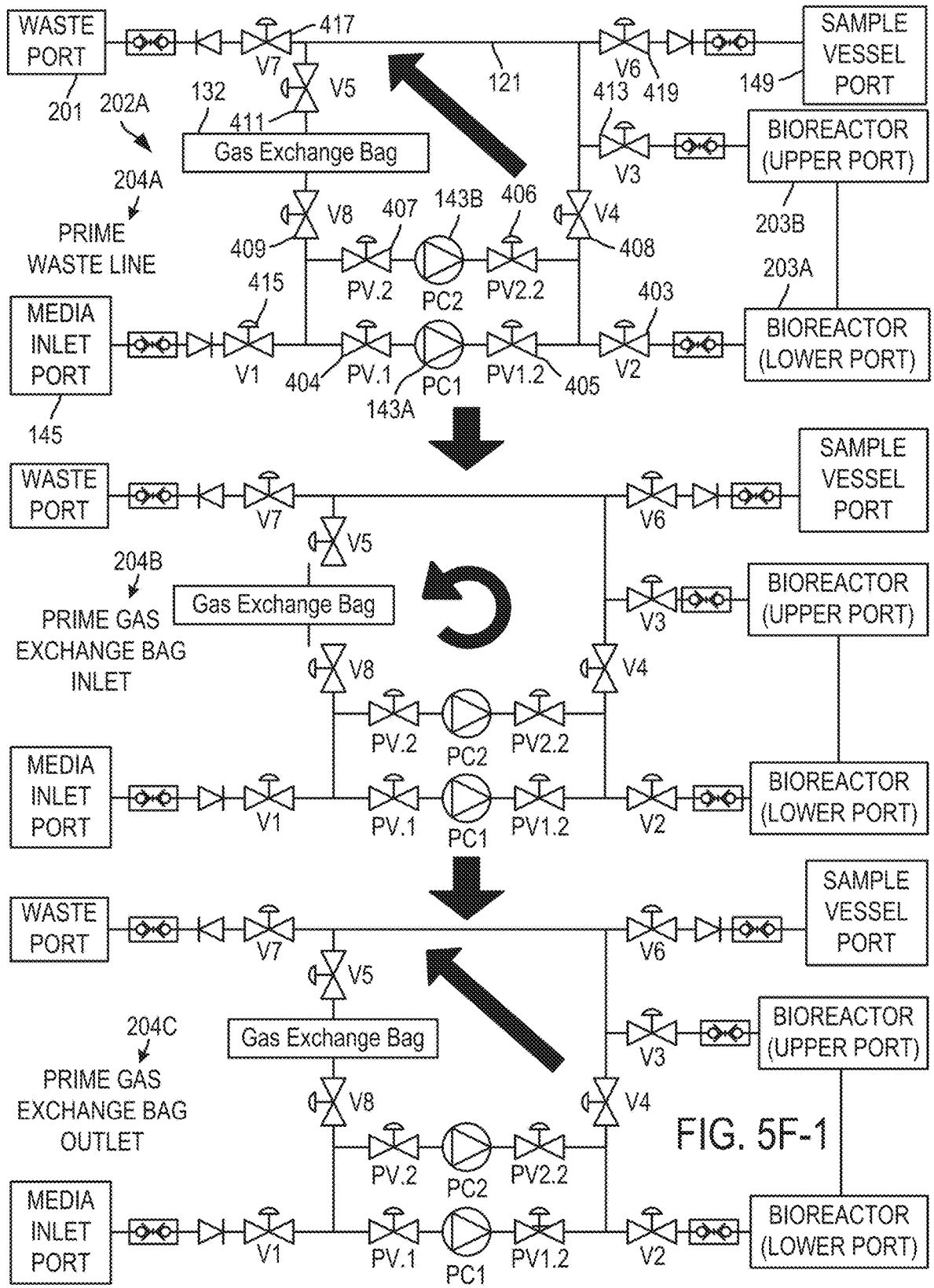

Referring now to FIGS. 5C-5E, various configurations of cassette 111 (FIG. 5) can include cassette layout 200A (FIG. 5C), cassette layout 200B (FIG. 5D), and cassette layout 200C (FIG. 5E). Layouts 200A (FIG. 5C) and 200B (FIG. 5D) include seven fluid valves, and gas exchange can be conducted through pumping/membrane valves rather than including a dedicated gas exchange area. Layout 200B (FIG. 5D) illustrates a possible position of sensor block 1046. Layout 200C (FIG. 5E) includes eight fluid valves and gas exchange zone 132 (FIG. 5E). The eighth valve can be used to accommodate a compliant gas exchange zone, to selectively fill or drain the compliant space in the gas exchange zone.

Referring now to FIGS. 5F-1 through 5I-2, cassette layout 200C (FIG. 5D) is shown in various flow path examples. An exemplary priming sequence 202A (FIG. 5F) can include the flow paths through cassette layout 200C (FIG. 5E) for priming 204A waste line 121 in which fluid valves V4 408, V1 415, and V7 417 are open and the rest of the fluid valves are closed. PV1.2 405/PV2.1 407 and PV1.1 404/PV2.2 406 alternate being open and closed. The fluid proceeds from media inlet port 145 to waste port 201, bypassing bioreactor ports 203A/B and sample port 149. Priming 204B the inlet of gas exchange zone 132 can include the flow paths through cassette layout 200C (FIG. 5E) in which fluid valves V4 408, V1 415, and V5 411 are open and the rest of the fluid valves are closed. PV1.2 405/PV2.1 407 and PV1.1 404/PV2.2 406 alternate being open and closed. Priming 204C the outlet of gas exchange zone 132 can include the flow paths through cassette layout 200C (FIG. 5E) in which fluid valves V4 408, V1 415, and V8 409 are open and the rest of the fluid valves are closed. PV1.2 405/PV2.1 407 and PV1.1 404/PV2.2 406 alternate being open and closed. Priming 204D sample line 116B can include the flow paths through cassette layout 200C (FIG. 5E) in which fluid valves V4 408, V1 415, and V6 419 are open and the rest of the fluid valves are closed. Priming 204E bioreactor 113 (FIG. 1B) through bioreactor upper port 203B and bioreactor lower port 203A can include the flow paths through cassette layout 200C (FIG. 5E) in which fluid valves V7 417, V1 415, V2 403, and V3 413 are open and the rest of the fluid valves are closed. Setting 204F the cassette ready for circulation can include an idle state in which all valves can be closed, for example. Alternatively, the system can proceed from the previous step to the next step.

Figures 2, 5F:
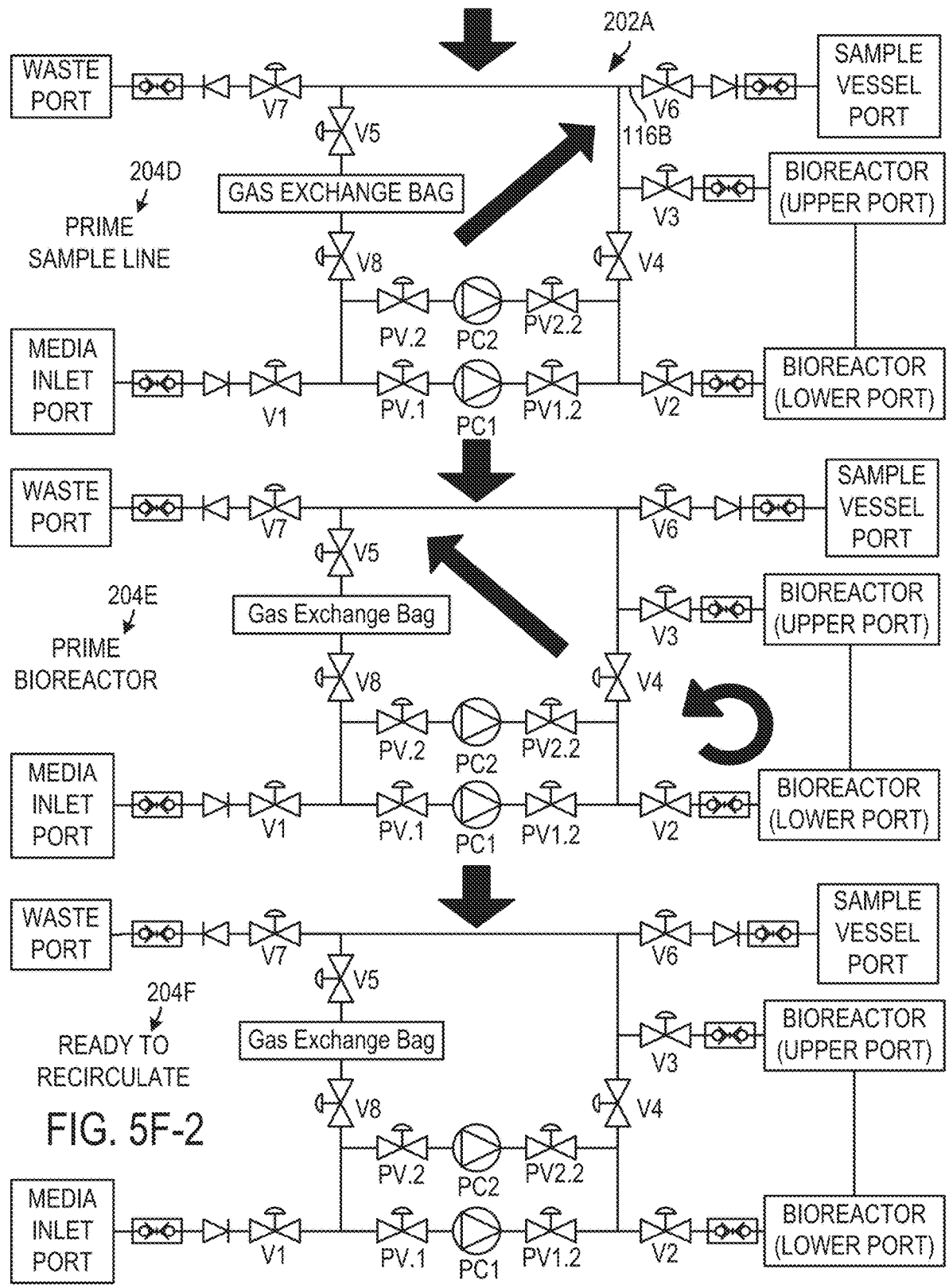
Figure 5G:
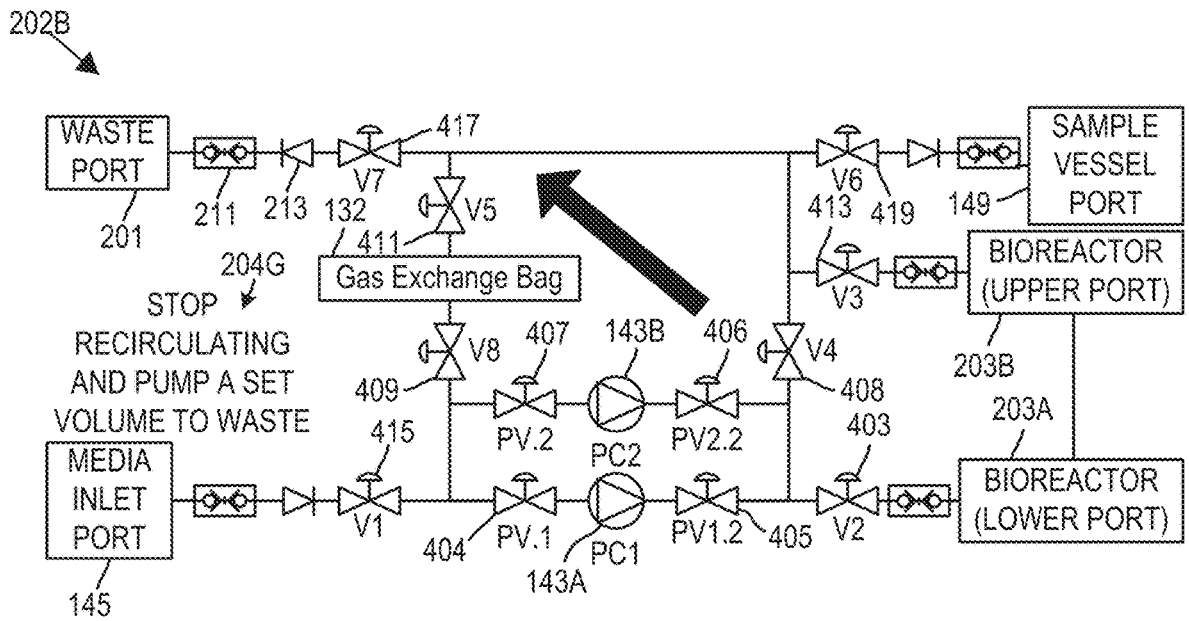
FIG. 5G is a fluid flow path for a partial replenishment of the media for the cassette of FIG. 5D.
Figure 5G:
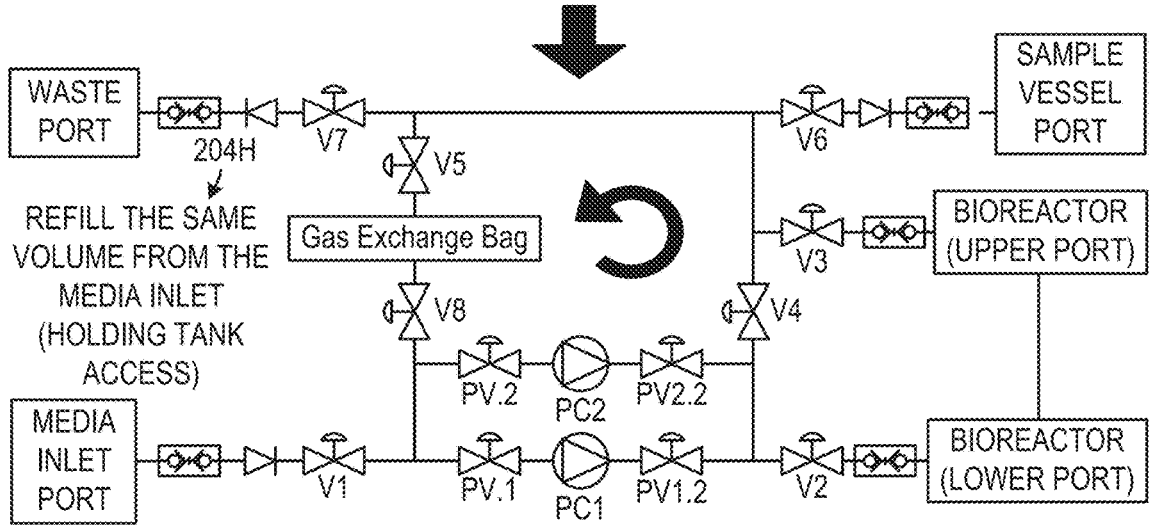
Figure 5G:
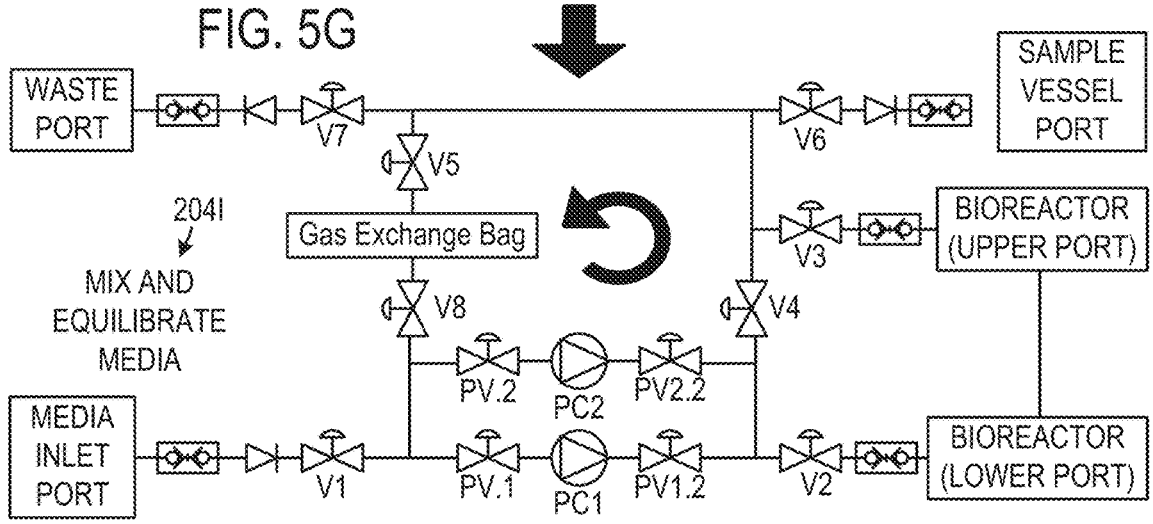

Referring now to FIG. 5G, exemplary sequence 202B of steps for partial replenishment of the media can include stopping 204G recirculating and pumping a set volume to waste, refilling 204H the same volume from media inlet port 145, and mixing 204I and equilibrating the media. Stopping 204G recirculating and pumping a set volume to waste can include the flow paths through cassette layout 200C (FIG. 5E) in which fluid valves V7 417, V8 409, and V4 408 are open and the rest of the fluid valves are closed. PV1.2 405/PV2.1 407 and PV1.1 404/PV2.2 406 alternate being open and closed. Refilling 204H the same volume from media inlet port 145 can include the flow paths through cassette layout 200C (FIG. 5E) in which fluid valves V1 415, V5 411, and V4 408 are open and the rest of the fluid valves are closed. Mixing 204I and equilibrating the media can include the flow paths through cassette layout 200C (FIG. 5E) in which fluid valves V5 411, V8 409, and V4 408 are open and the rest of the fluid valves are closed.

Figure 5H:
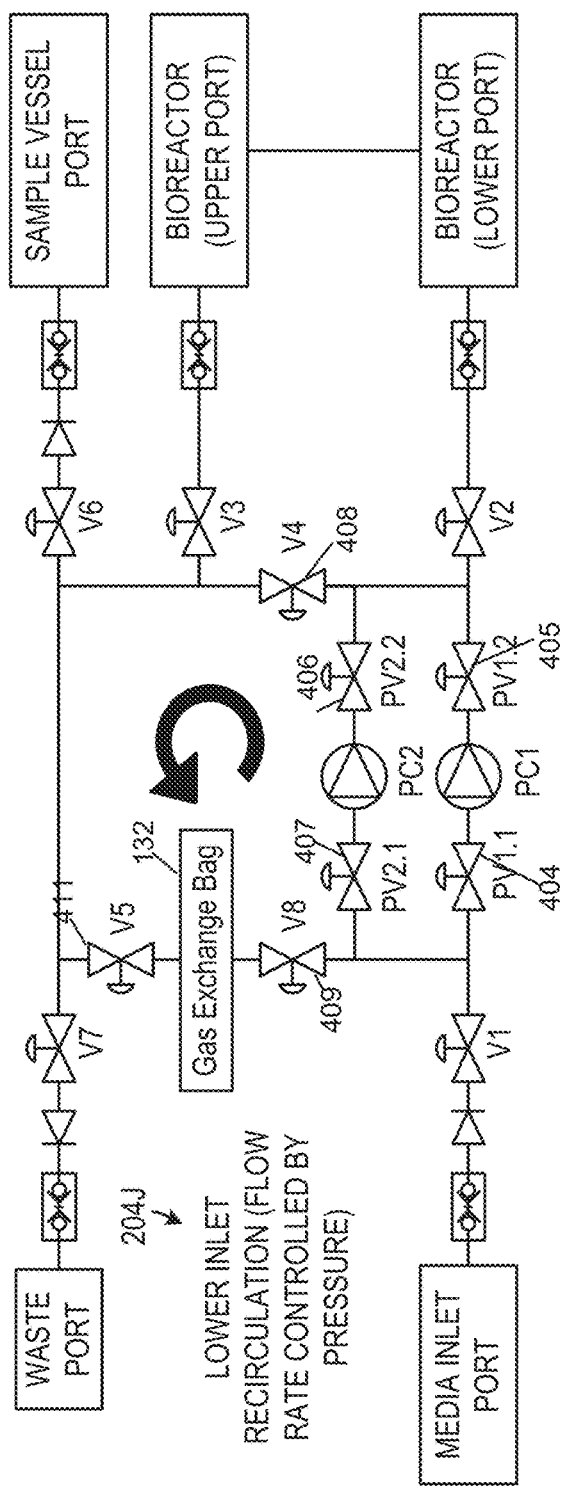
FIG. 5H is a fluid flow path for mixing the media and purging stale media for the cassette of FIG. 5D.
Figure 5H:
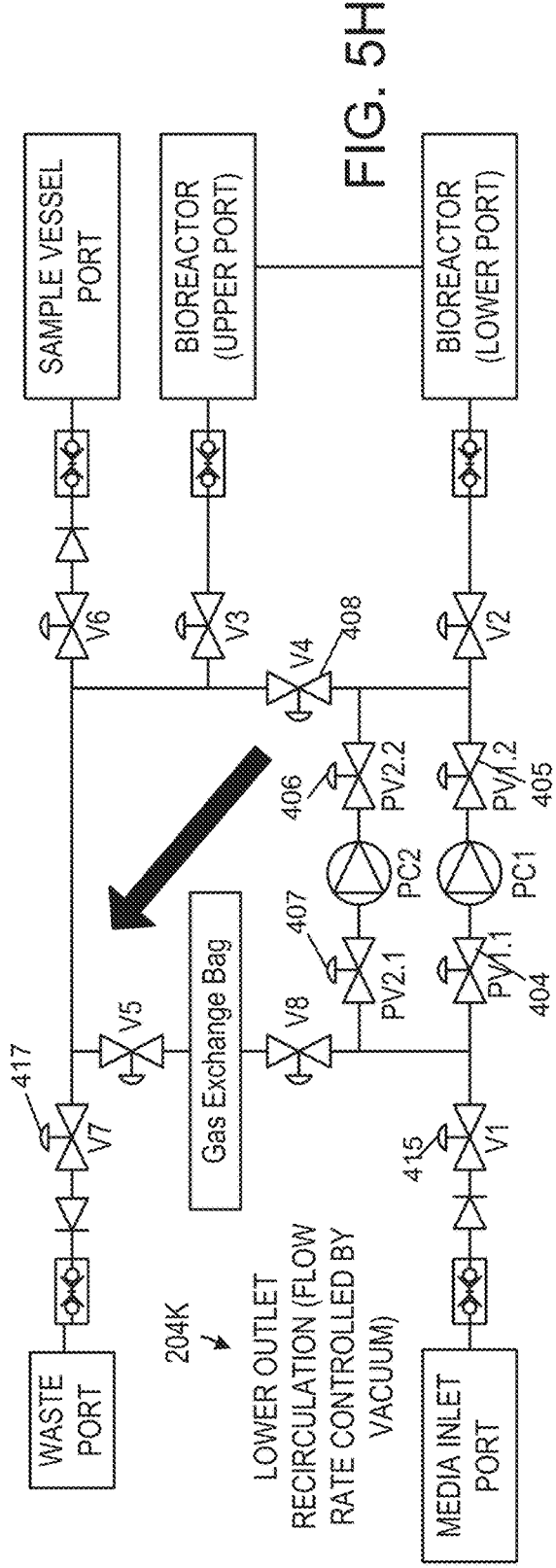

Referring now to FIG. 5H, mixing 204J the media in gas exchange zone 132 can include the flow paths through cassette layout 200C (FIG. 5E) in which fluid valves V5 411, V8 409, and V4 408 are open and the rest of the fluid valves are closed. PV1.2 405/PV2.1 407 and PV1.1 404/PV2.2 406 alternate being open and closed. Purging 204K stale media in module line 119 can include the flow paths through cassette layout 200C (FIG. 5E) in which fluid valves V7 417, V1 415, and V4 408 are open and the rest of the fluid valves are closed.

Figures 2, 5I:
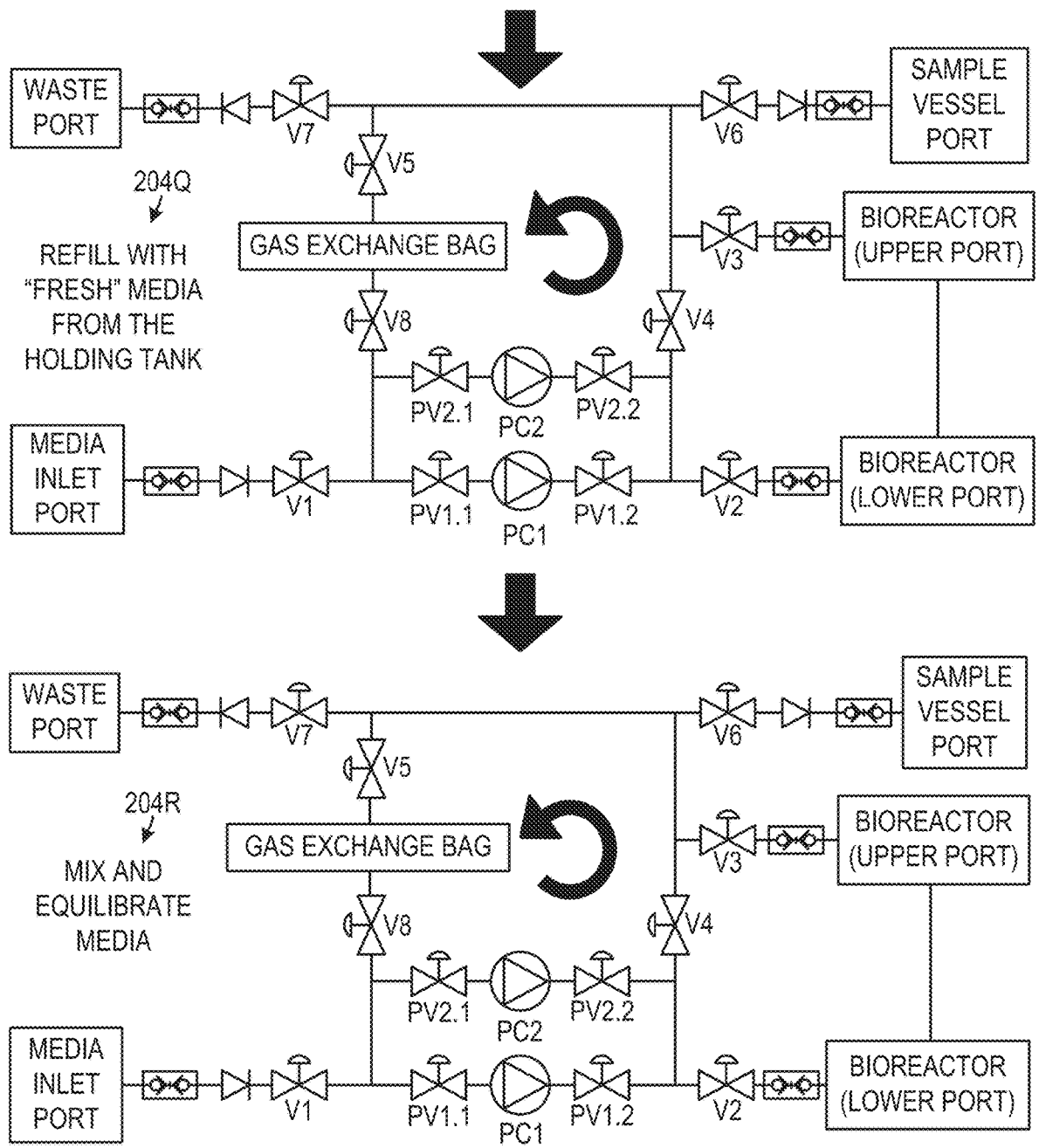

Referring now to FIGS. 5I-1 and 5I-2, exemplary sequence 202D of steps for providing a media sample for offline analysis can include flushing 204N stale media in sample line 116B with new media, mixing 204O while waiting for a switch between a stale media container and a spent media container, delivering 204P spent media to sample line 116B, refilling 204Q with fresh media, and mixing 204R and equilibrating the media. Flushing 204N stale media in sample line 116B with new media can include the flow paths through cassette layout 200C (FIG. 5E) in which fluid valves V8 409, V6 419, and V4 408 are open and the rest of the fluid valves are closed. PV1.2 405/PV2.1 407 and PV1.1 404/PV2.2 406 alternate being open and closed. Mixing 204O while waiting for a switch between a stale media container and a spent media container can include the flow paths through cassette layout 200C (FIG. 5E) in which fluid valves V5 411, V8 409, and V4 408 are open and the rest of the fluid valves are closed. Delivering 204P spent media to sample line 116B can include the flow paths through cassette layout 200C (FIG. 5E) in which fluid valves V6 419, V8 409, and V4 408 are open and the rest of the fluid valves are closed. Refilling 204Q with fresh media can include the flow paths through cassette layout 200C (FIG. 5E) in which fluid valves V6 419, V8 409, and V4 408 are open and the rest of the fluid valves are closed. Mixing 204R and equilibrating the media can include the flow paths through cassette layout 200C (FIG. 5E) in which fluid valves V5 411, V8 409, and V4 408 are open and the rest of the fluid valves are closed.

Referring now to FIGS. 6A-6D, second/third configuration cassettes 699 (FIGS. 6A/6B)/700 (FIGS. 6C/6D) can include many features discussed herein in relation to first configuration cassettes 107/111 (FIG. 5). Second/third configuration cassettes 699/700 can include on-cassette gas exchange and on-cassette media characteristics sensing in addition to the features discussed herein with respect to first configuration cassettes 107/111 (FIG. 5). Second/third configuration cassettes 699/700, though normally disposable, can be durable as well. Second/third configuration cassettes 699/700 can include, but are not limited to including, pump side 699A (FIG. 6A)/700A (FIG. 6C) and channel side 699B (FIG. 6B)/700B (FIG. 6D), and can include one or more pump chambers 705/707. Each of pump chambers 705/707 can include a variable volume chamber that can be defined, in part, by cassette membrane that can act as a displaceable diaphragm. Pressure applied to the cassette membrane or membrane associated with one or more pump chambers 705/707 can cause fluid to be drawn into or forced out of one or more pump chambers 705/707. Second/third configuration cassettes 699/700 can include, but are not limited to including, a number of fluid valves V1 805-V9 745 (FIG. 6C) that can include, but are not limited to including, volcano or diaphragm valves. In some configurations, fluid valves V1 805-V9 745 can be independently opened and closed to make and break fluid communication with fluid pathways on channel side 699B/700B. In some configurations, valves V2 743/V8 747 (also referred to as 747V) and V3 741/V9 745 (also referred to as 745V) can be tied together. Each of fluid valves V1 805-V9 745 can be associated with a valve seat. Cassette membrane can be forced against or pulled away from the valve seats to close or open the valves. The valves can be opened and closed to direct fluid flow when fluid is pumped via one or more of pump chambers 705/707.

Continuing to refer primarily to FIGS. 6A-6D, the cassette membrane can create a fluid tight seal for the fluid pathways on second/third configuration cassettes 699/700 such that fluid in the fluid pathways can be confined within the fluid pathways. Second/third configuration cassettes 699/700 can include a number of fluid ports, for example, but not limited to, media inlet port 723, sample vessel port 721, bioreactor lower port 719, bioreactor upper port 717, and waste port 715. Each of the ports can be connected to fluid lines, or conduits leading to fluid sources or reservoirs. Operation of pump chambers 705/707, and fluid valves V1 805-V9 745 can allow fluid to be pumped into, out of, or around second/third configuration cassettes 699/700 through one or more of the ports. Closing all of the fluid valves that are not associated with a desired fluid pathway to one or more of the ports can allow one or more pump chambers 705/707 to be in exclusive communication with the desired of the ports.

Continuing to refer primarily to FIGS. 6A-6D, each of pump chambers 705/707 may be of different or identical geometry. For example, first pump chamber 705 can have a generally circular footprint while second pump chamber 707 can be, for example, but not limited to, ovoid, elliptical, oblong, and stadium shaped, and vice versa. In some configurations, pump chambers 705/707 can be at least partially formed as a generally hemispherical or spherical cap-like depression in second/third configuration cassettes 699/700. Pump chambers 705/707 can be defined at least partially by flat bottomed depressions in second/third configuration cassettes 699/700. One or more of pump chambers 705/707 may include spacers (not shown).

Continuing to refer to FIGS. 6A-6D, second/third configuration cassettes 699/700 can include a membrane or cassette membrane that can include generally planar pieces of material overlaying both pump side 699A/700A and channel side 699B/700B of second/third configuration cassettes 699/700. The membrane can at least partially include, for example, but not limited to, substantially gas impermeable and flexible material, for example, a flexible plastic or elastomeric material. The membrane can be attached to second/third configuration cassettes 699/700 by, for example, but not limited to, heat bonding, adhesive, ultrasonic welding or other means. The membrane can at least partially include a high gas propagation barrier because high pressure in pump chambers 705/707 can drive gas transfer.

Continuing to still further refer to FIG. 6A-6D, when second/third configuration cassettes 699/700 are assembled, each pump chamber 705/707 can be, for example, defined in part by walls extending from the body of second/third configuration cassettes 699/700 to create depressions in pump chambers 705/707. Application of pressure to the cassette membrane over pump chambers 705/707 can cause the volume of pump chambers 705/707 to vary. When negative pressure is applied to pump side 699A/700A of second/third configuration cassettes 699/700, the cassette membrane may be pulled away from walls 704 (FIG. 6A), enabling fluid travel in fluid busses 706. In communication with a fluid source such as, for example, but not limited to, media 101 (FIG. 1B), fluid may be drawn into one or more of pump chambers 705/707 when negative pressure is applied, executing a fill pump stroke. Positive pressure exerted on pump side 699A/700A can depress the cassette membrane against the valve seat. The pressure can, for example, form fluidically sealed chambers and pathways in cassette 700. The cassette membrane can be, but is not limited to being, prevented from being forced against each of the valve seats because walls may be, for example, proud of the valve seats. One or more piece of the cassette membrane can optionally include one or more preformed region. The preformed regions can include, but are not limited to including, depression-like features in the cassette membrane that can generally conform to the contours of various portions of second/third configuration cassettes 699/700. The preformed regions can be added to the cassette membrane during manufacture. The cassette membrane can be, for example, generally formed as a flat member and preformed regions can later be thermoformed. In some configurations, the preformed regions can correspond to pump chambers 705/707. Dome-like preformed shapes can, for example, conform to the depressions of pump chambers 705/707. A vacuum form mold can press a sheet of the cassette membrane against second/third configuration cassettes 699/700 and bond the membrane to second/third configuration cassettes 699/700. At least one piece of the cassette membrane can be formed of a rigid sheet of material that can be bonded or otherwise made integral with second/third configuration cassettes 699/700. In some configurations, at least one piece of the cassette membrane need not necessarily be, or include, a flexible member. The cassette membrane need not be flexible over its entire surface, but instead can include one or more flexible portions to permit pump and/or valve operation, and one or more rigid portions, e.g., to close fluid buses of second/third configuration cassettes 699/700. In some configurations, second/third configuration cassettes 699/700 can include fluid buses or pathways that can be otherwise sealed or fully enclosed within second/third configuration cassettes 699/700 without the cassette membrane.

Continuing to refer to FIGS. 6A-6D, second/third configuration cassettes 699/700 can include gas exchange areas 701A/701 that can enable modification of the characteristics of the circulating media through exposure to specific gases as described herein. Gas exchange between the circulating media and the specific gases can occur in gas exchange areas 701A/701. Fluid can enter gas exchange area 701A/701 through gas exchange inlet 727, and can return to second/third configuration cassettes 699/700 through gas exchange outlet 725. Second configuration gas exchange area 701A (FIGS. 6A/6B) can include fluid bus circulation points 706A/706B/708 that can enable the circulation of fluid on both sides of second configuration cassette 699 around channels 702 and back to the pumping portion of second configuration cassette 699 through gas exchange outlet 725. Gas exchange areas 701A/701 can be covered on both sides by a gas-permeable membrane. The membrane can enable gas exchange between the fluid in channels 702 and pressurized gas applied to the gas-permeable membrane. When it is determined, based on the data gathered by on- and/or off-board sensors, that the characteristics of the fluid circulating on second/third configuration cassettes 699/700 requires modification, gas of a desired composition can be delivered to the circulating fluid and become dissolved therein through the gas-permeable membrane. In some configurations, a glucose sensor can be located on channel side 700B. Locating the glucose sensor downstream of media inlet port 723 can enable calibration of the glucose sensor 133 while third configuration cassette 700 is operational by minimizing the mixing of fresh and spent media prior to the media passing by the glucose sensors, and having knowledge of the glucose concentration of the fresh media. Media entering the cassette can be prevented from mixing with spent media.

Figure 6B:
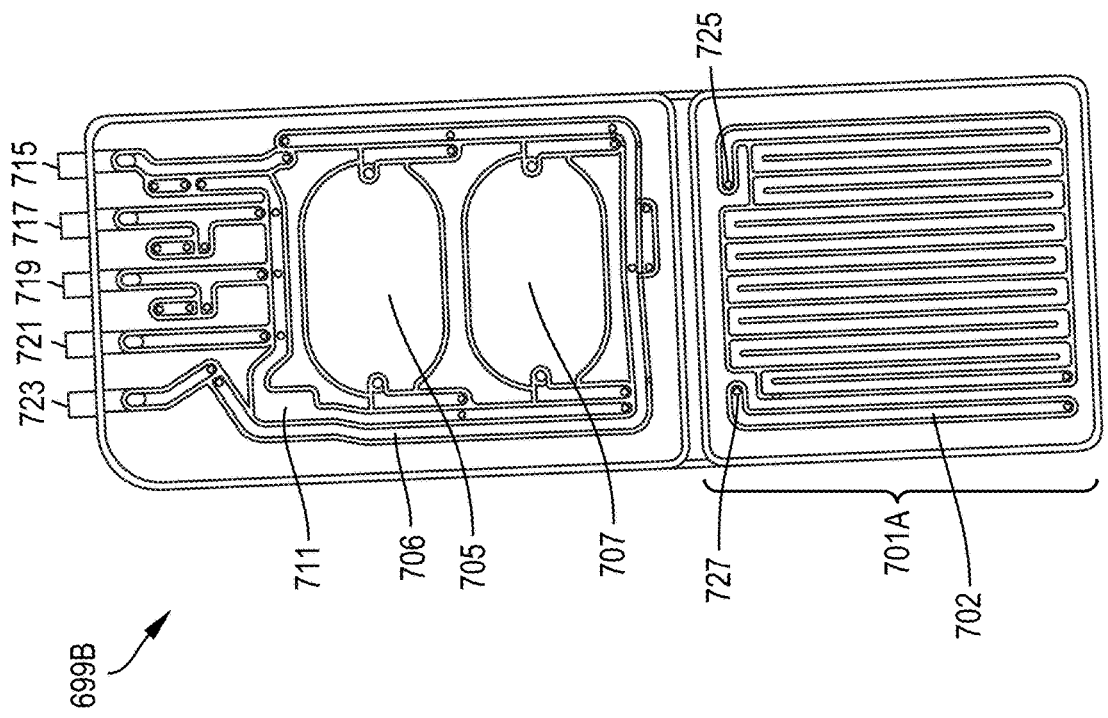
FIGS. 6A and 6B are pictorial representations of front and rear views of configuration of a pumping cassette having on-board gas exchange.
Figure 6A:
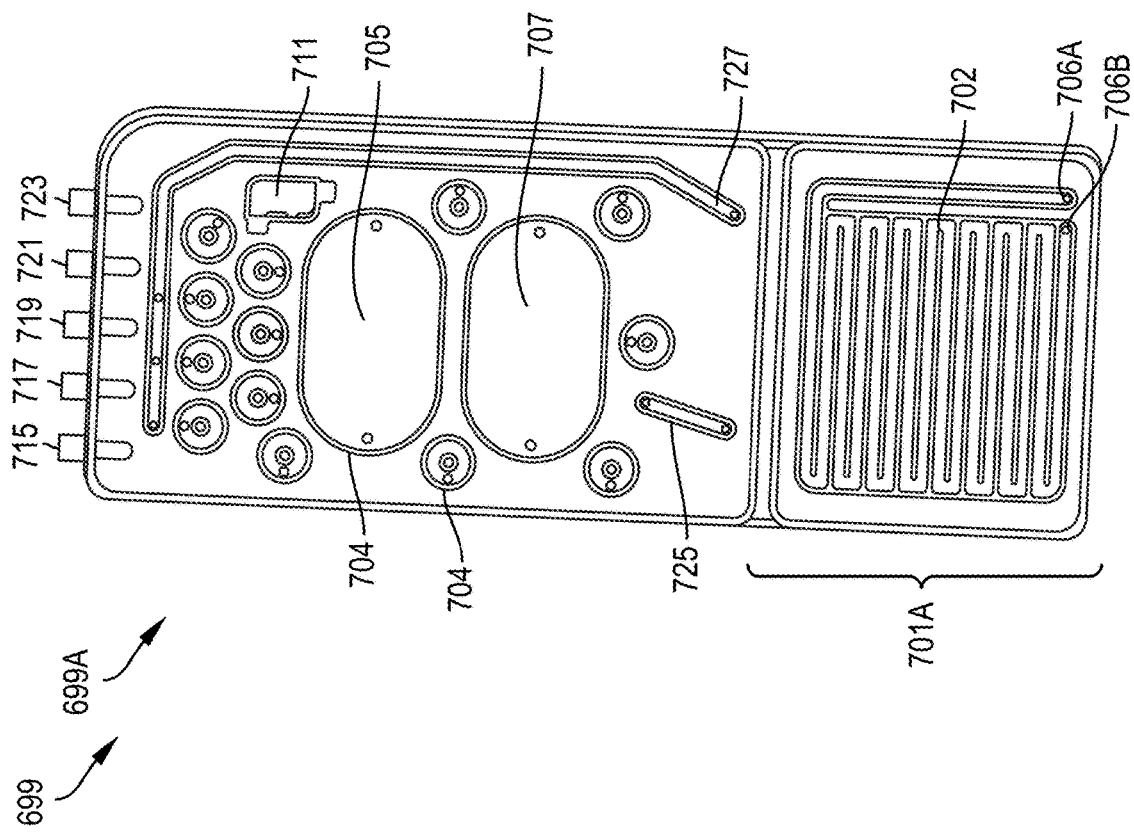
Figure 6C:
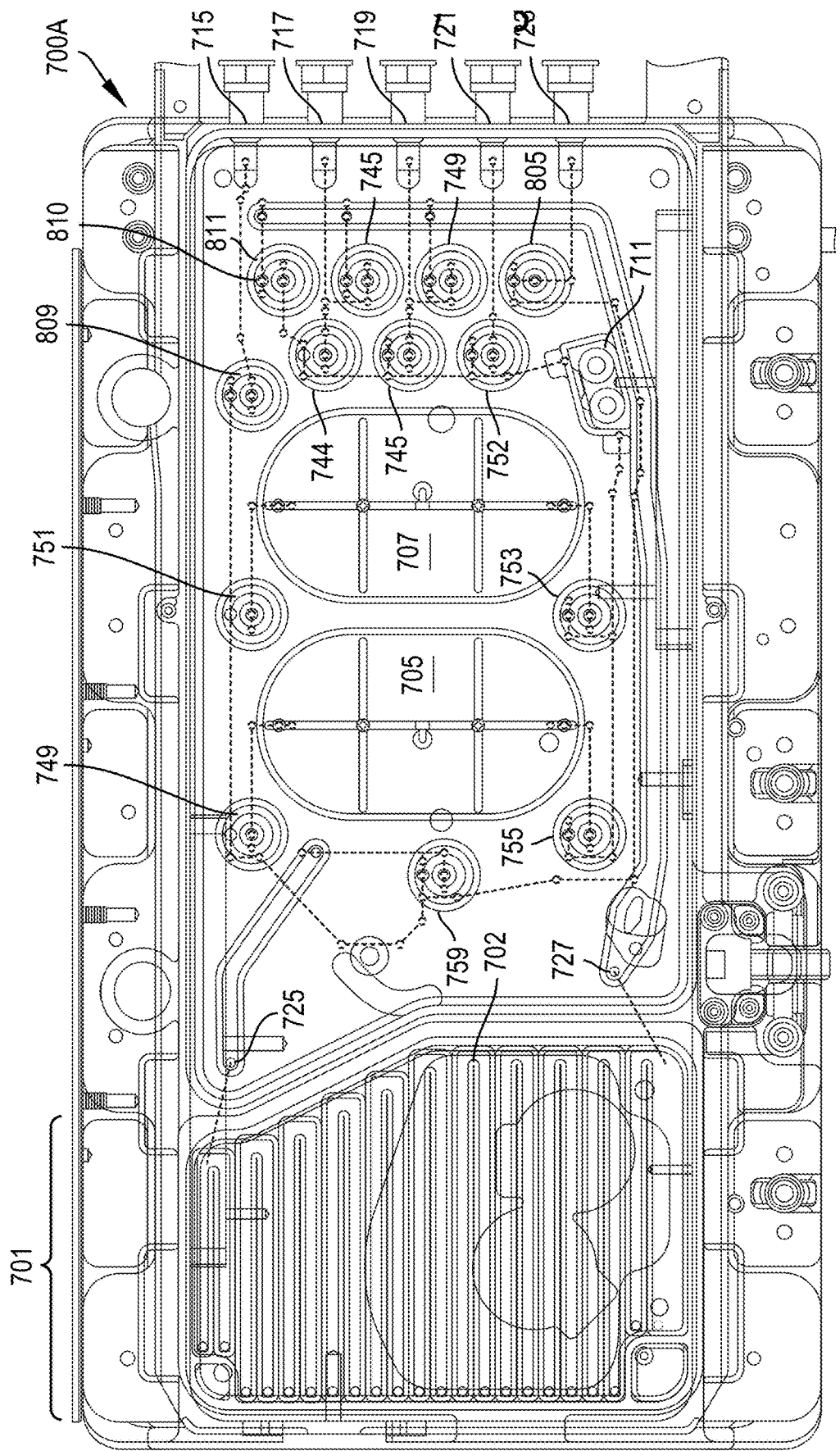
FIGS. 6C and 6D are pictorial representations of front and rear views of another configuration of a pumping cassette having on-board gas exchange.
Figure 6D:
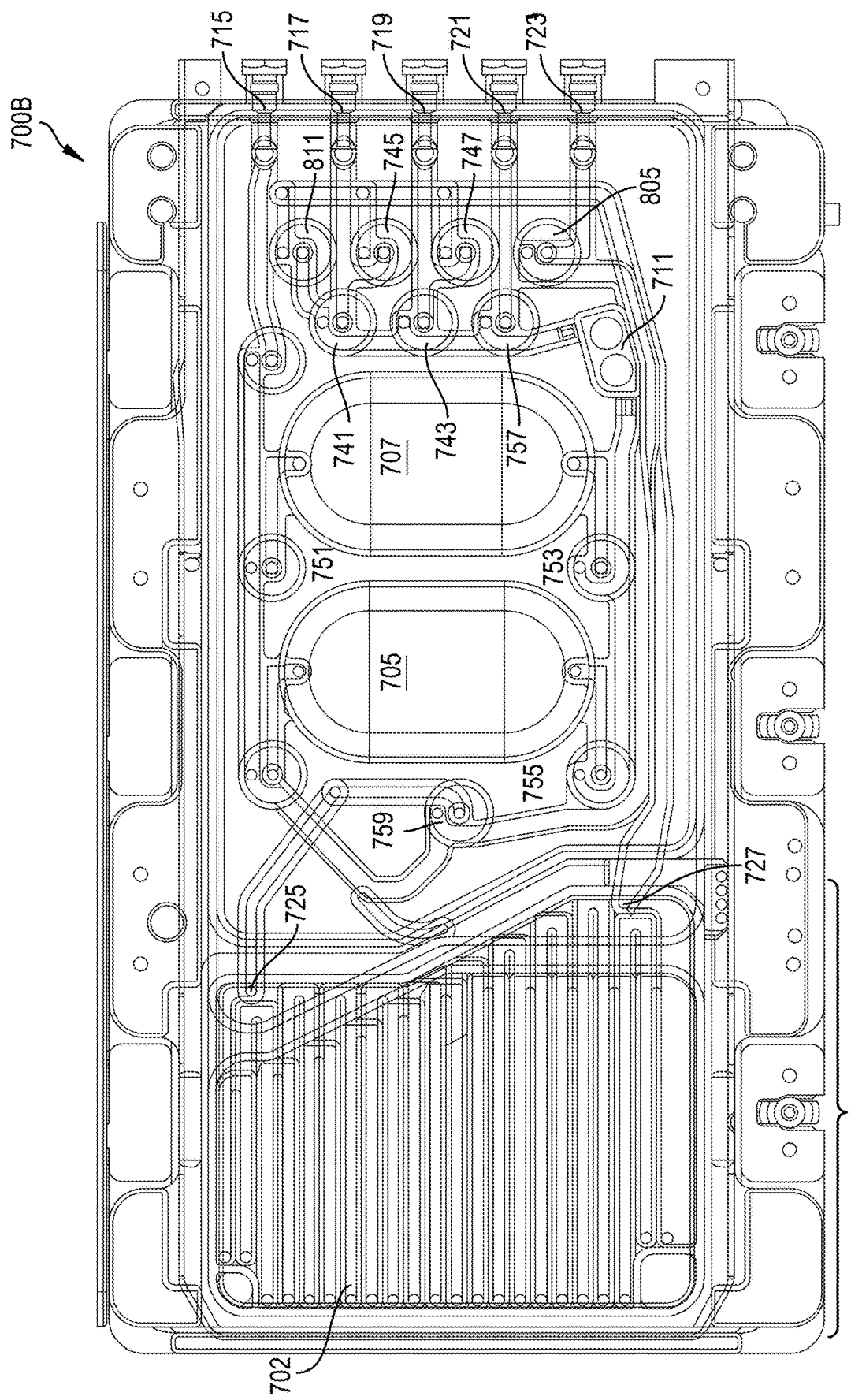
Figure 6E:
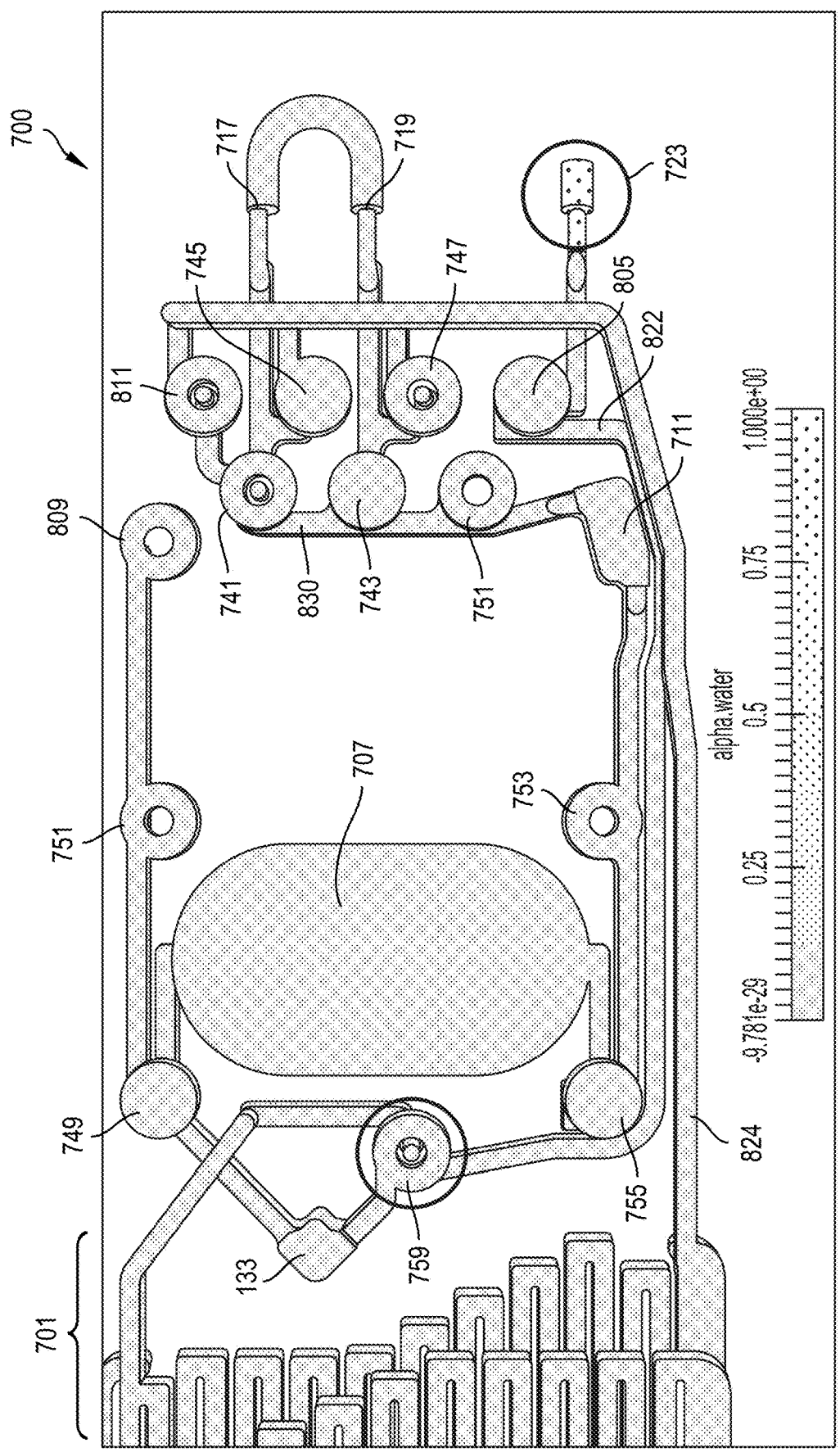
FIGS. 6E and 6F are pictorial representations of exemplary fluid flow paths from a media inlet to the gas exchange region, and bypassing bioreactor entry of the cassette of FIGS. 6C and 6D.

Referring now to FIG. 6E, exemplary fluid flow from media inlet 723 through a bioreactor to gas exchange area 701 is shown. Media can enter cassette 700 at media inlet 723 and travel through valve 805, down channel 822, through valve 755 (also referred to as 755V) and through channel 828. Fluid can travel past glucose sensor 133, through valve 749 (also referred to as 749V), and into pumping chamber 707. The fluid can be pumped out of pumping chamber 707 according to the process described herein, can travel through valve 755, down a channel, past sensors 711, and into another channel. Fluid can travel through valve 743 and into bioreactor through bioreactor inlet 719. Fluid can re-enter cassette 700 through bioreactor outlet 717, through valve 745, and down channel 824 into gas exchange area 701.

Figure 6F:
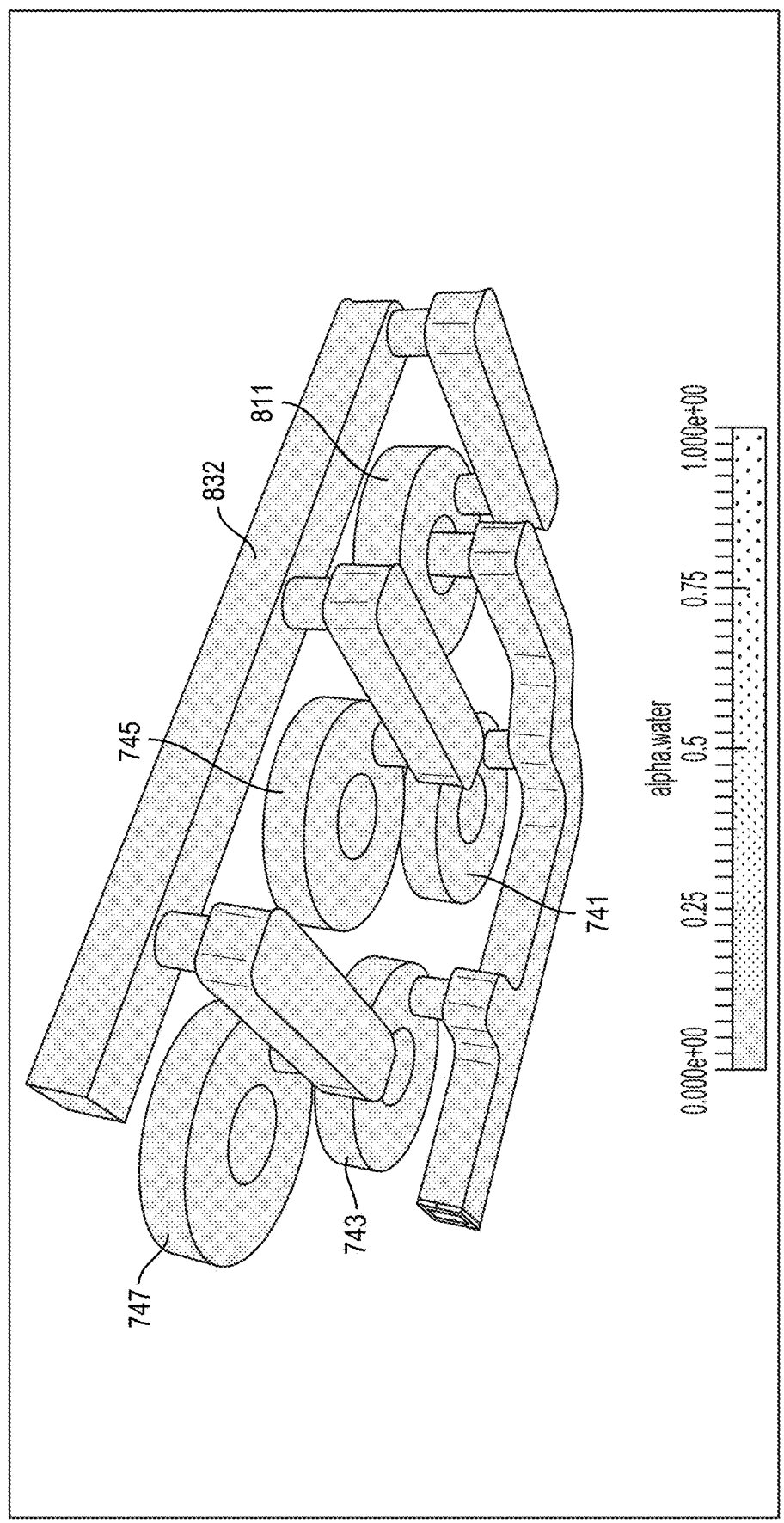

Referring now to FIG. 6F, in a second exemplary fluid flow, media can be flowing through channel 830 past closed valves 743 and 741, into open valve 811, and into channel 832, bypassing bioreactor entry, heading towards gas exchange area 701.

Figure 7A:
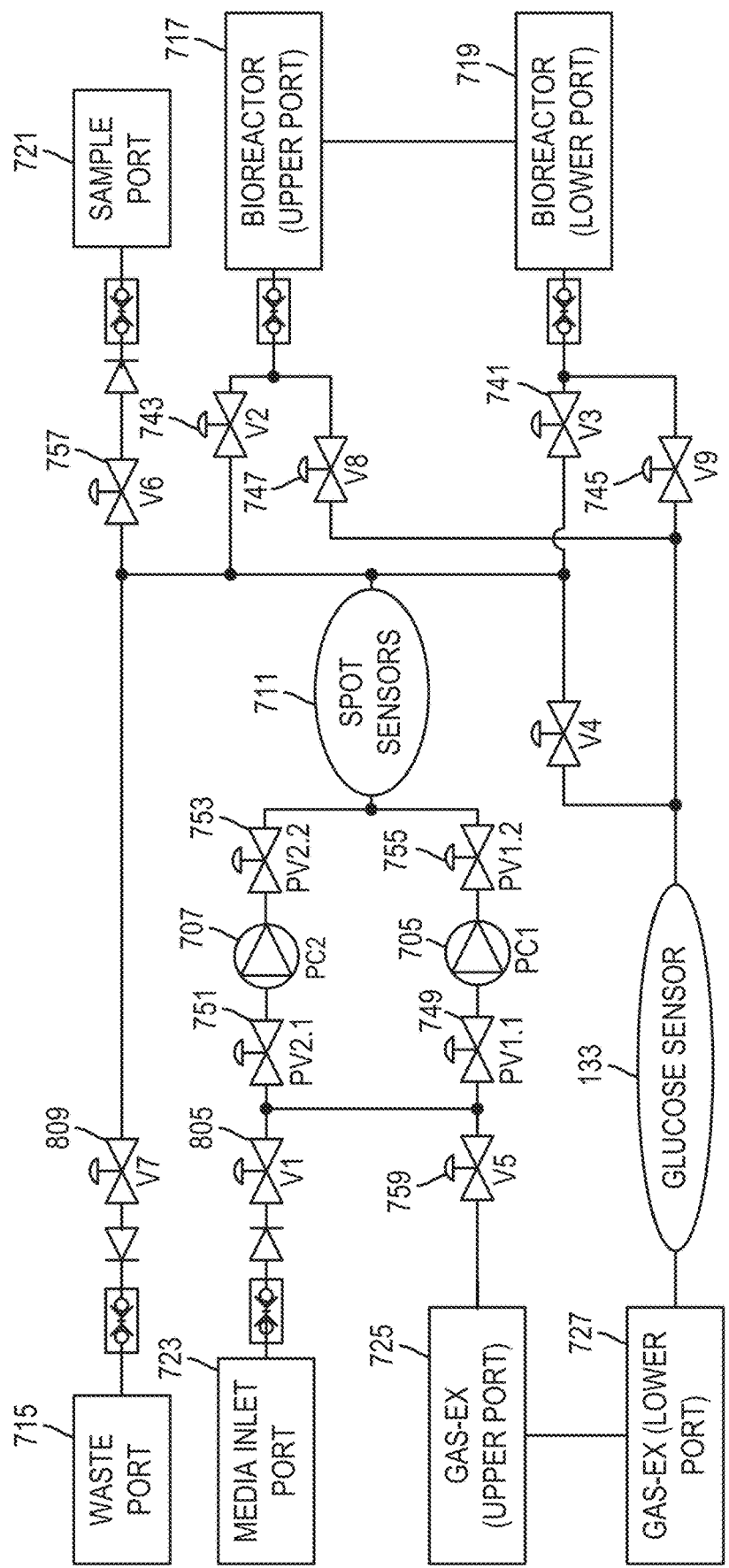
FIGS. 7A-7C are fluid flow paths for various valve and port configurations.
Figure 7B:
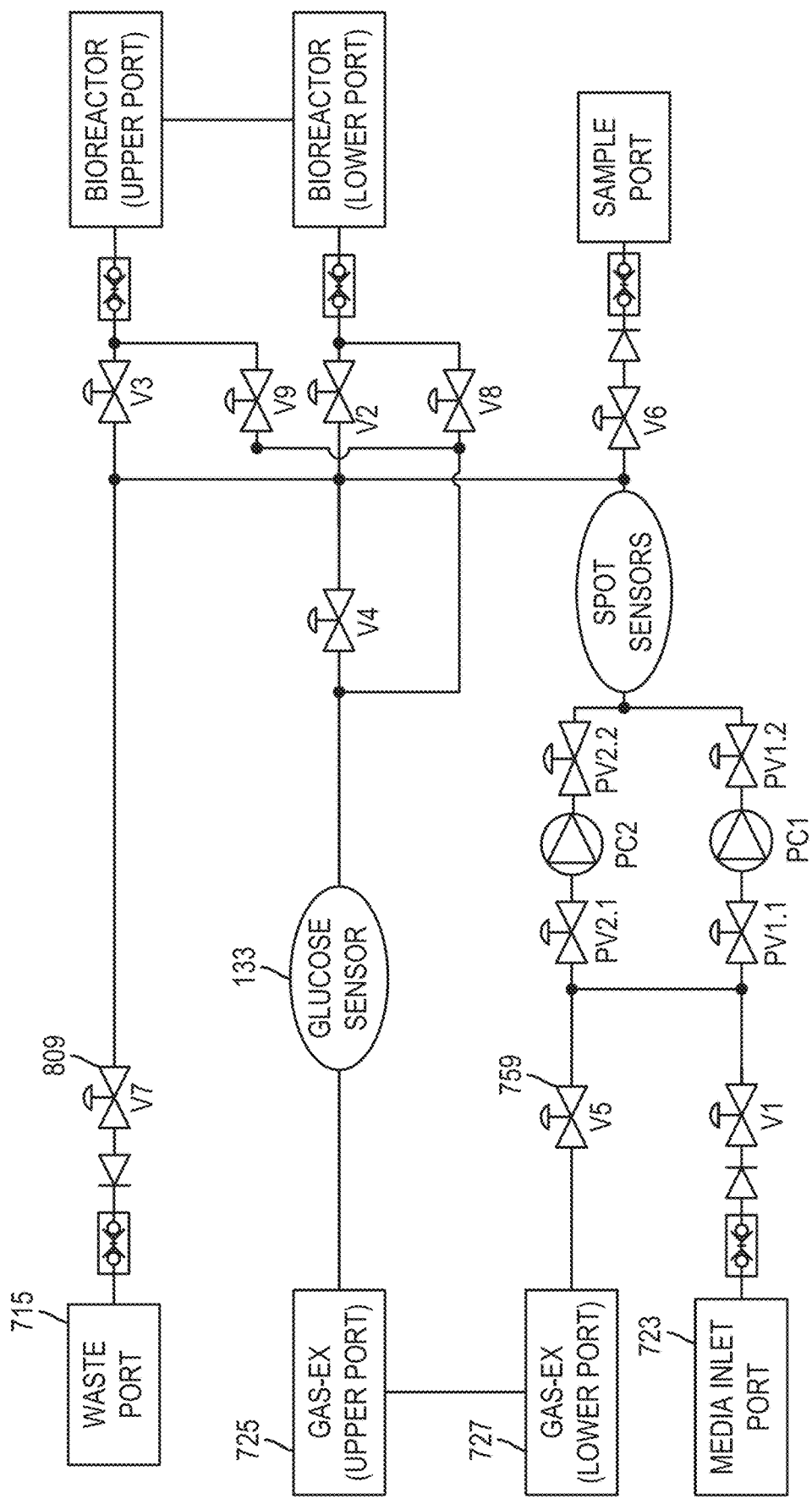
Figure 7C:
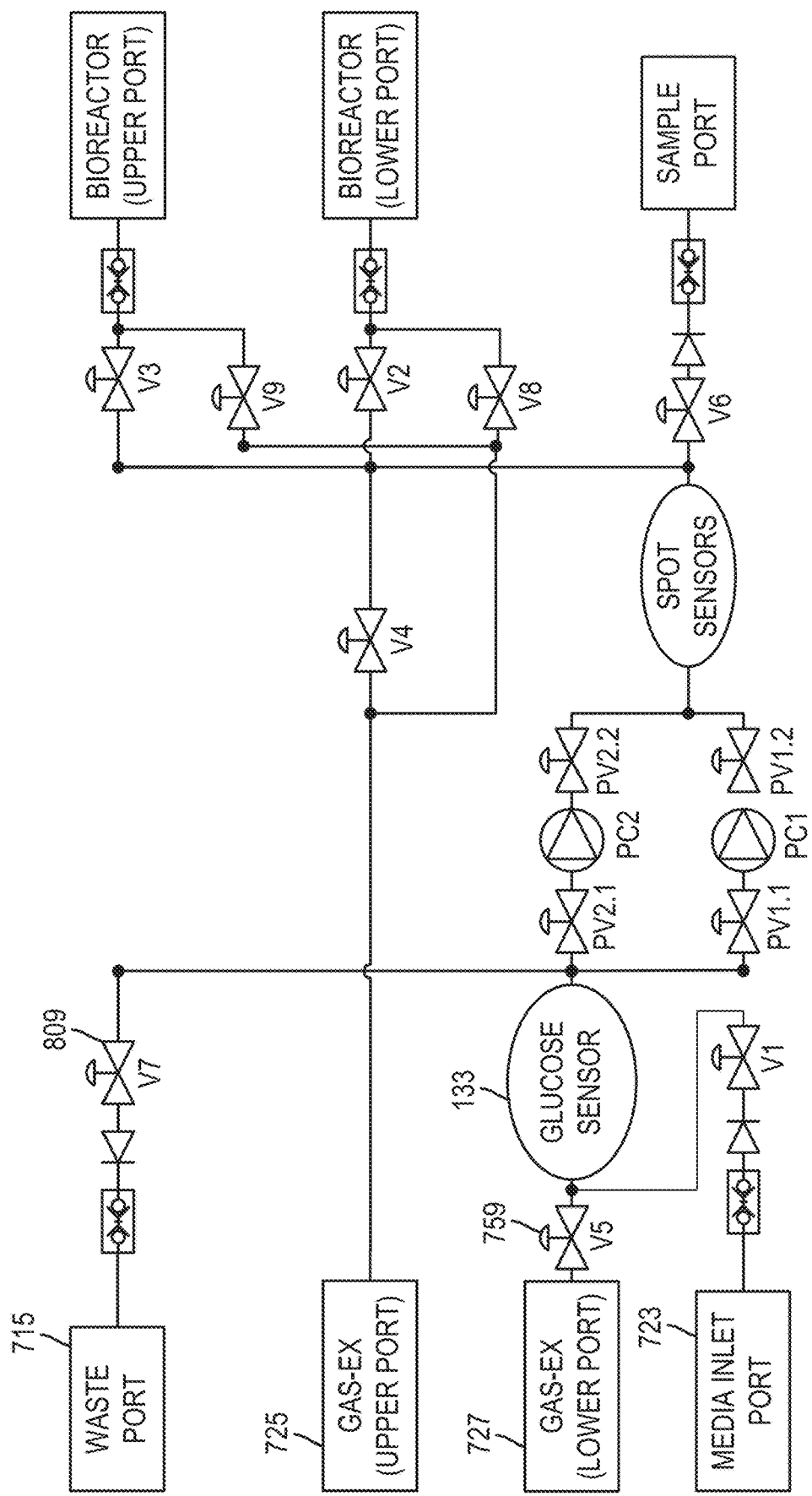
Figure 8:
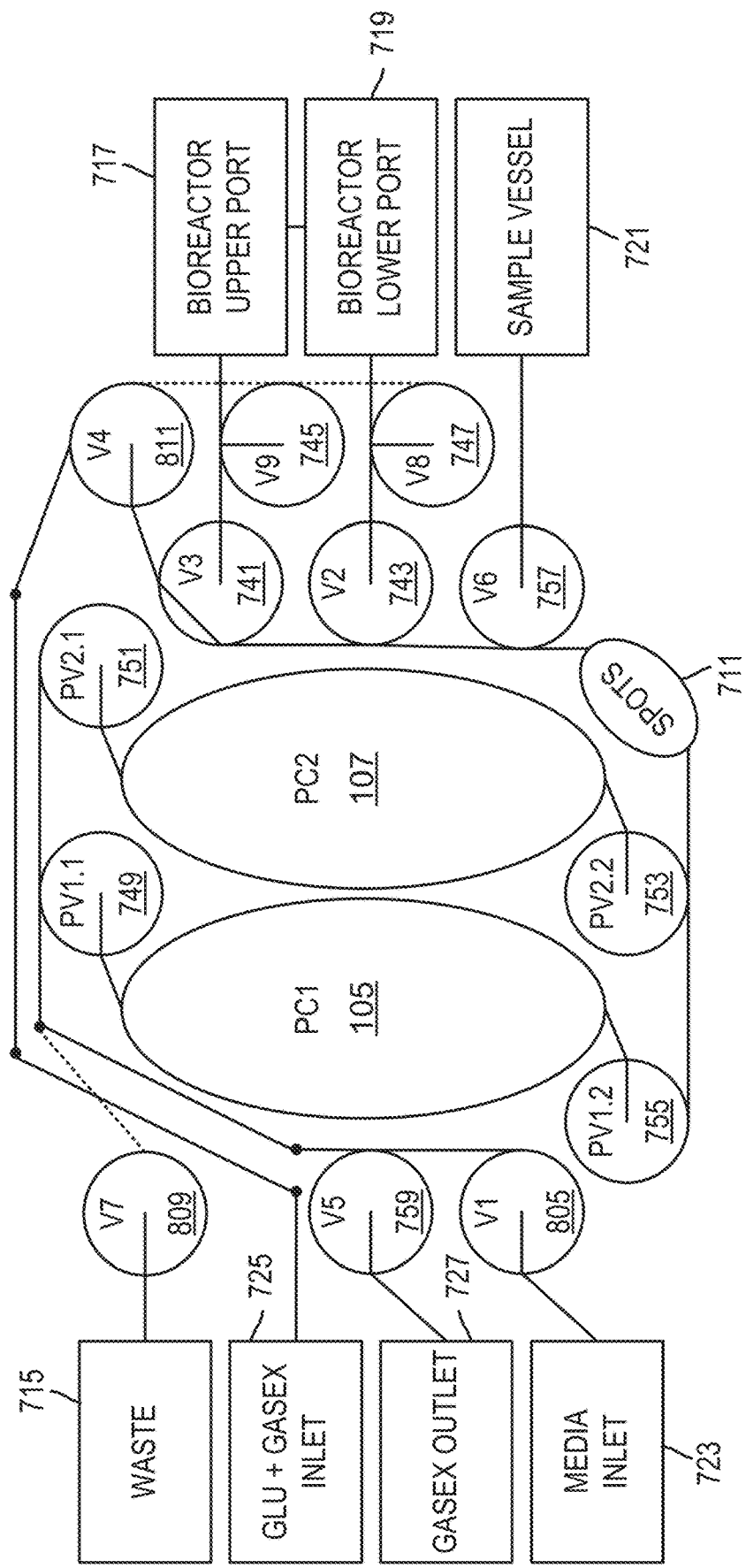
FIG. 8 is a pictorial representation of a cassette layout implementing the fluid flow paths in FIGS. 7B and 7C.
Figure 9A:
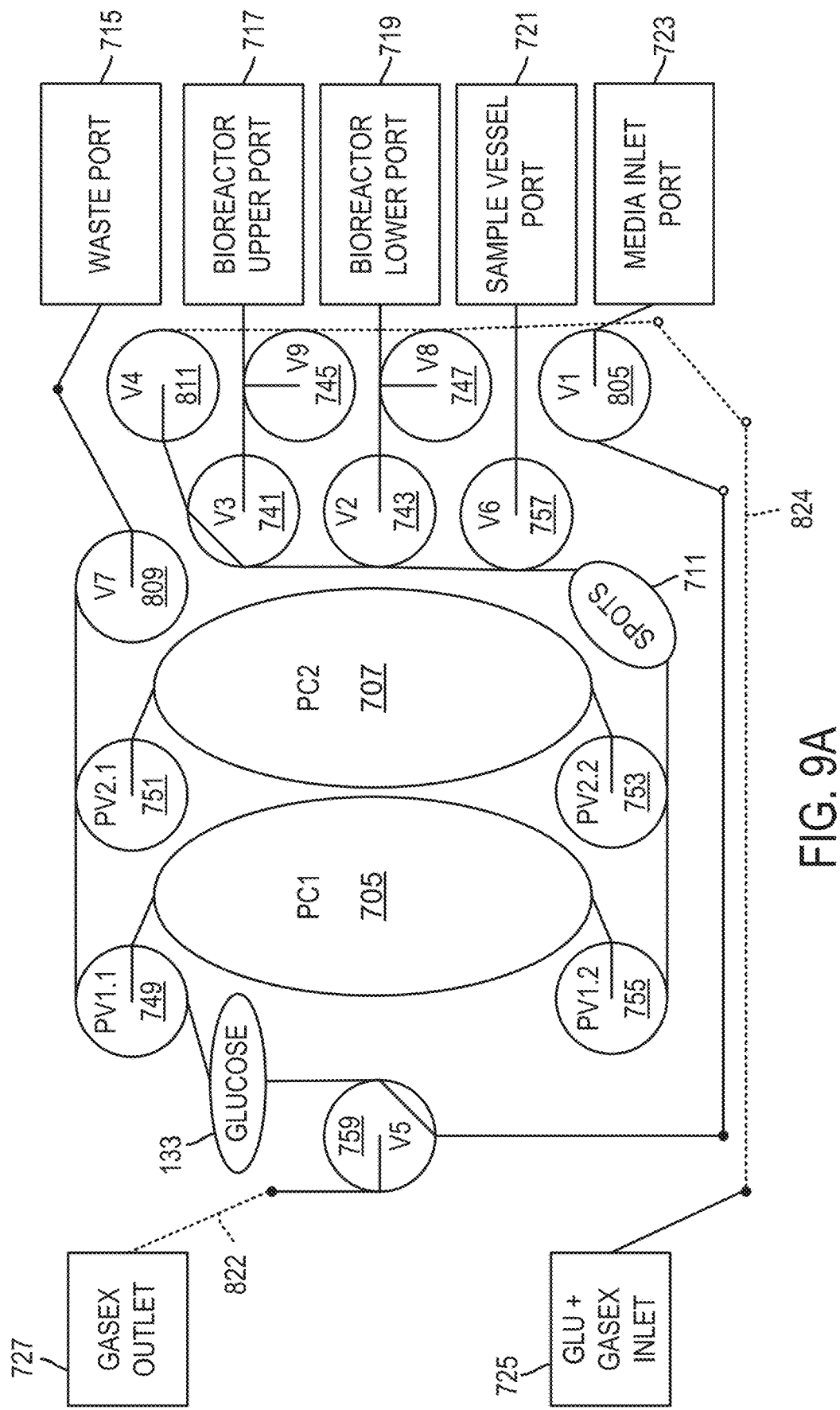
FIGS. 9A and 9B are fluid flow paths and cassette layout for the cassette in FIGS. 6C and 6D.
Figure 9B:
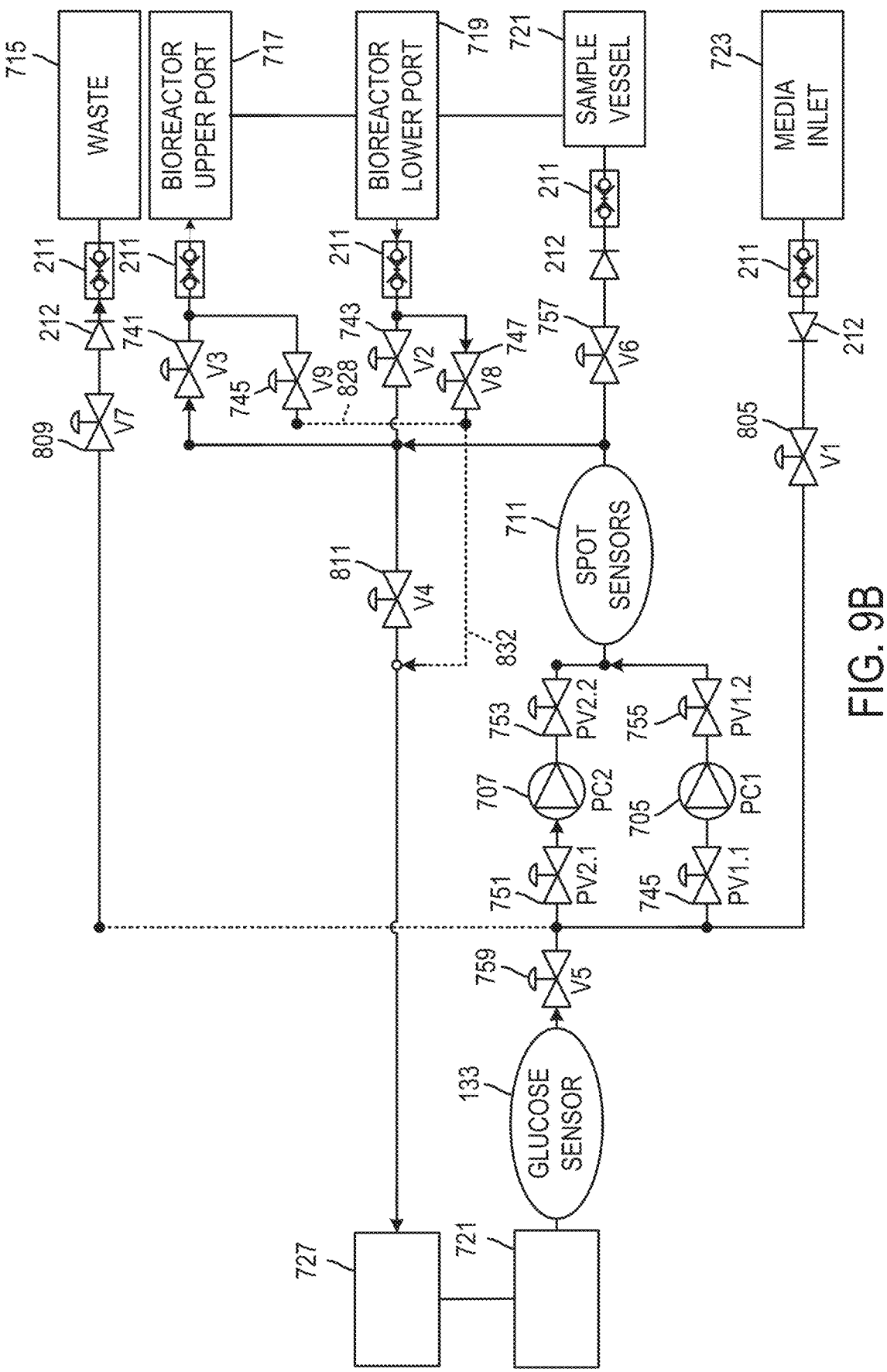

Referring now to FIGS. 7A, 7B, 7C, 8 through 9B, and 9C, cassettes can include various valve and port configurations. In some configurations, waste port 715 can be associated with valve V7 809 (also referred to in the drawings as 809N) and can be located on the same side of cassettes 699/700 as gas exchange ports 725/727. In some configurations, glucose sensor 133 can fall in the fluid path of gas exchange lower port 727 or gas exchange upper port 725. In some configurations, valve V5 759 can fall in the direct fluid path of gas exchange upper port 725 or gas exchange lower port 727. FIGS. 7A and 7B illustrate moving media in to the lowest port to promote air collection and purging to waste. FIGS. 7C, 8, and 9B illustrate positioning the waste for air purging via backpumping, preventing air being trapped in the bioreactor channels. Glucose sensor 133 can be positioned directly between media inlet port 723 and pumping chambers 705/707 to enable ease of calibration of glucose sensor 133. In some configurations, sensors 711 can be located in different positions on the cassette, and can encounter the circulating fluid at different locations in the flow path. Valve V4 811, associated with gas inlet 727, can be located in various positions on the cassette, depending on the desired flow path. Referring to FIG. 9A, the bus to gas exchange inlet 727 can be positioned to promote the purging of air in the gas exchange area during initial priming.

Figure 9C:
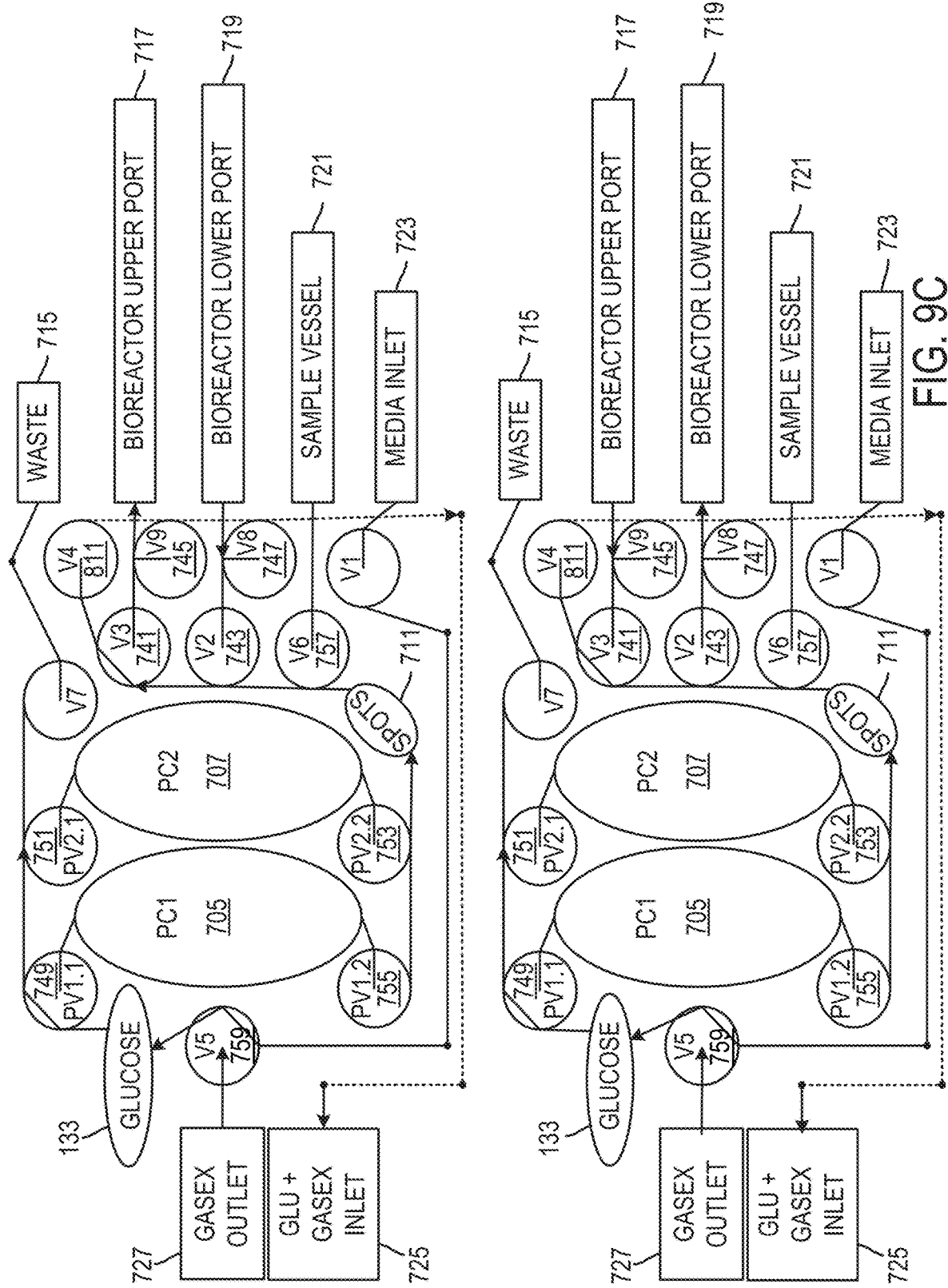
FIG. 9C illustrates fluid flow paths for clockwise and counterclockwise flow for cassettes in FIGS. 6A/6B and 6C/6D.
Figure 10A:
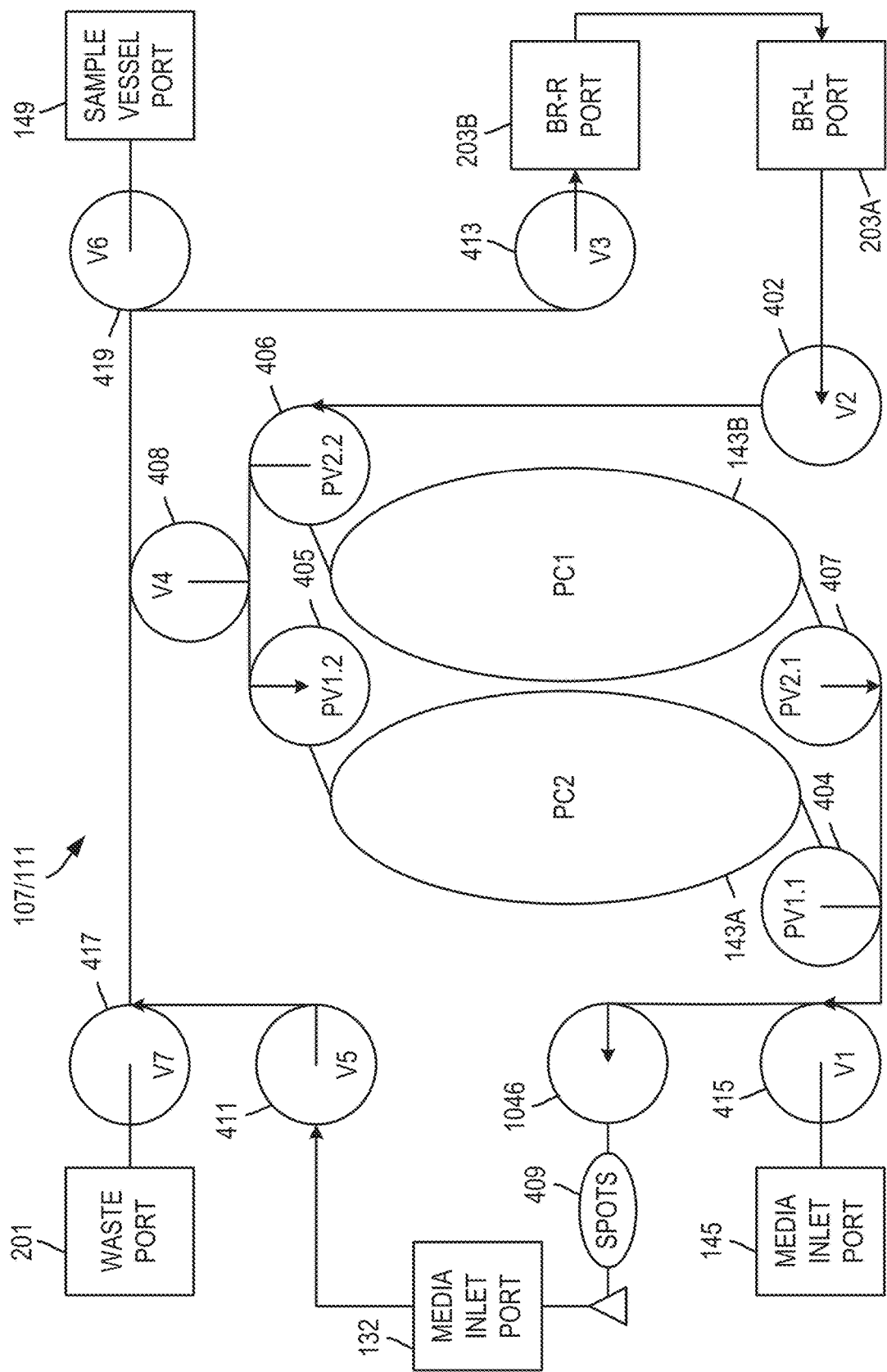
FIGS. 10A-10D are comparative fluid flow paths for clockwise and counterclockwise flow for cassettes in FIG. 4 and FIGS. 6A-6D.
Figure 10B:
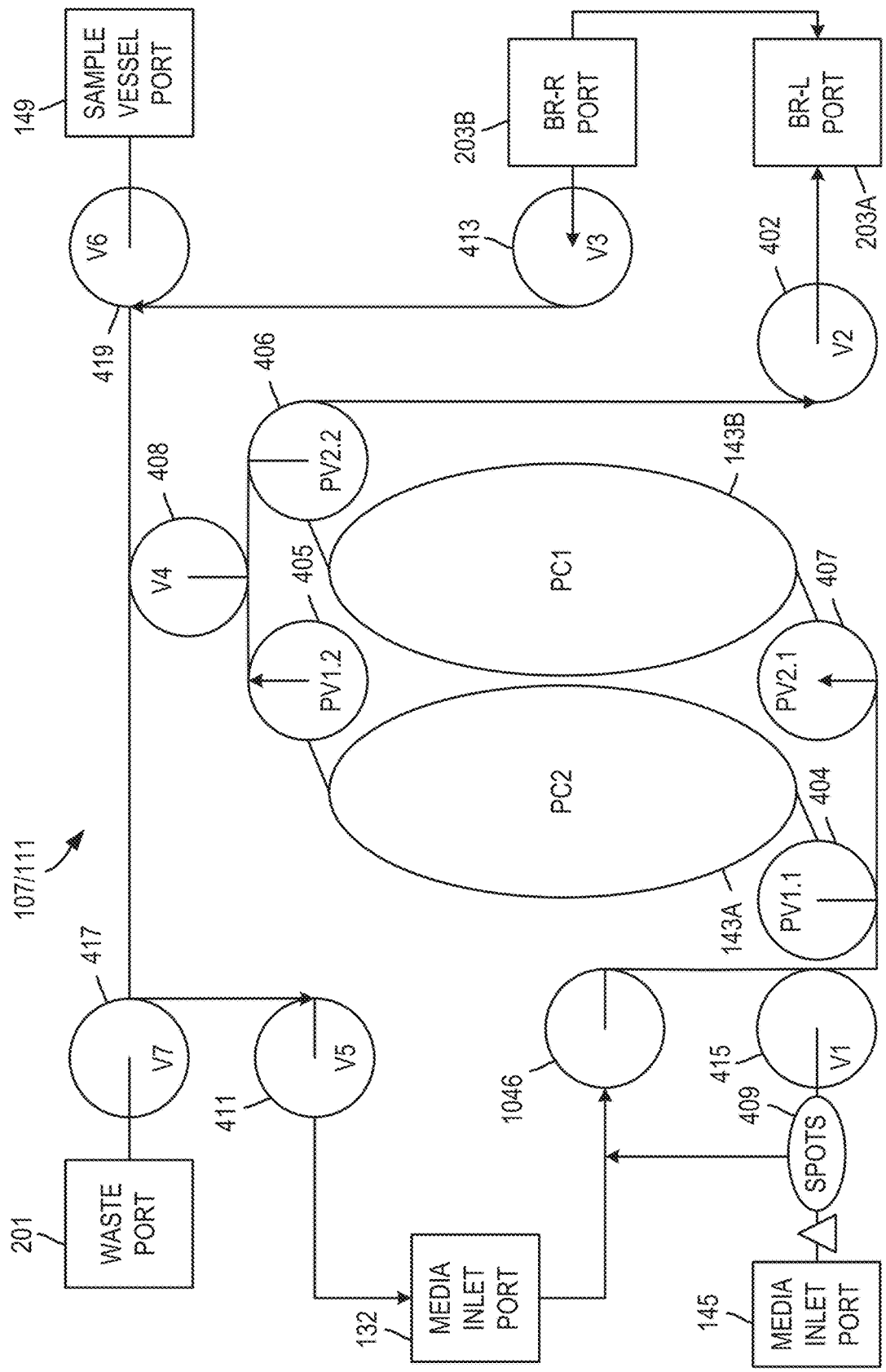
Figure 10C:
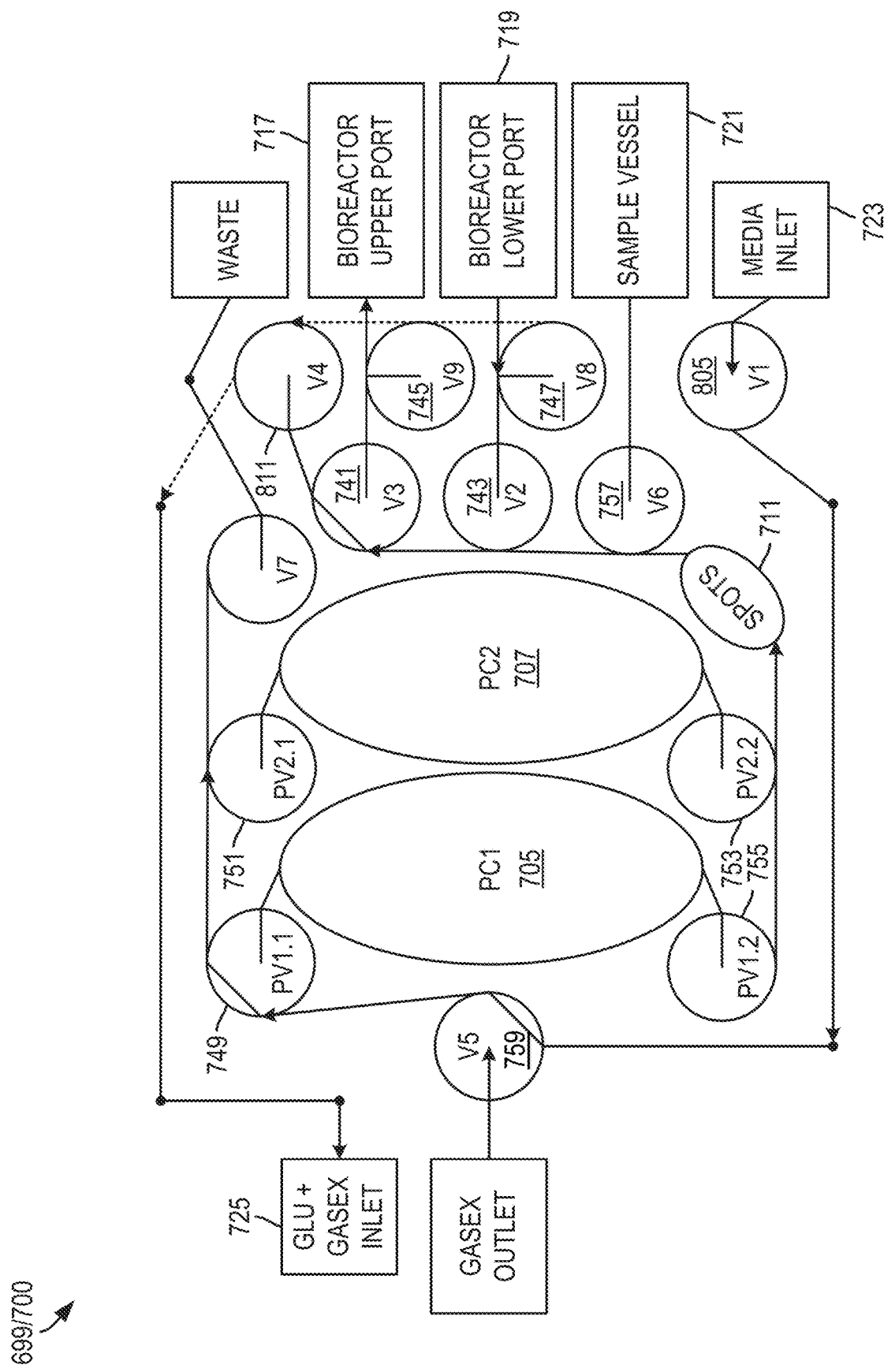
Figure 10D:
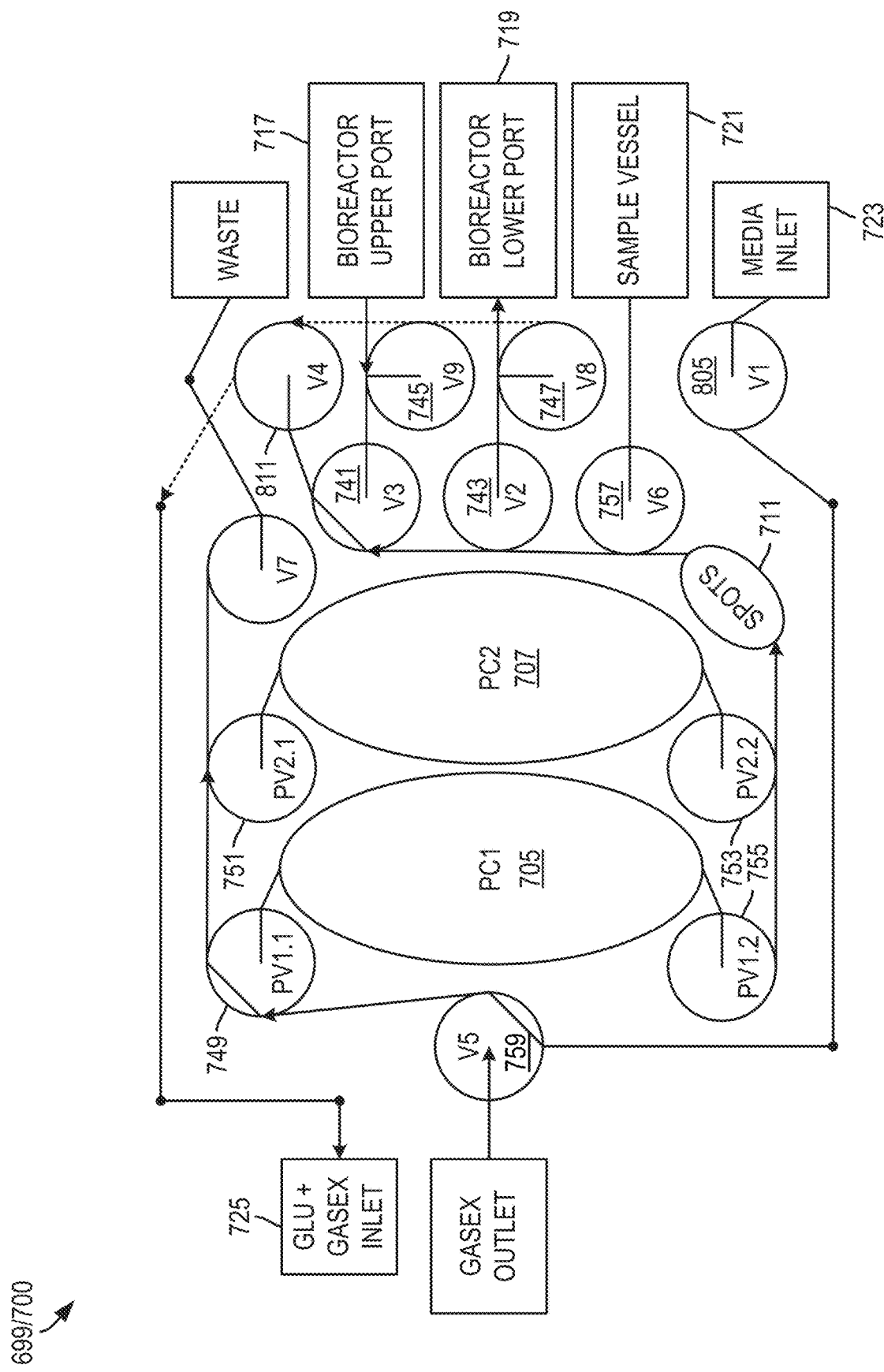

Referring to FIGS. 9B and 9C, the fluid paths are identical to FIG. 7C, but waste port 715 and media inlet port 723 are positioned on the same side in FIG. 9B. This port positioning can support a configuration in which the cassette is inserted into a housing, rather than being placed in a door, thus enabling more than one side to be accessed. Inserting the cassette can enable a footprint for building multiple stacking units, and can protect the manifold gasket from dust and debris, for example.

Referring now to FIG. 9C, clockwise flow and counterclockwise flow from/to and to/from bioreactor lower port 719/bioreactor upper port 717 for second/third configuration cassettes 699/700 (FIGS. 6A-6D) are shown. The cassette/valve layout can enable fluid that is entering the system from different directions to pass through valves, gas exchange, and past sensors in the same order. Fluid can flow alternately in one direction and then another through user-supplied device 113 (FIG. 1B). This alternating flow can enable, for example, but not limited to, purging of air, and can enable fluid pressure to be applied to all sides of the HCT/P. Second/third configuration cassettes 699/700 (FIGS. 6A-6D) can change the direction of fluid flow past the HCT/P without changing the direction of fluid flow through pumping chambers 705/707 or past inline sensors 711. To accomplish this, second/third configuration cassettes 699/700 (FIGS. 6A-6D) can include a valve organization in which clockwise and counterclockwise flow pathways are identical with the exception of port selection valves V3 741/V8 747/V2 743/V9 745, which can minimize the difference in fluid resistance when pumping in each direction. To change the direction of fluid flow past the HCT/P without changing the direction of fluid flow through pumping chamber 705/707 or past inline sensors 711, pneumatic pressure can be applied to the pumping chamber cassette membrane with the corresponding pumping valve PV1.2 755 or PV2.2 753 (also referred to as 753V) open. PV1.1 and PV2.1 will not be open at the same time during recirculation. PV 1.1 and PV2.2 should be open, then once the fill/delivery is finished, PV 1.2 and PV 2.1 should be open. The fluid can be pushed past sensors 711 and towards bioreactor lower port 719 if valve V2 743 is open, bioreactor upper port 717 if valve V3 741 is open, gas exchange area inlet 727 if valve V4 811 is open, or sample vessel port 721 if valve V6 757 is open. When pumping to the bioreactor, the fluid can return using the opposite port to the one described herein. Valve 4 811 corresponding to this path can be open and valves 3/9 741/745 and 2/8 743/747 can be closed to prevent flow from entering pumping chambers 705/707. The fluid can be routed to a pumping chamber inlet via an upper bus using valve V9 745, if valve V2 743 is open, or valve V8 747, if valve V3 741 is open. Because fluid valves V2 743 and V9 745 are always opened or closed at the same time, the pneumatic valves controlling the position of these valves can be tied together, decreasing costs and complexity while improving reliability. The same is true of valves V3 741 and V8 747. This configuration can enable simplification of the number of ports and tubing pathways outside second/third configuration cassettes 699/700 (FIGS. 6A-6D). To enable this type of fluid flow, valves V2 743, V3 741, V8 747, and V9 745 can be topographically organized on second/third configuration cassettes 699/700 (FIGS. 6A-6D) such that, when valves V2 743 and V9 745 are closed, fluid can enter second/third configuration cassettes 699/700 (FIGS. 6A-6D) through bioreactor lower port 719 and travel through open valves V3 741 and V8 747.

Continuing to refer to FIG. 9C, clockwise and counterclockwise circulations are shown, including on-board glucose sensor 133. Recirculation to bioreactor lower port 719, or counter-clockwise circulation, can include fluid valves V2 743, V9 745, and V5 759, and pumping valves PV 1.1, PV 2.1 open, and the rest closed. When valves V3 741 and V8 747 are closed, pumping chamber 707 can push the media through pumping valve PV 1.2 755, past sensors 711 and through valve V2 743 to bioreactor lower port 719. The media can pass to user-supplied device 113 (FIG. 1B) through bioreactor lower port 719, can return to the pumping system from bioreactor upper port 717 through valve V9 745, and can pass through an upper bus to gas exchange area 701A/701 (FIGS. 6A-6D) through gas exchange area inlet 727. At the same time, pumping chamber 705 can pull fluid from gas exchange area 701A/701 (FIGS. 6A-6D) through gas exchange outlet 727 past glucose sensor 133 through valves V5 759 and V2.1 751 (also referred to as 751V), in order to be prepared to start pumping once pumping chamber 707 is depleted. Recirculation to bioreactor upper port 717, or clockwise circulation, can include fluid valves V3 741, V8 747, and V5 759, and pumping valves PV 1.1, PV 2.1 open, and the rest closed. In this configuration, pumping chamber 707 can push the media through pumping valve PV1.2 755, past sensor 711, through valve V3 741 to bioreactor upper port 717. The media can pass to user-supplied device 113 (FIG. 1B) through bioreactor upper port 717, can return to the pumping system from lower bioreactor port 719 through valve V8 747 and can pass through an upper bus to gas exchange area 701A/701 (FIGS. 6A-6D) through gas exchange area inlet 727. At the same time, pumping chamber 705 can pull fluid from gas exchange area 701A/701 (FIGS. 6A-6D) through gas exchange area outlet 727 through valve V5 759, possibly past glucose sensor 133, and through pumping valve V2.1 751, in order to be prepared to start pumping once pumping chamber 707 is depleted. In gas exchange area 701A/701 (FIGS. 6A-6D), gas can be exchanged with the media as described herein.

Referring now to FIGS. 10A, 10B, 10C, and 10D, a comparison between the flow paths in clockwise and counterclockwise flows for first configuration cassettes 107/111 and second/third configuration cassettes 699/700 is shown. In first configuration cassettes 107/111, spot sensors 146 (FIGS. 10A/10B) are encountered in the fluid path before gas exchange during clockwise flow, and after gas exchange during counterclockwise flow. In second configuration cassettes 699/700, sensors 711 (FIGS. 10C/10D) are encountered in the fluid path after gas exchange in both clockwise and counterclockwise flow paths, i.e. whether heading into bioreactor upper port 717 or bioreactor lower port 719.

Figures 1, 11A:
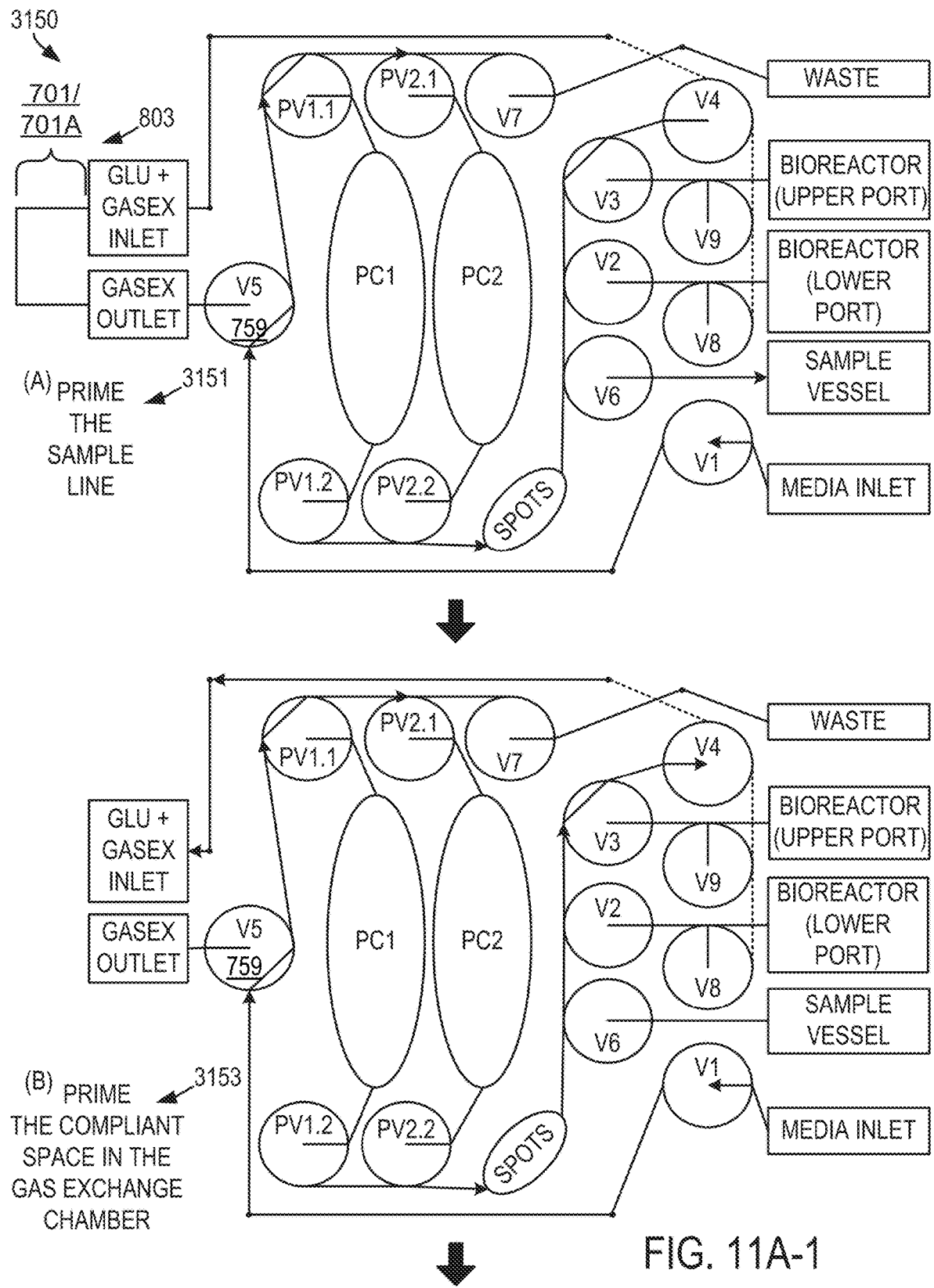
Figures 2, 11A:
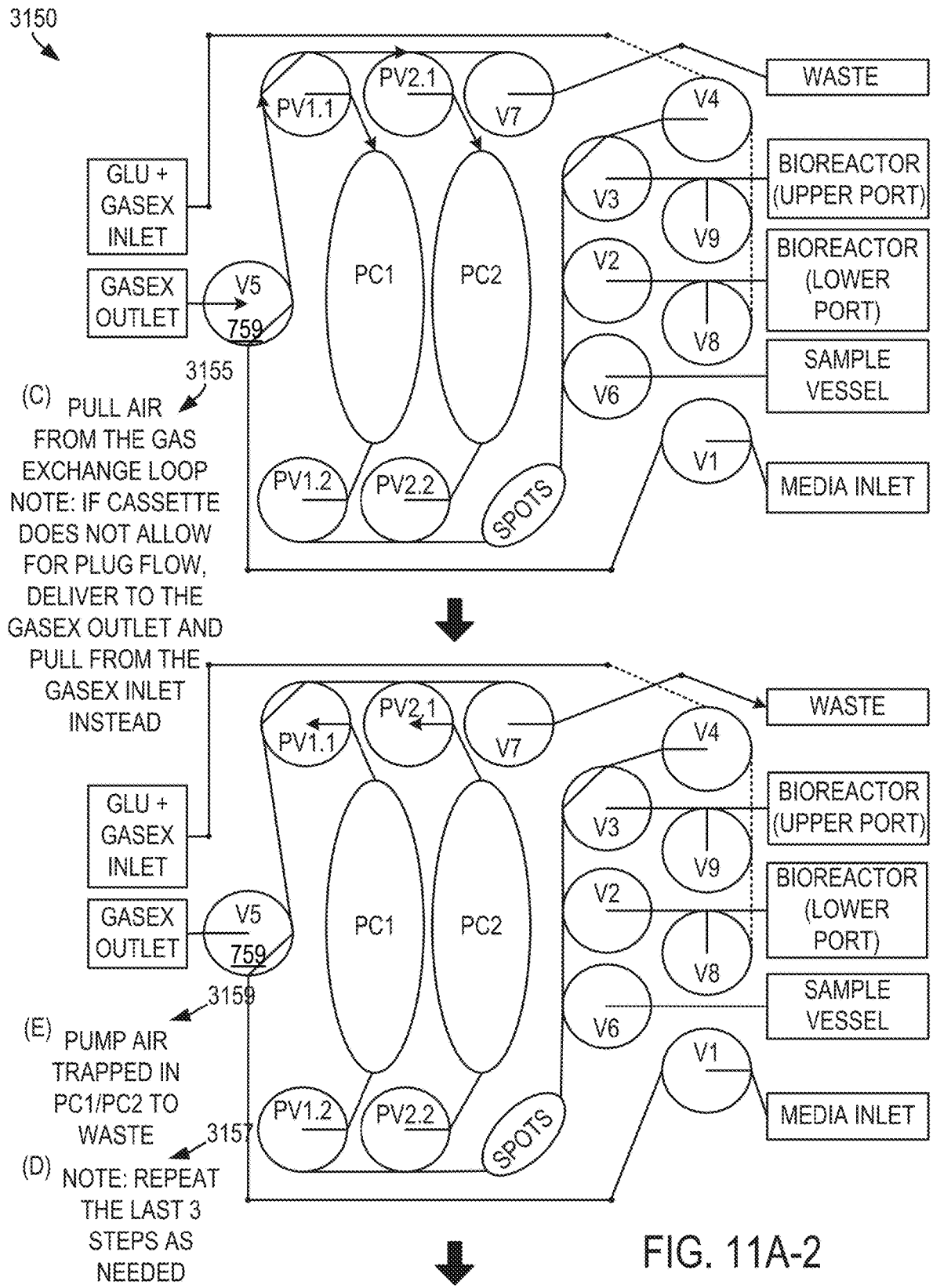
Figures 3, 11A:
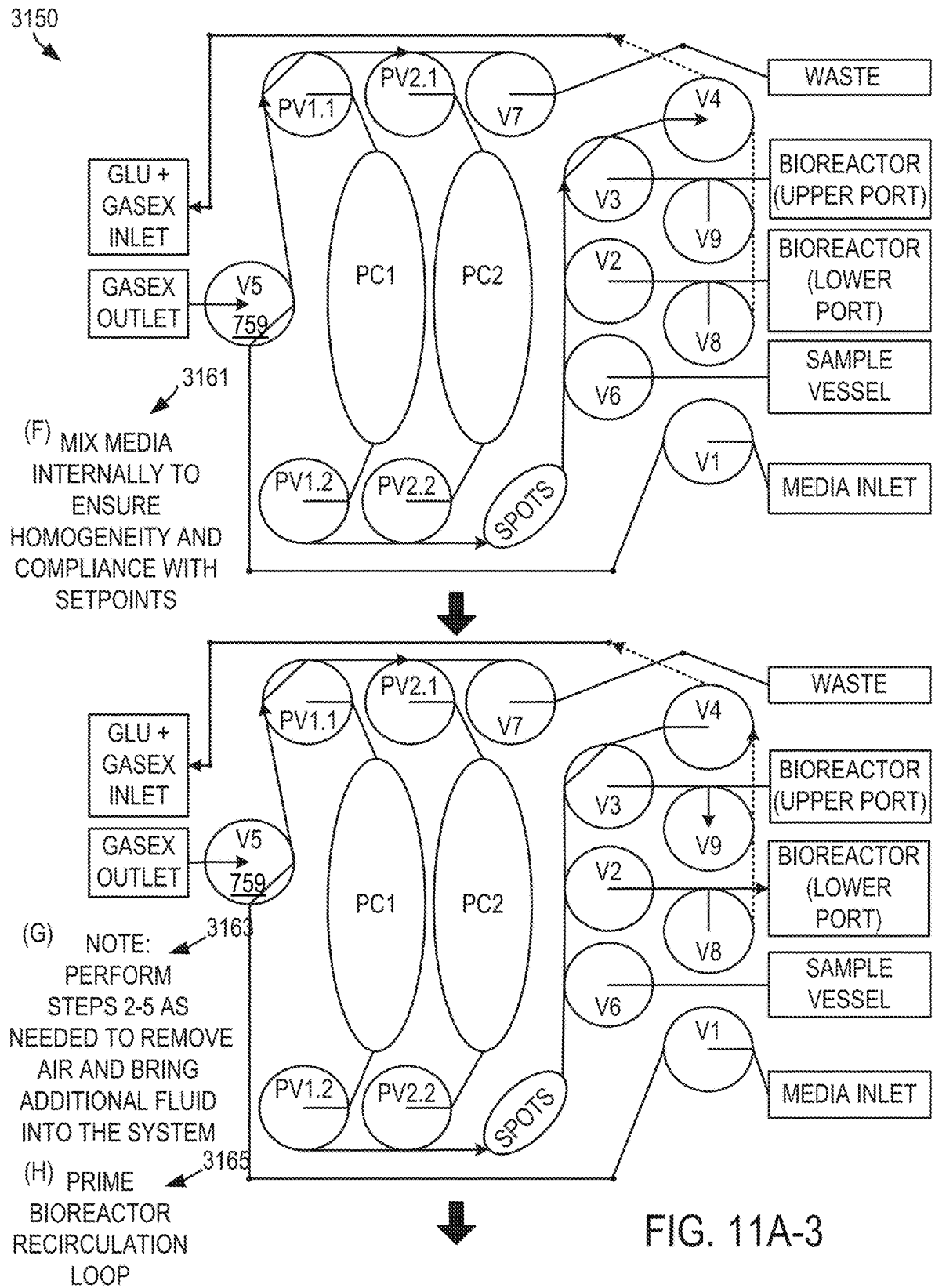
Figures 1, 11B:
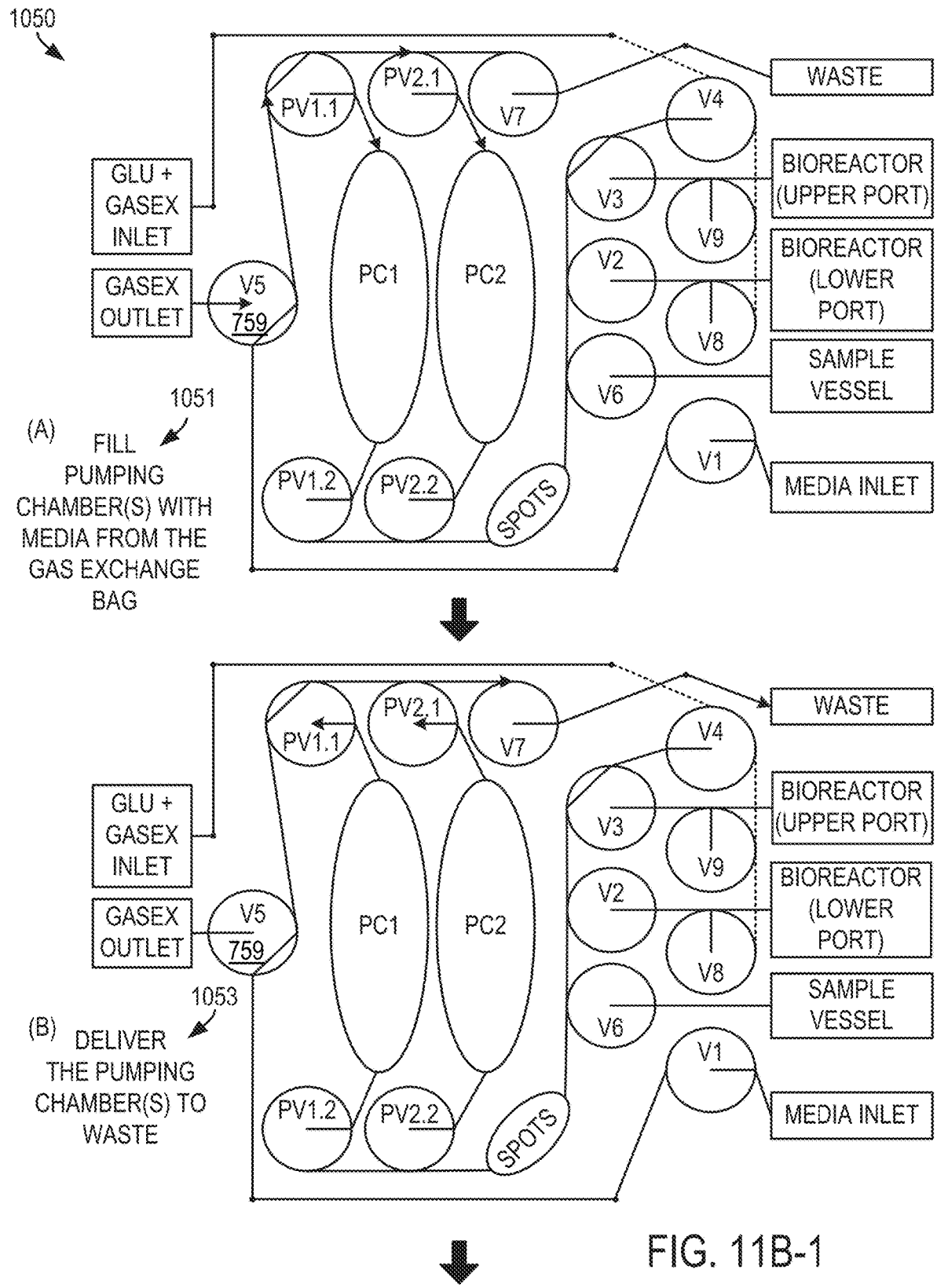
Figures 2, 11B:
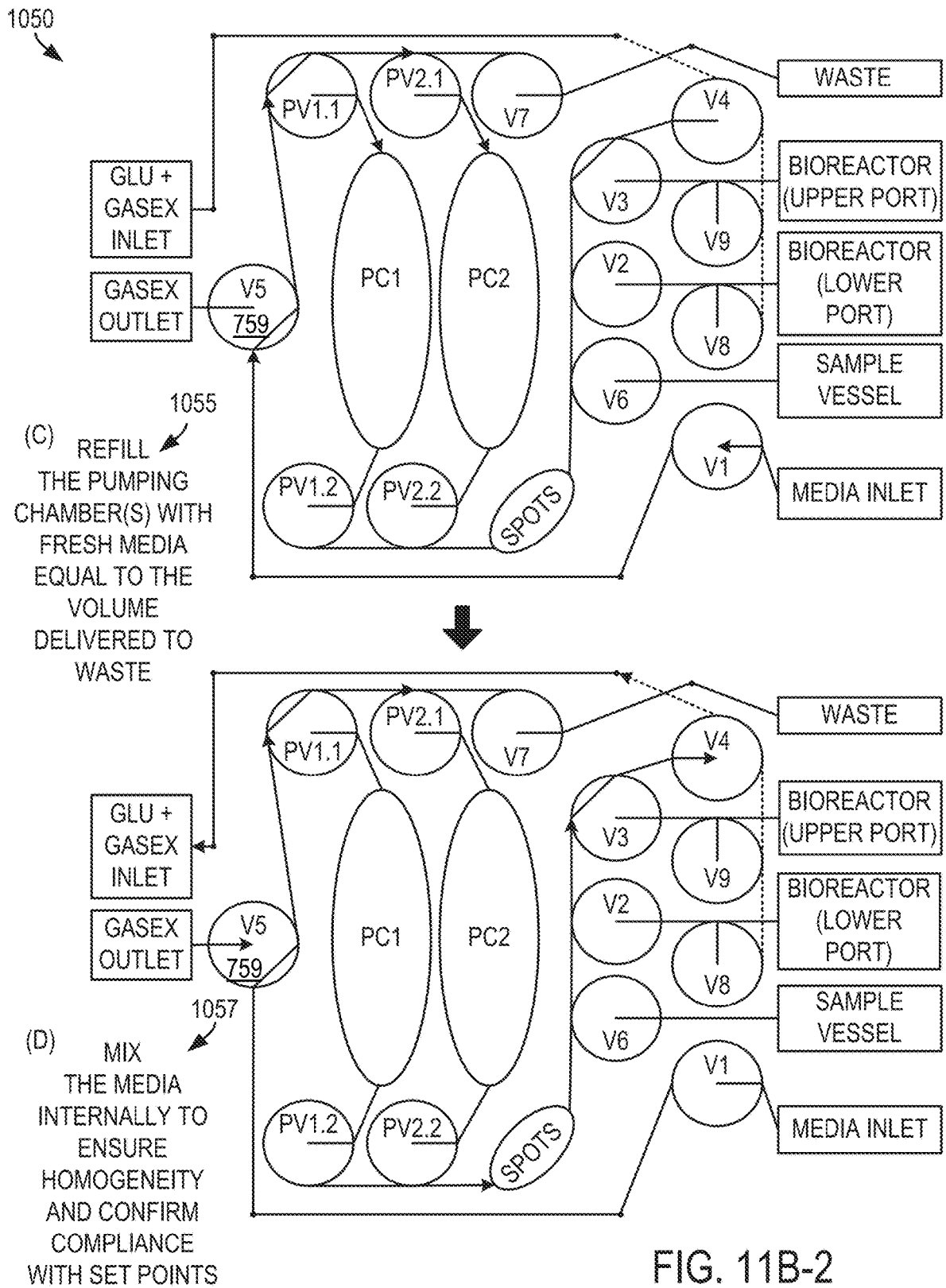
Figure 11C:
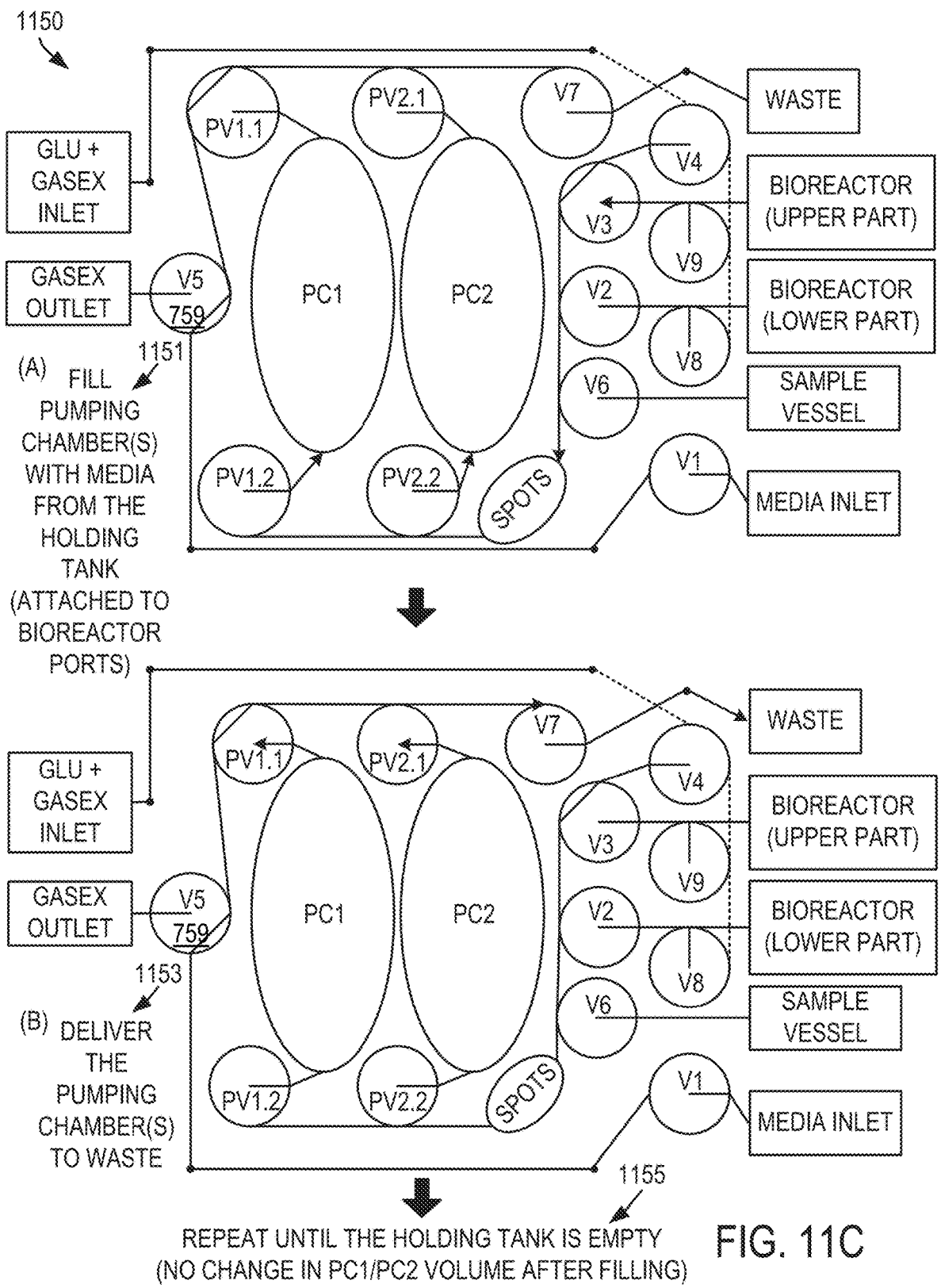
FIG. 11C is a fluid flow diagram of isolating the bioreactor from the cassette of FIGS. 6A-6D.
Figures 1, 11D:
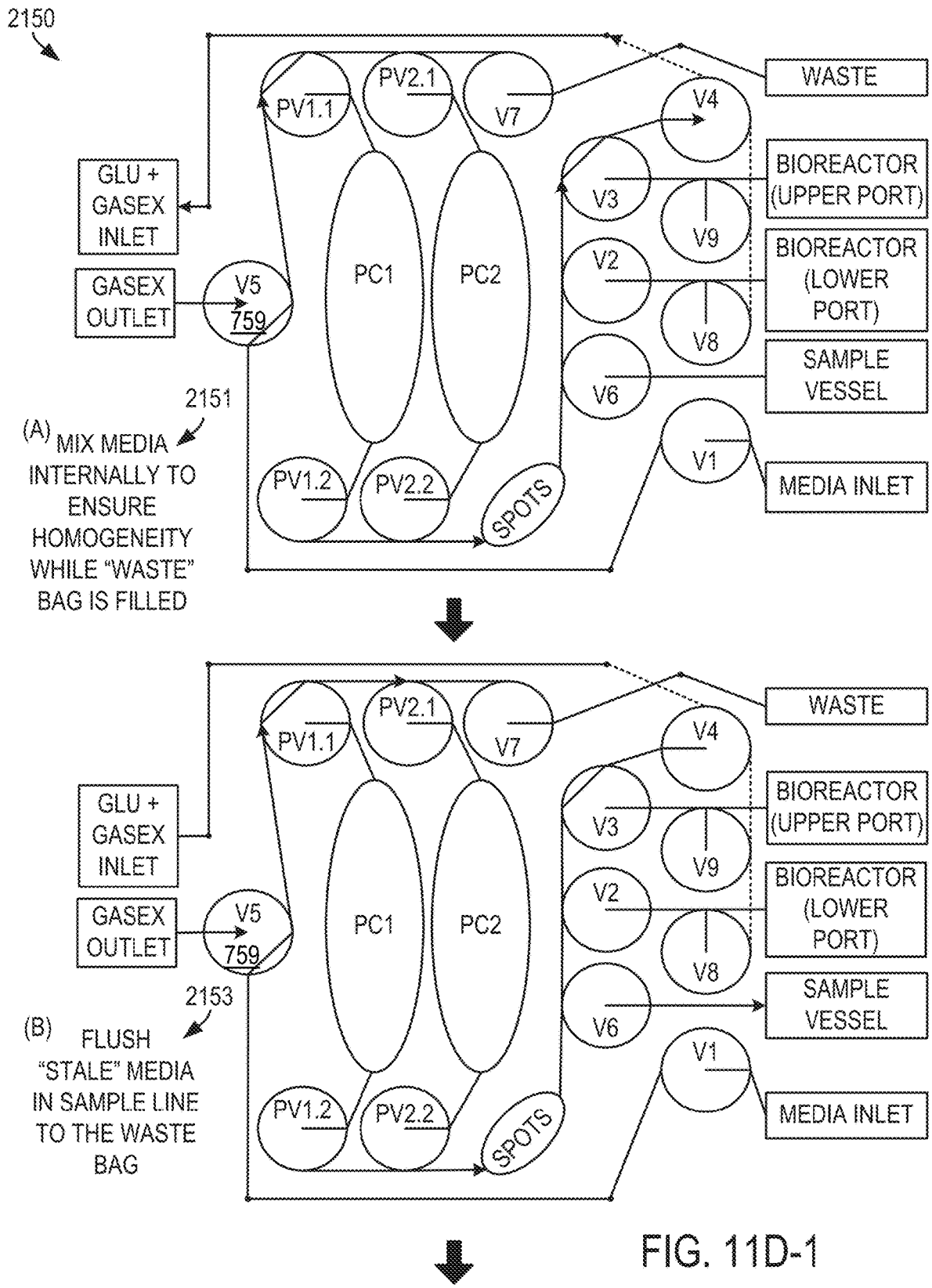
Figures 2, 11D:
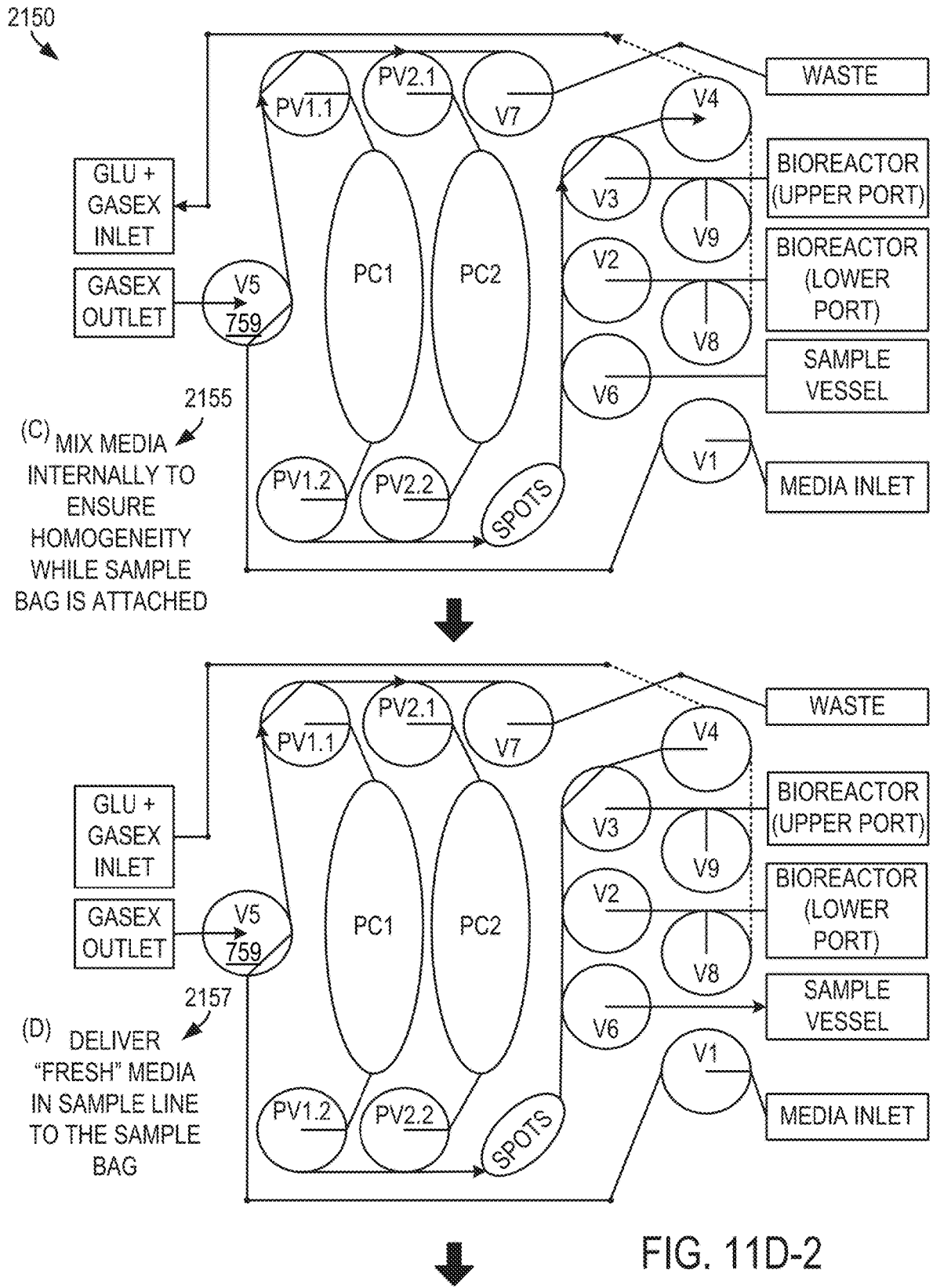
Figures 3, 11D:
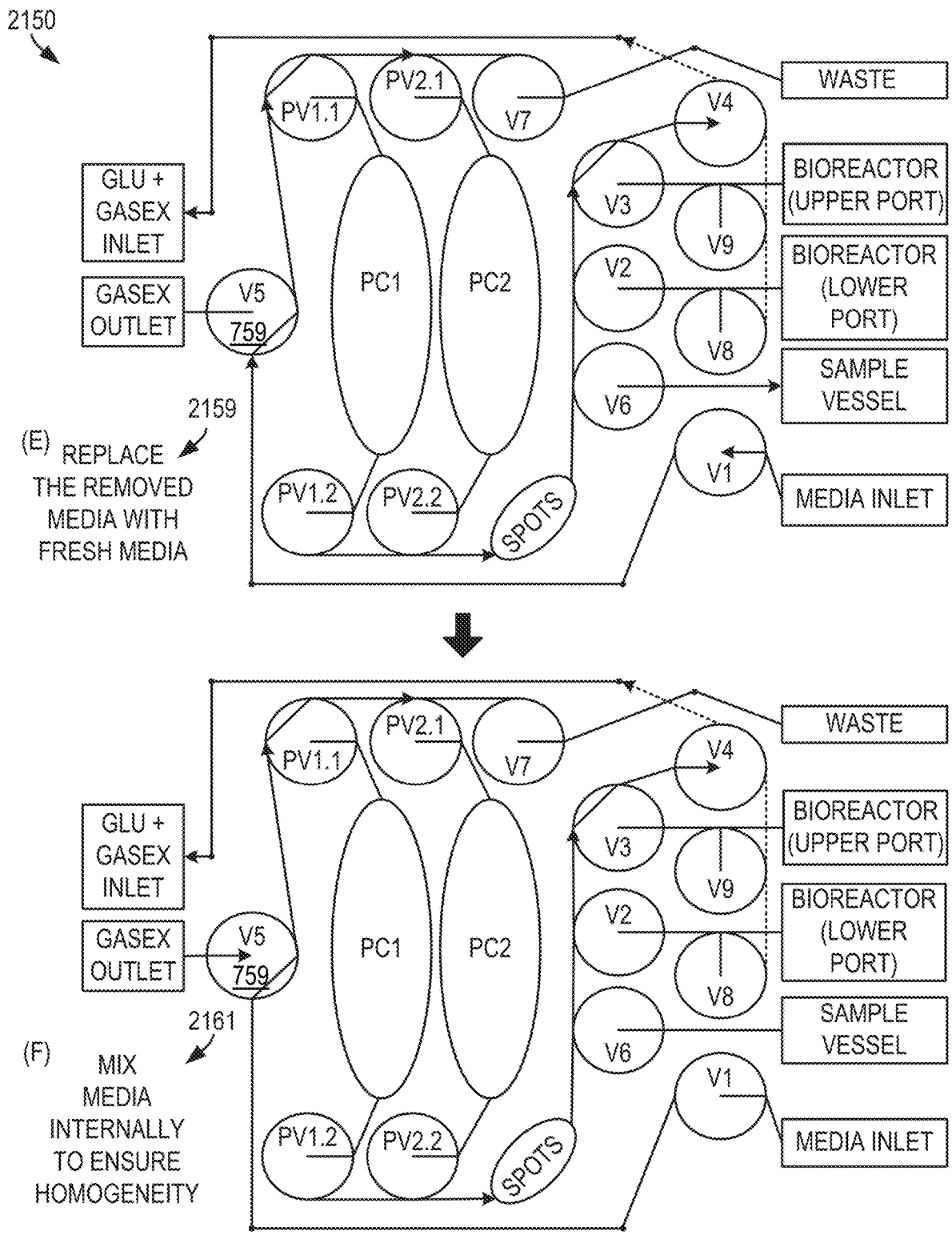
Figure 11E:
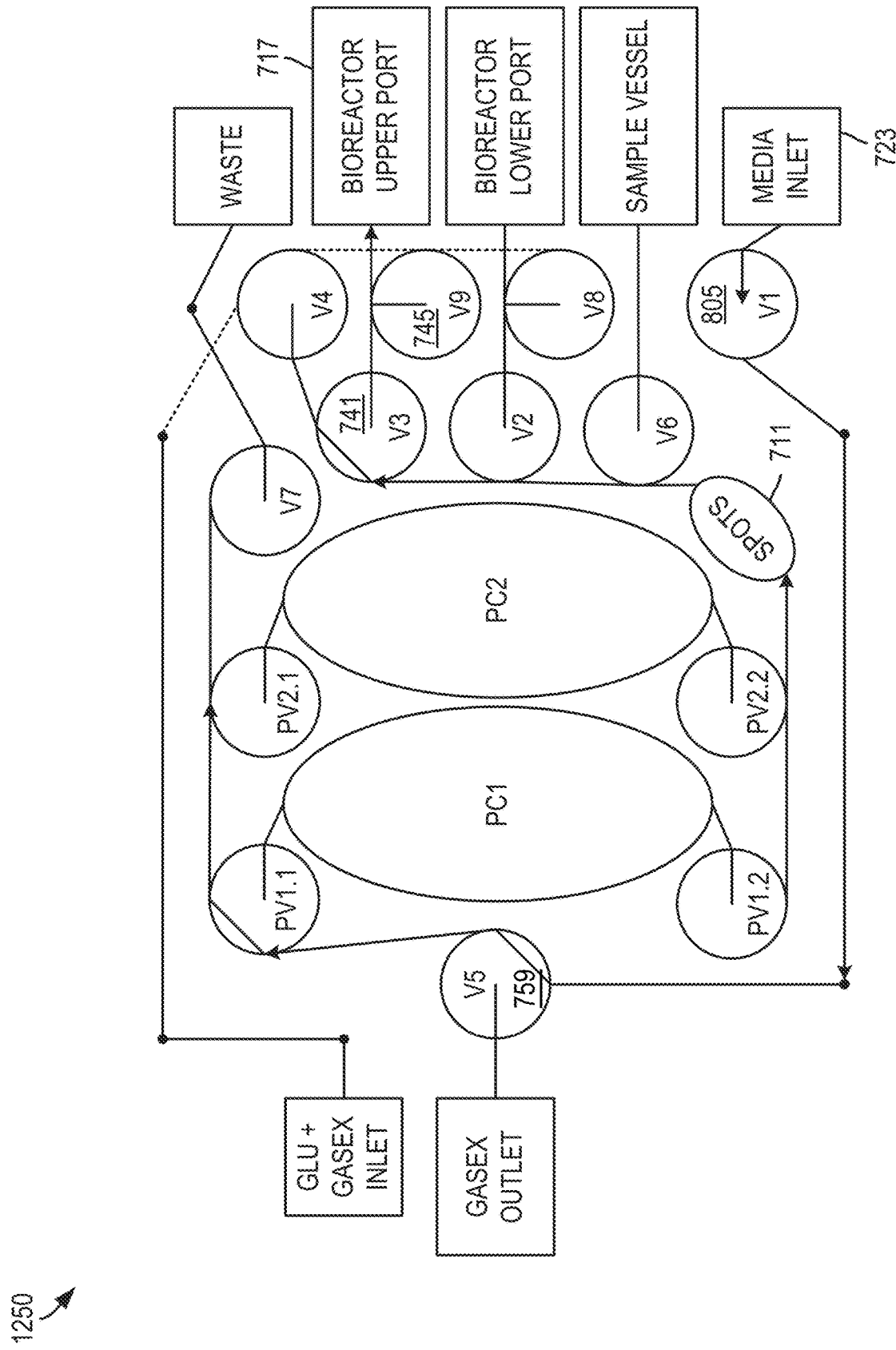
FIG. 11E is a fluid flow diagram of the intermediate steps through which the fluid passes between temperature management and the bioreactor.
Figure 11F:
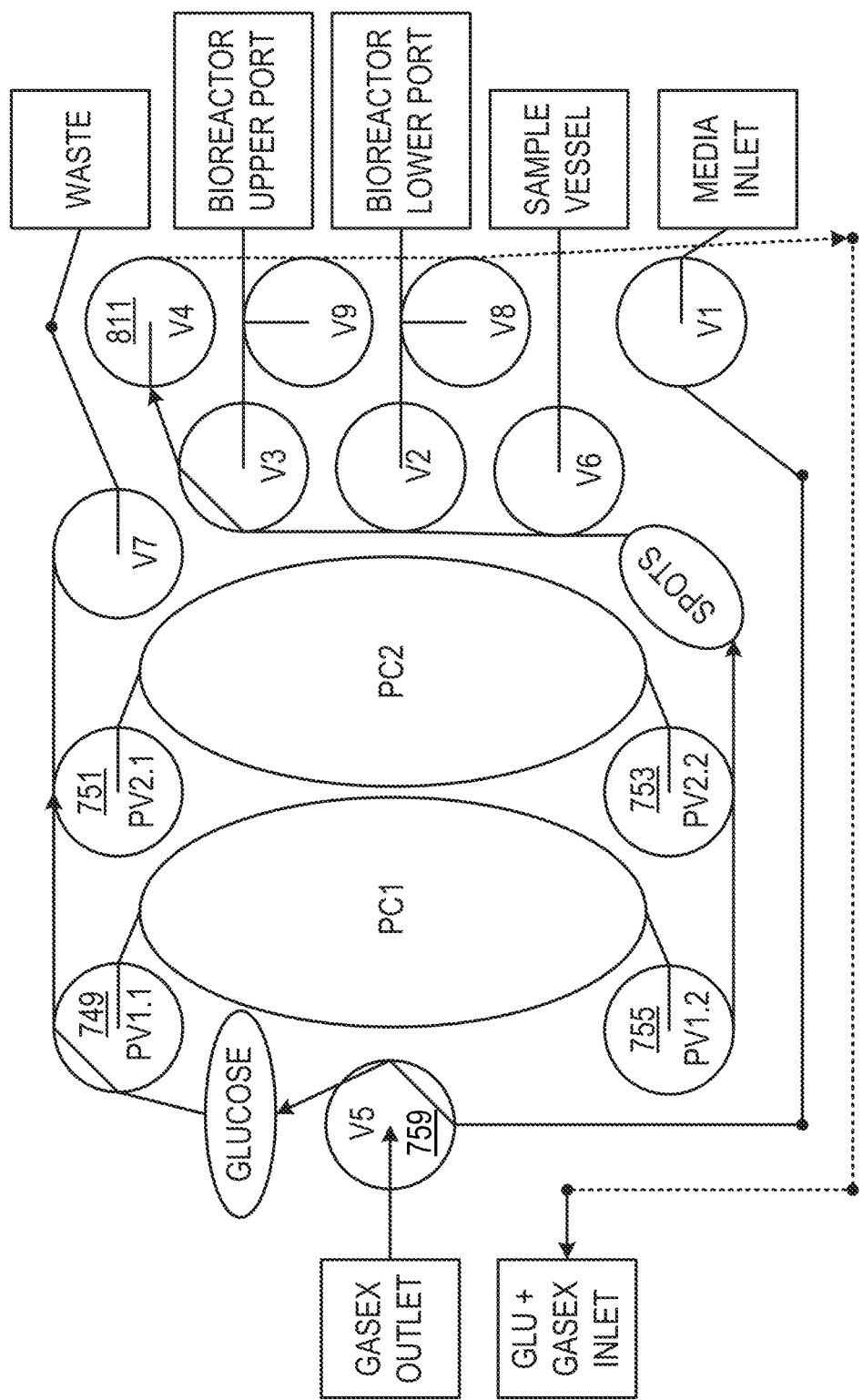
FIG. 11F is a fluid flow diagram of bioreactor isolation.

Referring now to FIGS. 11A-1 through 11F, in some configurations, flow paths for specific situations can be established. For example, flow path scenarios for priming the system, partial media replenishment, purging media to waste, and delivery of media to a sample vessel can be pre-configured. Flow paths to fill a holding tank and isolate the bioreactor can be frequently used and also pre-configured.

Referring now to FIGS. 11A-1 and 11A-2, initial setup can include configuring media reservoir, reservoir line, reservoir module cassette, module line, and waste line. Bioreactor setup can include loading the bioreactor module cassette and the user supplied device. The media can be sampled during the production process by removing a fraction of the media from the production run for offline analysis. The current recipe can be modified, for example, through a user interface. If the media reservoir is not sized appropriately, or if the media supplements have a short half-life, or if excessive sampling is performed, a scheduled or unscheduled swap of the current media reservoir for a new reservoir of fresh media can be performed. The user-supplied device can be removed after the production is finished. Bioreactor module cassette can be removed or sealed and left in place while the user-supplied device is removed. After all the HCT/P production runs for a given row have completed, the row can be reset to prepare for the next initial setup. Rack sensors, temperature regulation sensors, module sensor blocks, and user-supplied sensors can be calibrated as needed to maintain their accuracy. System 3000 (FIG. 1A) can include automatic identification and data capture (AIDC) technology that can enable quick scan of disposable components, media, user identification such as, for example, but not limited to, electronic signatures, and hardware information relevant to the current production run. System 3000 (FIG. 1A) can access hardware information such as, for example, but not limited to, board revisions and other information related to the specific configurations. This information can be recorded by system 3000 (FIG. 1A), and can provide traceability for reporting the results of production runs and diagnosing failures.

Referring now to FIGS. 11A-1 through 11B-2, the module fluid handling system can support, but is not limited to supporting, the following pumping actions: (a) priming second/third configuration cassettes 699/700 (FIGS. 6A/6B), (b) recirculating, both clockwise and counterclockwise, the media within user-supplied device 113 (FIG. 1B), (c) partially replenishing the media in the system, (d) purging the media except the media in user-supplied device 113 (FIG. 1B), to waste container 117 (FIG. 1C), (e) priming/flushing sample line 116B (FIGS. 2A/2B), filling sample vessel 115 (FIGS. 2A/2B), (f) resupplying the media to second/third configuration cassettes 699/700 (FIGS. 6A/6B) after priming/flushing sample line 116B (FIGS. 2A/2B), and (g) recirculating the media internally within second/third configuration cassettes 699/700 (FIGS. 6A/6B).

Referring again to FIGS. 11A-1 through 11A-3, to prime second/third configuration cassettes 699/700 (FIGS. 6A/6B) and user-supplied device 113 (FIG. 1B), the module fluid handling system can confirm that the media in holding container 109 (FIGS. 2A/2B) is within a pre-selected range of temperature, dissolved oxygen, and pH. In some configurations, the temperature setpoint can include the range of about 37° C.±0.5° C. In some configurations, the dissolved oxygen setpoint can include the range of about 0.65 to 6.75 mg/L. In some configurations, the pH setpoint can include the range of about 6.8 to 7.8 pH. The module fluid handling system can withdraw media from holding container 109 (FIGS. 2A/2B), pump the media through user-supplied device(s) 113 (FIG. 1B), and pump the media out waste line 121 (FIGS. 2A/2B). The flow rate of the priming action can be established to prevent damage to fragile HCT/Ps if necessary. The flow rate can include a default value, a user-supplied value, or a dynamically determined value. In some configurations, the flow rate can include the range of 1-100 mL/hr. The direction of flow during priming can be fixed, and the inlet/outlet to/from bioreactor module cassette 700 can be oriented to prevent air from becoming trapped in user-supplied device 113 (FIG. 1B) during priming. Method 3150 for priming the fluid flow of cassette 700 can include, but is not limited to including, (a) priming 3151 sample line 116B, (b) priming 3153 a compliant space in gas exchange area 701A/701 (FIGS. 6A-6D), (c) pulling 3155 air from gas exchange loop 803, (d) repeating 3157 steps (a)-(c) until the steps are completed according to pre-selected thresholds, (e) pumping 3159 air trapped in pumping chamber 1 705 and pumping chamber 2 707 to waste port 715, (f) mixing 3161 media internally to ensure homogeneity and compliance with setpoints of various characteristics, (g) repeating 3163 steps (b)-(f) until air is removed according to a pre-selected amount such as, for example, when <1 mL is detected in the pumping chamber, thus bringing additional fluid into second/third configuration cassettes 699/700 (FIGS. 6A-6D), and (h) priming 3165 bioreactor recirculation loop 803. In some configurations, the compliant space can be part of the gas exchange area. In some configurations, the gas exchange membrane can be welded on the sides the center section of the membrane, and the membrane can bow in or out providing >1 pumping chamber worth of available fluid, depending upon the priming process. The pre-selected thresholds can include, for example, pumping until <1 mL of air is detecting in the pumping change after a fill stroke. Flow in second/third configuration cassette 699/700 (FIGS. 6A-6D) that can accomplish priming can include, but is not limited to including, with respect to step (a), priming 3151 sample line 116B can include pumping fluid from media inlet port 723 through valve V1 805, past sensors 711, through valve V6 757 and sample port 721, and into sample container 116. With respect to step (b), priming 3153 a compliant space in gas exchange chamber 701/701A can include pumping fluid through media inlet port 723 through valve V1 805, past sensors 711, through valve V4 811, through gas exchange inlet 727, and into gas exchange area 701/701A. With respect to step (c), pulling 3155 air from gas exchange loop 803 can include pumping whatever is in gas exchange area 701/701A from gas exchange outlet 727 through valve V5 759 and into pumping chambers 1/2 705/707. In some configurations, pumping from gas inlet 727 can accomplish step (c). With respect to step (e), pumping 3159 air trapped in pumping chambers 1/2 705/707 to waste port 715 can include coordinated pumping whatever is located in pumping chambers 1/2 705/707 through valve V7 809 into waste port 715. With respect to step (f), mixing 3161 media internally can include pumping whatever is in pumping chambers 1/2 705/707 past sensors 711 through valve V4 811, through gas exchange inlet 727 into gas exchange area 701A/701 (FIGS. 6A-6D), then back through gas exchange outlet 727, through valve V5 759, and past sensors 711 again. With respect to step (h), priming 3165 bioreactor recirculation loop 803 can include pumping media from bioreactor upper port 717 through valve V9 745 into gas exchange inlet 727, through gas exchange area 701A/701 (FIGS. 6A-6D), through gas exchange outlet 727 through valve V5 759, past sensors 711, through valve V2 743, and through bioreactor lower port 719. It is determined that air and not fluid is being pumped by evaluating the difference in volume between the pumping chamber and the reference chamber. If there is air in the chamber, it will expand when negative pressure is applied and shrink when positive pressure is applied. If there is no air that is being pumped, there should be no difference in the volumes.

Referring now to FIGS. 11B-1 and 11B-2, to perform a partial replenishment of media, the module fluid handling system can confirm that the media in holding container 109 (FIG. 1B) is within temperature, dissolved oxygen, and pH ranges. Ranges can include 37±0.5° C., 0.65 to 6.75 mg/L of dissolved oxygen, and 6.8 to 7.8 pH. The ranges can be default values, user-defined, and dynamically determined. A predetermined volume such as, for example, but not limited to, about 10 mL, of media can be withdrawn from holding container 109 (FIG. 1B), pump the media through user-supplied device 113 (FIG. 1B), and pump the output from user-supplied device 113 (FIG. 1B) out waste line 121 (FIGS. 2A/2B). The volume of media replaced can be user adjustable, a default value, or dynamically determined. To avoid, for example, but not limited to, any of large swings in media quality, such as, for example, when all the media is replaced, removal of beneficial signaling molecules, or media waste that exceeds a pre-selected threshold, partial media replenishment can enable a fraction of the total volume to be added during initial priming process 150 (FIG. 11A), according to a pre-selected recipe, for example. Avoiding large swings is possible by performing partial media exchanges, removing a pre-selected amount, for example, but not limited to, removing 10 mL from a total recirculating volume of 30-140 mL, of the media at a time, but not the entire amount. The pre-selected amount can include a default amount, a user-settable amount, and/or a dynamically-determined amount. The media can be adjusted for glucose without replacing the entire amount of media. Replacing the entire amount of media, a typical part of a manual media management process, can rid the media of beneficial molecules as well as waste. If flow continuity is a priority, the direction of flow during partial replacement can be fixed, using, for example, the same valve states used in priming process 150 (FIG. 11A). If the direction of flow is a priority, temporary isolation of user-supplied device 113 (FIG. 1B) during the replenishment exchange can be enabled, and user-supplied device 113 (FIG. 1B) can rejoin the fluid circulation when the fluid is flowing in the desired direction. Method 1050 for partial replenishment with fresh media can include, but is not limited to including, (a) filling 1051 pumping chambers 705/707 with media from gas exchange area 701A/701 (FIGS. 6A-6D), (b) delivering 1053 contents from pumping chamber 705/707 to waste port 715, (c) refilling 1055 pumping chambers 705/707 with media, and (d) mixing 1057 the media internally as discussed herein. With respect to step (a), filling 1051 pumping chambers 705/707 with media from gas exchange area 701A/701 (FIGS. 6A-6D) can include pumping media from gas exchange area 701A/701 (FIGS. 6A-6D) through gas exchange outlet 725 and valve V5 759. With respect to step (b), delivering 1053 contents from pumping chamber 705/707 to waste port 715, can include pumping of the media from pumping chambers 705/707 through valve V7 809 into waste port 715. With respect to step (c), refilling 1055 pumping chambers 705/707 with media, possibly equal to the volume delivered to waste port 715, can include pumping media through media inlet 723 into pumping chambers 1/2 705/707. With respect to step (d), media can be mixed internally pumping of the media through valve V4 811, through gas exchange inlet 727 to gas exchange area 701A/701 (FIGS. 6A-6D). The media can re-enter the cassette circulation system through gas exchange outlet 725, valve V5 759, past sensors 711 and back through valve V4 811.

Referring now to FIG. 11C, if the media in media inlet 145, reservoir line 105 (FIGS. 2A/2B), module line 119 (FIGS. 2A/2B), or second/third configuration cassettes 699/700 (FIGS. 6A-6D) is to be disposed of without circulating through user-supplied device 113 (FIG. 1B), for example, but not limited to, if the quantity of air exceeds a pre-selected threshold, or if the pH/temperature fall outside pre-selected ranges such as, for example, but not limited to, >42° C., <6 pH, or >8 pH, user-supplied device 113 (FIG. 1B) can be isolated, and pumping of the media directly from media inlet 145, reservoir line 105 (FIGS. 2A/2B), and/or module line 119 (FIGS. 2A/2B) to waste line 121 (FIGS. 2A/2B) can be done. The pre-selected ranges can be based at least on how sensitive the components in the media are. Purging can also be conducted on a schedule to clear out any media components that degrade at 37° C. The pre-selected threshold can include, for example, 1 mL per fill stroke, and enables prevention of filling the holding tank with air. Purge to waste method 1150 can include, but is not limited to including, (a) filling 1151 pumping chambers 705/707 with media from holding tank 109 (FIGS. 2A/2B), (b) delivering 1153 the media from pumping chambers 705/707 to waste port 715, and repeating 1155 steps (a) and (b) until holding container 109 (FIG. 1B) is empty. Degraded media may be replaced with fresh media from media reservoir 101 after a pre-selected amount of the degraded media is disposed of. Holding container 109 (FIG. 1B) can be determined to be empty by determining that there was no change in pumping chamber volume after step (a). In removing media and/or air from lines in the system, the contents from media inlet 723 can be pumped directly to sample vessel 115 (FIGS. 2A/2B) without going through user-supplied device 113 (FIG. 1B). A volume of fluid can be delivered to sample vessel 115 (FIGS. 2A/2B) to allow for offline analysis. With respect to (a), filling 1151 pumping chambers 705/707 with media from holding container 109 (FIG. 2A) can include pumping fluid from bioreactor upper port 717 through valve V3 741, past sensors 711, and into pumping chambers 1/2 705/707. With respect to (b), delivering 1153 the media from pumping chambers 1/2 705/707 to waste port 715 can include pumping fluid from pumping chambers 705/707 through valve V7 809 and through waste port 715. As user-supplied device 113 (FIG. 1B) can be isolated from the rest of cassette 699/700 while purging to waste port 715, recirculation can be temporarily suspended for the duration of this pumping action.

Referring now to FIGS. 11D-1 through 11D-3, other circulation scenarios can include sample line priming/flushing, sample vessel fill, restoring media after sample vessel fill, and sensor recirculation and mixing. With respect to sample line priming and flushing, in preparation for filling sample vessel 115 (FIGS. 2A/2B), it may be necessary to remove any old media or air from sample line 116B (FIGS. 2A/2B). To support this, the module fluid handling system can pump fluid from media inlet port 723 (FIG. 6E) directly to sample vessel 115 (FIGS. 2A/2B) without going through user-supplied device 113 (FIG. 1B), thus isolating user-supplied device 113 (FIG. 1B) from the rest of cassette 699/700 (FIGS. 6A-6D) during priming/flushing of sample line 116B (FIGS. 2A/2B). As such, recirculation can be temporarily suspended for the duration of this pumping action.

Continuing to refer to FIGS. 11D-1 through 11D-3, with respect to filling sample vessel 115 (FIGS. 2A/2B), the contents of sample vessel 115 (FIGS. 2A/2B) can be used for offline analysis, such as, for example, chemical analysis. To avoid diluting the sample, inlet line 723 can remain closed during the filling of sample vessel 115 (FIGS. 2A/2B), and the volume to be delivered to sample vessel 115 (FIGS. 2A/2B) can be drawn from the compliant sections of cassette 699/700, for example, pumping chambers 705/707. The maximum volume allowed for this action can be limited by the volume of the compliant space within cassette 699/700. User-supplied device 113 (FIG. 1B) can be isolated from the rest of cassette 699/700 while filling sample vessel 115 (FIGS. 2A/2B) to avoid flow to/from complaint parts of user-supplied device 113 (FIG. 1B). As such, recirculation can be temporarily suspended for the duration of the pumping action. After a sample vessel fill operation, the volume of media within cassette 699/700 can be restored. Media can be withdrawn from holding container 109 (FIGS. 2A/2B) and delivered to depleted of pumping chambers 1/2 705/707. Unlike a typical partial replenishment, no media can be delivered to waste container 117 (FIGS. 2A/2B) during this time, and flow of media through user-supplied device 113 (FIG. 1B) can be temporarily suspended. Flow can be suspended during a partial replenishment of media if needed. In some configurations, it may be necessary to isolate user-supplied device 113 (FIG. 1B) for extended periods, such as, for example, hours to days, to simulate static culture. In some configurations, in a manual static culture, media exchanges can be performed 2-3 times/week, depending, for example, on cell density. During these periods, the valves leading to bioreactor lower port 719, bioreactor upper port 717, media inlet port 723, sample vessel port 721, and waste line port 201 can be closed. To maintain media homogeneity and ensure the accuracy of the sensors, media can be recirculated internally within cassette 699/700 for the duration of this pumping action.

Continuing to refer to FIGS. 11D-1 through 11D-3, method 2150 for filling sample vessel 115 (FIGS. 2A/2B) can include, but is not limited to including (a) mixing 2151 media on cassette 699/700 to ensure homogeneity while a sacrificial container is attached, (b) flushing 2153 stale media in sample line 116B (FIGS. 2A/2B) to the sacrificial container and detaching waste container 117 (FIGS. 2A/2B), (c) mixing 2155 media on cassette 699/700 to ensure homogeneity while sample container 116 (FIGS. 2A/2B) is attached, (d) delivering 2157 spent but not stale media in sample line 116B (FIGS. 2A/2B) to sample container 116

(FIGS. 2A/2B) and detaching sample container 116 (FIGS. 2A/2B), (e) replacing 2159 the removed media with fresh media, and (f) mixing 2161 the media internally to ensure homogeneity. With respect to (a), internal circulation can include pumping media through valve V4 811, through gas exchange inlet 727 through gas exchange area 701A/701 (FIGS. 6A-6D), through gas exchange outlet 727, valve V5 759, past sensors 711, and back to valve V4 811. Homogeneity is determined by recognizing no spikes or rapid shifts in sensor readings during recirculation. Circulation can proceed for a pre-selected, user-defined, or dynamic amount of time, based at least on information supplied by sensors associated with cassette 699/700, until the media is substantially homogeneous. With respect to (b), flushing stale media can include pumping media from gas exchange area 701A/701 (FIGS. 6A-6D) through gas exchange outlet 727, valve V5 759, past sensors 711, through valve V6 757, through sample vessel port 721, and into sample vessel 116 (FIGS. 2A/2B). With respect to (c), another internal mixing step as in (1) can be taken. With respect to (d), delivering fresh media in sample line 116B (FIGS. 2A/2B) to sample vessel 116 (FIGS. 2A/2B) can include pumping media from gas exchange area 701A/701 (FIGS. 6A-6D) through gas exchange outlet 727, valve V5 759, past sensors 711, through valve V6 757, through sample port 721, and into sample vessel 116 (FIGS. 2A/2B). With respect to (e), replacing the removed media can include pumping media through media port 723, through valve V1 805, past sensors 711, through valve V4 811, through gas exchange inlet 727, and into gas exchange area 701A/701 (FIGS. 6A-6D). With respect to (f), mixing the media to ensure homogeneity can include steps as in (c).

Referring now to FIG. 11E, post purge/sample refilling 1250 can include pumping media from media inlet 723 through valve V1 805, past sensors 711, through valve V3 741, through valve V9 745, and through bioreactor upper port 717 into the bioreactor.

Referring now to FIG. 11F, bioreactor isolation from cassette fluid circulation (internal recirculation) can be accomplished by opening fluid valves V4 811 and V5 759, and closing the rest of the valves. Pumping valves PV2.1 751 and PV1.2 755 alternate being open and closed with PV2.2 753 and PV1.1 749 during pumping.

Referring now to FIGS. 12A through 13E, the pumping action and fluid flow of the cassettes described herein can be enabled by pneumatic valves operating cooperatively. In some configurations, pumping and directing of fluid through reservoir and bioreactor cassettes 699/700 (FIGS. 6A-6D) can be driven, e.g., pneumatically as described in, for example, U.S. Pat. No. 8,292,594, filed Apr. 13, 2007, issued Oct. 23, 2012, entitled "FLUID PUMPING SYSTEMS, DEVICES AND METHODS, incorporated herein by reference in its entirety. In addition, gasses such as, for example, but not limited to, nitrogen, carbon dioxide, and oxygen can be supplied to gas exchange areas to condition the media as described herein.

Continuing to refer to FIGS. 12A through 13E, in the various configurations, a pneumatic block can enable positive and negative pressures through system 3000 (FIG. 1A). The positive and negative pressures can ultimately supply the force necessary to pump fluid through the fluid circuit of the present teachings. For each rack 205 (FIG. 1B), each row 207 (FIG. 1B), and each module—reservoir module 116A (FIG. 1B) and bioreactor module 118A (FIG. 1B)—the pneumatic block can enable accurate, independent, adjustable control of bladders, valves, and pumping pressures. In some configurations, regulators can be arranged to enable the control of pressure in groups of valves. In some configurations, gas sources can supply pressure to manifolds through a series of devices that can include, but are not limited to including, connectors, solenoid valves, proportional valves, pressure relief valves, and gauges, that together can provide varying levels of control of the pressure of sources. Connectors can include, but are not limited to including, sterile connectors. Solenoid valves can include, but are not limited to including, normally closed valves. The pneumatic valve arrangement can allow for independent pressurization of reference chambers and pumping chambers to maximize pressure differential during measurements. In some configurations, reference chambers can be located in manifolds. Pneumatic valves can isolate reference chambers and associated pressure sensors, and pneumatic valves can vent reference chambers. The stroke volume of pump chambers can be precisely computed by charging reference chambers with air, measuring the pressure, and then opening the valves to pumping chambers. The volume of air on the pump side of the cassette can be computed based on the fixed volume of reference chambers and the change in pressure when reference chambers are connected to pump chambers. The initial and final pressures in pumping chambers and reference chambers can be used in a thermodynamic model to calculate the air volume in pumping chambers. The volume of air on the pneumatic side can be measured before and after a fill or deliver stroke. The difference in the air volume is equal to the amount of fluid delivered during the pump stroke. Prior to the volume measurement, pumping chambers 705/707 can be pressurized to a pre-charge value. In some configurations, the pre-charge value, for positive pressure, can potentially reach a maximum positive rail pressure, for example ~135-150 kPa absolute/~+35 to ~+50 gauge. In some configurations, the pre-charge value, for negative pressure, can potentially reach as low as the minimum negative rail pressure, for example, ~30 kPa absolute/~−70 kPa gauge. This is done in order to create a pressure difference between pumping chambers 705/707 and reference chambers 911A/B. Taken together, the typical difference between the reference and pumping chamber is ~11001 kPa. The pre-charge pressure can be either positive or negative relative to the atmospheric pressure. These situations are referred to as positive FMS (+FMS) and negative FMS (−FMS), respectively. Two different measurements of the air volume on the pneumatic side, which can be used to detect air volume on the hydraulic side when the membrane is at a hard stop, can be taken. Once the fluid measurement system has been calibrated to measure air volume, positive and negative FMS can be used to detect air on the fluid side of the membrane. Under normal operating conditions, only positive FMS is used. If, when the chamber is in the full position, a positive FMS value that is larger than expected is detected, air detection is triggered and a negative FMS measurement is made. When the cassette membrane is against the manifold wall in the full position or against the cassette pump chamber in the empty position, any air on the fluid side can be measured by either positive or negative FMS, but not by both. In these cases, the difference between the two FMS values is used to determine the air volume on the fluid side of the cassette.

Referring again to FIGS. 12A through 13E, determining the amount of fluid in pumping chamber 705/707 can include sequencing the pressurizing of pumping chamber 705/707 and reference chamber 911A/B to determine the volume in pump chamber 705/707. Filling pumping chamber 705/707 with fluid can include detecting end-of-stroke when pumping chamber 143A/705 is full, and confirming the volume of the fluid. The average volume of pump chamber 705/707 and the average number of pulses needed to deliver the average volume to pumping chamber 705/707 can be determined, and the period of the pulses needed to obtain a desired flow rate can be determined. When orifice valves need to be pulsed can be determined, and when the flow rate can be controlled by the differential pressure controls without pulsing orifice valves can be determined. Determinations can be made based on FMS measurements and system clock time measurement to calculate the measured flow rate, and then adjustment of the orifice valve pulse rate can raise/lower the flow rate as needed, for example, under PID control.

Referring now to FIGS. 12A through 13E, in some configurations, section A of pneumatic block 2011B (FIG. 12B) can include connectors 211 such as, for example, quick disconnect connectors that can include, for example, sterile filters or oil filters, solenoid valves 901, pressure gauges 906, and pressure relief valves 907, but no proportional valves 905x. In some configurations, sections B 1203 (FIG. 12A), C 1205 (FIG. 12A), D 1207 (FIG. 12A), . . . X 1209 (FIG. 12A) can include proportional valves, but no 3/2 valves. In some configurations, section I 1223 (FIG. 12A) can include a single valve on positive pressure bus 1505 (FIG. 12B), and possibly a valve on negative pressure bus 1507 (FIG. 12C). In some configurations, section A 1201 (FIG. 12A) can include manual pressure regulators 914 for each gas source. In some configurations, section M 1221 (FIG. 12A) can include seven pneumatic valves (FIGS. 12B/C) or eight pneumatic valves (FIG. 12D/E) or nine pneumatic valves (FIGS. 12F/G/H). In some configurations, section E (FIG. 12E) can include gas vent valve 1502 (FIG. 12D) to enable venting of gas exchange chamber 701/701A. In some configurations, sections J1/J2 of pneumatic block 2011F (FIGS. 12F and 13D) can include a single positive pressure bus valve and a single negative pressure bus valve for each pumping chamber, for five valves total. In some configurations, section L1 1227 (FIG. 12A) in pneumatic block 2011F (FIGS. 12F and 13D) can include a common reference chamber for two pumping chambers. The reference chamber valve can receive both positive and negative pressures, and can be unvented. In some configurations, sections J1/J2 1225/1229 (FIG. 12A) of pneumatic block 2011G (FIGS. 12G and 13C) can include a pump through reference configuration including three valves associated with both pumping and reference chambers, for a total of six valves. Both pumping and reference chambers can receive both positive and negative pressures, and the reference chambers can be unvented. In some configurations, sections J1/J2 1225/1229 (FIG. 12A) and L1/L2 1227/1231 (FIG. 12A) of pneumatic block 2011H (FIGS. 12H and 13E) can include single valves enabling positive and negative pressure on both pumping chambers, and a single reference chamber, for a total of four valves. The valves enabling pressure on the pumping chambers can enable pressure on the reference chamber as well.

Referring now to FIGS. 12A-12F, for description purposes, pneumatic block 2011 can be divided into sections such as, for example, but not limited to, rack section 1233, row section 1235, and manifolds 1211. Rack section 1233 can include gas/air 903, air/gas interface section A 1201, and gas supply section B 1203 (FIG. 12C). Row section 1235 can include reservoir manifold section C 1205 (FIG. 12D), and at least one bioreactor manifold section C/D . . . /X 1205/1207/ . . . /1209. Manifold section 1211 can include gas section E 1213 (FIG. 12E), negative/positive pressure section F/H 1219, flow valve section N 1221, bladder section G 1217, pumping chamber sections J1/J2 1225/1229, reference chamber sections L1/L2 1227/1231, and pumping valve interface section I 1223. Each air/gas source can interface with pneumatic block 2011 through air/gas interface section A 1201. For each air/gas source, air/gas interface section A 1201 can possibly include, for example, but is not limited to including, connectors 211 such as, for example, quick disconnect connectors that can include, for example, sterile filters or oil filters, normally closed solenoid valves 901, valves such as proportional, 2/2, or 2/3 valves, pressure gauges 906, and passive pressure relief valves 907. Various pneumatic block configurations may or may not include each of the above-listed elements, depending on the desired result. Gas supply section B 1203 can supply gas to a thermal management area where the media reservoir is located. If the air in the thermal management area is purged with a low solubility gas for example, but not limited to, nitrogen, outgassing when warming up the chilled media could be decreased. In some configurations, a coarse adjustment of the oxygen and carbon dioxide levels could decrease their equilibration time. Gas supply section B 1203 can include, in some configurations, a valve for each gas source 903, pressure gauge 906x, and temperature manager 810 through which the gas can flow according to the valve settings. In some configurations, the pressure/vacuum control of gas supply section B can be included in air/gas interface section A 1201, rather than accommodating individual control. The valve can include a 2/2 valve, for example. Reservoir manifold section C 1205 and bioreactor manifold sections D/E . . . /X can include one valve for each of air and vacuum sources, and one valve 808N/O/CO (FIG. 14L) and one orifice 4326N/O/CO (FIG. 13A-4) heading into reservoir module gas exchange chamber 701/701A (FIG. 13A-4) for each gas source 903 ($O_2$ 1401, $CO_2$ 1403, and $N_2$ 1405 (FIG. 12B)). In some configurations, gas control can be part of manifold 1211. The valve can include, for example, a proportional valve. In some configurations, each of the valves can be accompanied by pressure gauge 906, while the combination of gas sources 903 can by accompanied by a single pressure gauge 906, measuring the pressure of the air/gas entering reservoir/bioreactor manifold 1211.

Continuing to refer to FIGS. 12A-12F, manifold 1211 can include gas exchange section E 1213 (FIG. 12E), positive/negative pressure bus section F/H 1219, pneumatic valve section M 1221, bladder door section G 1217, PCB section I 1223, control section K 1224, pumping chamber sections J1/J2 1225/1229, and reference chamber sections L1/L2 1227/1231. Gas exchange section E 1213 can provide gas exchange with the fluid circulating in the cassette by enabling the gas to move from gas sources 903 to gas exchange chamber 701/701A. Pressure from the gas in gas exchange section E 1213 upon fluid in gas exchange area 701A/701 (FIGS. 6A-6D) can enable specific quantities of specific gasses to be taken up by the liquid, thus modifying the characteristics of the liquid to desired levels. For example, the fluid can be oxygenated, or the pH level of the liquid can be adjusted. Gas section E 1213 can include, but is not limited to including, valve 1501 that can be used to vent gas exchange chamber 701/701A. Valve 1501 can include, but is not limited to including, a 3/2 valve. Positive/negative pressure bus section F/H 1219 can include air bus 1505 that can provide air at a desired pressure and negative pressure bus 1507 that can draw a vacuum on pneumatic valves to which negative pressure bus 1507 is connected. The combination of the pressure supplied by the air and the vacuum moves the fluid in the cassette. Pneumatic valve section M 1221 can include as many pneumatic valves and pumping valves as are required to interface with the fluid valves on the cassette. The valves can include, but are not limited to including, 3/2 valves. In some configurations, for example, pneumatic block 1200E (FIG. 12E), there are fewer pneumatic valves than there are fluid valves on the cassette, for example, when fluid valves are configured to operate simultaneously and therefore only require a single pneumatic valve. Bladder door section G 1217 can include bladder 1319 and bladder valve 935. Bladder 1319 can provide the pressure necessary, when inflated, to press the cassette against the manifold. Bladder valve 935 can be pressurized by positive pressure bus 1505. PCB section I 1223 can include, in some configurations, at least one valve, and at least one pressure gauge 906. Control section K 1224 can throttle the pressure on pressure bus 1505. Control section K 1224 can include, for example, but not limited to, at least one valve and at least one pressure gauge 906. Pumping chamber sections J1/J2 1225/1229 can manage the pressure upon pumping chambers 705/707 on the cassette. Pumping chamber sections J1/J2 1225/1229 of pneumatic block 2011 (FIGS. 12A and 13B) can include positive pressure valves 310A/B, negative pressure valves 312A/B, pumping chambers 705/707, and pressure gauges 906 associated with pumping chambers 705/707. Positive pressure valves 310A/B can enable the supply of positive pressure to both pumping and reference chambers through their respective positive pressure valves. Reference chamber sections L1/L2 1227/1231 can operate in conjunction with pumping chamber sections J1/J2 1225/1229 to deliver specific amounts of fluid. Reference chamber sections L1/L2 1227/1231 can include isolation valves 306A/B, vent valves 308A/B, and reference chambers 911A/B. In some configurations, the valves can include 3/2 valves.

Figure 12A:
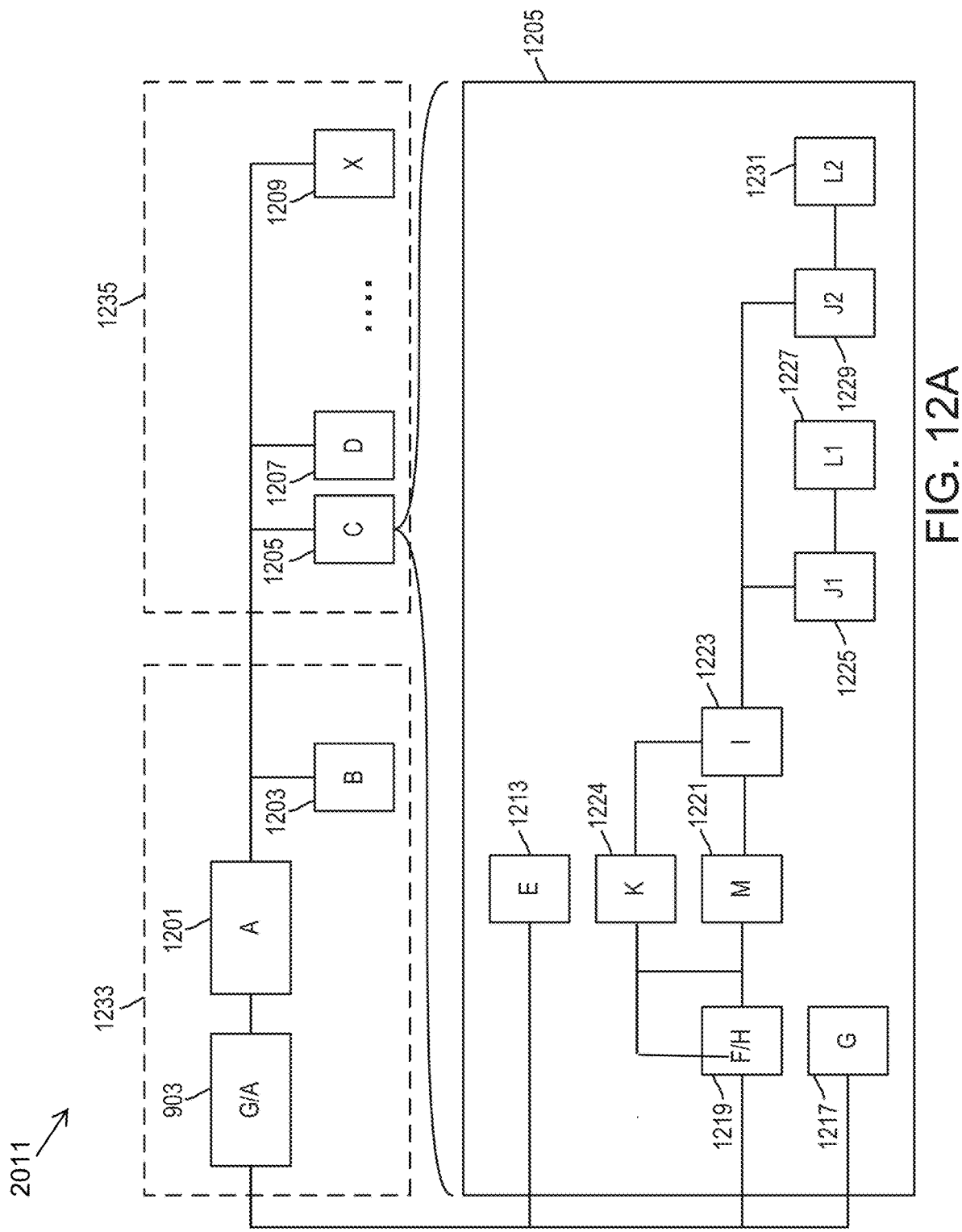
FIG. 12A is a schematic block diagram of the components of the pneumatic system of one configuration of the present teachings.
Figure 12B:
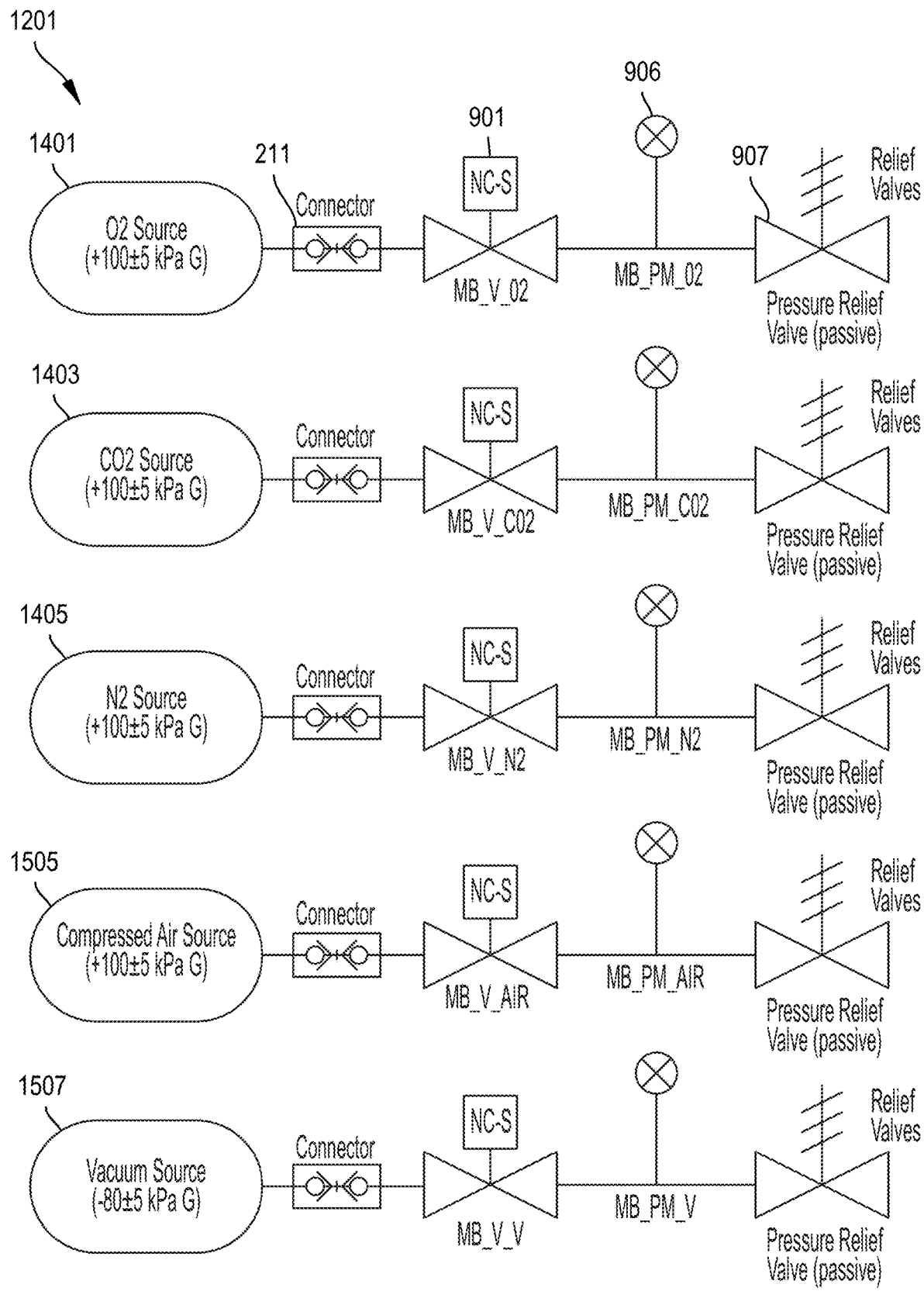
FIGS. 12B-12F are pneumatic diagrams of selected of the components of FIG. 12A.
Figure 12C:
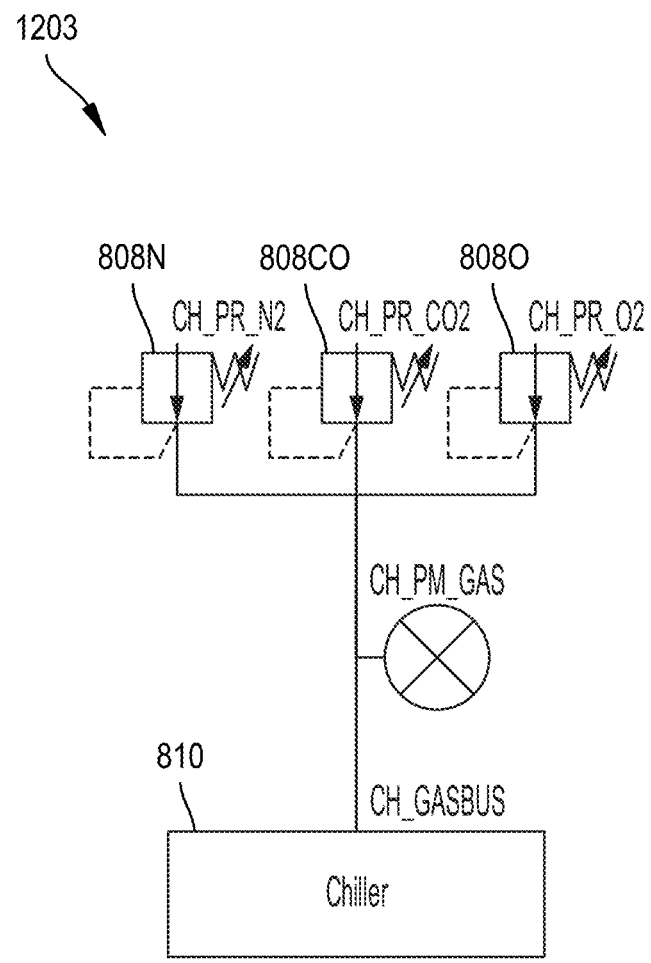
Figure 12D:
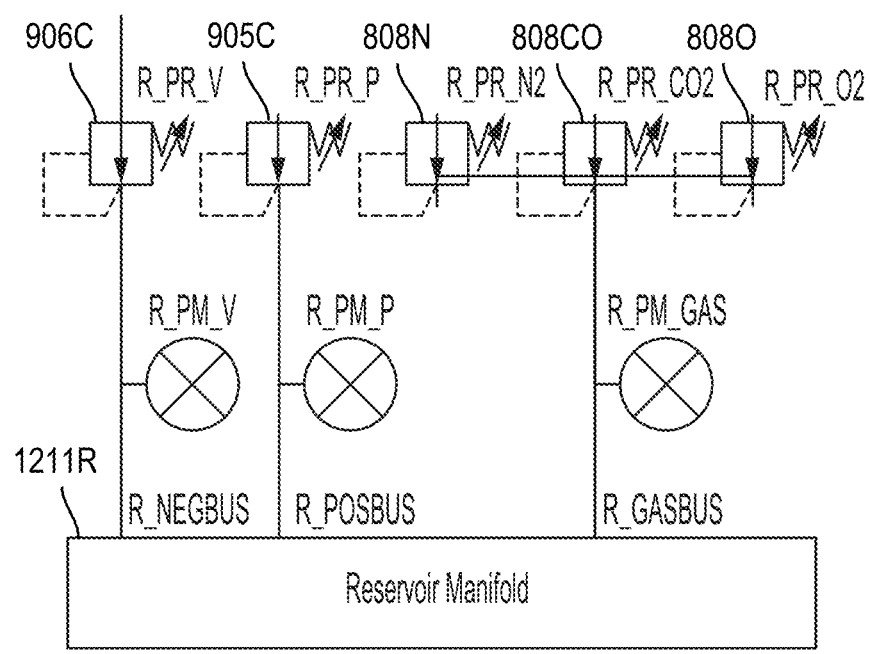
Figure 12E:
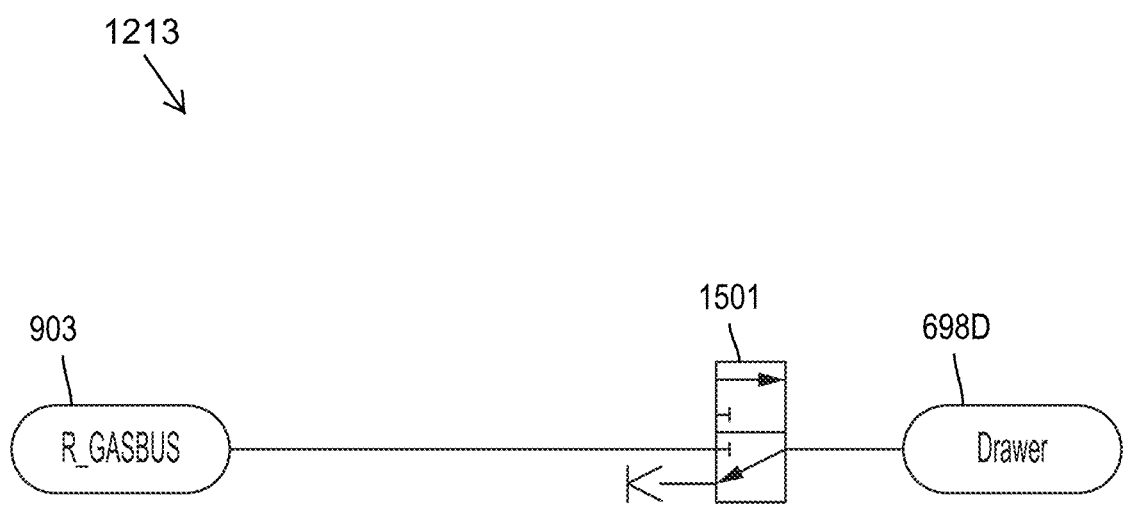
Figure 12F:
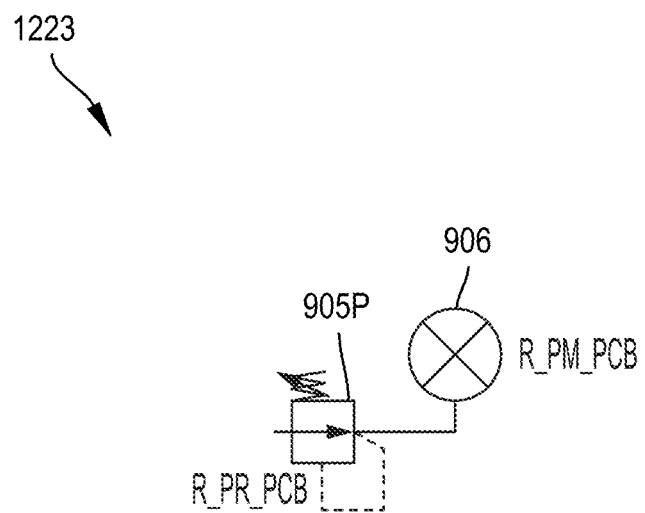
Figure 12G:
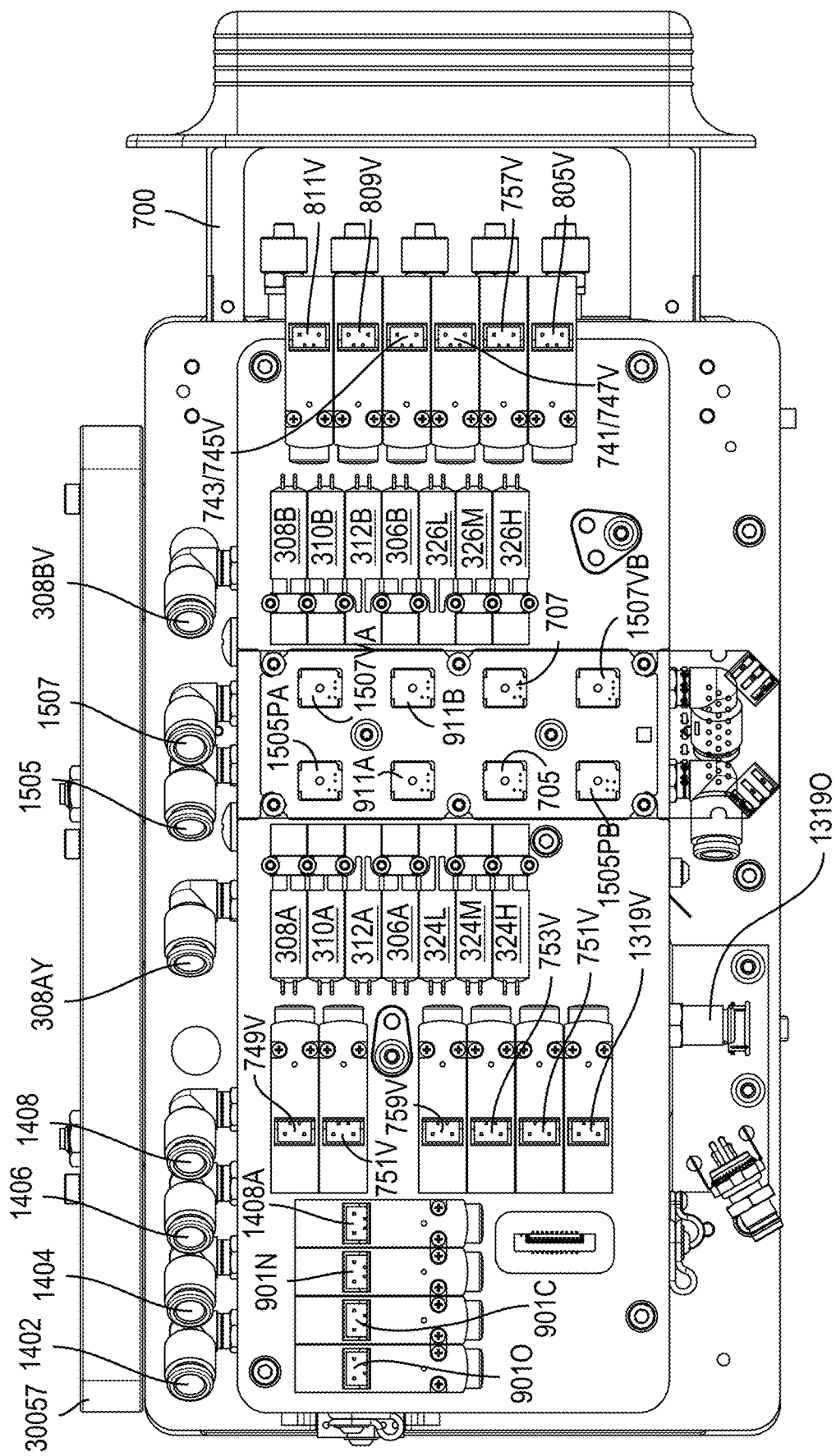
FIGS. 12G-12I are valve layout diagrams of the system of the present teachings that can implement, in whole or in part, the pneumatic diagrams in FIGS. 12AA-12AI.
Figure 12H:
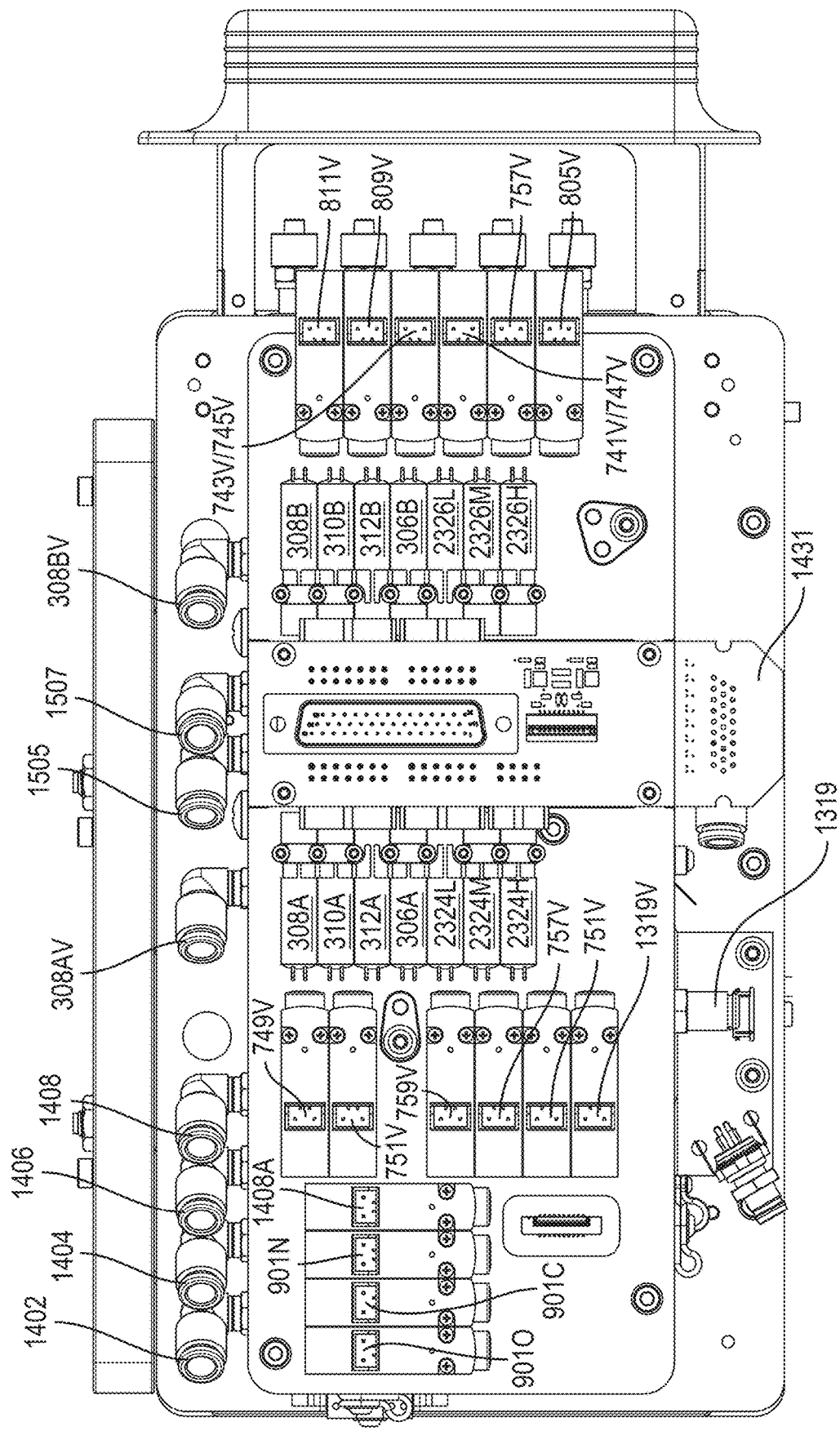
Figure 12I:
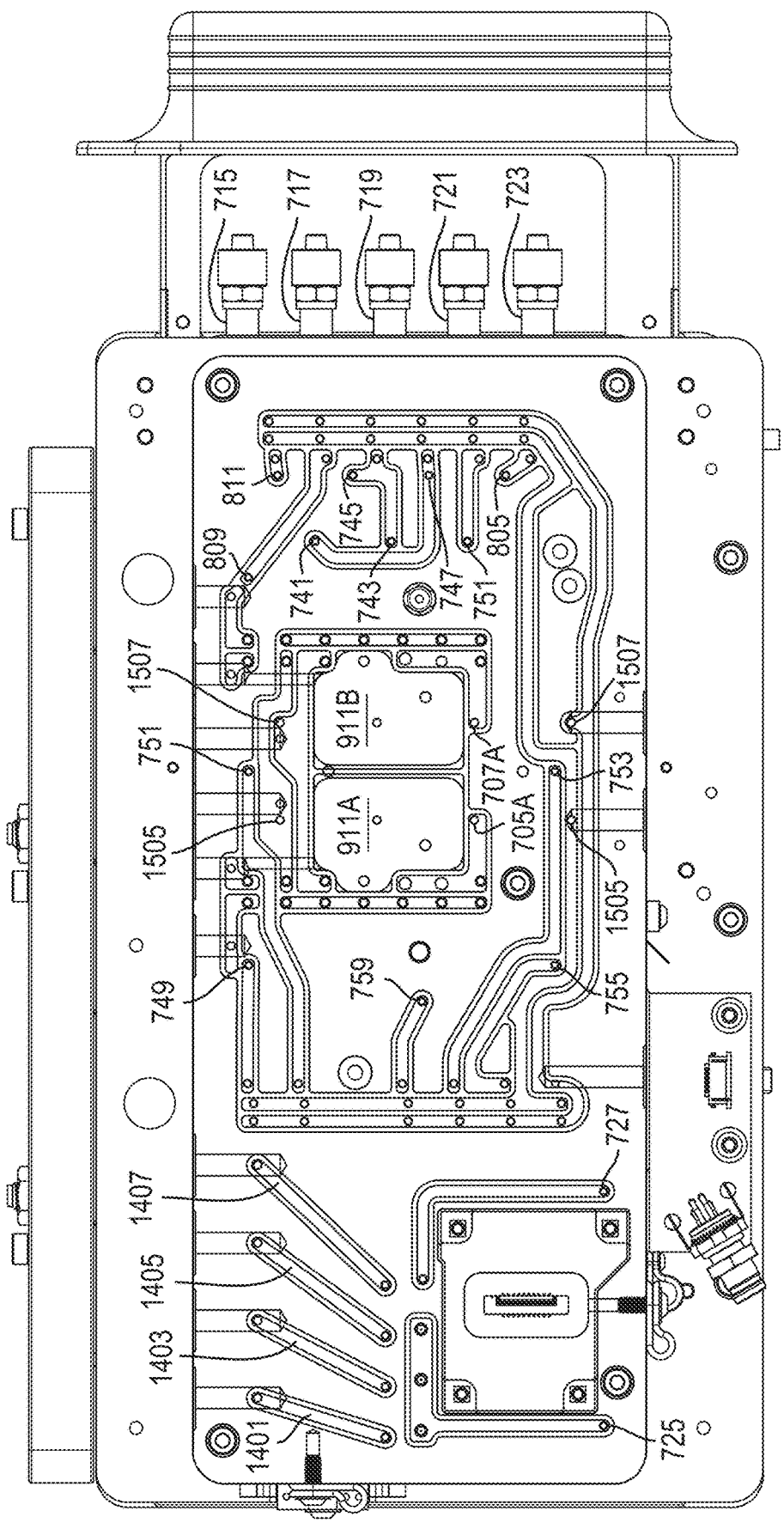
Figure 12A:
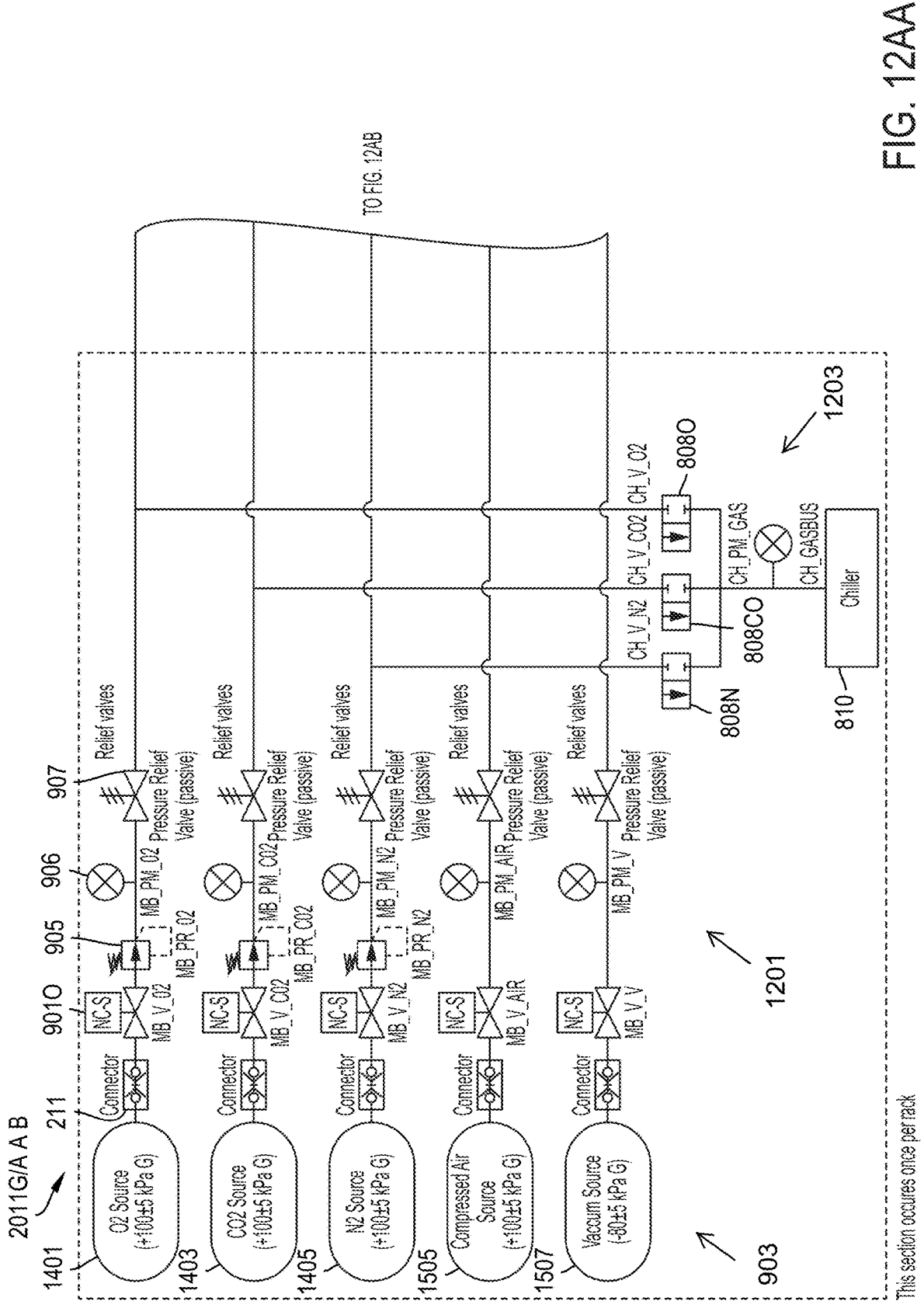
Figure 12A:
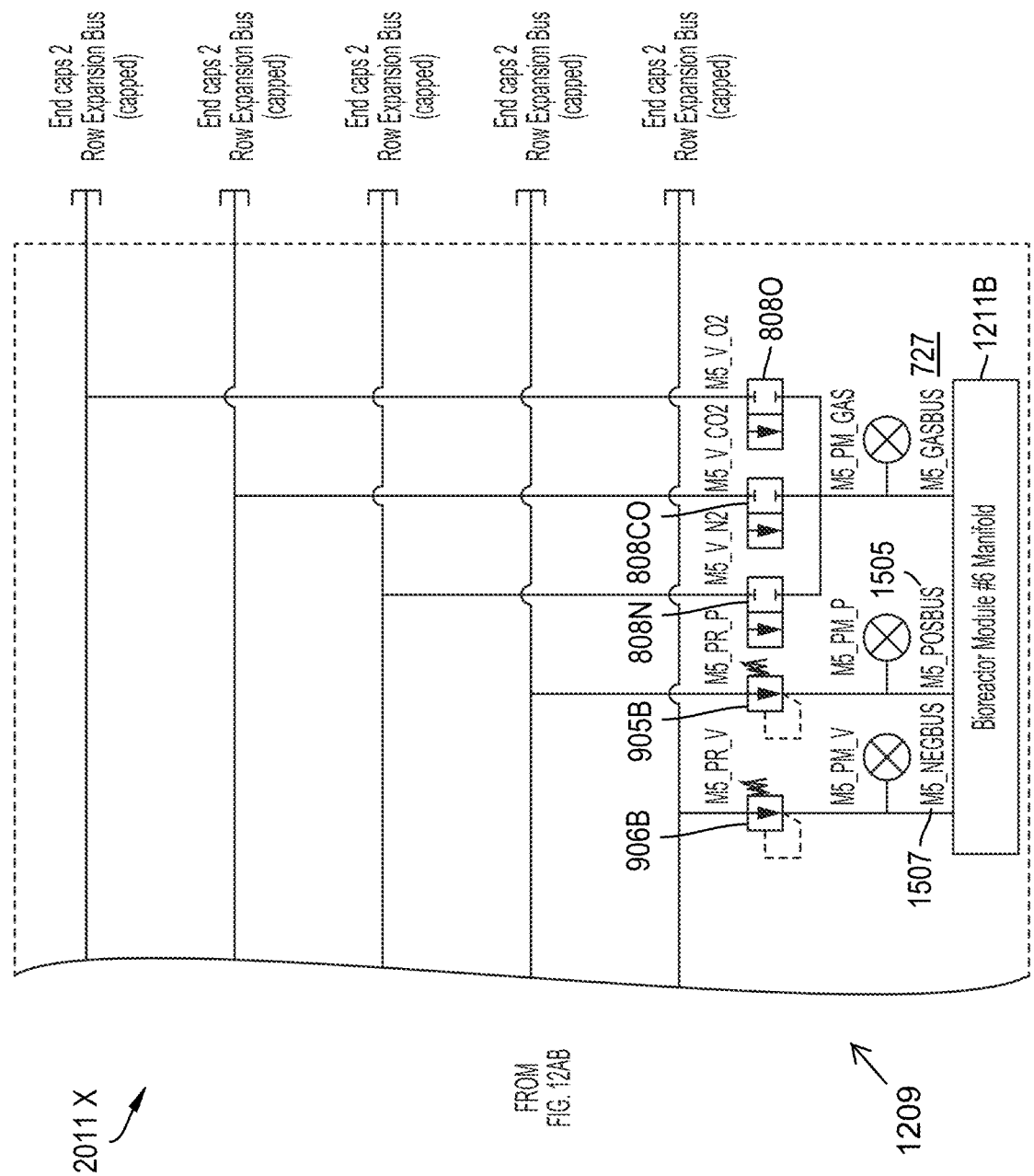
Figure 12A:
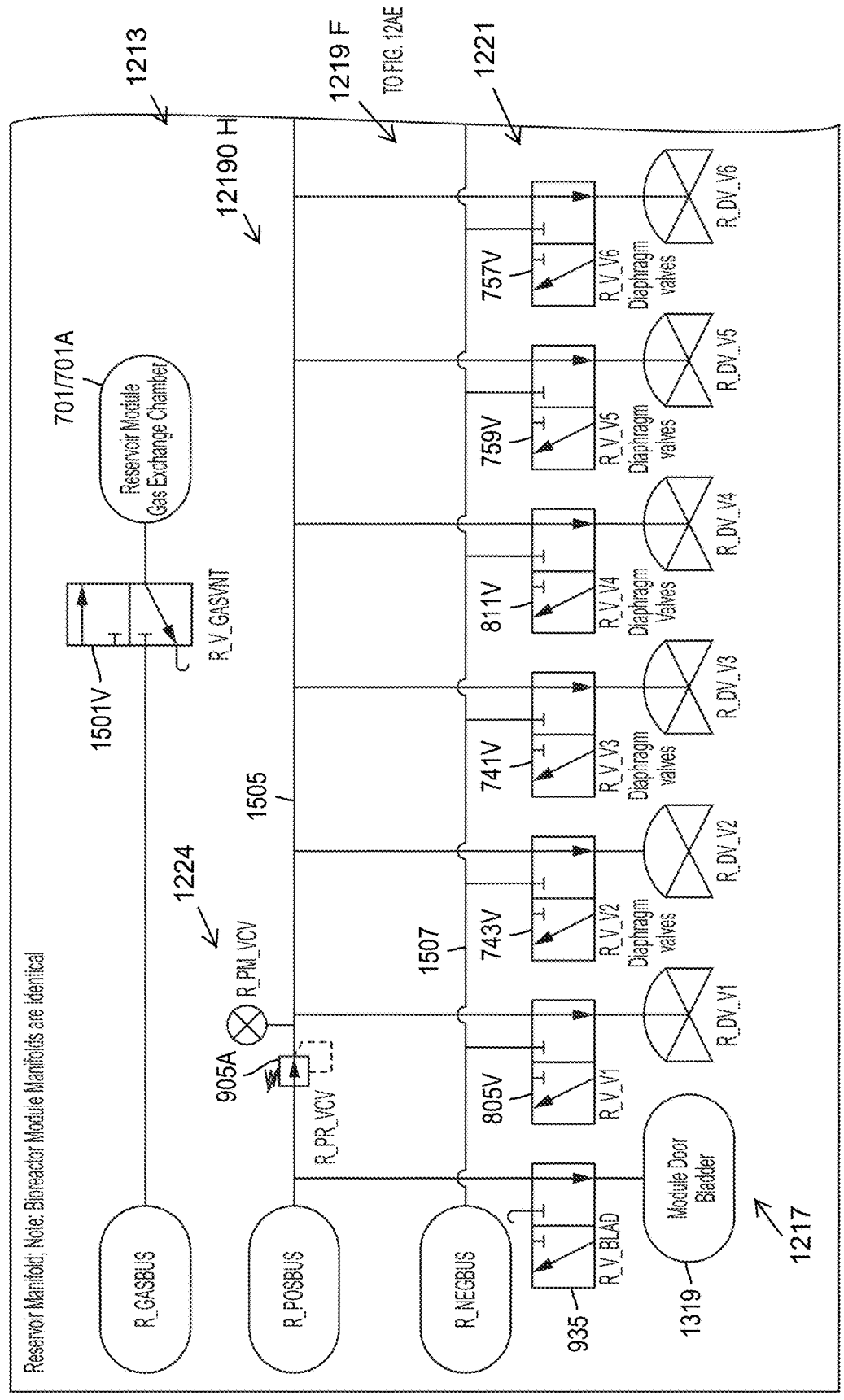
Figure 12A:
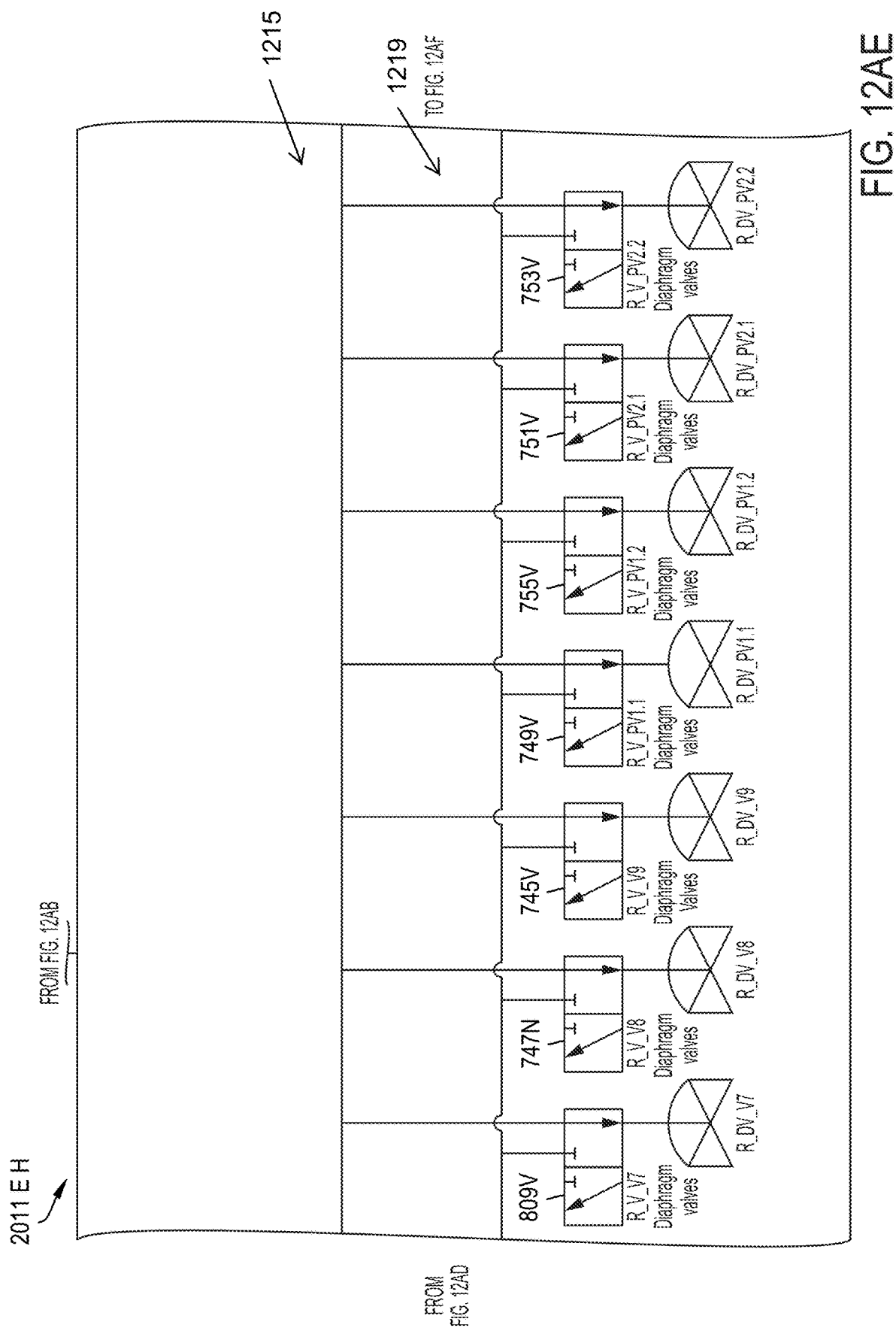
Figure 12A:
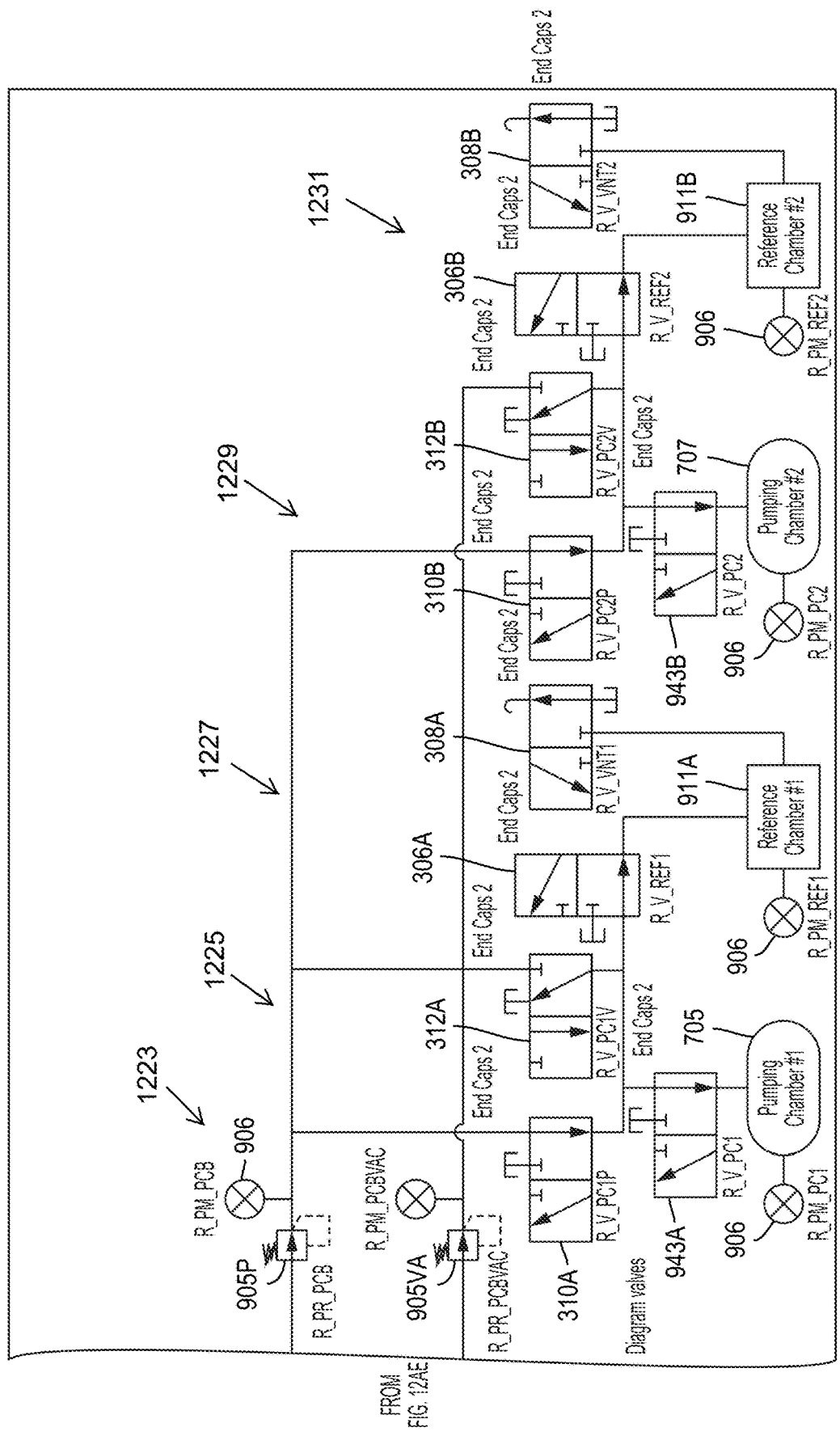
Figure 12B:
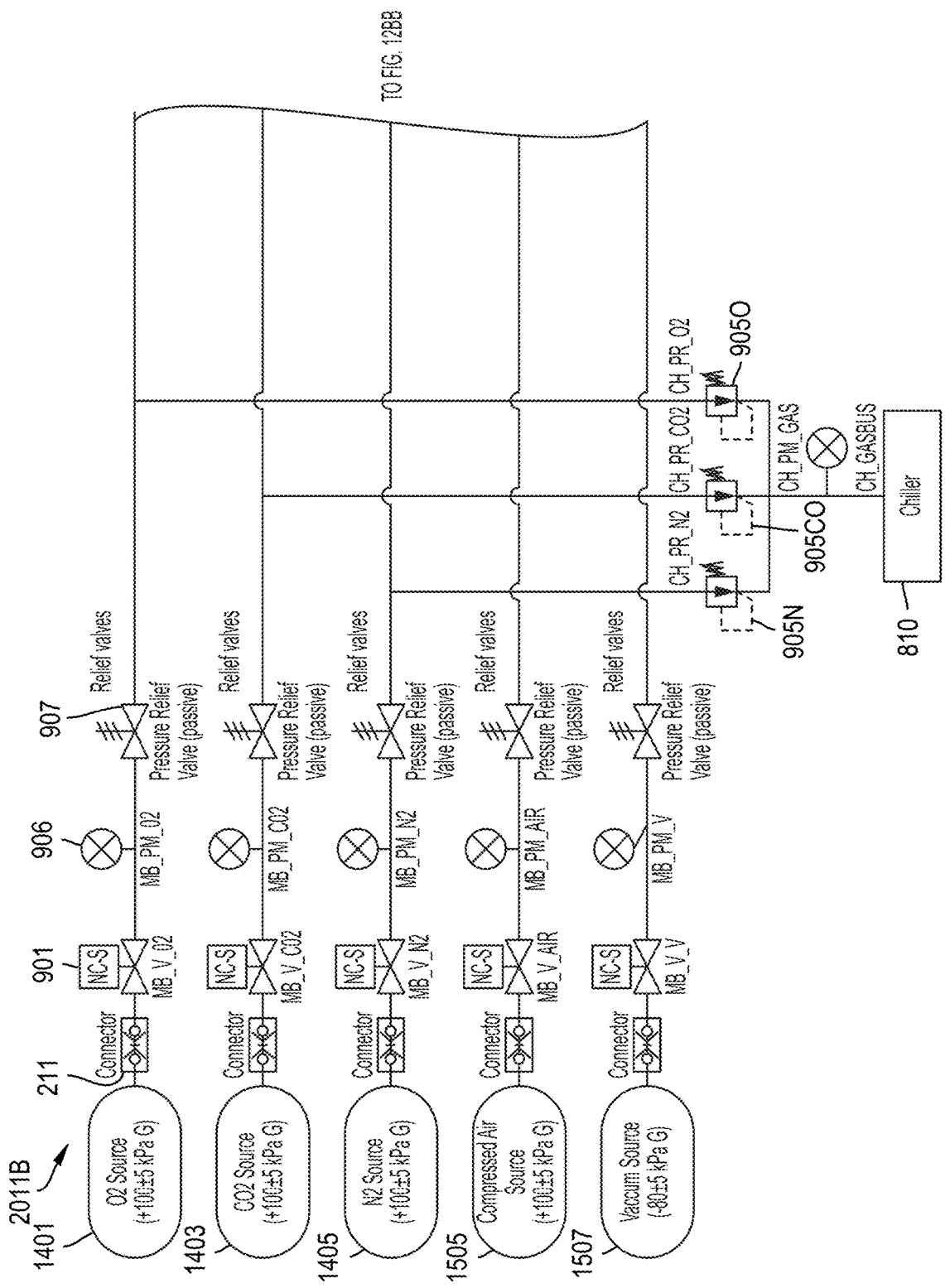
Figure 12B:
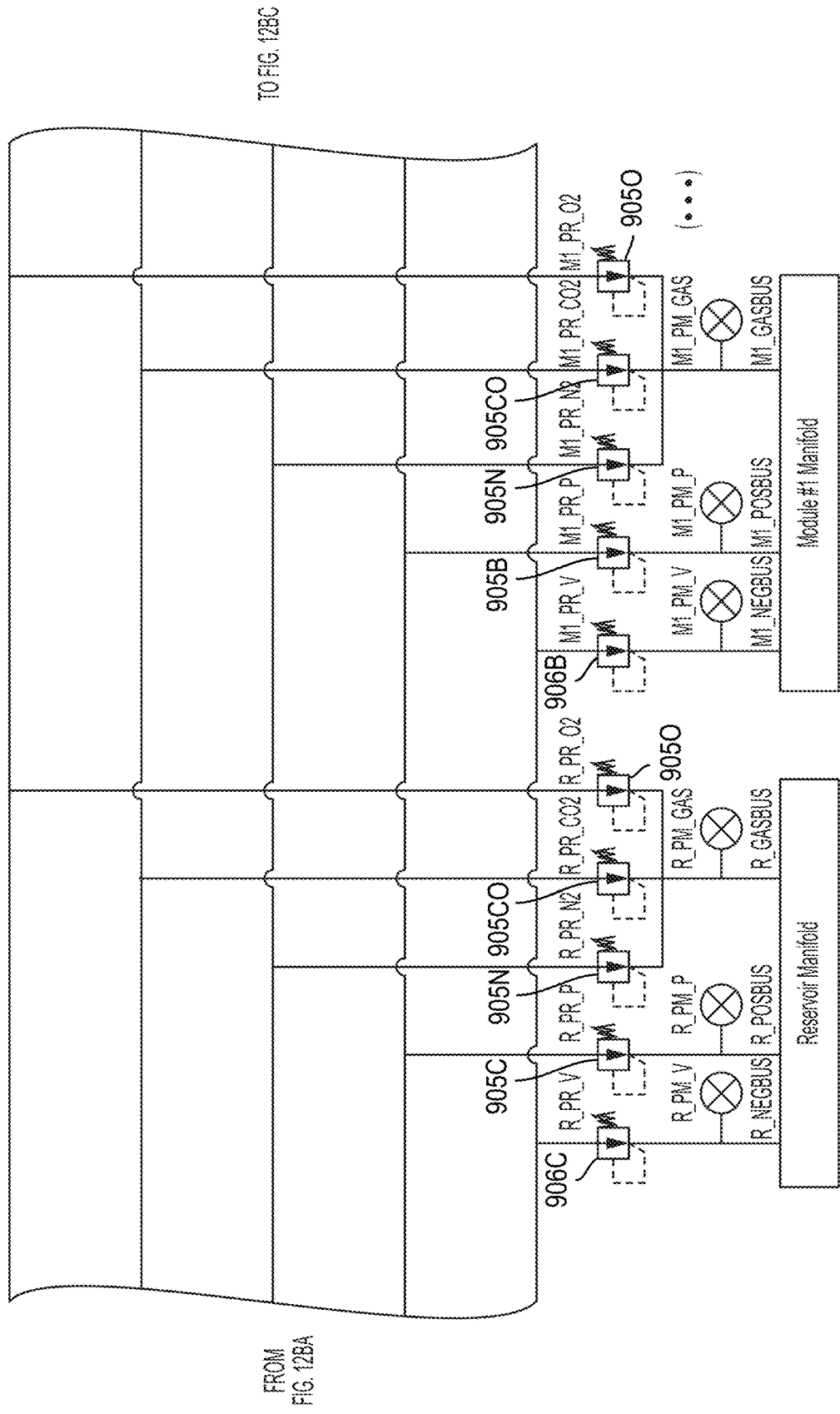
Figure 12B:
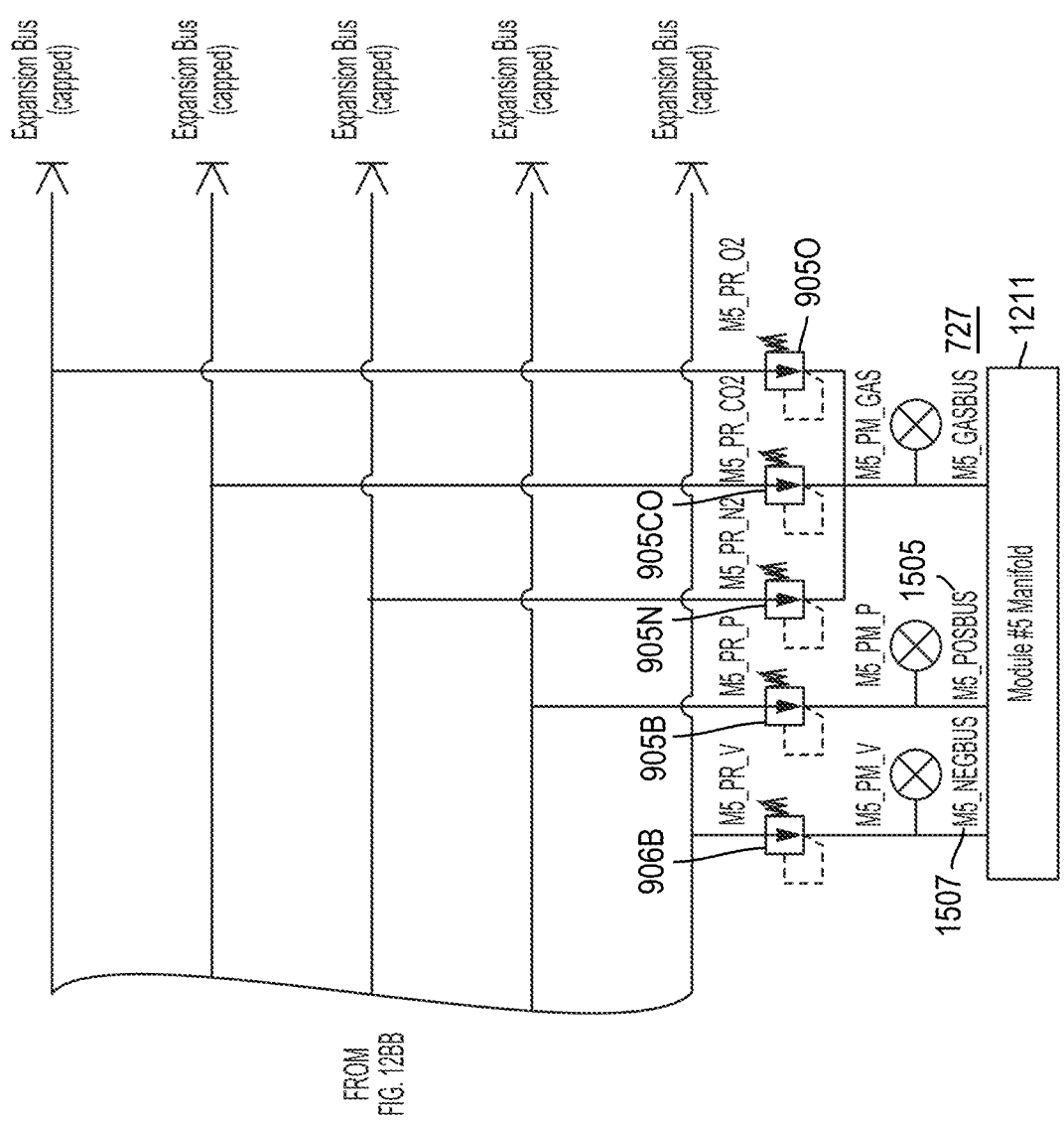
Figure 12B:
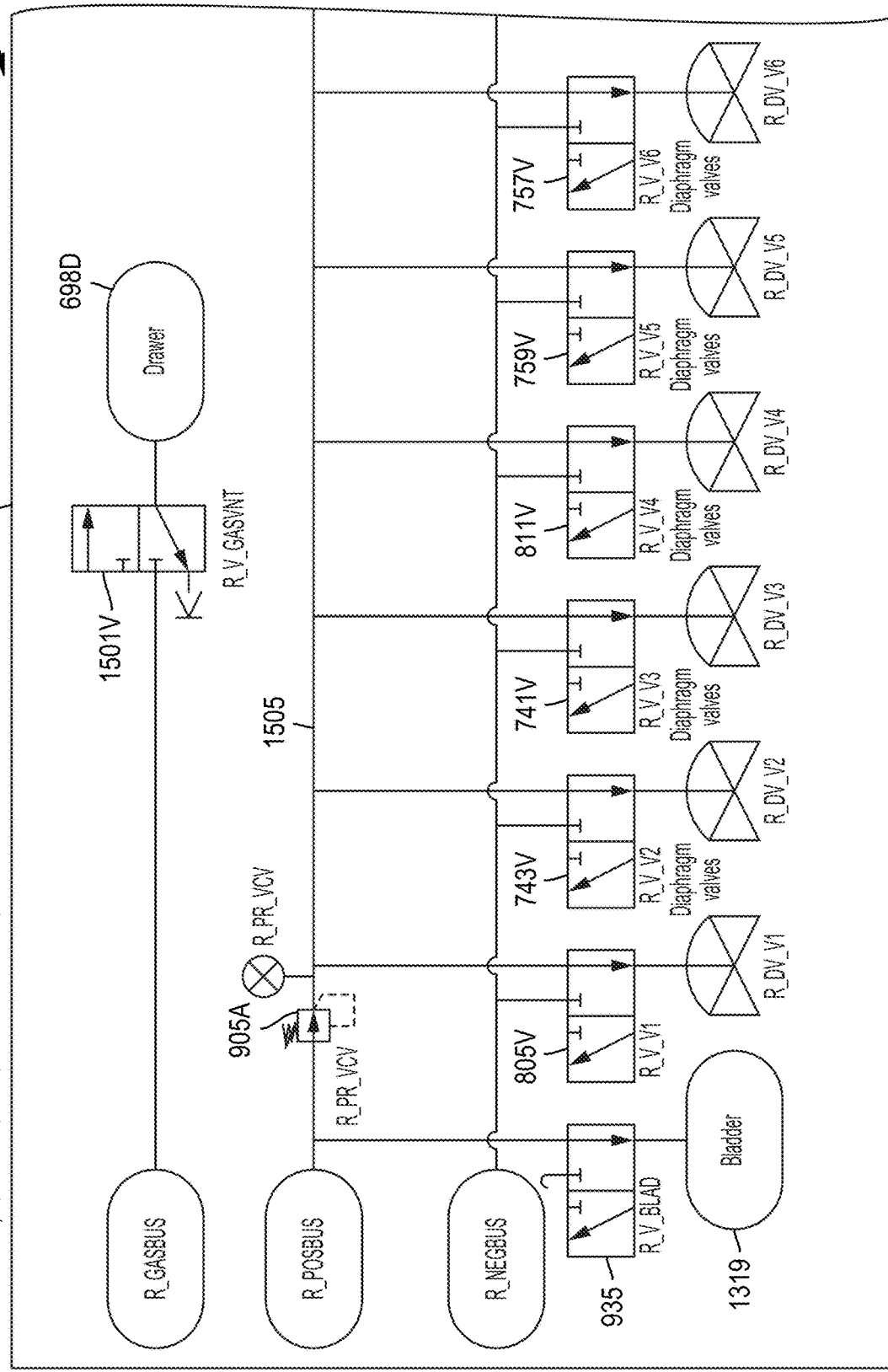
Figure 12B:
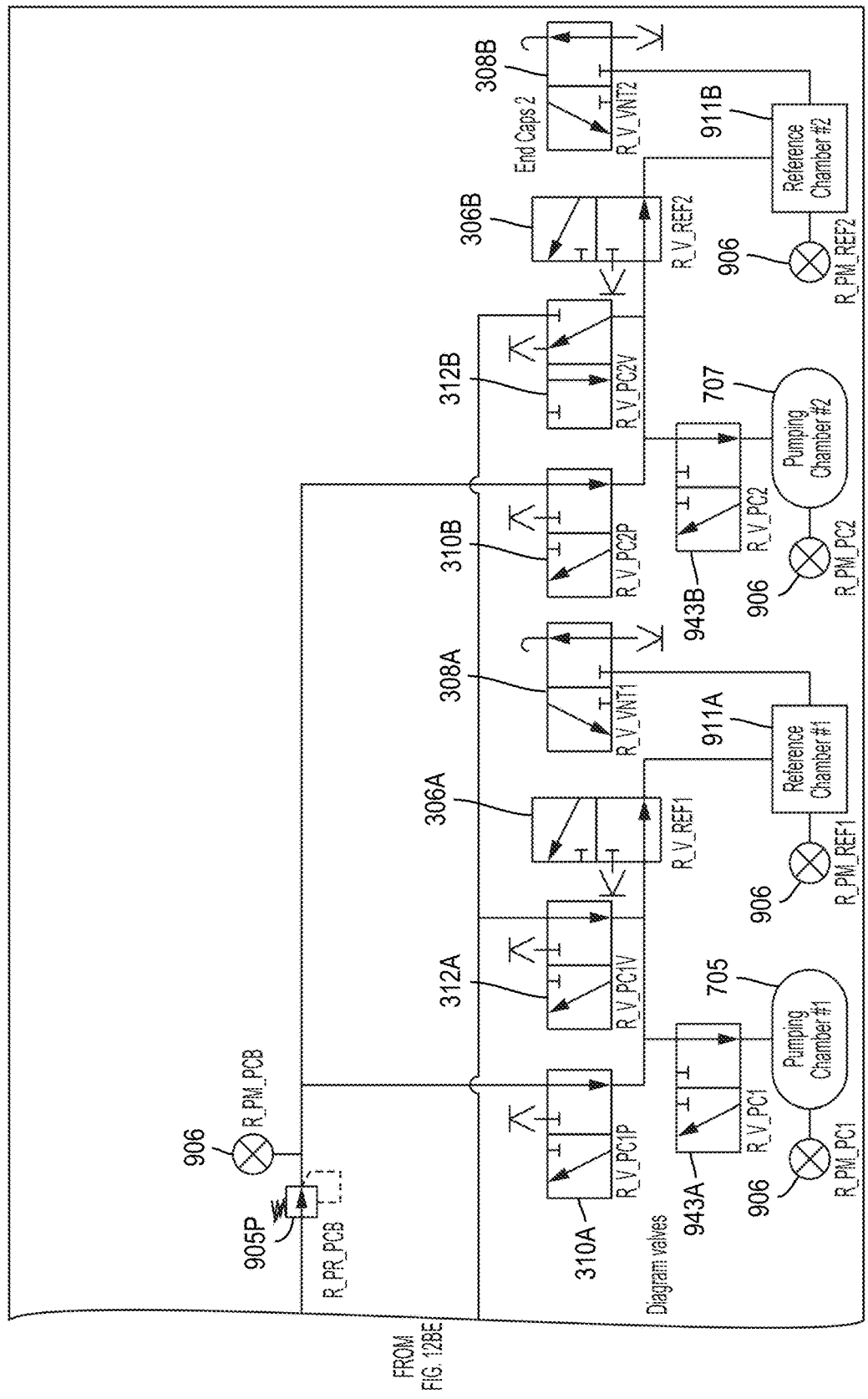
Figure 12C:
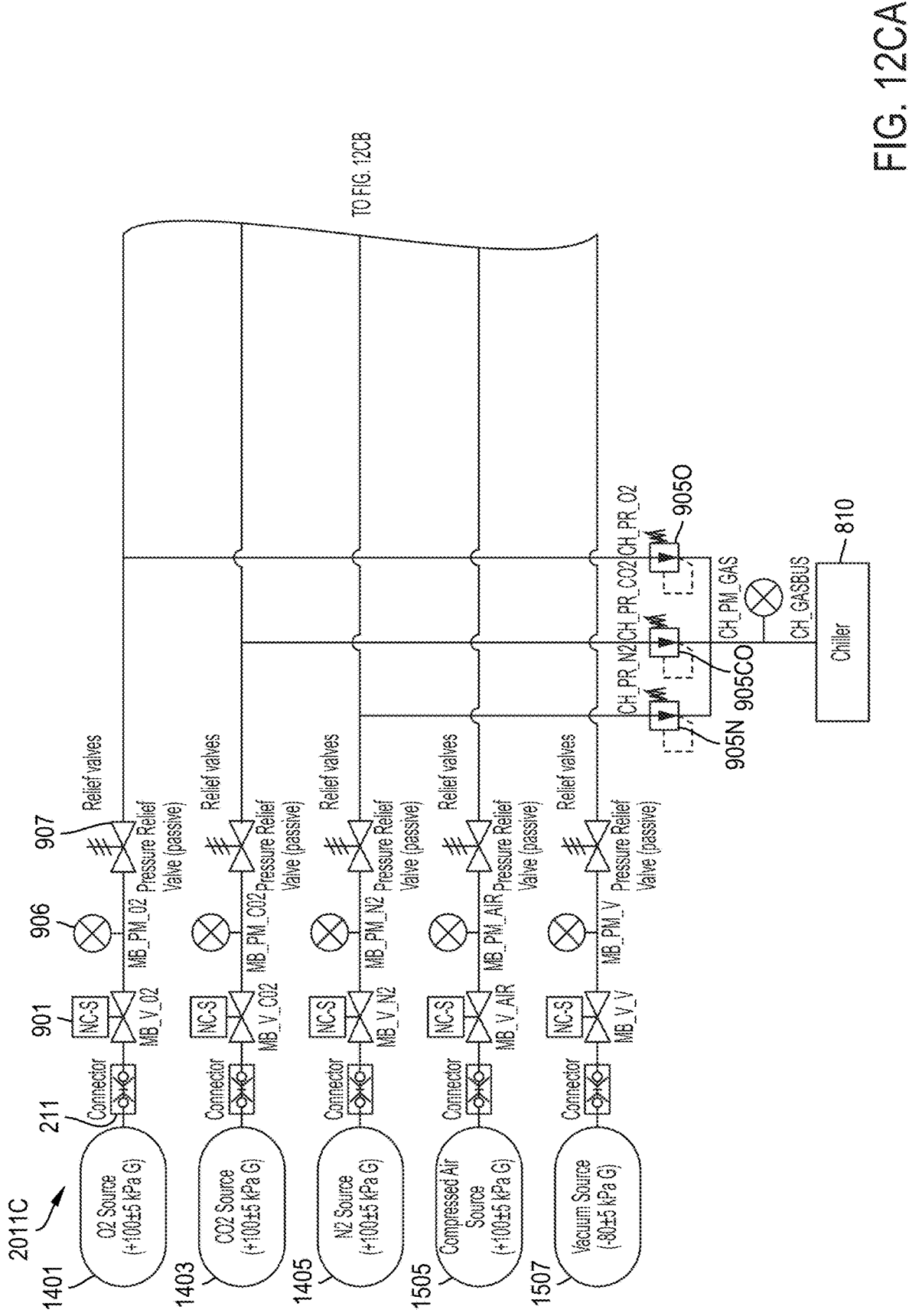
Figure 12C:
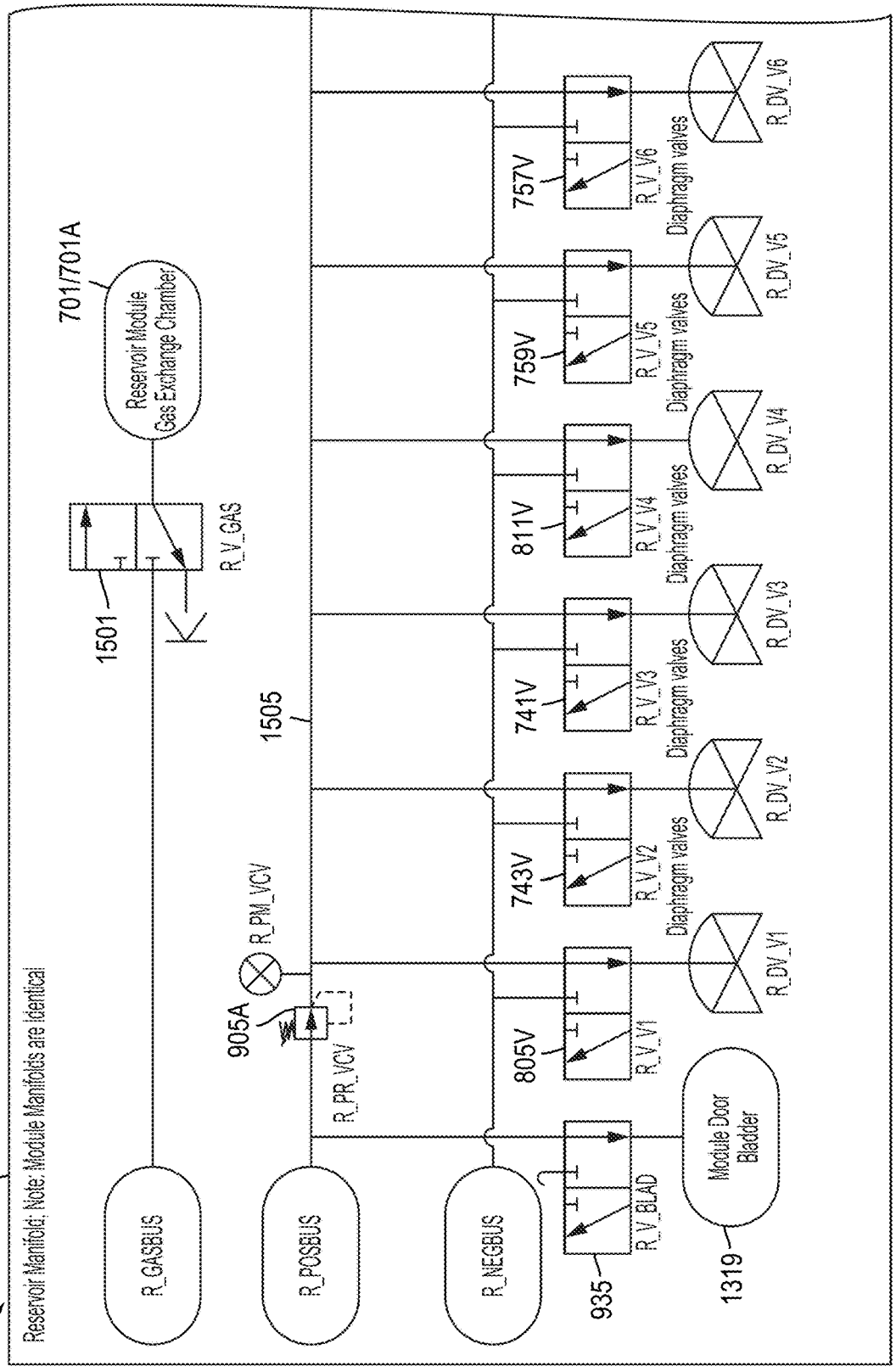
Figure 12C:
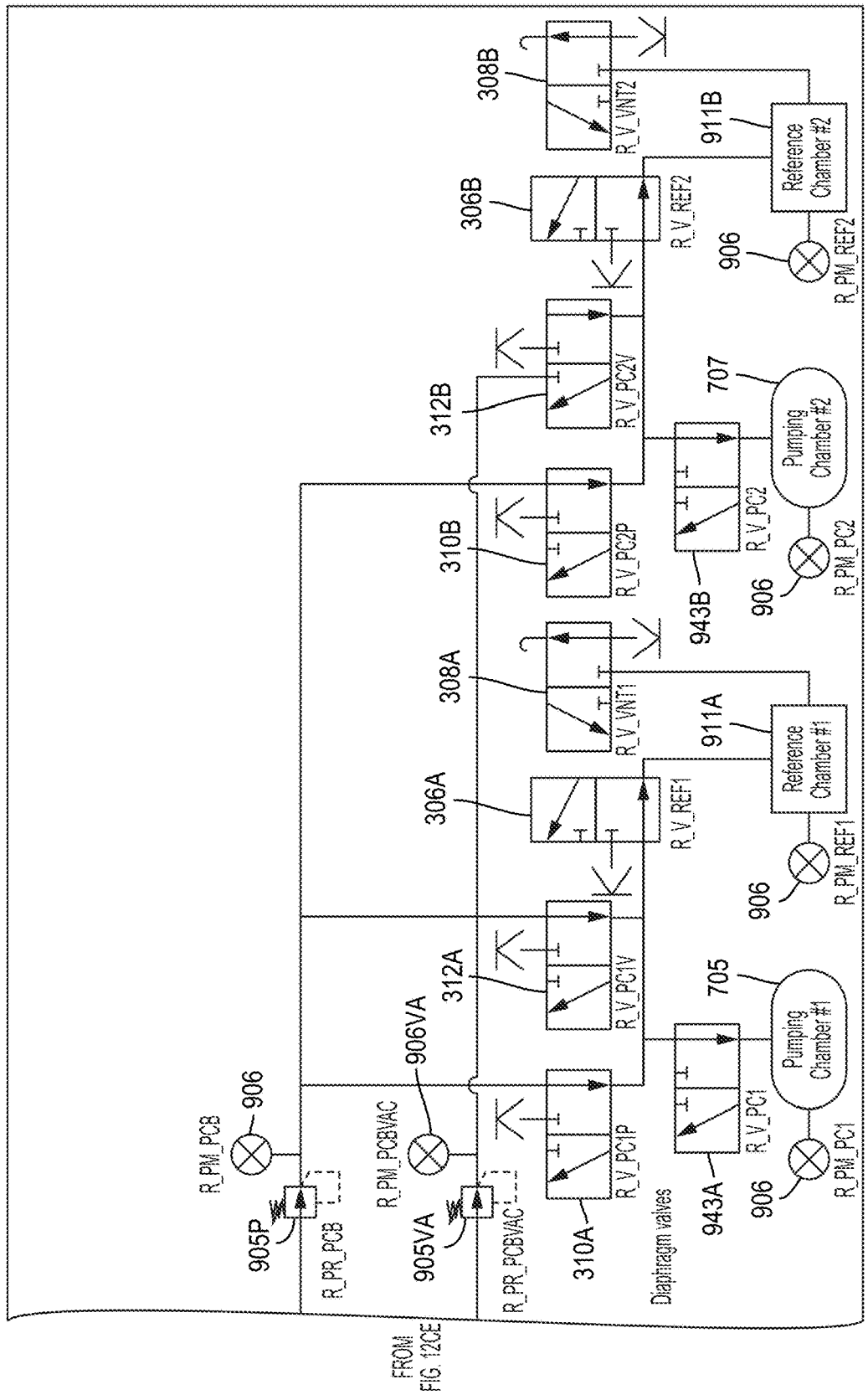
Figure 12D:
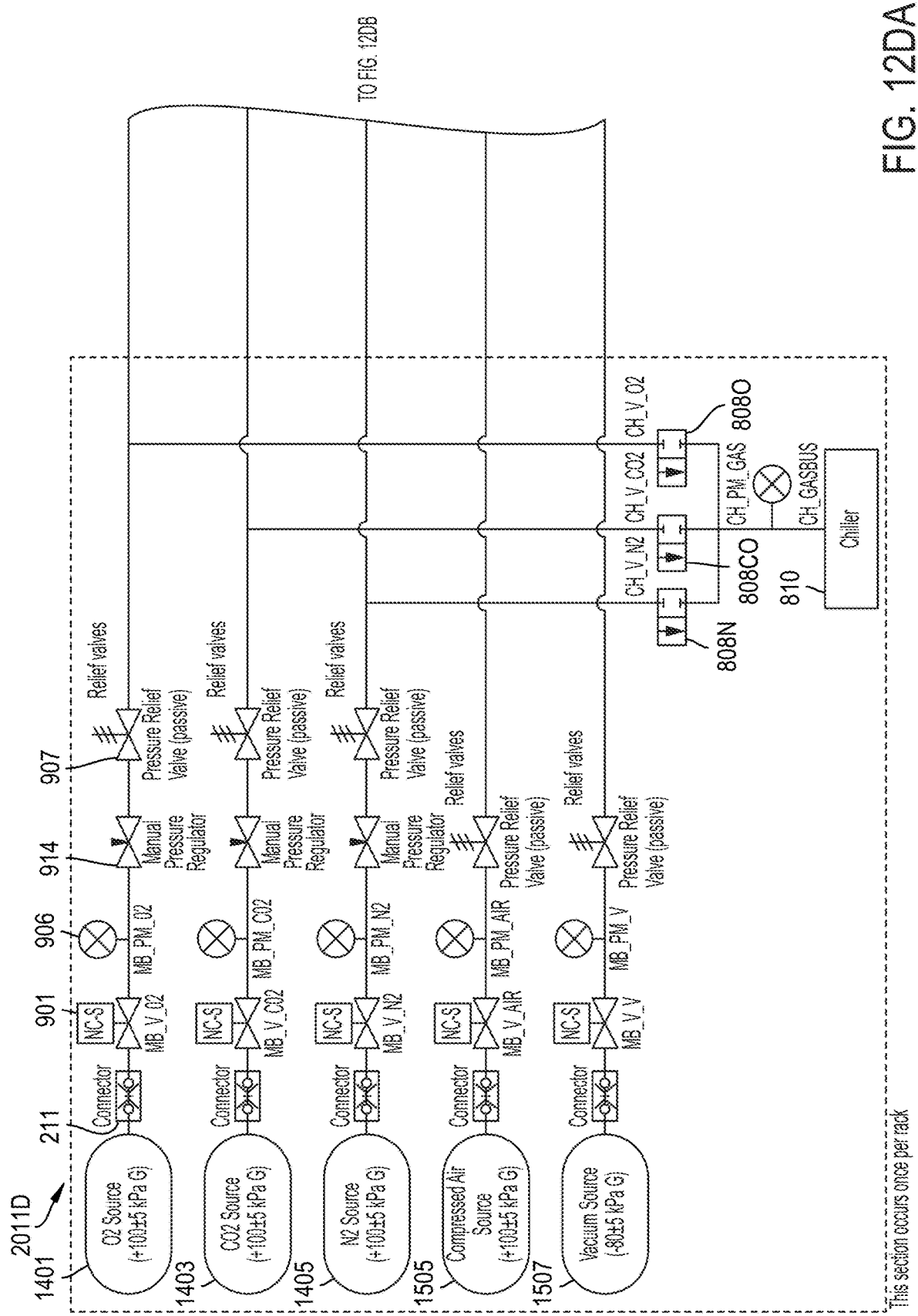
Figure 12D:
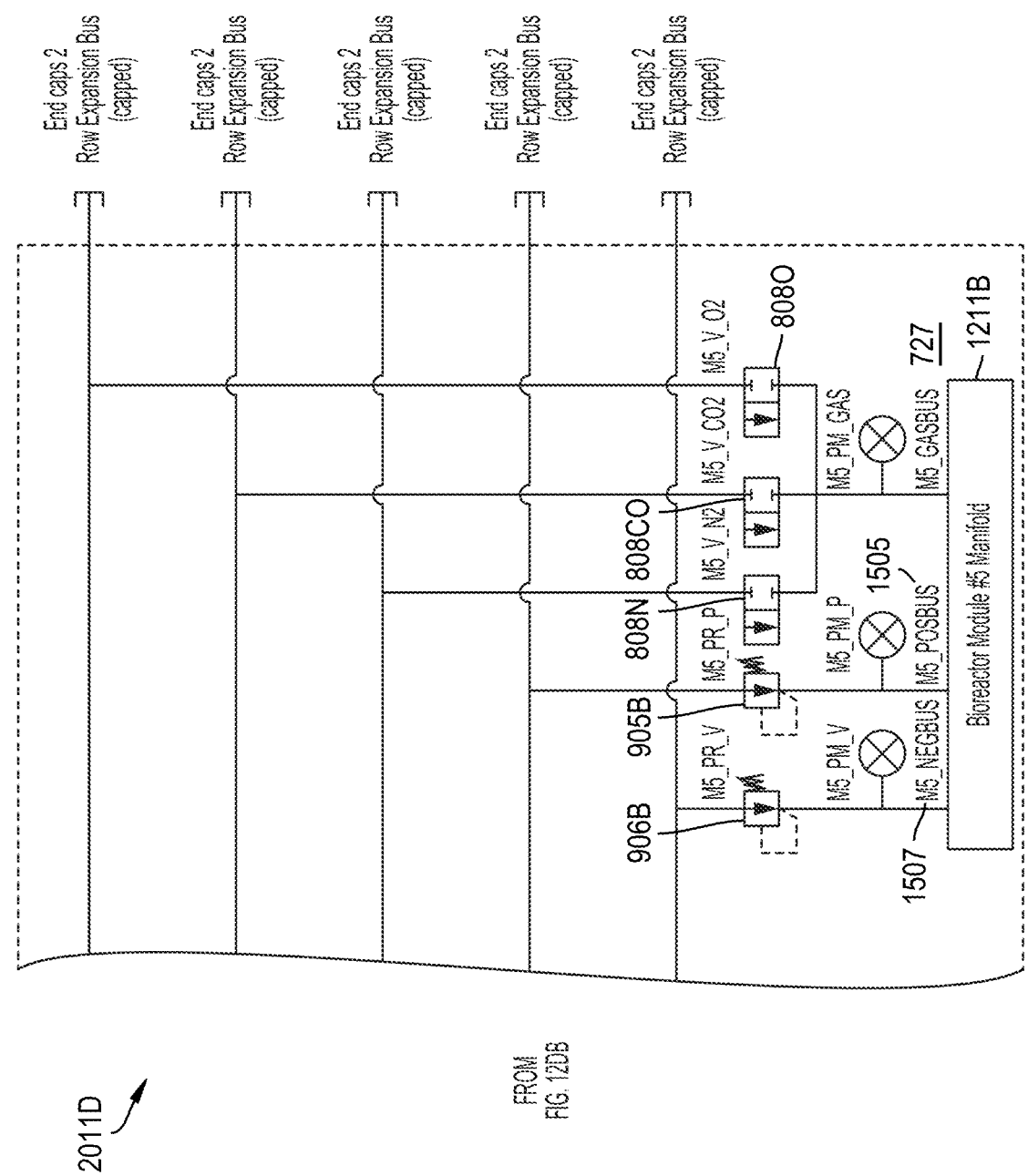
Figure 12D:
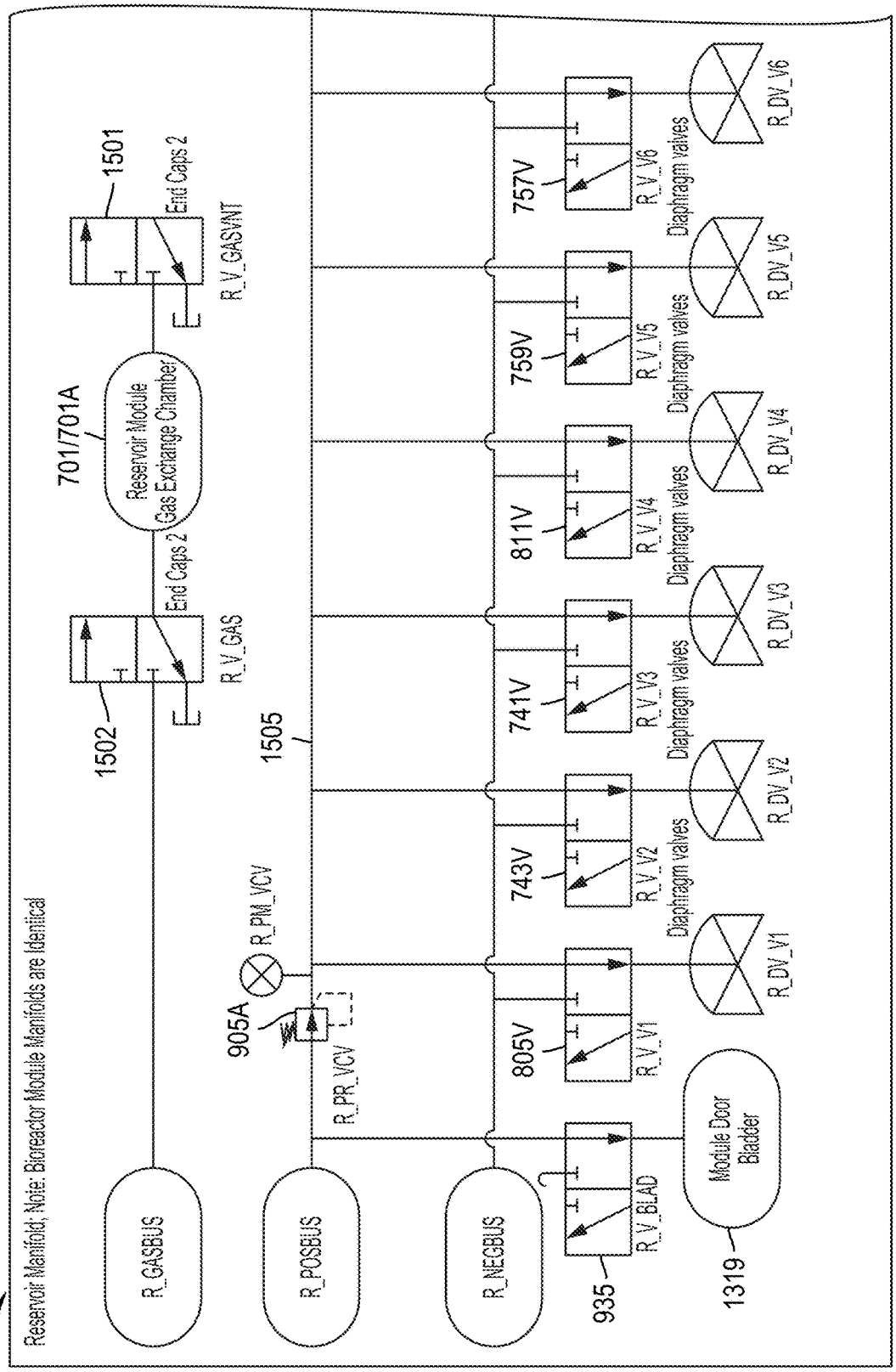
Figure 12D:
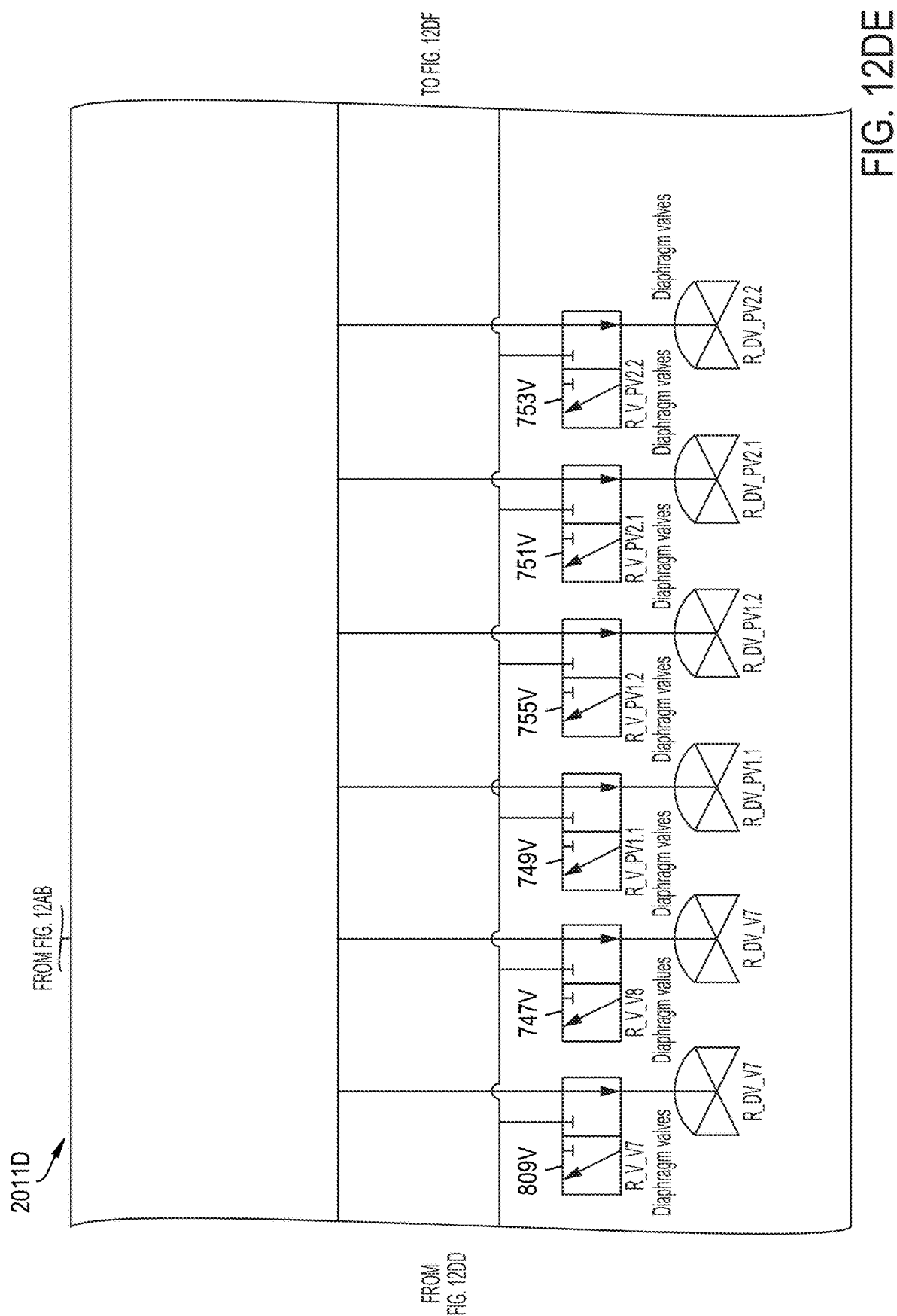
Figure 12D:
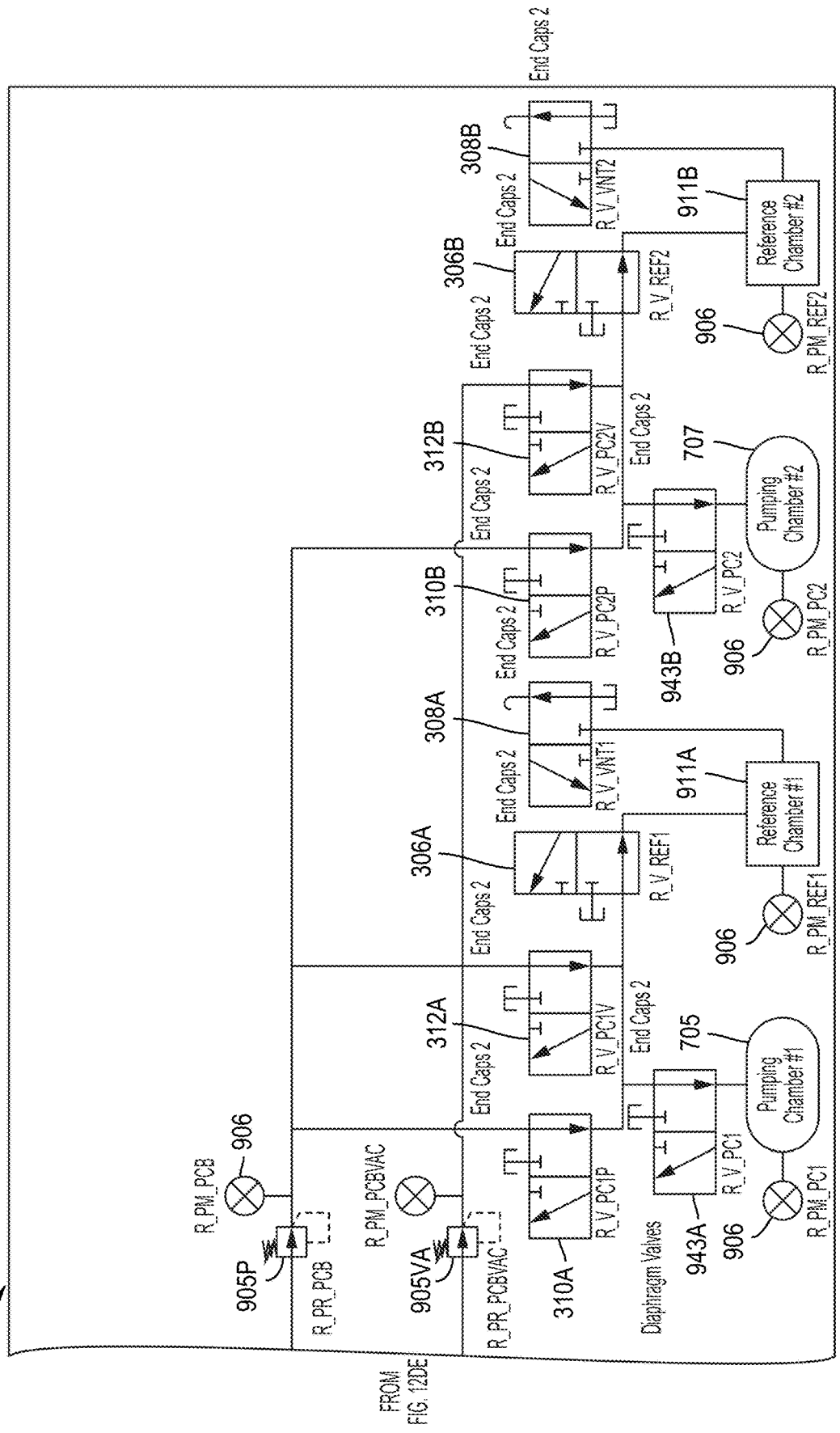
Figure 12E:
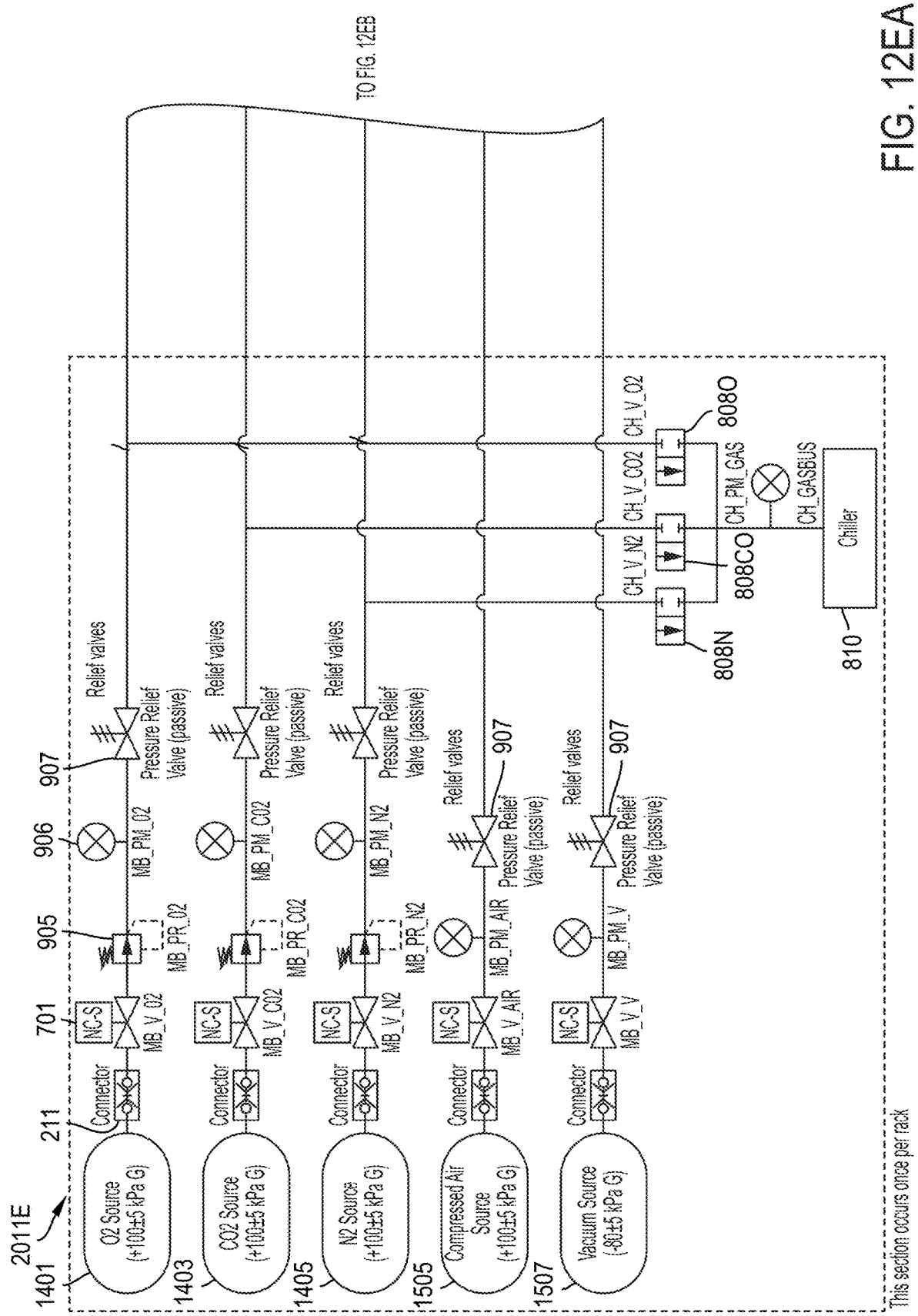
Figure 12E:
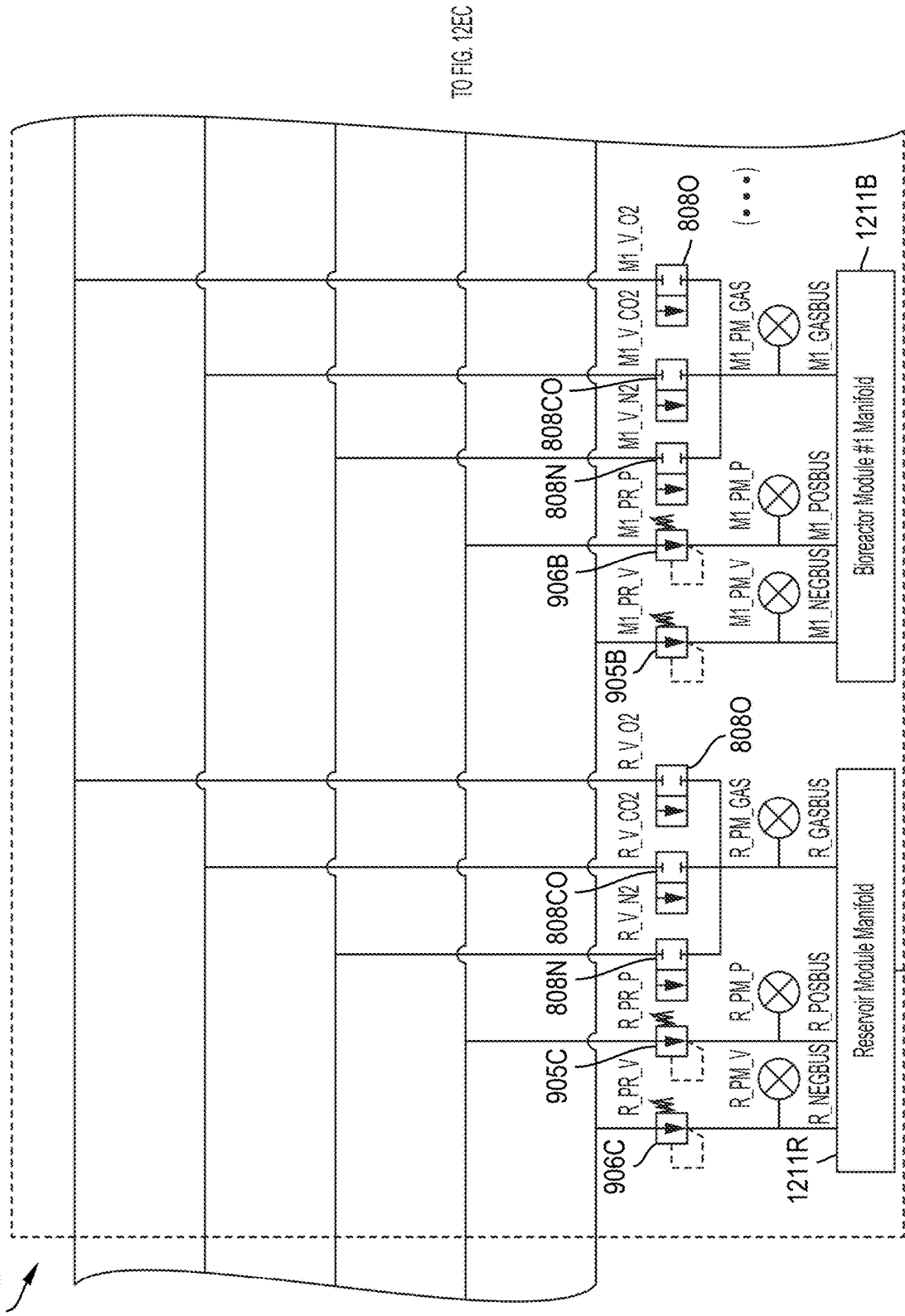
Figure 12E:
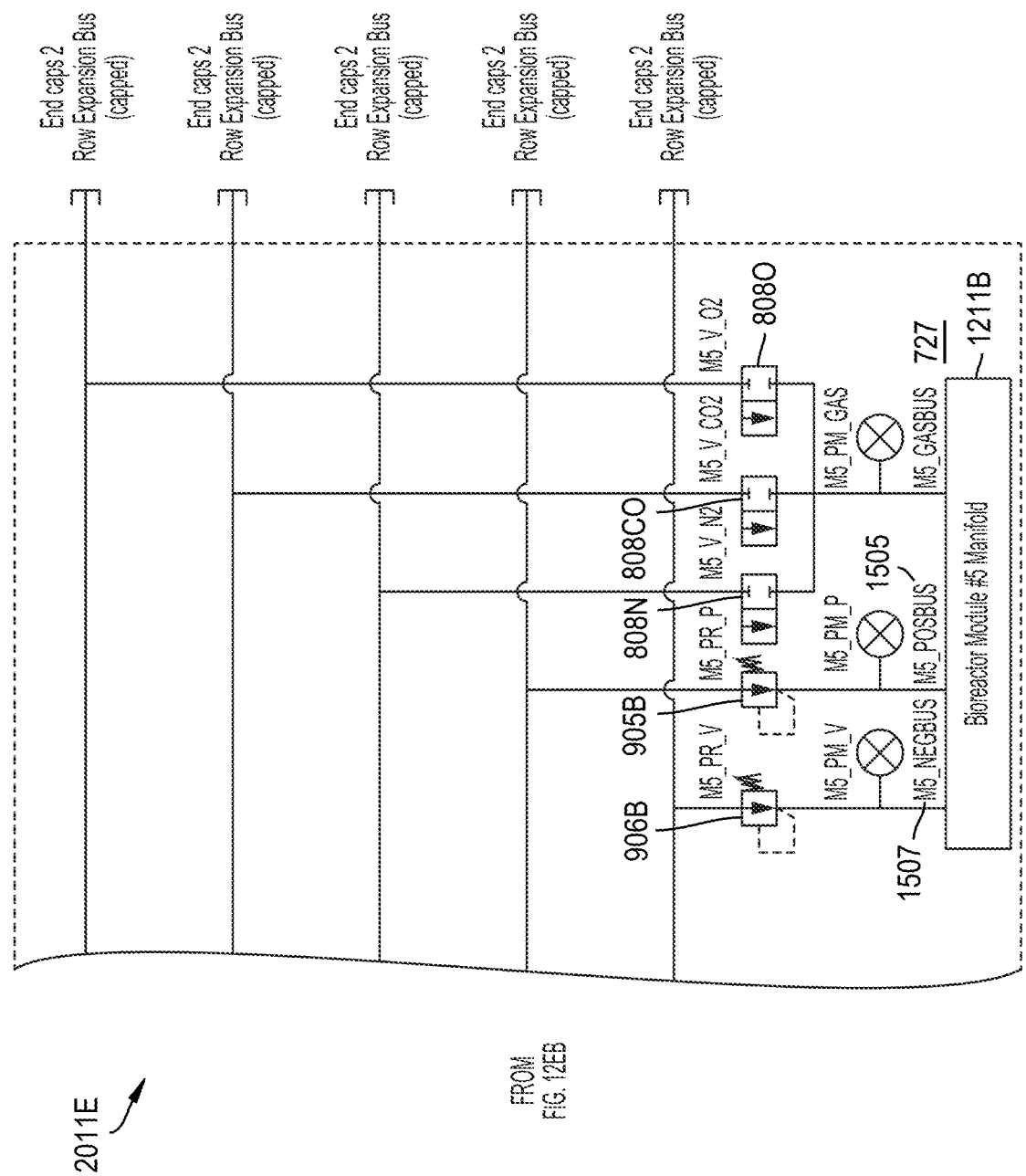
Figure 12E:
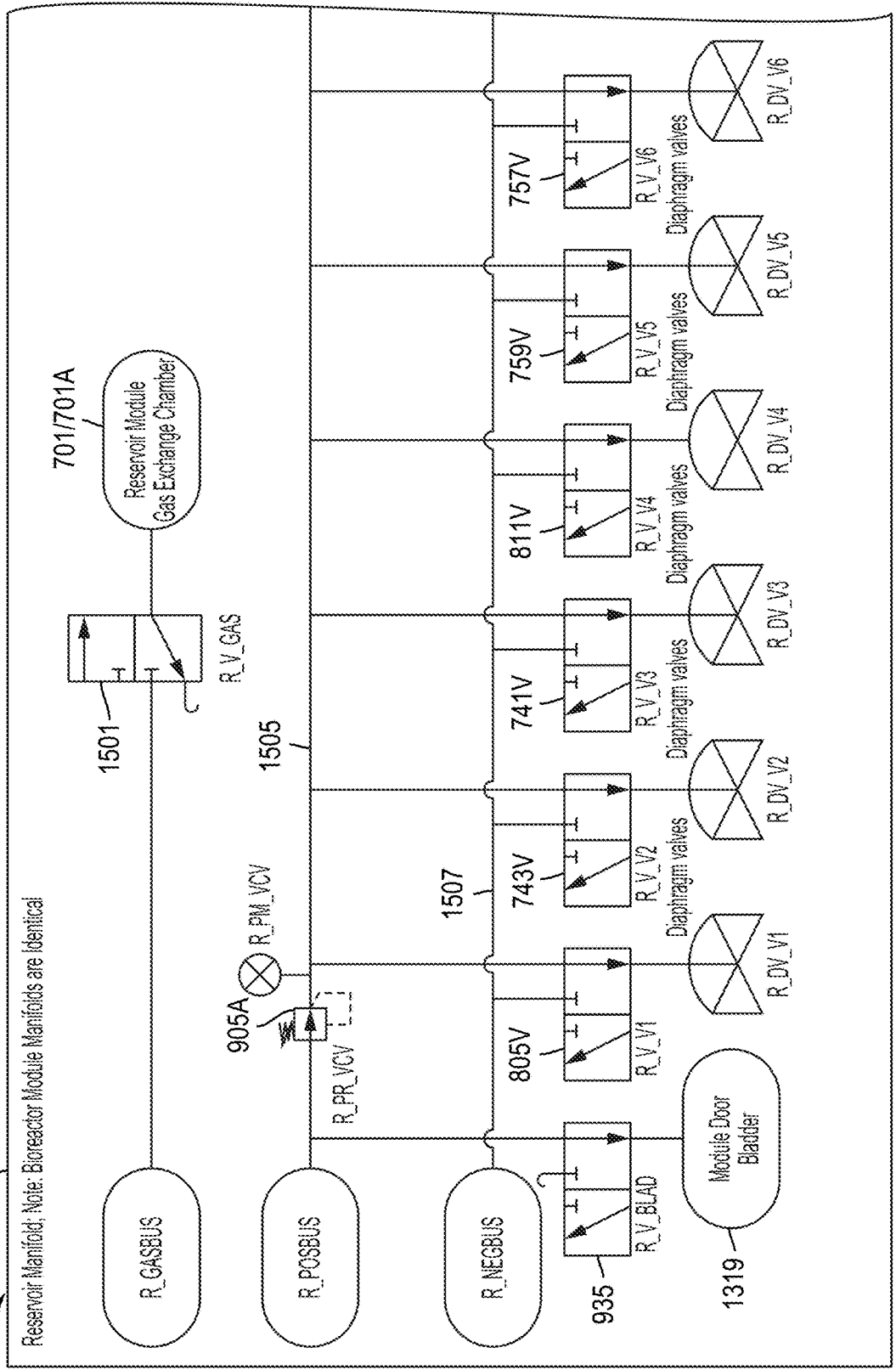
Figure 12E:
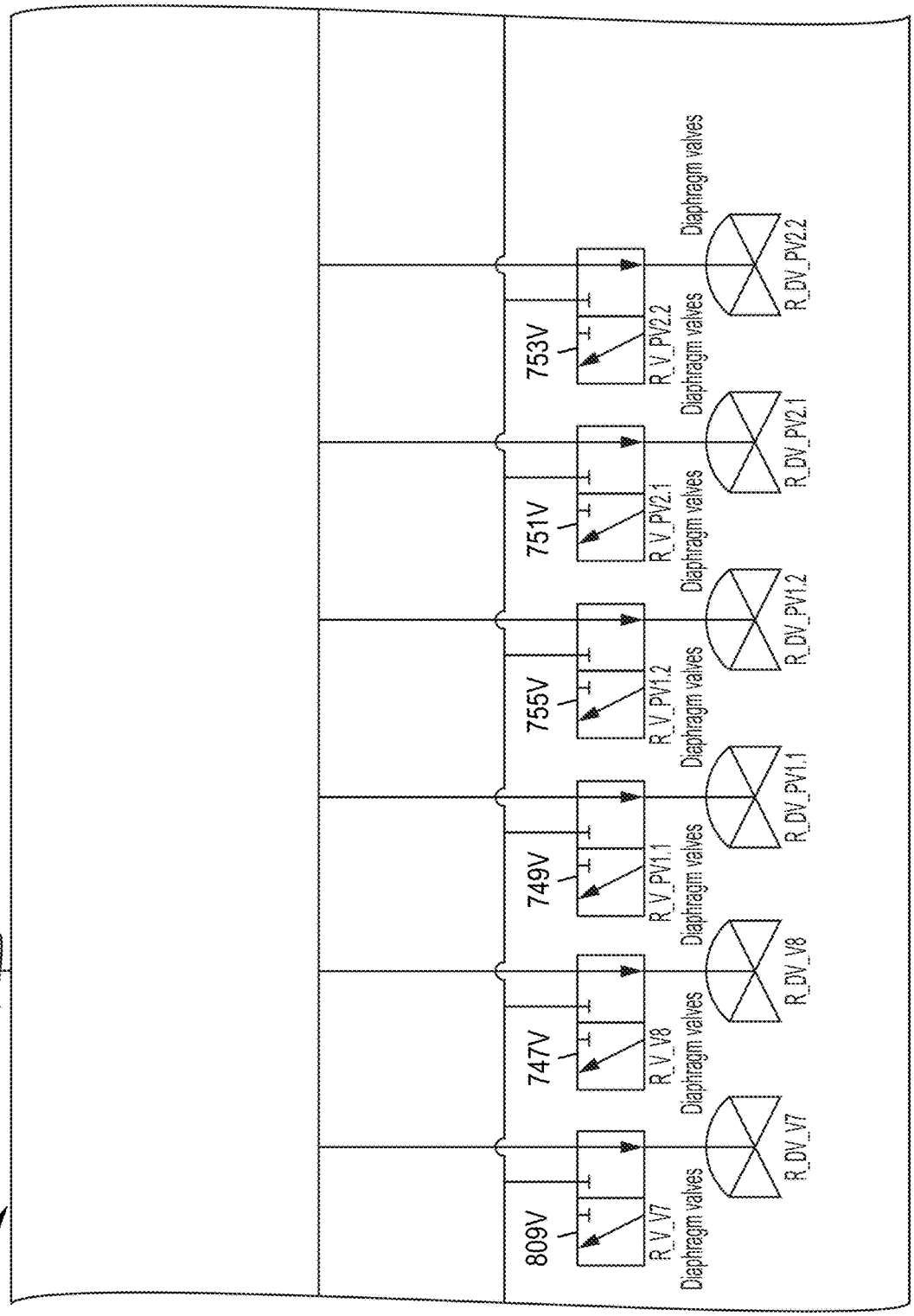
Figure 12E:
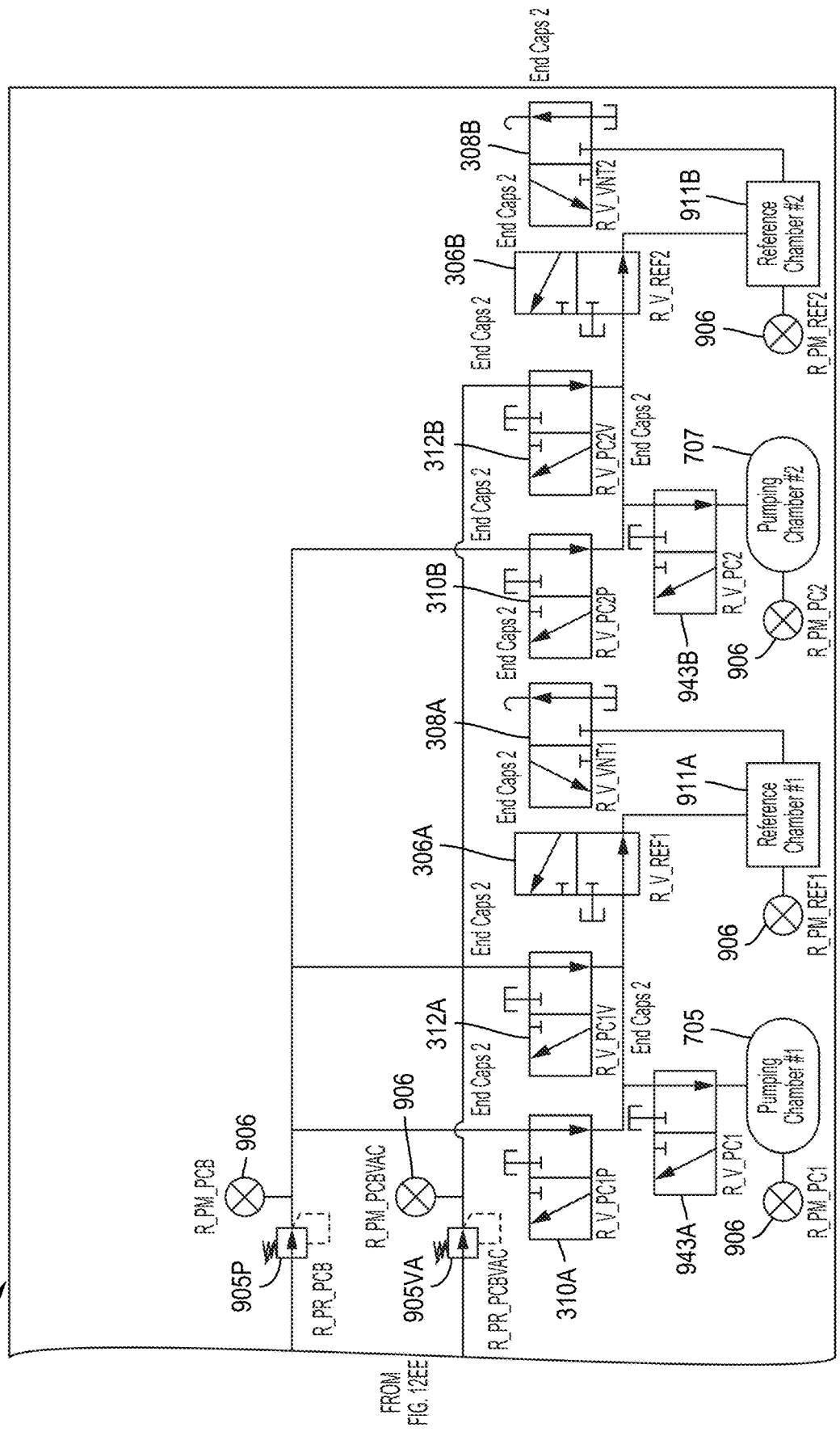
Figure 12F:
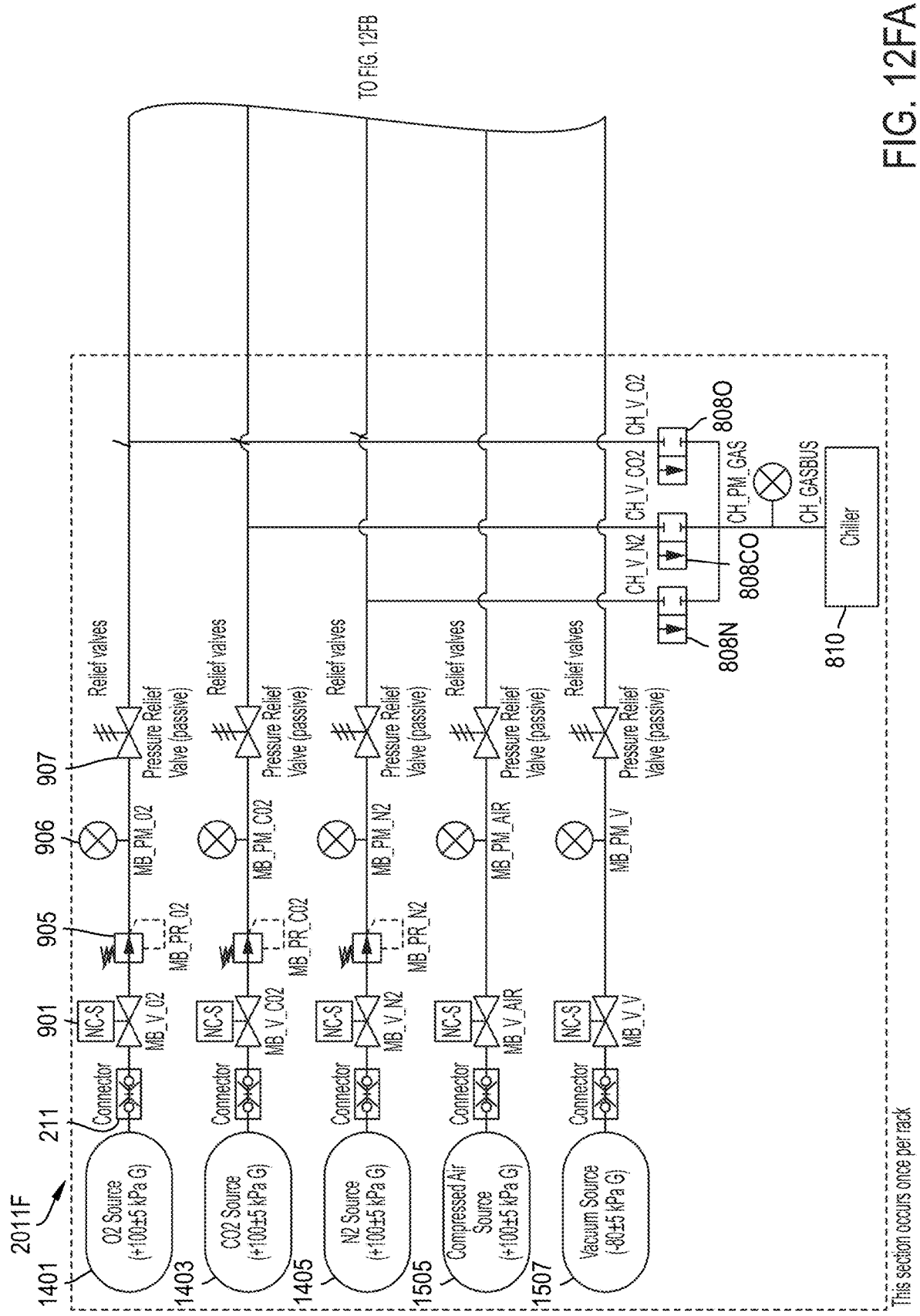
Figure 12F:
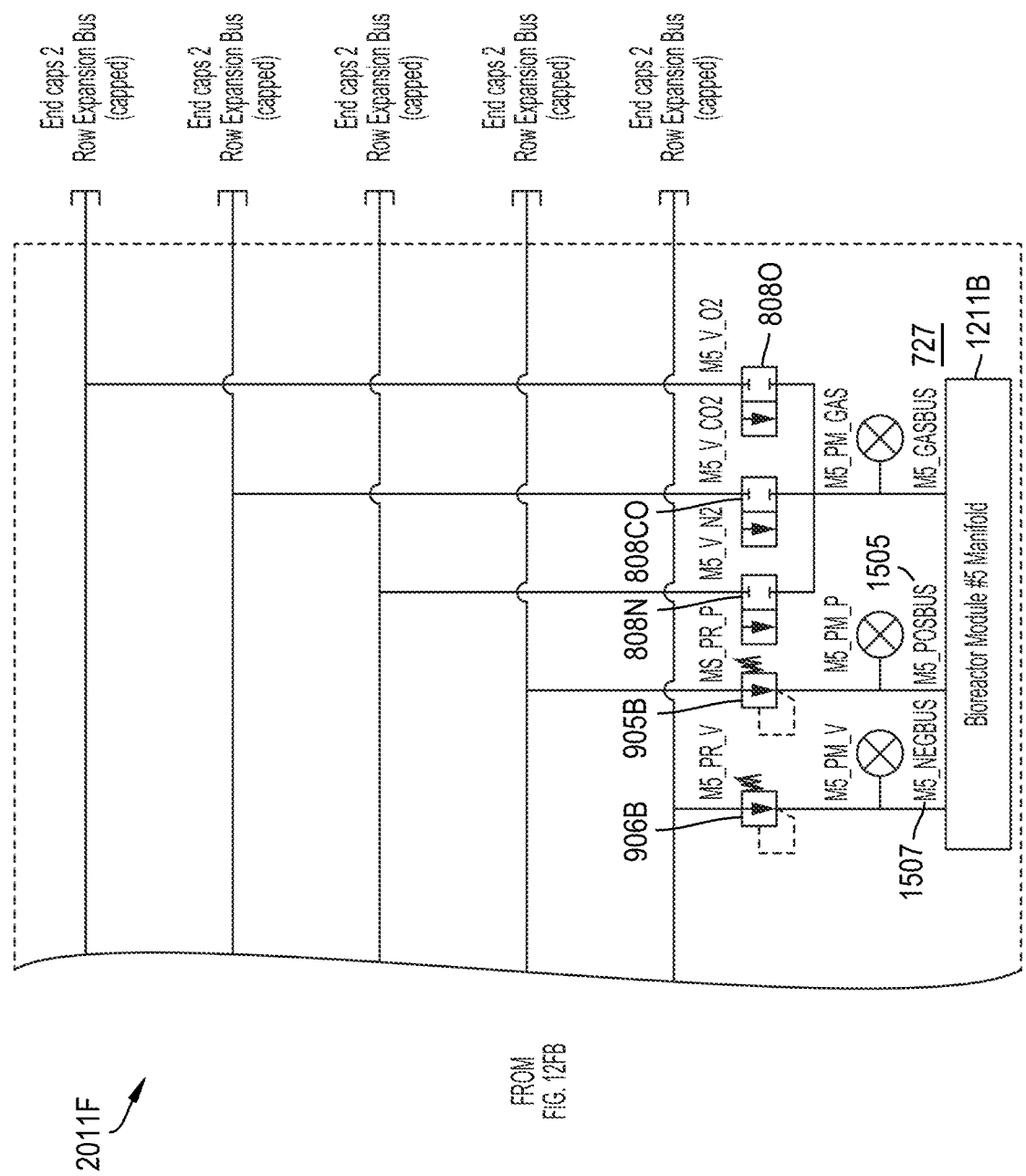
Figure 12F:
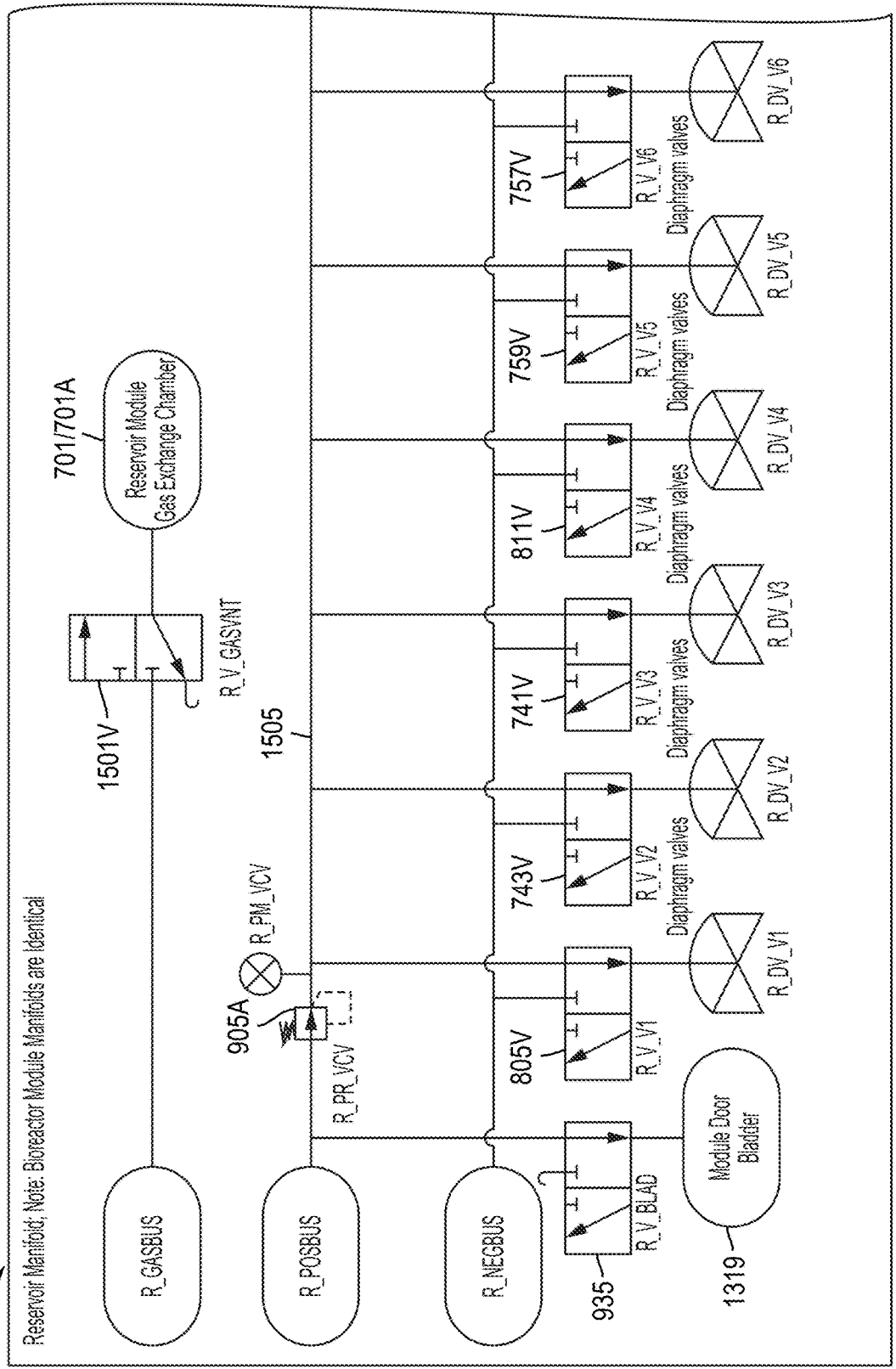
Figure 12F:
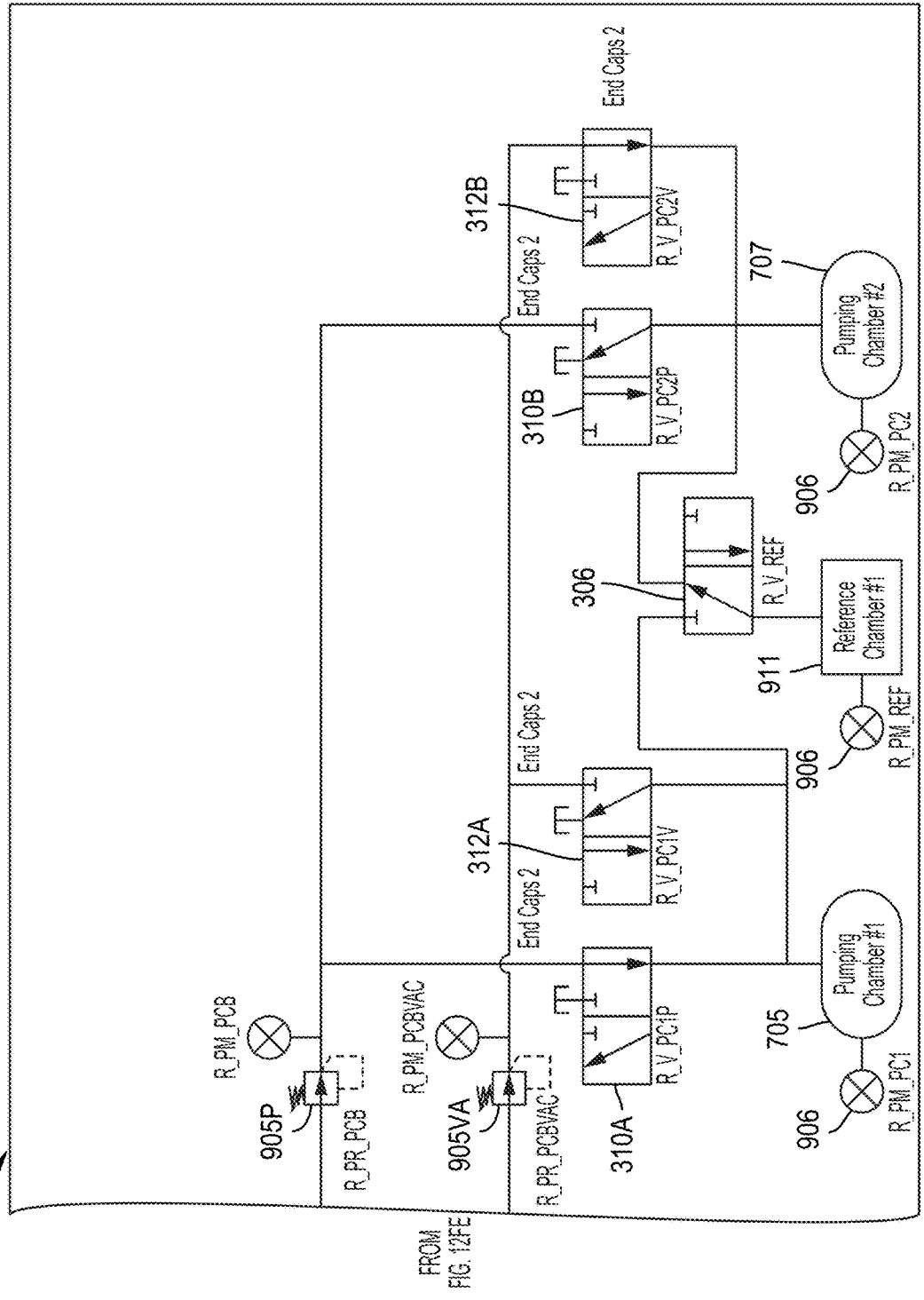
Figure 12G:
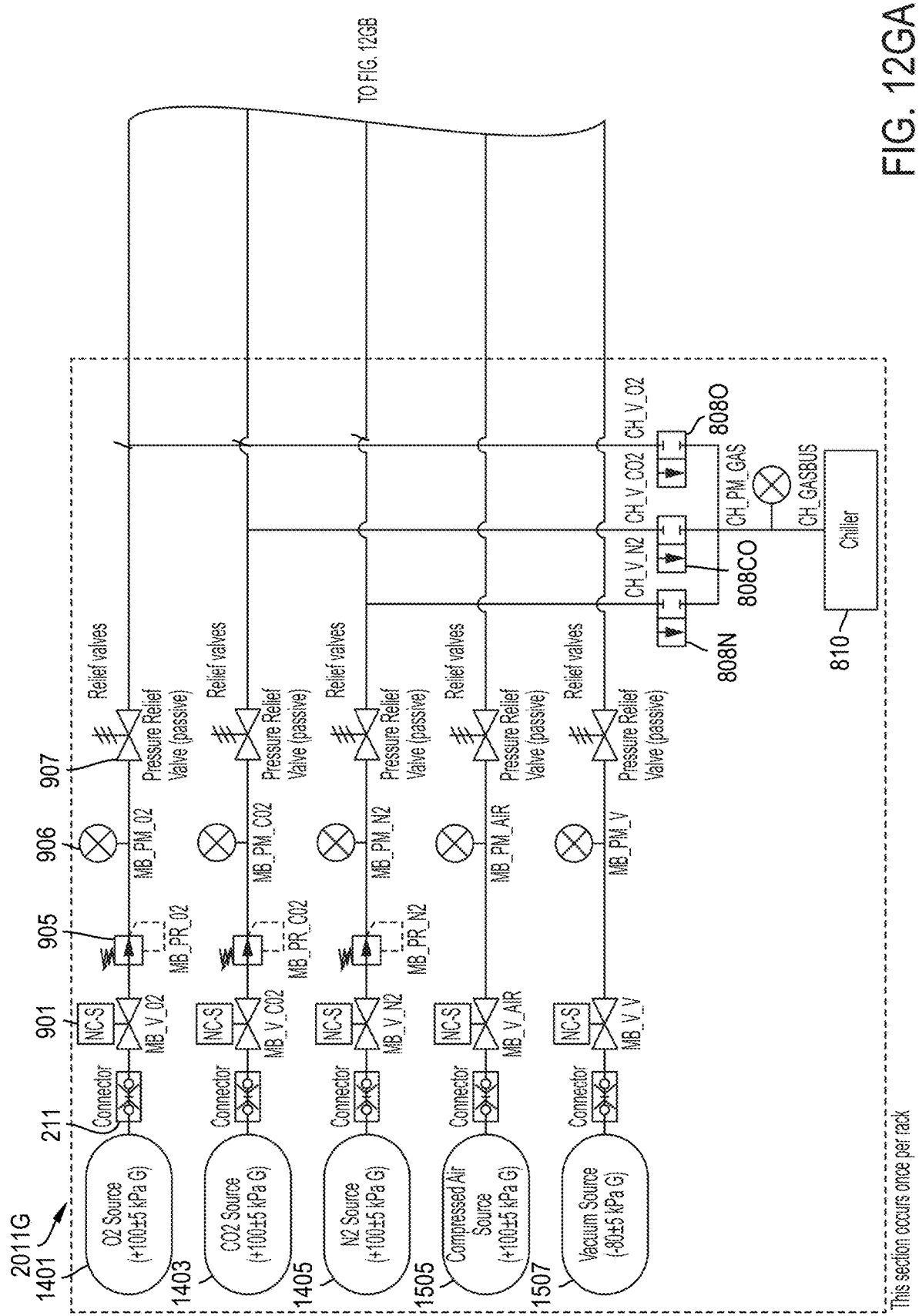
Figure 12G:
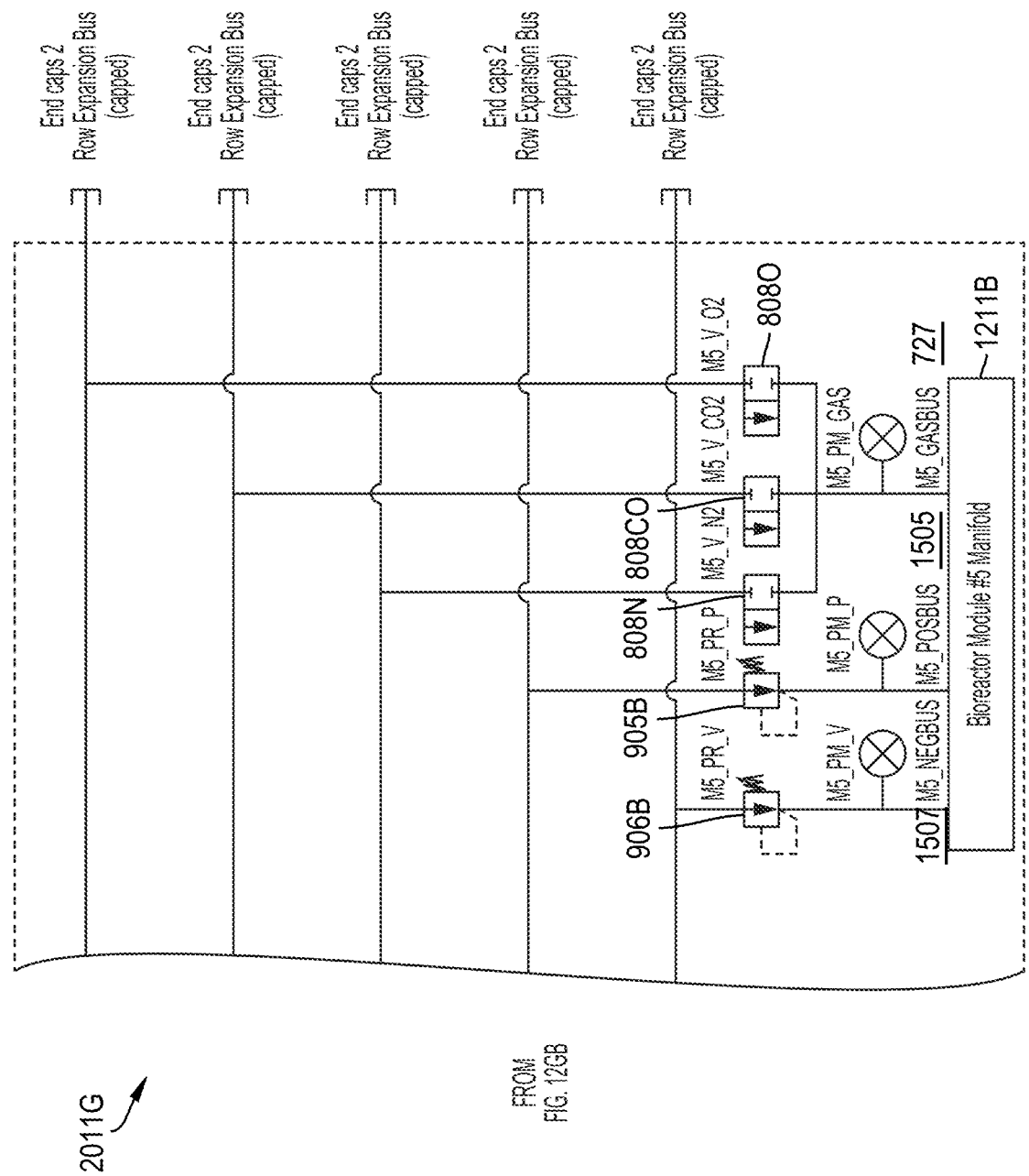
Figure 12G:
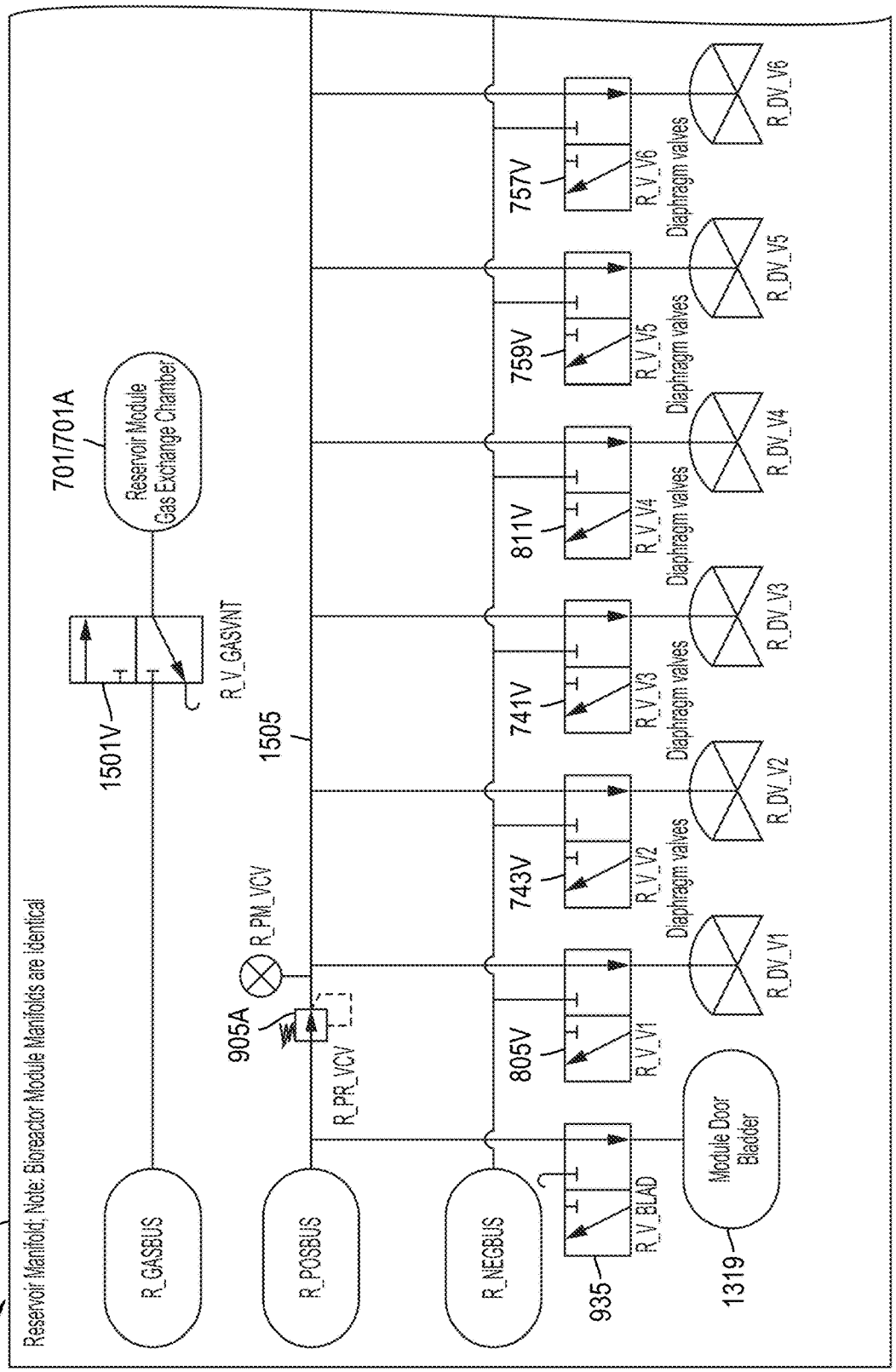
Figure 12G:
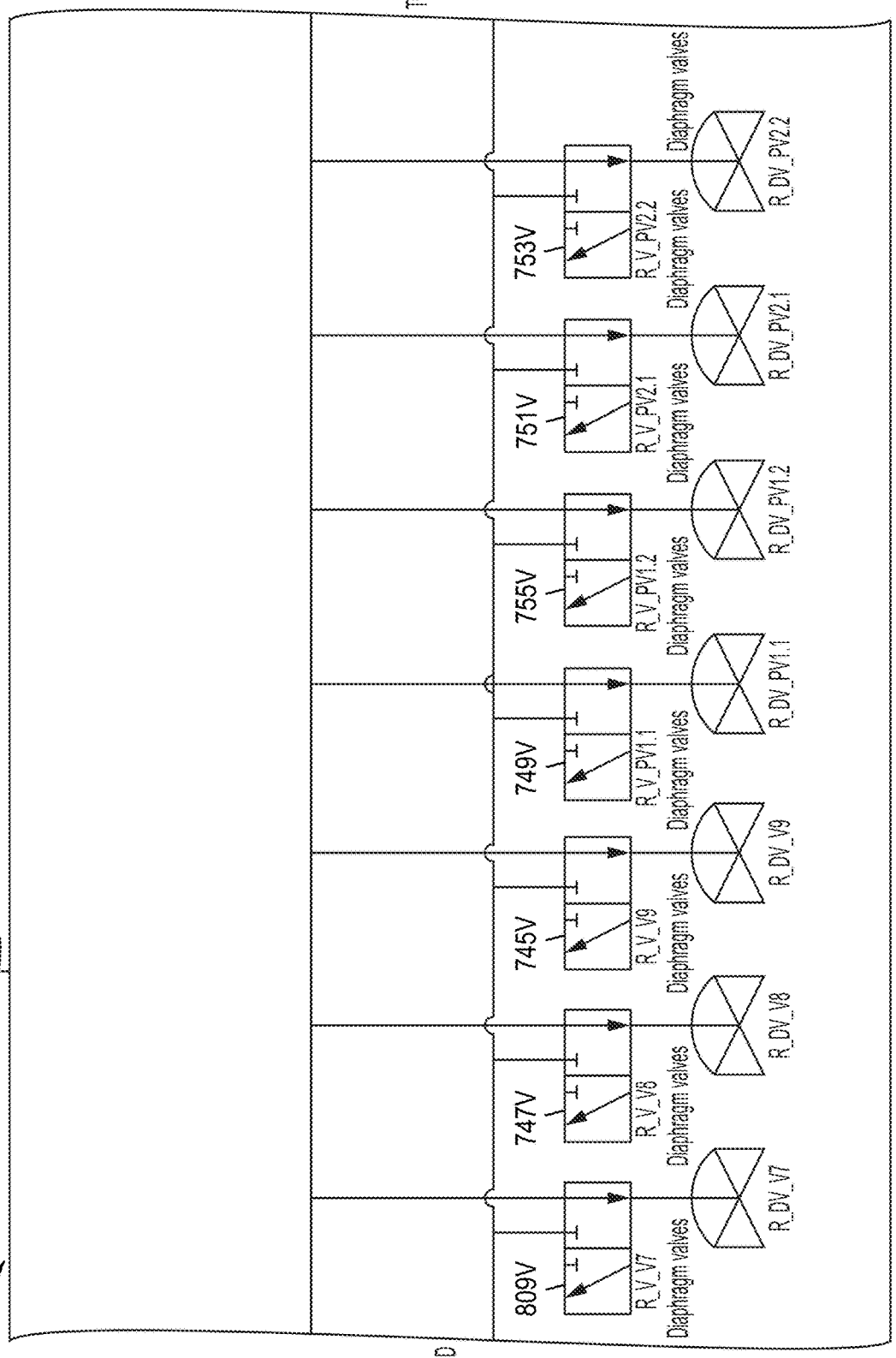
Figure 12G:
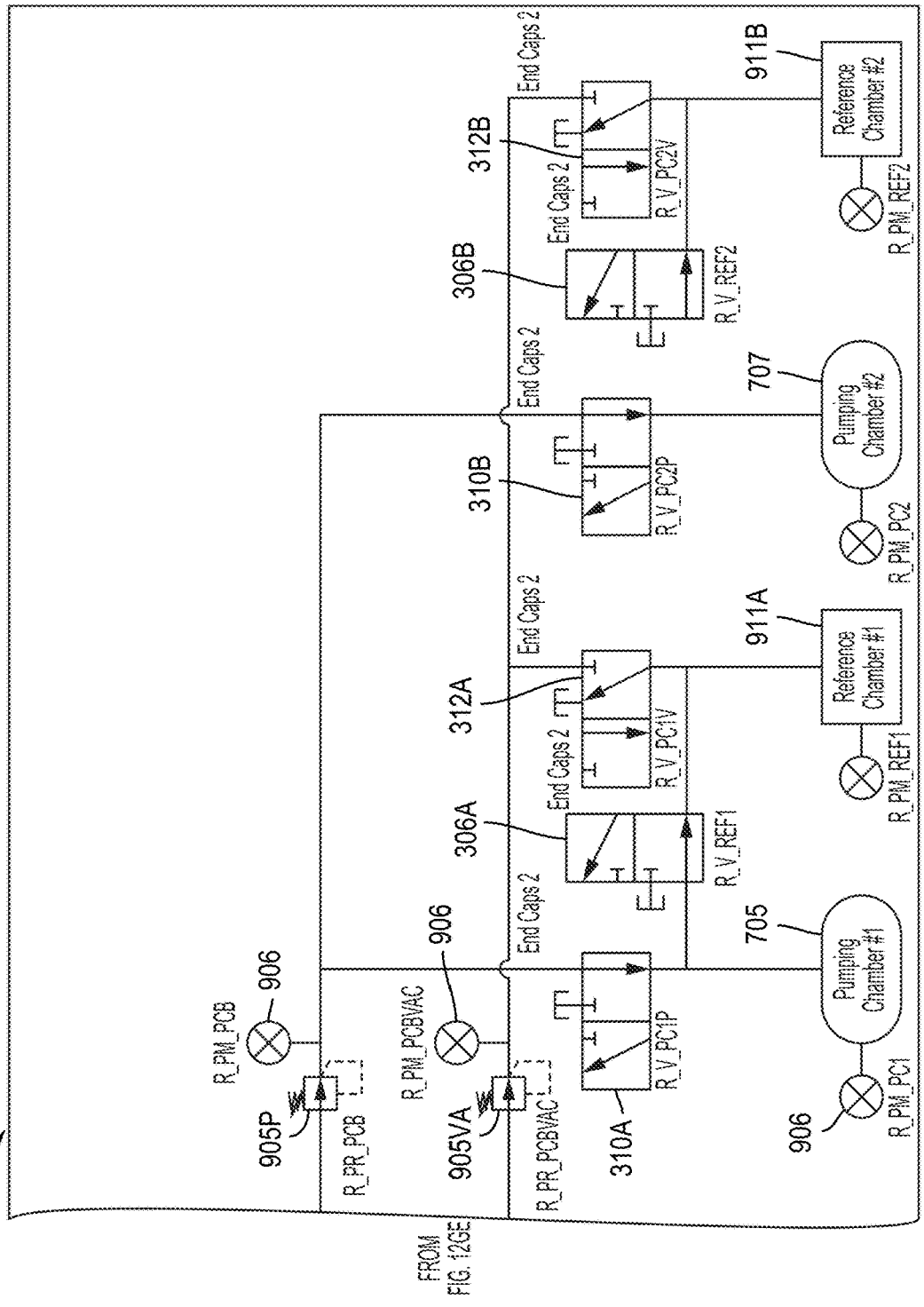
Figure 12H:
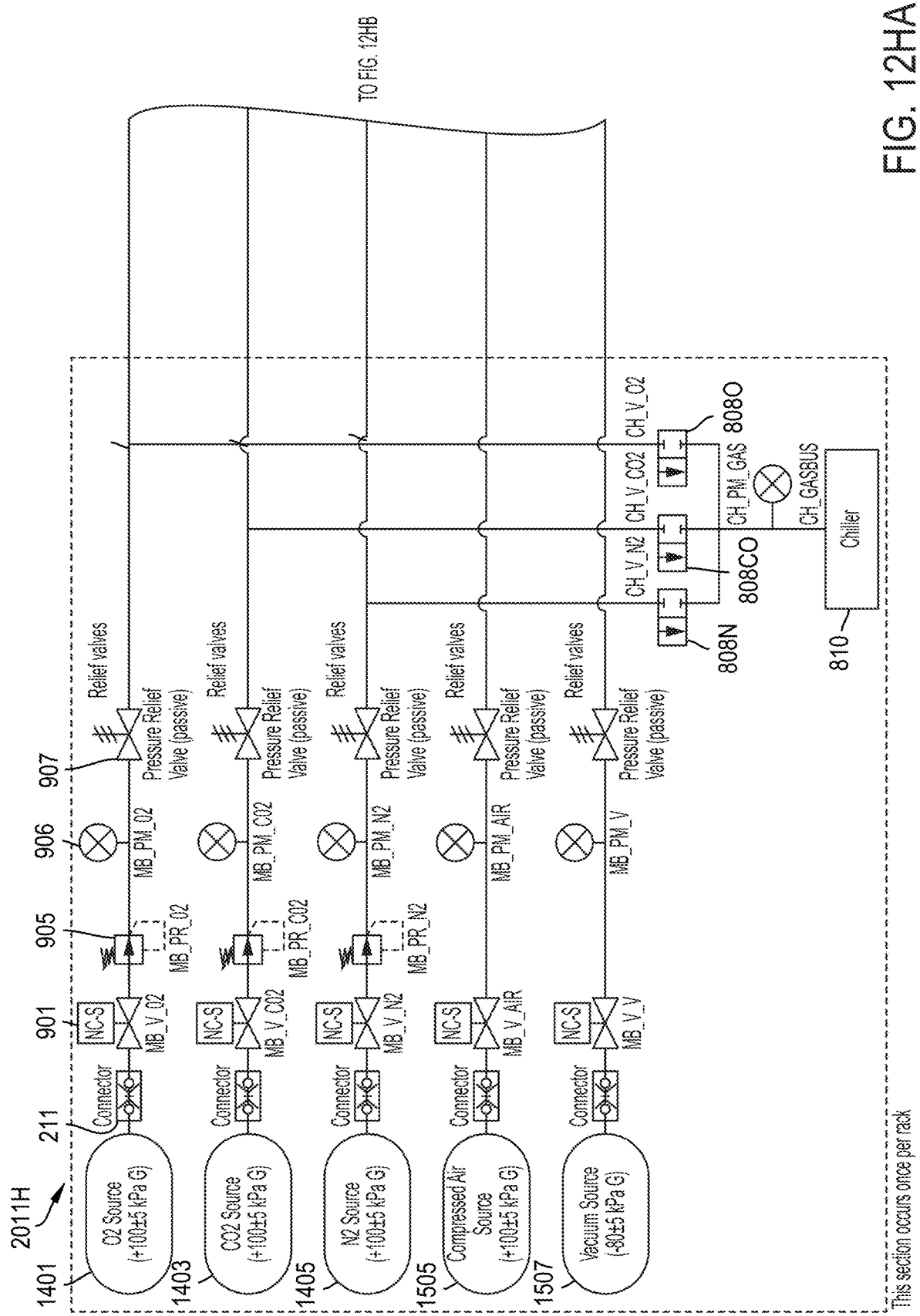
Figure 12H:
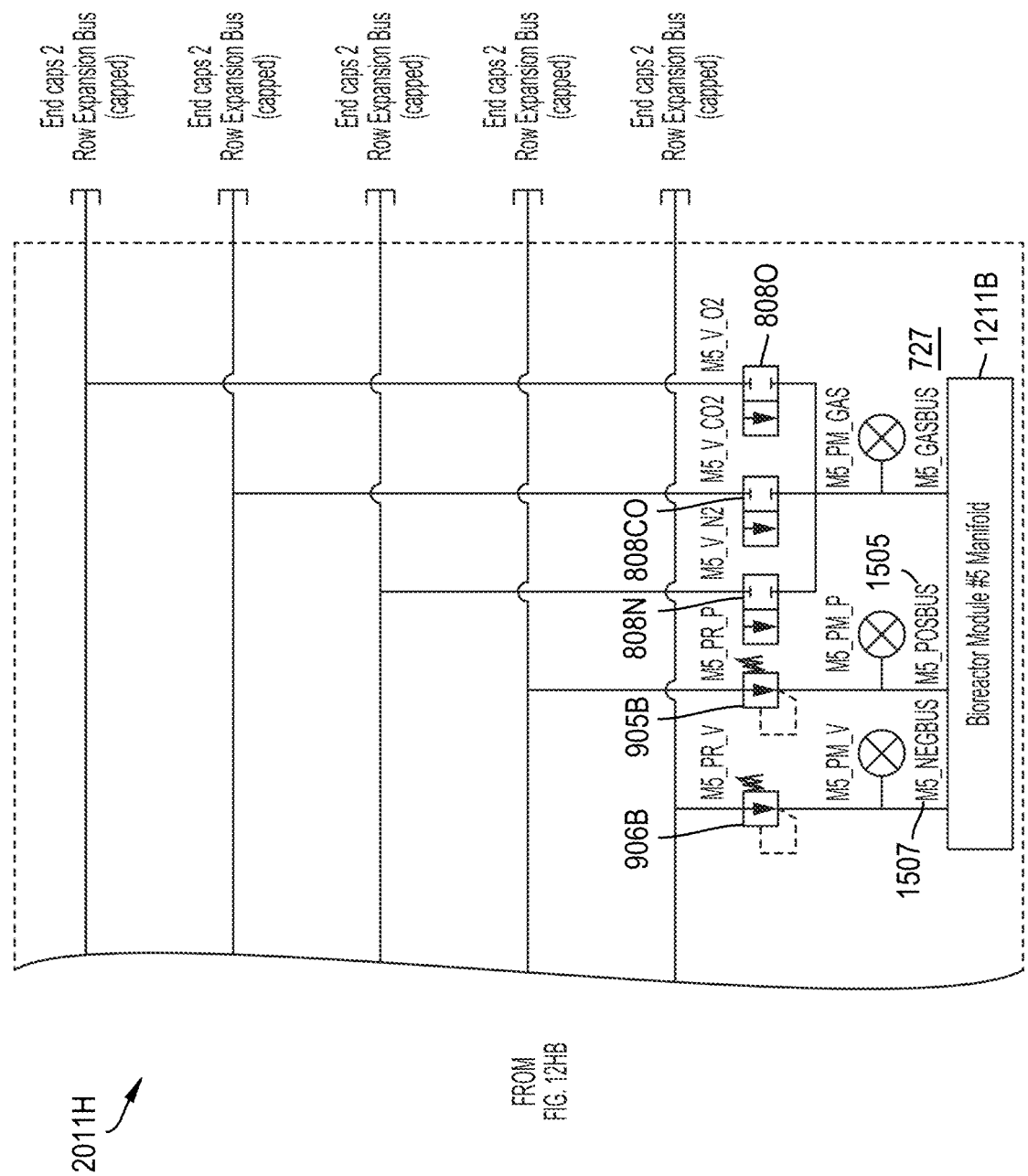
Figure 12H:
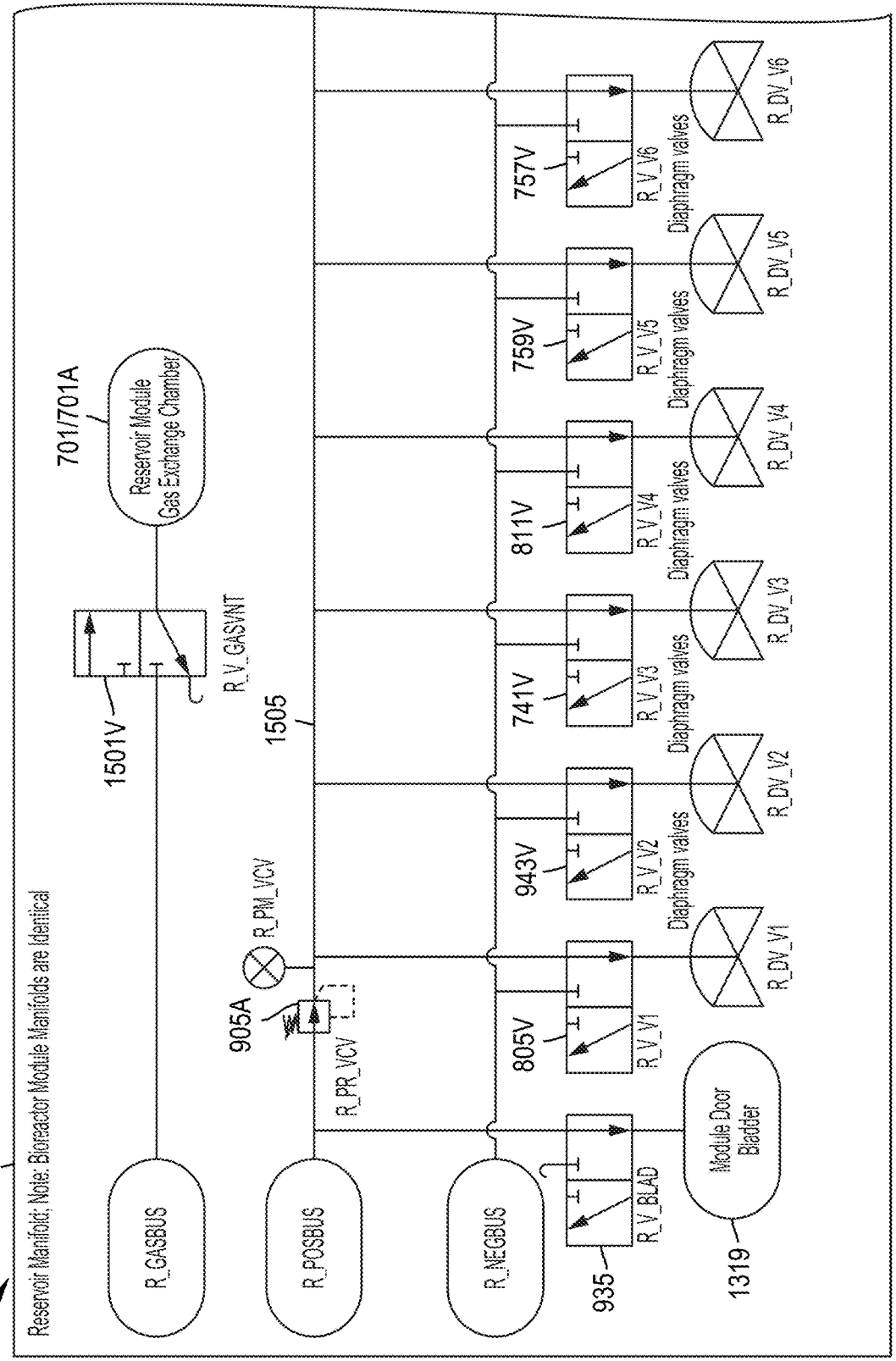
Figure 12H:
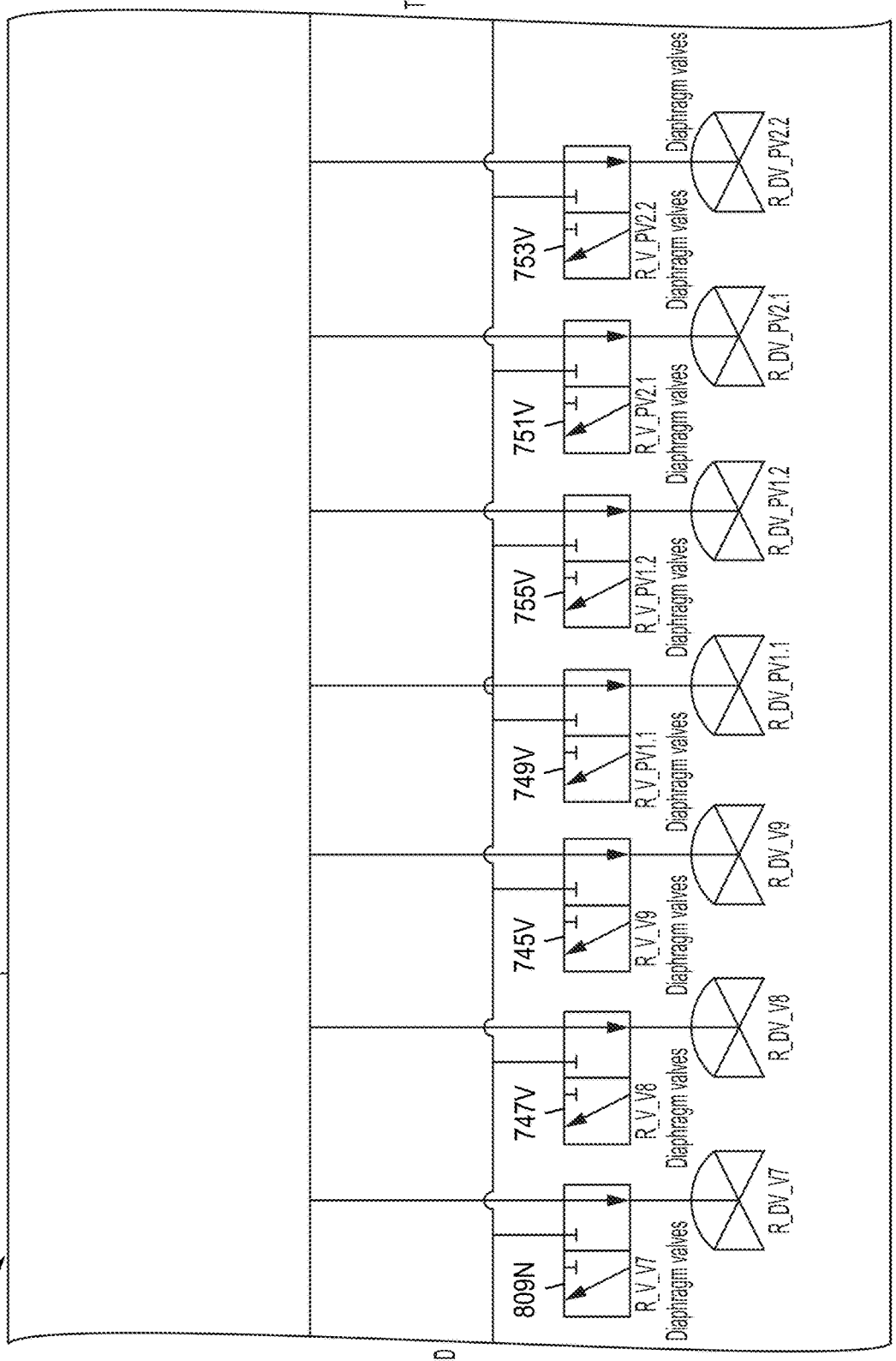
Figure 12H:
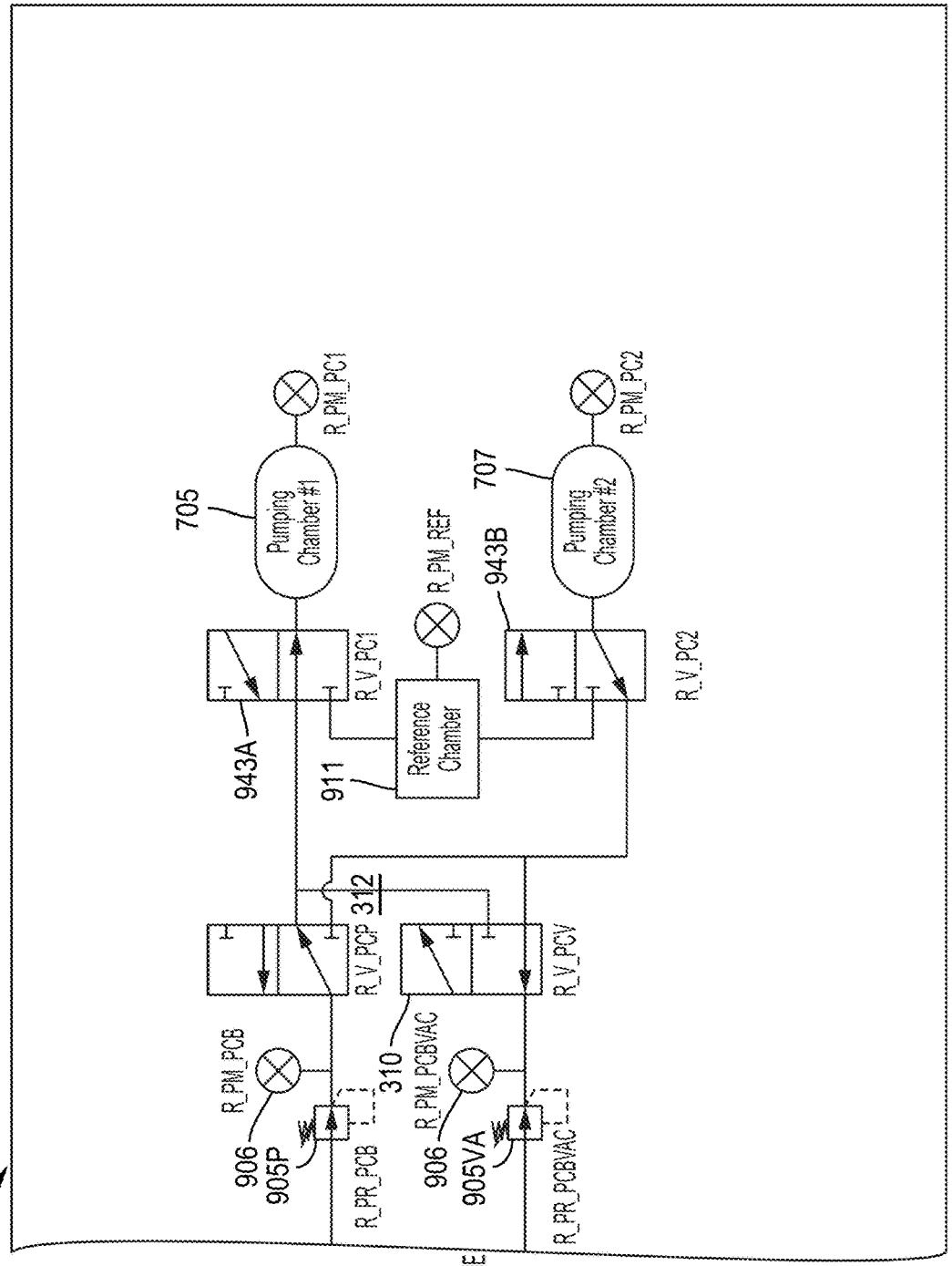

Referring now to FIGS. 12G-12I, an implementation of pneumatic rails 2011 (FIG. 12A), shown in conjunction with top plate 30055 (FIG. 14K) can include a component topography that can accommodate placement of groups 901/1305/1303 (FIG. 14K) of solenoid and 3/2 NC valves, and manifold pressure sensor board gasket 30071 (FIG. 14M), for example. In some configurations, cassette valves V1 805V-V9 745V, pumping valves 1.1 749V-2.2 753V, bladder valve 1319V, gas valves 901O, 901C, and 901N, pressure meters 705V/707V for pumping chambers 1/2, pressure meters for inlet FMS pressure and vacuum 1505PA/1505PB-1507VA/1507VB, reference chamber valves, vent 1408/1408a (FIG. 12H), vent bus 1407 (FIG. 12I), and vent valve 1408V for the gas exchange chamber can be implemented with FESTO® 3/2 NC valves, 10 l/min, for example. In some configurations, pumping chamber valves positive and negative pressure 310A-312B, reference chamber valves 306A/B, and vent valves 308A/B, and variable metering valves 2324L-2326H can be implemented with LEE® Company 3-port solenoid valves, for example (see also FIG. 14J). Manifold pump side plate 30053 can include flow paths that can route air according to valve orientation. Valve definitions laid out with respect to cassette 700 are likewise shown in FIG. 12I, along with reference chambers 911A/B, described herein.

Continuing to refer to FIGS. 12AA through 13E, at least one source 903 can include, but is not limited to including, compressible fluids such as, for example, compressed air and components of compressed air. In some configurations, positive pressure can be applied in the range of about 130 kPa to about 160 kPa. Positive pressure can be applied to reservoir module manifold 1211R through a proportional valve, and to bioreactor module manifold(s) 1 through proportional valve(s). In some configurations, there can be multiple of bioreactor module manifolds and proportional valves all receiving positive pressure from the same positive pressure source flowing along positive pressure bus. When positive pressure reaches reservoir module manifold 1211R, positive pressure can be applied to module door bladder 1319, according to bladder valve 935. Positive pressure can be applied to fluid valves V1 805 through V9 745 and pumping valves PV1.1 749 through PV2.2 753, each of which can be associated with a solenoid valve, through a valve monitored by pressure gauge 906. Positive pressure can travel from positive pressure bus through valve 941, which can control the pressure in pumping chamber 705. A similar positive pressure path can be followed for pumping chamber 707. Positive pressure can be provided to reference chamber 911A as described herein.

Continuing to still further refer to FIGS. 12AA through 13E, in some configurations, negative pressure, i.e. vacuum, can be applied in the range of about 30 kPa to about 60 kPa. Negative pressure can be applied to reservoir module manifold 1211R through a proportional valve, and to bioreactor module manifold(s) 1211B through proportional valve(s). In some configurations, there can be multiple of bioreactor module manifolds 1211B and proportional valves all experiencing negative pressure applied along negative pressure bus.

Continuing to refer to FIGS. 12A through 13E, in some configurations, proportional valves 1301 (FIG. 12B) can be positioned upstream of pumping chambers 705/707 and reference chambers 911A/B to provide gas delivery flow rate control at varying flow rates. In a configuration including ten valves, the system can provide independent control of each pumping and reference chamber. In some configurations, the number of valves can be reduced from ten to six to save cost and reduce footprint, but—FMS is not possible. In some configurations, the number of valves can be reduced to five, both pumping chambers 1/2 705/707 can operate from common reference chamber 911A, but FMS cannot be performed on both pumping chambers at the same time and pumping cannot occur while performing FMS. In some configurations, the number of valves can be reduced to four, and both pumping chambers 1/2 705/707 can operate from common reference chamber 911A, but pumping chambers cannot be operated independently.

Continuing to refer to FIGS. 12A through 13E, in some configurations, pumping and reference chamber valve configurations can be used to meter fluid flow at various pressures. In some configurations, proportional valves 1301 can be replaced with 2/2 direct operation valves. In some configurations, proportional valves can be configured in parallel with 2/2 or 3/2 valves. In some configurations, proportional valves can be used for delivery flow rate control at relatively larger flow rate ranges, for example, between <1 mL/min to >1000 mL/min, and 2/2 or 3/2 valves can enable a relatively large pressure differential for fluid management. Parallel placement of 2/2 or 3/2 valves and proportional valves can enable coarse control with the 2/2 or 3/2 valve and fine control with the proportional valve. This configuration can increase the total maximum flow rate because resistance can be reduced. In some configurations, a 2/2 or 3/2 valve can be configured in serial with the proportional valve that can enable the mitigation of pressure leaks.

Continuing to still further refer to FIGS. 12A through 13E, the pumping system of second/third configuration cassettes 699/700 can be controlled by, for example, but not limited to, a programmable logic controller (PLC) or a field programmable gate array (FPGA). Advantages of using a PLC can include the smaller footprint of the PLC with respect to the FPGA. Advantages of using a FPGA can include processor speed of the FPGA. The system of the present teachings can accommodate the use of any computing device. Each cassette can include two pump chambers that can pump asynchronously (one chamber can deliver while the other chamber can fill). These chambers can deliver and fill to the different ports on the manifold depending upon which valves are active. The pumping system can include delivery, fluid management, filling, and manifold control. The pumping system can include performing tasks such as, for example, but not limited to, (1) pumping the fluid from pumping chamber 705/707 to a location, (2) determining the volume of fluid in pumping chamber 705/707, (3) filling pumping chamber 705/707 with fluid, and (4) controlling manifold 1211.

Continuing to refer to FIGS. 12A through 13B, in some configurations, pneumatic block 2011 can include V_PCx 943A/B, valves that can enable isolation of pump chambers 705/707 from both positive and negative pressures, and V_PCxV 312A/B, valves that can enable the application of negative pressure to pump chambers 705/707. Valves V_REFx 306A/B can enable isolation of reference chambers 911A/B from pump chambers 705/707, the positive pressure bus, and the negative pressure bus. Pneumatic block 2011 can include valves V_VNTx 308A/B that can enable venting of reference chambers 911A/B and pumping chambers if valves 943A/B and 306A/B are open, and pressure gauges 906 that can measure the pressure in pumping chambers 705/707 and reference chambers 911A/B. The valves can include, for example, but not limited to, 2/2 valves and 3/2 valves. Pumping chambers 705/707 can include a volume of space on one side of the cassette membrane covering reservoir/bioreactor module cassette 699/700. Reference chambers 911A/B can include a fixed volume of space. The initial state of pressure and volume of reservoir/bioreactor module cassette 699/700 is based on the pressure in pumping chambers 705/707, the volume of pumping chambers 705/707, the pressure in reference chambers 911A/B, and the volume of reference chambers 911A/B. The values are the result of isolating pumping chambers 705/707 from the rest of the system by closing valves V_PCs 943A/B while pumping chambers 705/707 are under positive or negative pressure, opening valves V_PCxP 310A/B or V_PCxV 312A/B while valves V_VNTx 308A/B are closed and valves V_REFx 316A/B are opened to create the largest possible pressure offset between pumping chambers 705/707 and reference chambers 911A/B, and closing valves V_PCxP 310A/B and V_PC1V 312A/B. Valves V_PCx 943A/B can be opened to allow the pressure between pumping chambers 705/707 and reference chambers 911A/B to equilibrate, which can result in a final pressure and volume. The volume of pumping chambers 705/707 can be computed based at least on the final pressure, the volume of reference chamber 911A/B, and the initial pressures of pumping chambers 705/707 and reference chambers 911A/B. The volume of the contents delivered can be calculated by measuring the change in the volume of pumping chambers 705/707 from the end of the fill stroke to the end of the delivery stroke. If the total volume of the cassette chambers and pumping chambers 705/707 are known (excluding the cassette membrane), the current volume of media in the cassette chambers can be approximated by subtracting the volume of pumping chambers 705/707 from the total volume. Once the volume delivered is known, the flow rate can be calculated by dividing the volume delivered by the time taken to deliver it. If the delivery flow rate is outside of pre-selected and/or user-defined flow rate limits, the pneumatic pressure applied to diaphragms of pumping chambers 705/707 can be adjusted. Negative pneumatic pressure can be applied to the cassette chamber membrane to refill pumping chambers 705/707 prior to delivery. Negative pneumatic pressure can be adjusted so that the chamber always fills faster than it delivers, which can allow time for volumetric measurements to be taken before and after filling without preventing the system from being able to constantly deliver fluid. This configuration can allow for precise control of the degree of flow pulsatility of the delivered media. One configuration of the interaction between reference chambers 911A/B and pump chambers 705/707 can be found in U.S. Pat. No. 9,022,969, filed Jan. 23, 2009, entitled FLUID LINE AUTOCONNECT APPARATUS AND METHODS FOR MEDICAL TREATMENT SYSTEM, which is incorporated herein by reference in its entirety.

Figures 1, 13A:
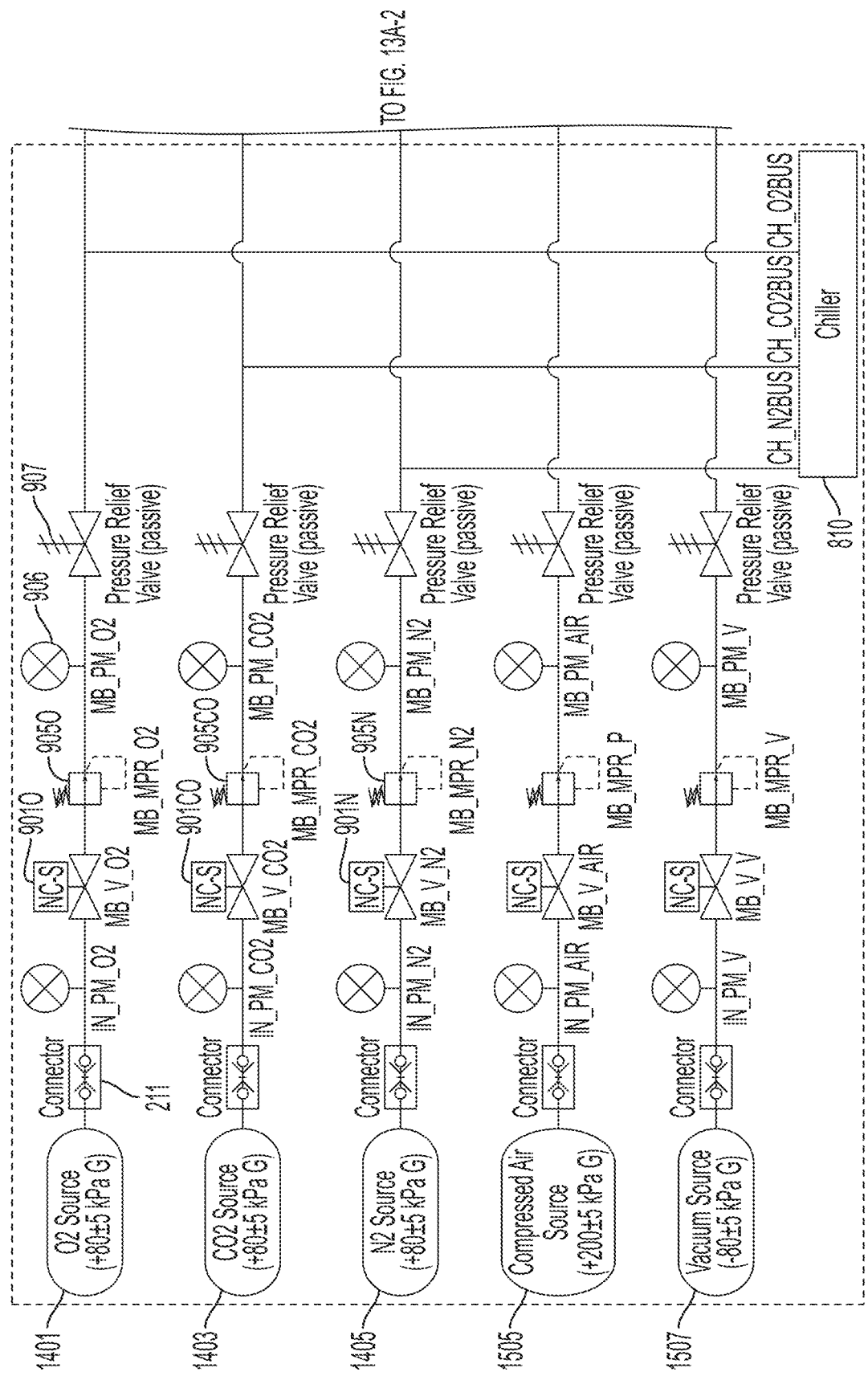
Figures 2, 13A:
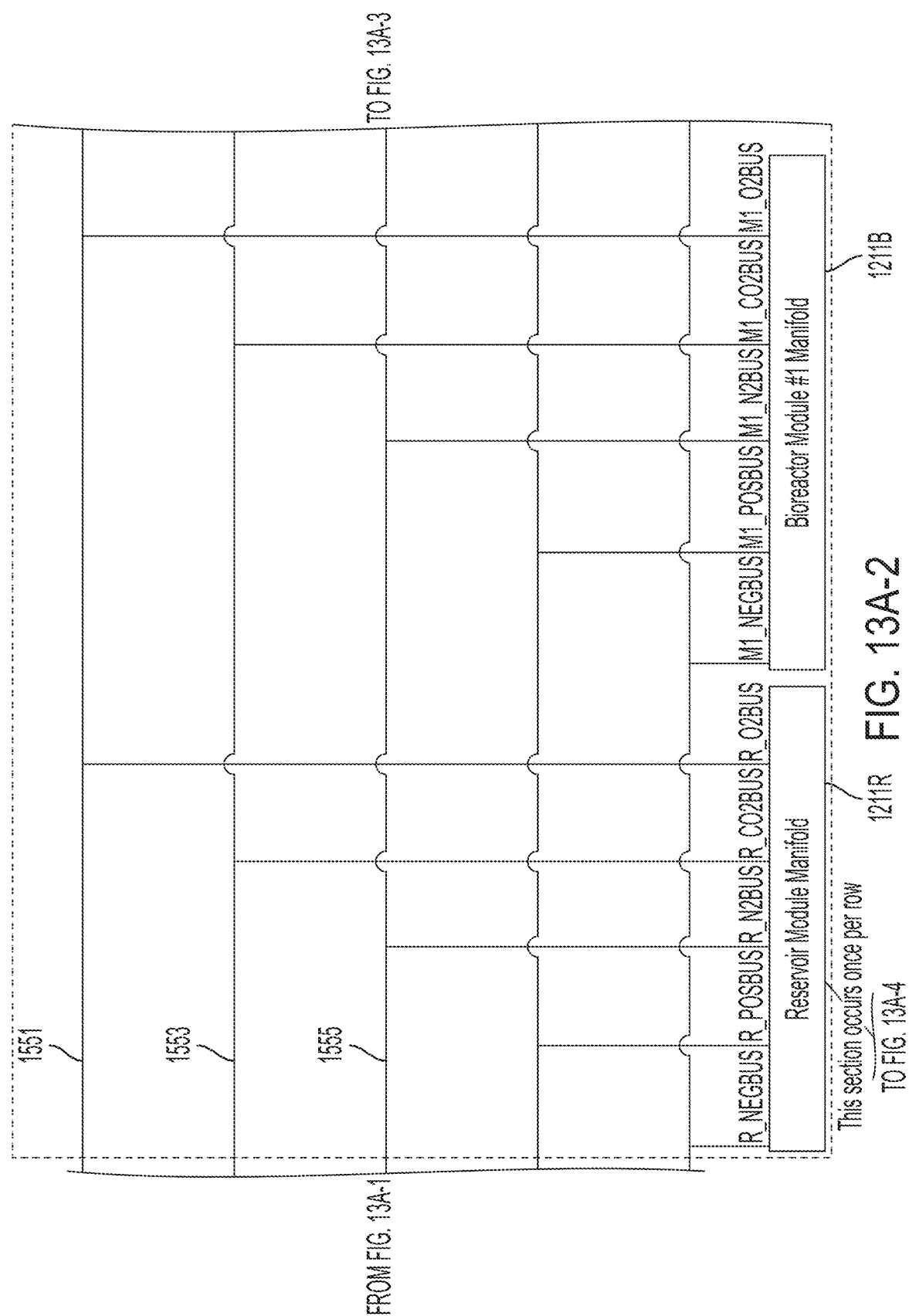
Figures 4, 13A:
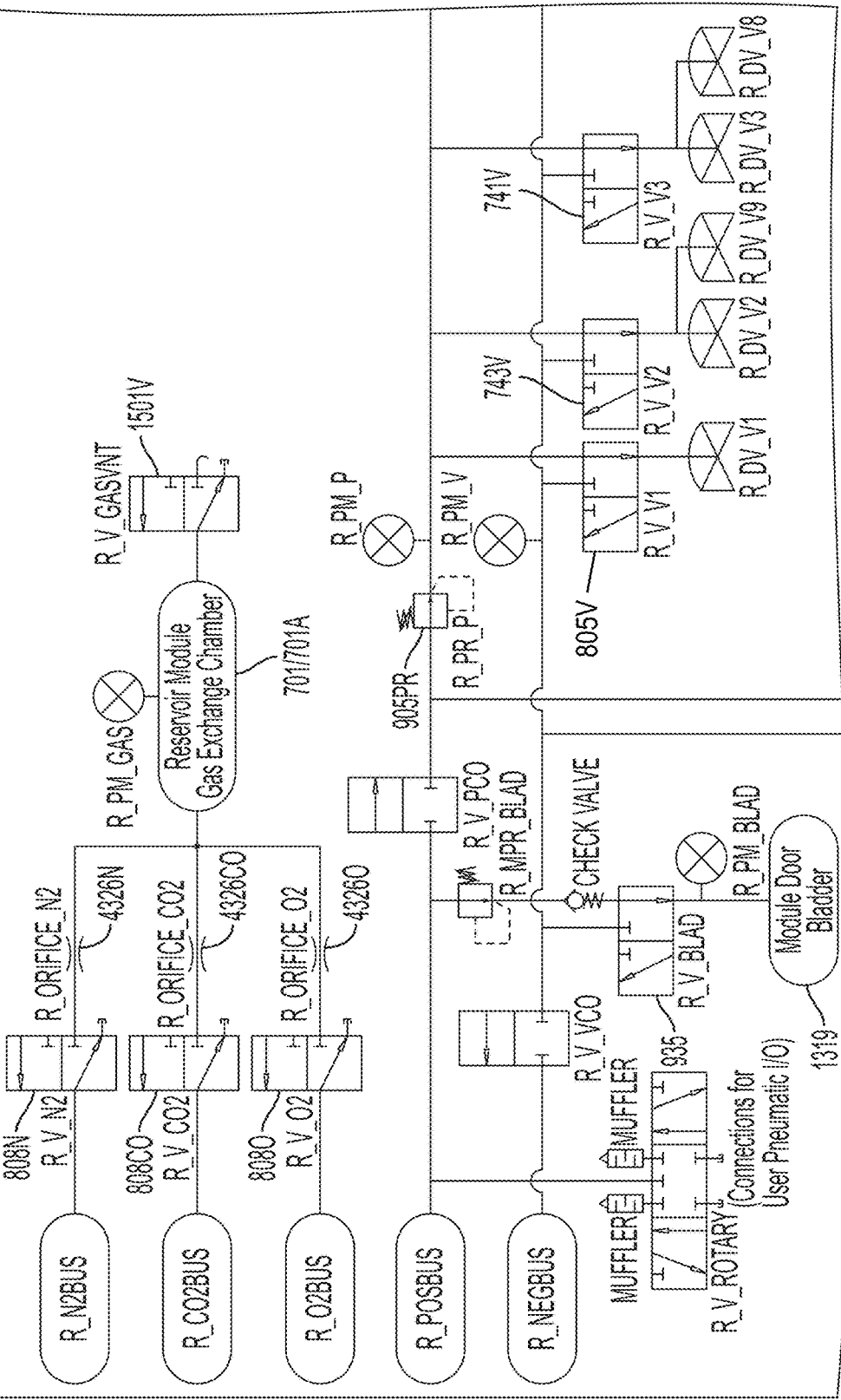
Figures 5, 13A:
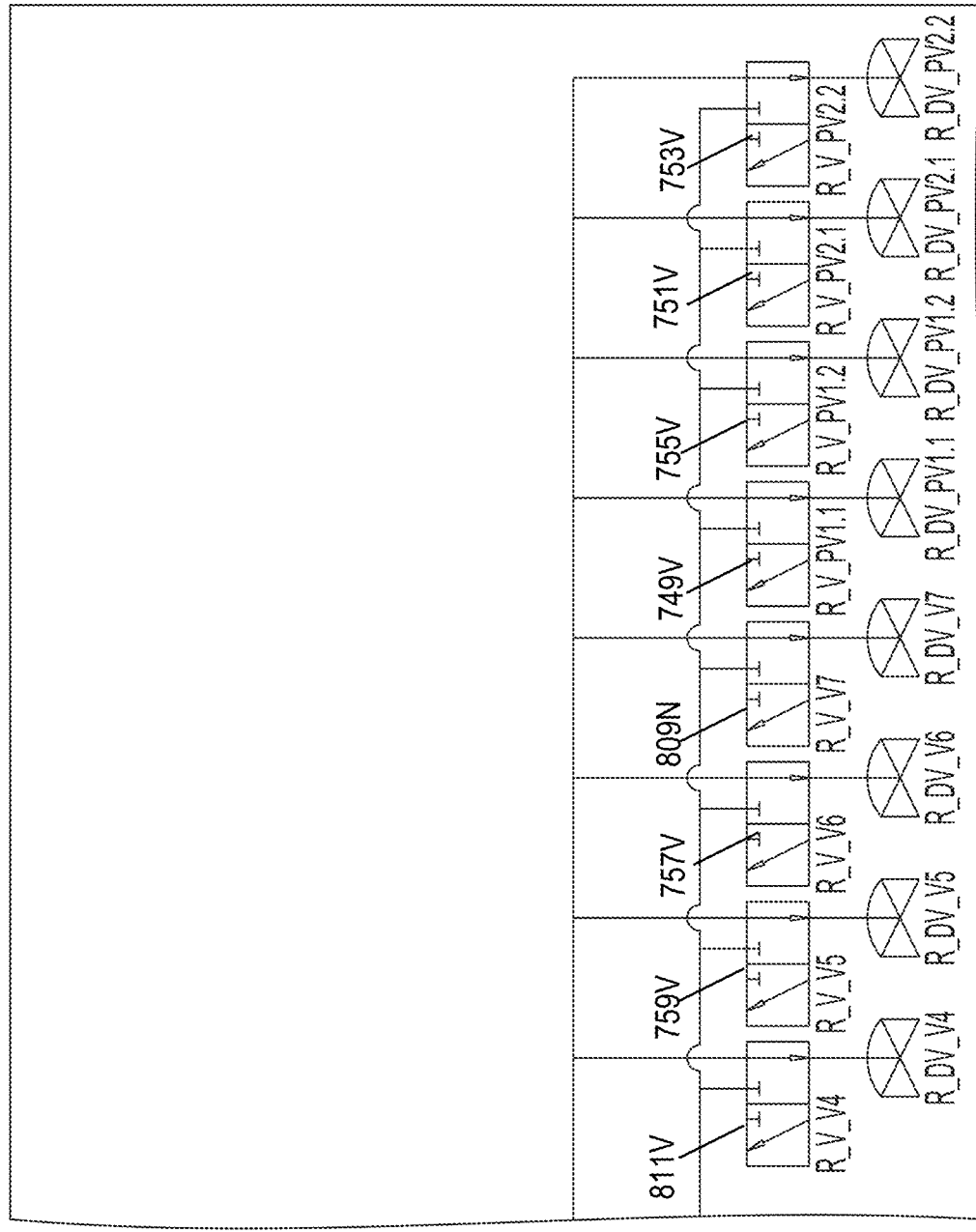
Figures 6, 13A:
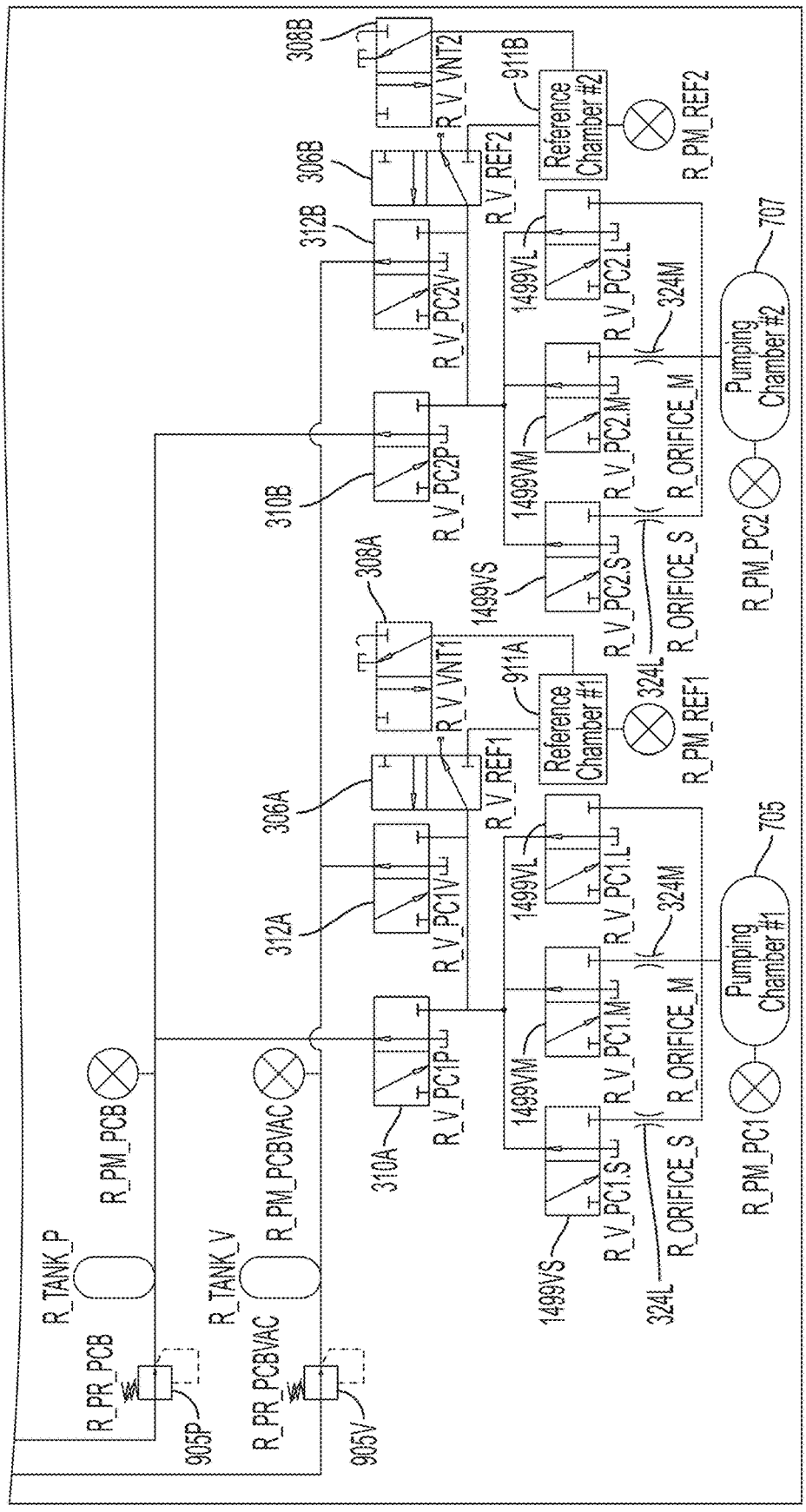
FIGS. 13B-13E are pneumatic diagrams of specific components having various numbers of valves.
FIGS. 13F-13H are pneumatic flow diagram for various configurations of the pneumatic system of the present teachings.
FIGS. 13I-13K are graphical representations of end of stroke trigger events.
Figure 13B:
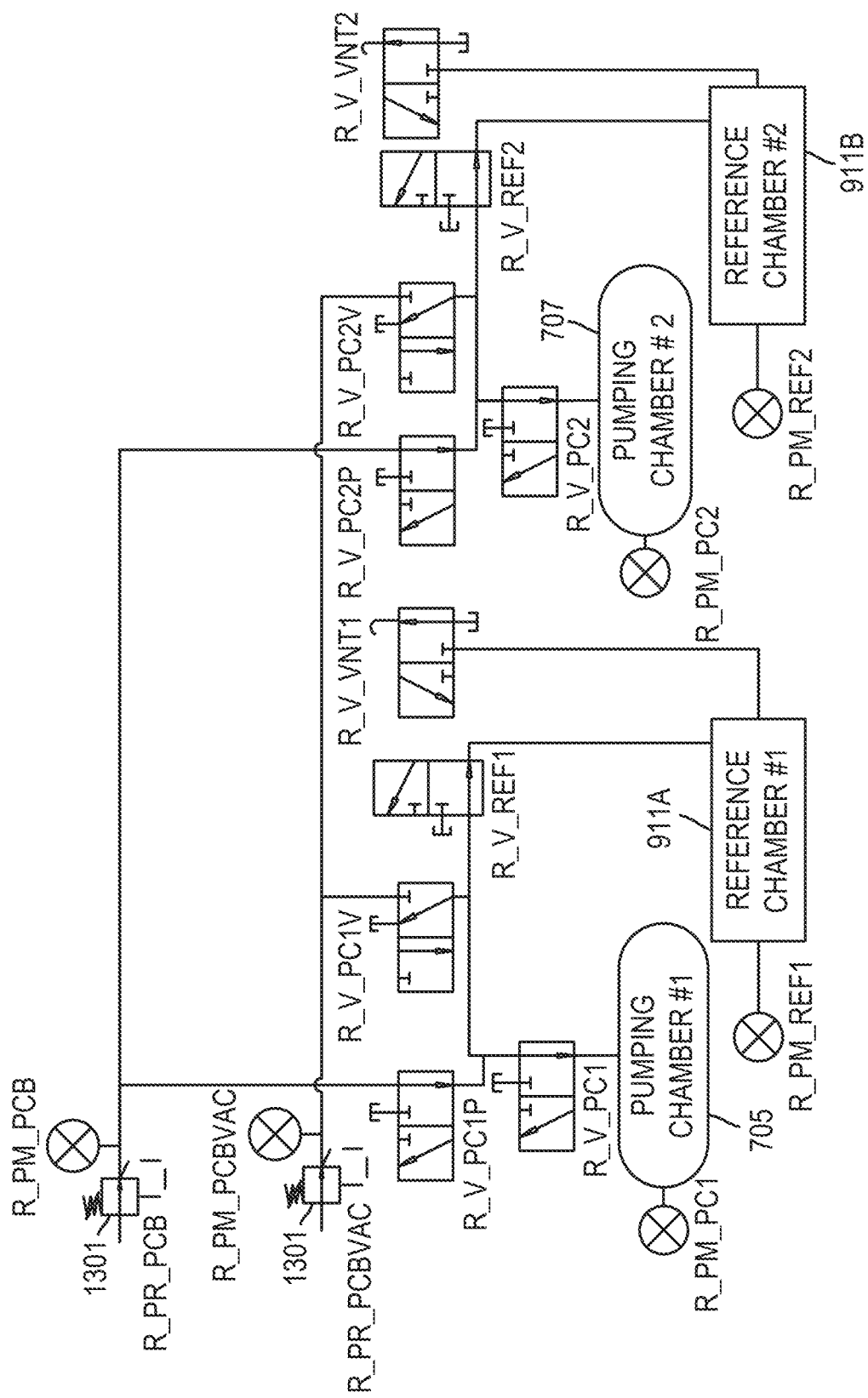
Figure 13C:
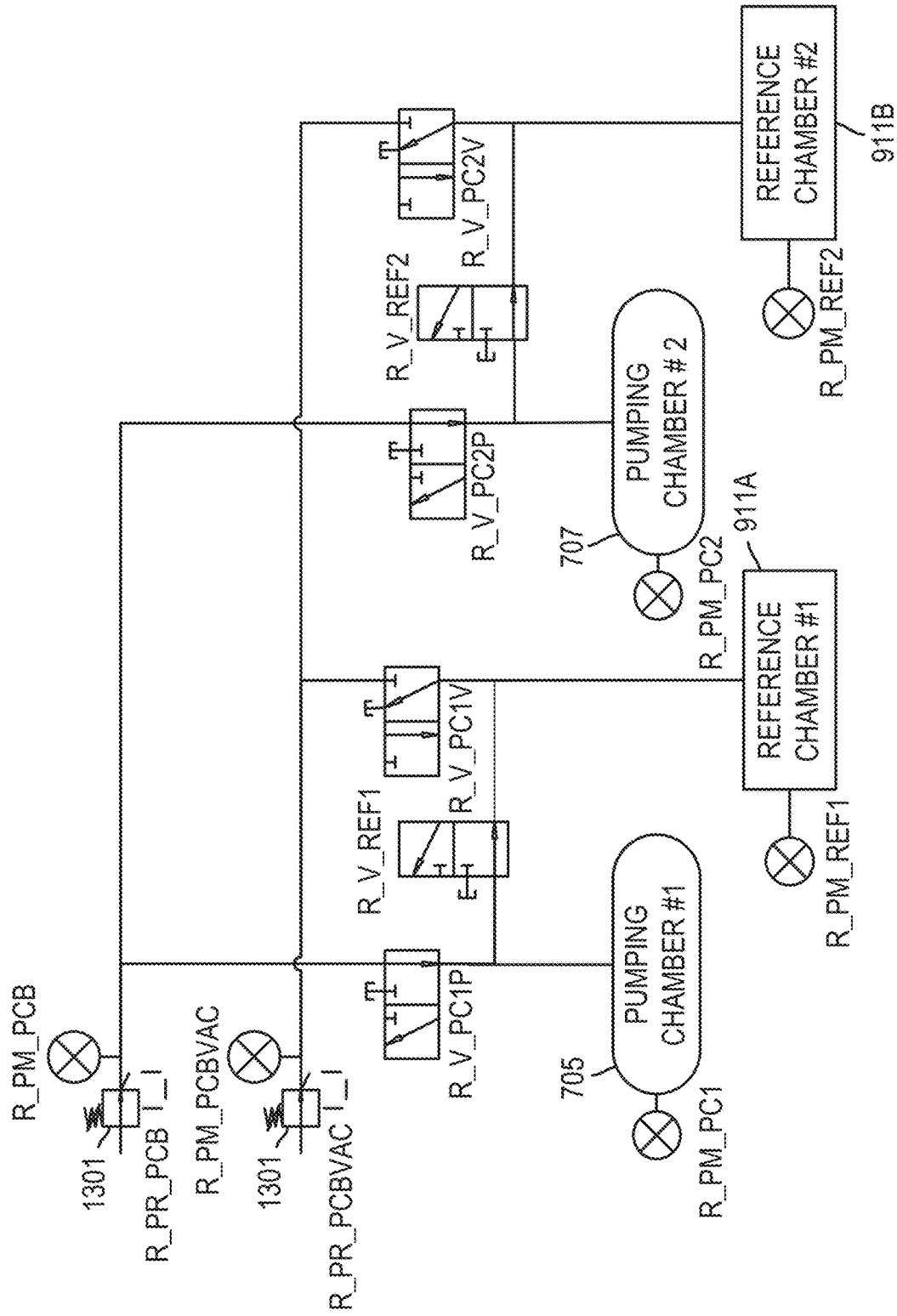
Figure 13D:
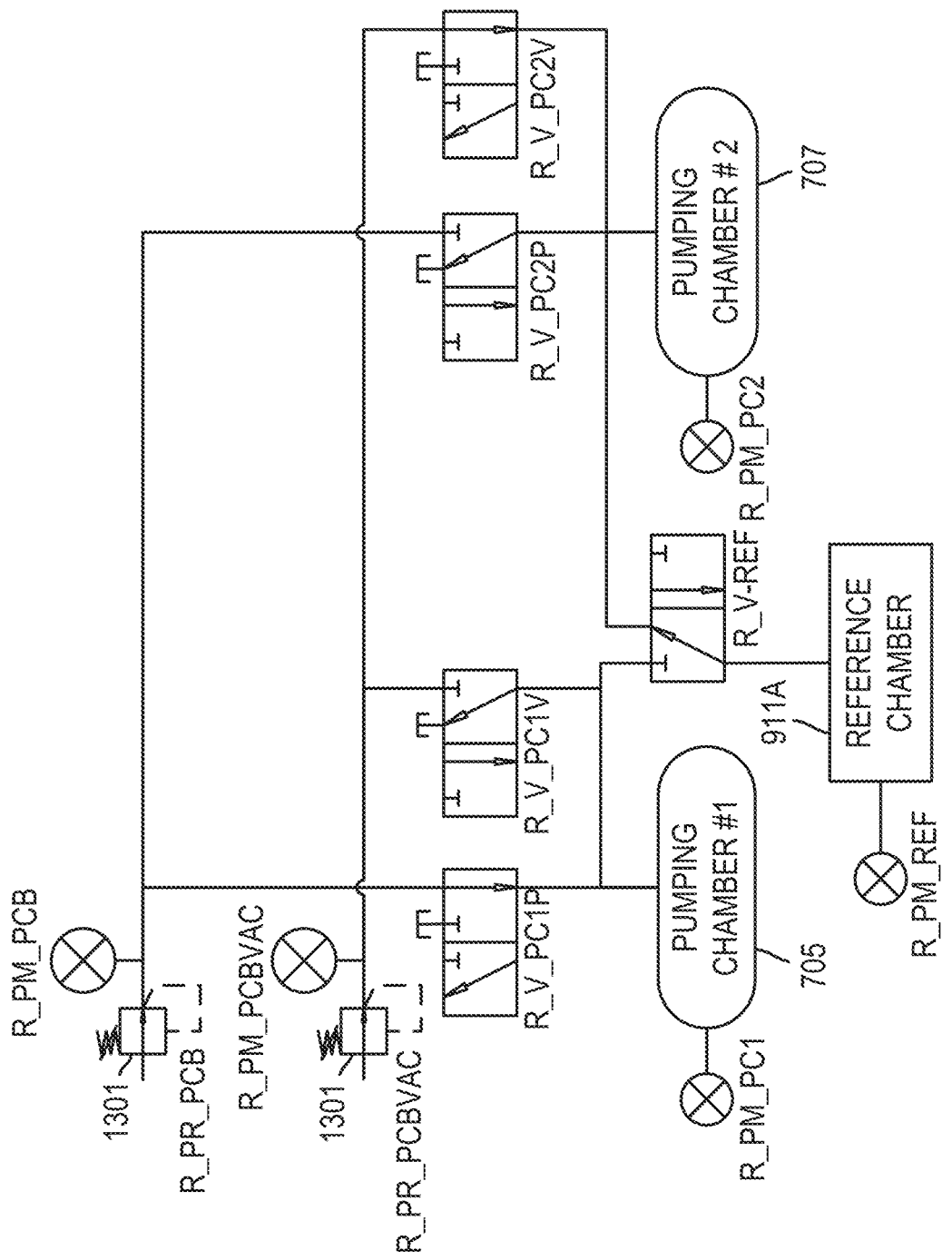
Figure 13E:
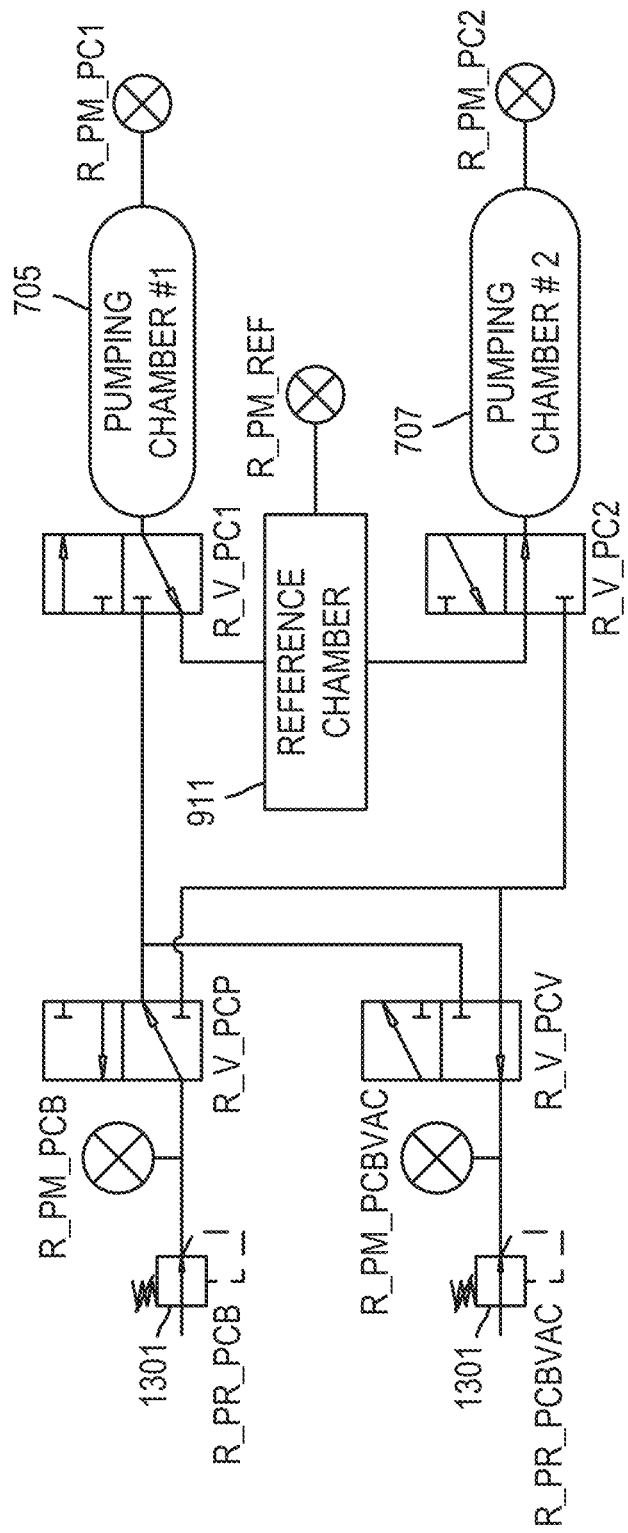
Figure 13F:
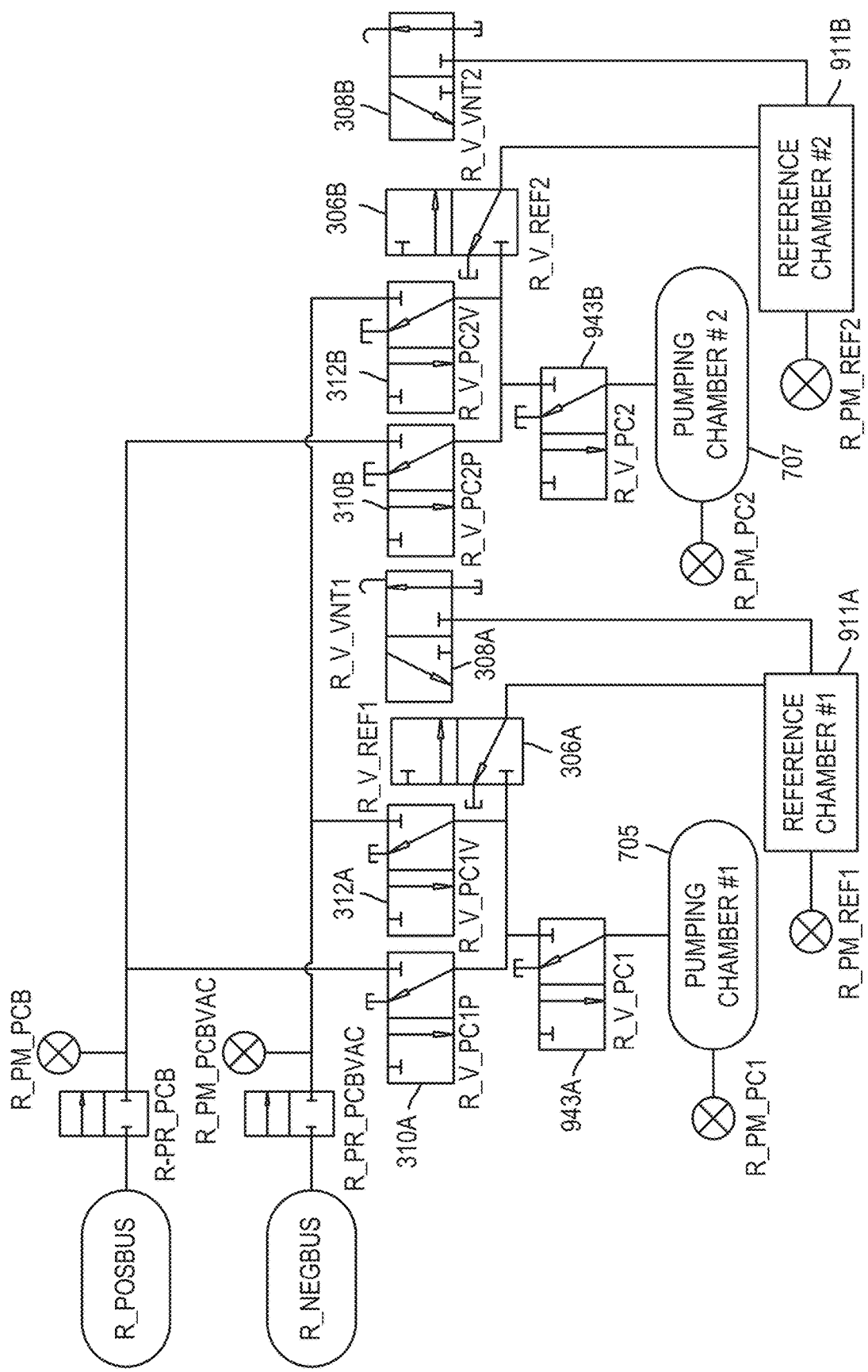
Figure 13G:
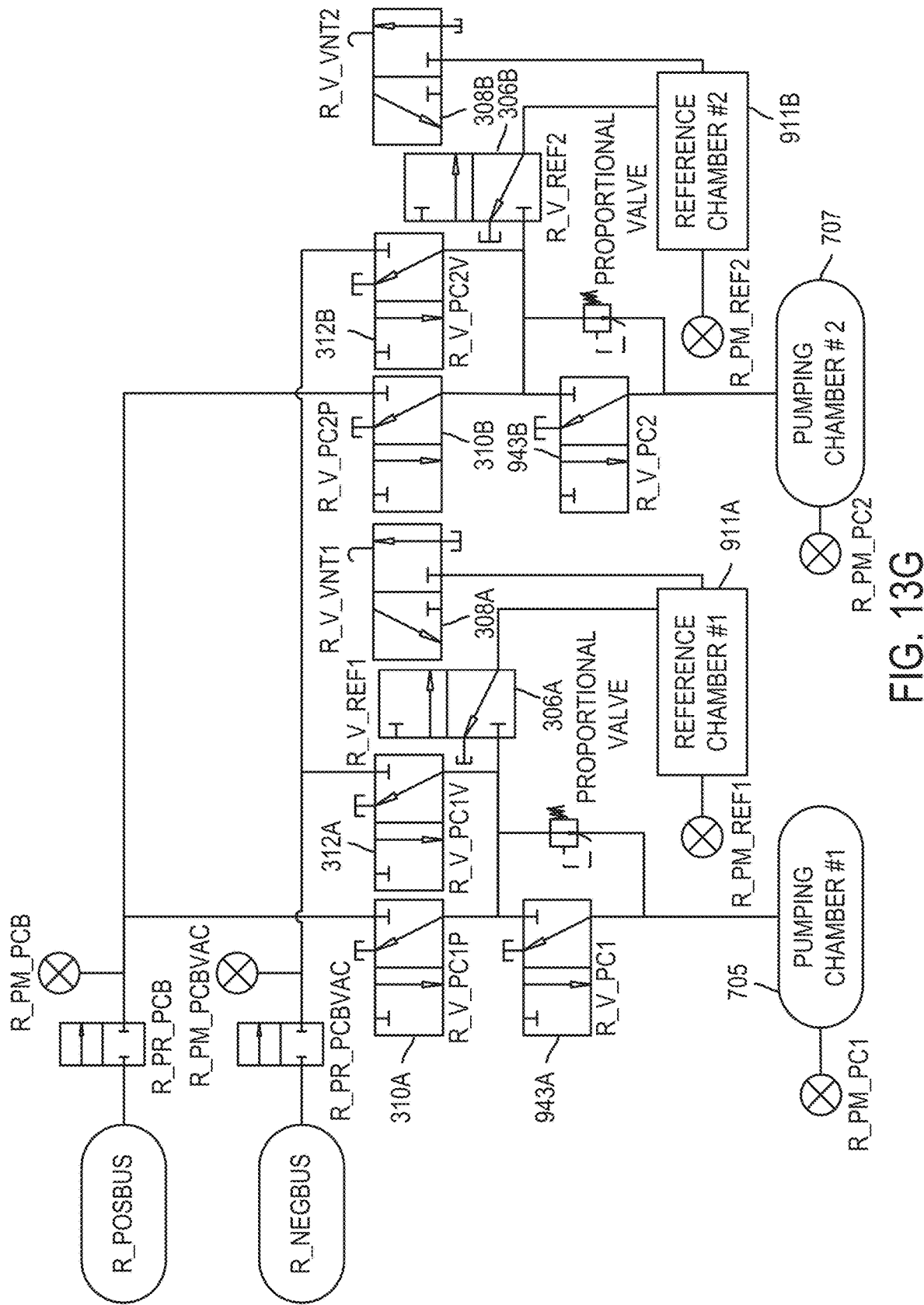
Figure 13H:
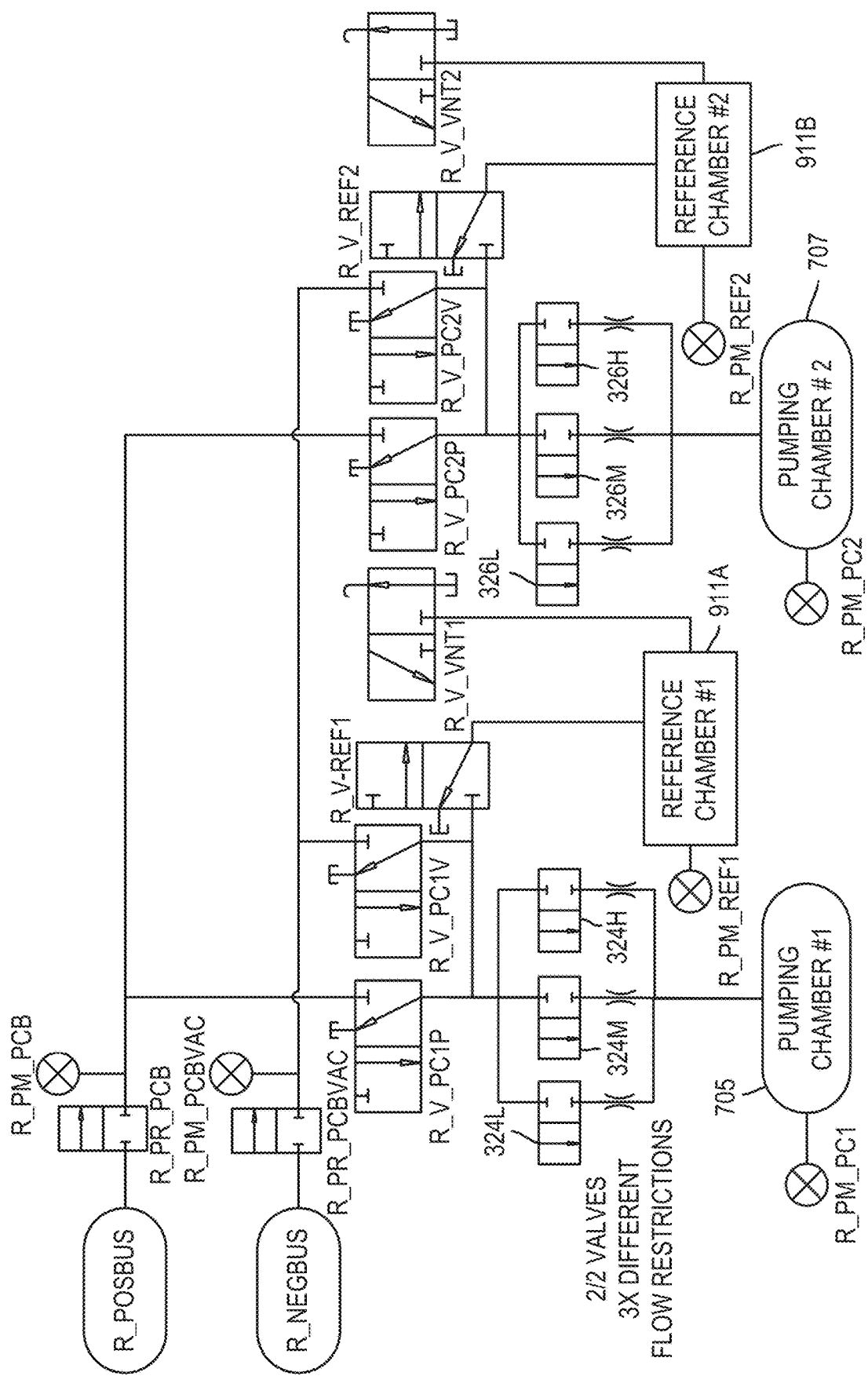

Referring now to FIGS. 13F-13H, measuring the current volume of the pumping chamber is necessary to determine how much fluid should be pumped around the system during each pump cycle. The systems of the present teachings focus on flow rate and flow continuity, and thus apply pressure to the pumping chambers in a consistent, controlled manner. The systems of the present teachings can support a wide range of flow rates including, but not limited to, 1-100 mL/min. The volume of fluid delivered from a pumping chamber can be measured through the application of Boyle's law, which states that at a constant temperature (isothermal), the pressure (P) and volume (V) behave of a closed system behave as follows:

$$P_{Initial} * V_{Initial} = P_{Final} * V_{Final}$$

Referring now to FIG. 13F, the pumping and reference chamber valve configuration of pneumatic block 2011 (FIG. 12A) is depicted. To minimize the effect of pressure sensor accuracy, in some configurations, pumping chambers 705/707 can be isolated from the rest of the system by (1) closing R_V_PCx 943A/B while pumping chambers 705/707 are under pressure or vacuum, (2) either opening R_V_PCxP 310A/B or R_V_PCxV 312A/B while R_V_VNTx 308A/B is closed, and opening R_V_REFx 306A/B to create the largest possible pressure offset between pumping chamber 705/707 (volume=V1, pressure=$P1_{Initial}$) and reference chamber 911A/B (volume=V2, pressure=$P2_{Initial}$), (3) closing R_V_PCxP 310A/B and R_V_PCxV 312A/B. These steps can result in an initial state conforming to a modified version of Boyle's law:

$$P_{Initial} * V_{Initial} = P1_{Initial} * V1 + P2_{Initial} * V2$$

R_V_PCx 943A/B can be opened to allow the pressure between pumping chamber 705/707 and reference chamber 911A/B to equilibrate, resulting in a final state, and the volume of pumping chamber 705/707:

$$P_{Final} = P1_{Final} = P2_{Final}$$

$$V_{Final} = V1 + V2$$

$$P_{Initial} * V_{Initial} = P_{Final} * V_{Final}$$

$$P1_{Initial} * V1 + P2_{Initial} * V2 = P_{Final} * (V1 + V2)$$

$$P1_{Initial} * V1 + P2_{Initial} * V2 = P_{Final} * V1 + P_{Final} * V2$$

$$P1_{Initial} * V1 - P_{Final} * V1 = P_{Final} * V2 - P2_{Initial} * V2$$

-continued
$$V1 = \frac{(P_{Final} * V2 - P2_{Initial} * V2)}{(P1_{Initial} - P_{Final})}$$

Continuing to refer to FIGS. 13F-13H, the volume of the fluid delivered can be calculated by evaluating the change in V1 from the end of the fill stroke to the end of the delivery stroke. If the total volume of the cassette chamber and pumping chamber 705/707 is known (excluding the membrane), the current volume of media in the cassette chamber may also be approximated by subtracting V1 from the total volume. Once the volume delivered is known, the flow rate may then be calculated by dividing the volume delivered by the time taken to deliver it. If the delivery flow rate is outside of pre-selected flow rate limits, which can be default values, user-defined, or dynamically-determined, the pneumatic pressure applied to the pumping chamber diaphragms can be adjusted by changing the positive pressure electronic pneumatic regulator orifice size (see FIG. 13G), control valve PWM rate (see FIG. 13F), or orifice valve selection and/or PWM rate (see FIG. 13H). Negative pneumatic pressure can be applied to the cassette chamber membrane to refill pumping chamber 705/707 prior to delivery. The negative pneumatic pressure can be adjusted so that pumping chamber 705/707 can fill faster than it delivers, allowing time for volumetric measurements to be taken before and after filling without preventing the system from being able to constantly deliver fluid. This can enable precise control of the degree of flow pulsatility of the delivered media.

Referring now to FIG. 13H, in some configurations, a pre-selected number of 2/2 valves can be configured in parallel and can include pre-selected-sized orifices 324L/M/H. The pre-selected number can include, for example, three orifices, and the pre-selected sizes can include, but are not limited to including, small and mid-range sizes, such as, for example, but not limited to, between 0.0003 in and 0.0015 in. In some configurations, small orifices 324L and accompanying valve 1499VS (FIG. 13A-6) can accommodate low flow rates, mid-size orifices 324M or a combination of sizes of orifices 324L/M/H and accompanying valves 1499VS/VM/VL (FIG. 13A-6) can accommodate medium flow rates, and all orifices 324L/M/H and accompanying valves 1499VS/VM/VL (FIG. 13A-6) together can accommodate high flow rates. Low flow rates can include, but are not limited to including, <0.5 mL/min to 5 mL/min, and orifice size ranges can include 0.0007 in. Medium flow rates can include, but are not limited to including, 5.0 m/L to 15 mL/min (inclusive), and can include orifices sized 0.0015 in. High flow rates can include, but are not limited to including, >15 mL/min to >100 mL/min, and can include completely open orifices. These valves can be based at least on the sizes of the orifices. In some configurations, combinations of orifices 324L/M/H can be used at different parts of the pump stroke to achieve relatively exact desired flow rates, and orifices of different sizes can be used to achieve target flow rate ranges. In some configurations, combining the orifices 324L/M/H or 326L/M/H can address cassette membrane stiffness issues, for example. Combining orifices can result in applying less pressure at the beginning of the stroke and more pressure at the end of the stroke through the combination of different valves/orifices. If the pumping chamber is completely full, the cassette membrane can actually pump, even if external pressure is not applied, because the cassette membrane aims to return to a midpoint position. If the pumping chamber is almost empty and the cassette membrane can resist further movement and can require extra pressure to completely empty the pumping chamber, again because the cassette membrane aims to return to a midpoint position. In some configurations, at very low flow rates (~1 mL/min) the smallest orifice can be pulsed and the other two orifice valves can remain closed. At slightly higher flow rates (>1 to ~10 mL/min) the smallest orifice can be left open, the medium orifice can be pulsed, and the largest orifice valve can remain closed. At the highest flow rates (>10 to 100 mL/min) the small and medium orifices can be left open and the largest orifice can be pulsed. Other combinations of the orifices being opened/closed/pulsed can be used to achieve target flow rate ranges.

Figure 13I:
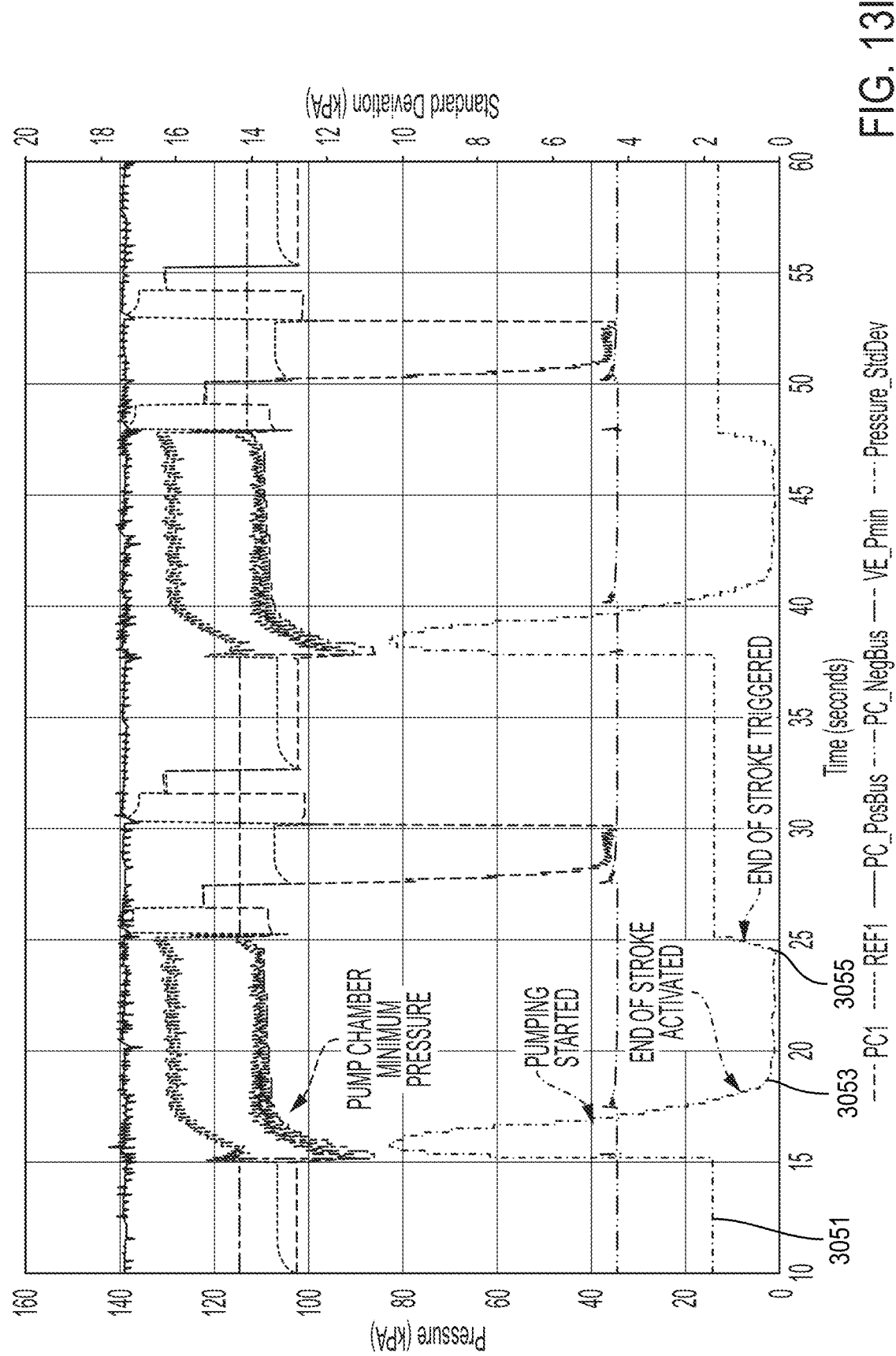
Figure 13J:
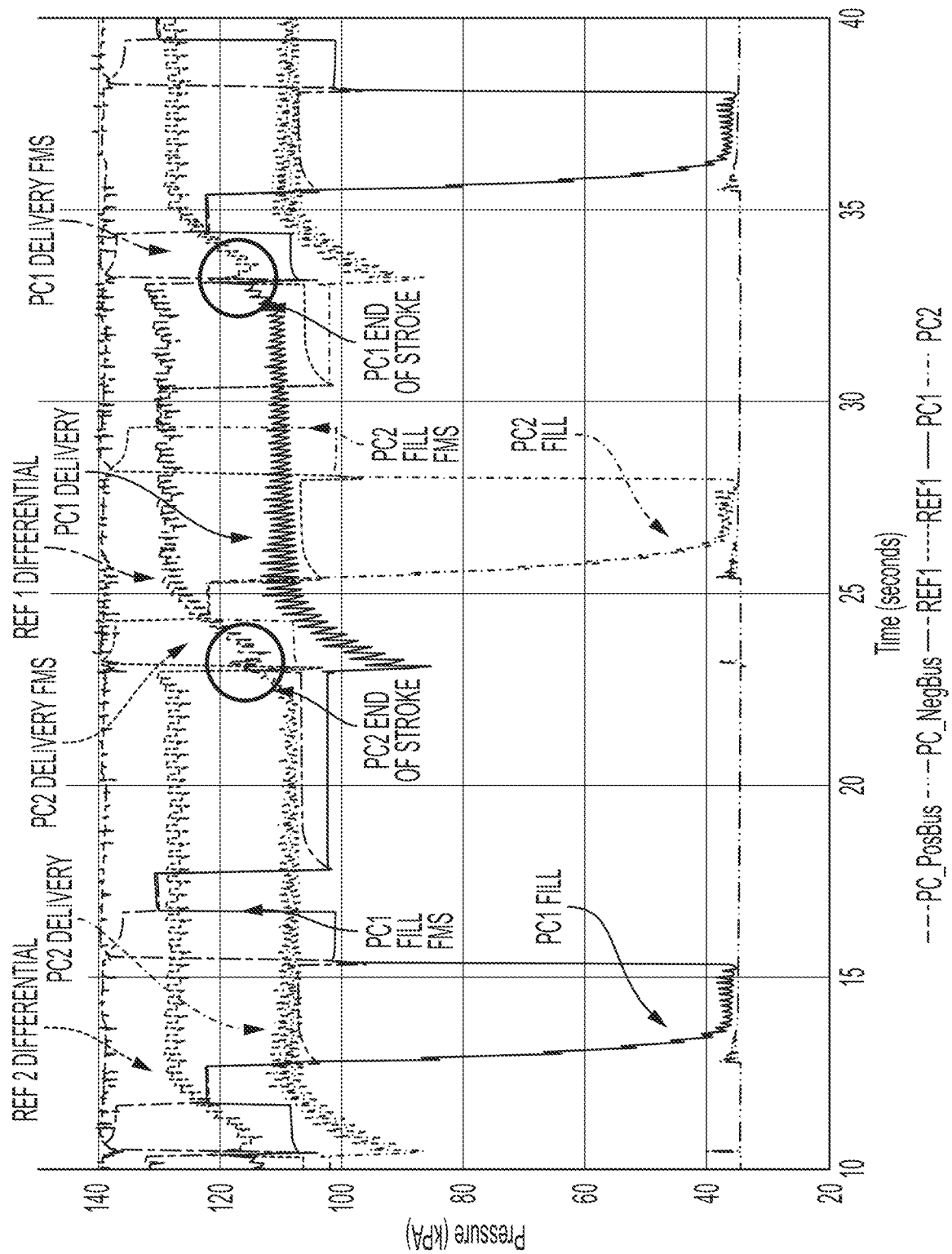
Figure 13K:
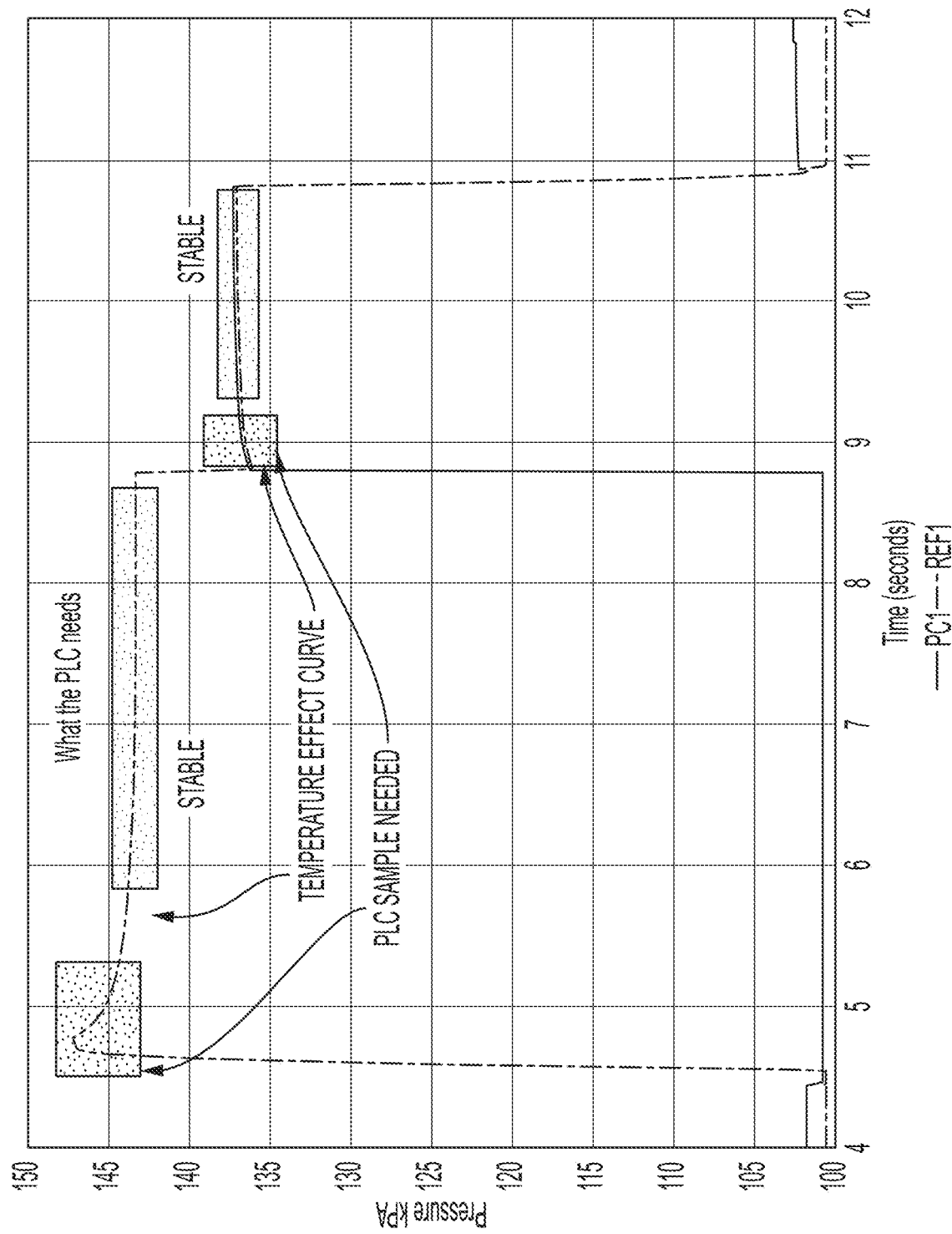

Referring now to FIGS. 13I-13K, pumping the fluid from pumping chamber 705/707 to a location can include determining when pumping chamber 705/707 has delivered the contents by determining an end-of-stroke, confirming the volume of fluid delivered, and regulating the differential pressure across the pump chamber fluid valve. End-of-stroke can be determined by (a) monitoring standard deviation 3051 (FIG. 13I) of the minimum value of the pump chamber pressure during a pulse until the standard deviation has substantially stopped changing 3053 (FIG. 13I), (b) evaluating changes in the standard deviation of the minimum value of the pump chamber pressure, (c) and, when the standard deviation begins to increase 3055 (FIG. 13I), triggering an end-of-stroke. The standard deviation can be computed over, for example, a rolling one-second window of the minimum values, and a sample of the minimum values can be taken, for example, each second. If the standard deviation does not settle during a pump cycle, a maximum pump chamber pressure threshold can trigger an end-of-stroke indication. The threshold can include a range of 8-12 kPa below the pressure of the pump chamber positive bus pressure. The standard deviation increase of the minimum pump chamber pressure can cause an end of stroke indication during a fill as described herein. If an end-of-stroke indication does not occur within a pre-selected amount of time, the system can proceed as if the end-of-stroke indication did occur. The pre-selected time can include a range of 2-6 seconds. By opening reference valve 306 A/B (FIG. 13F), and keeping vent valve 308A/B (FIG. 13F) closed, the resulting volume can enable pressure regulation using reference chamber pressure sensor 316A/B (FIG. 13F). Between delivery pulses, the pressure can be maintained in the pre-selected differential pressure range by controlling pump chamber pressure valve PCxP 310A/B (FIG. 13F) and vacuum valve PCxV 312A/B (FIG. 13F). When it is time to deliver the fluid, PCxP 310A (FIG. 13F) and PCxV 312A/B (FIG. 13F) can be closed and the pump chamber fluid valve can be opened. When orifice valves are used, a selected orifice can be open while the pressure in reference chamber 911A/B (FIG. 13F) is continuously controlled.

Figure 14B:
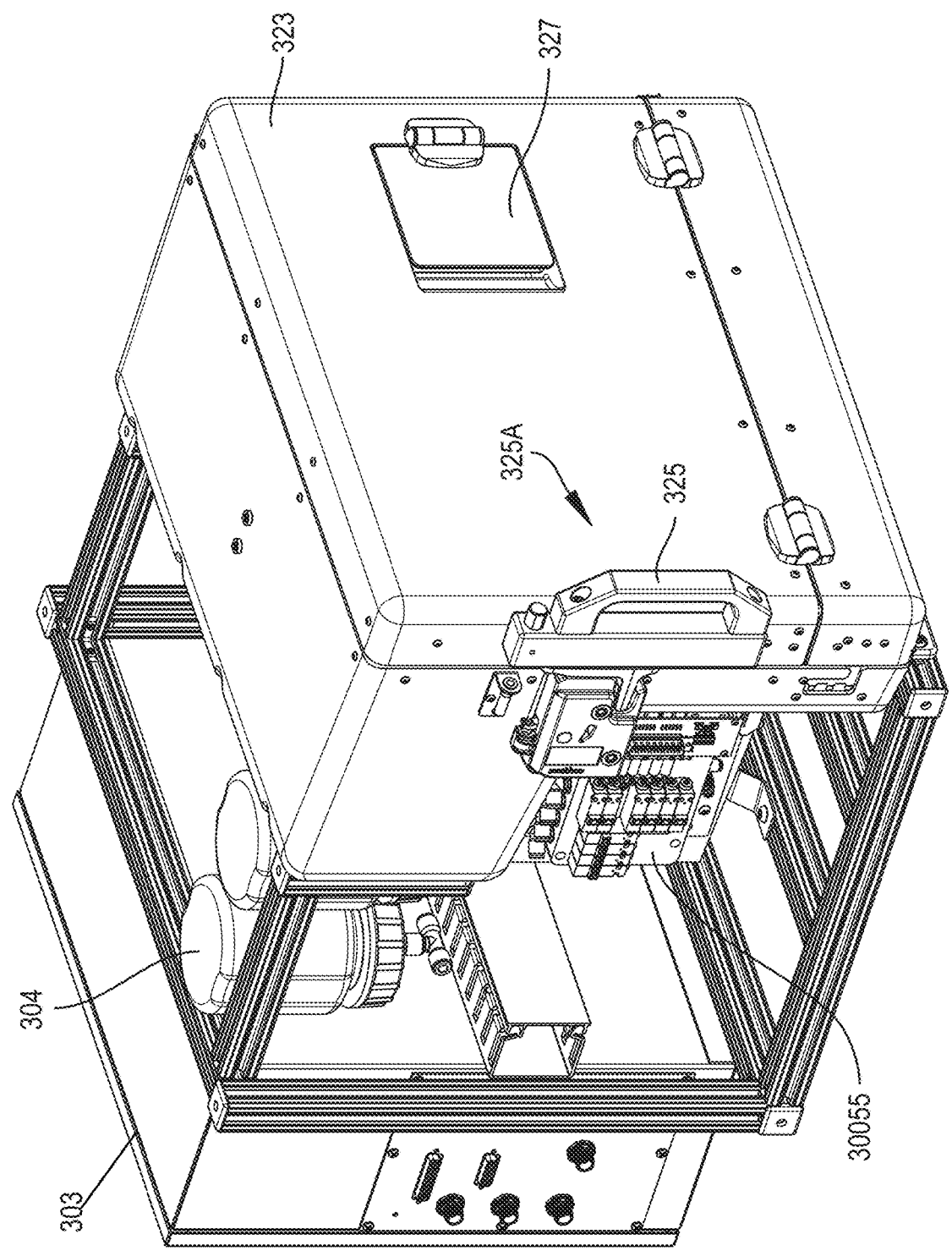
Figure 14C:
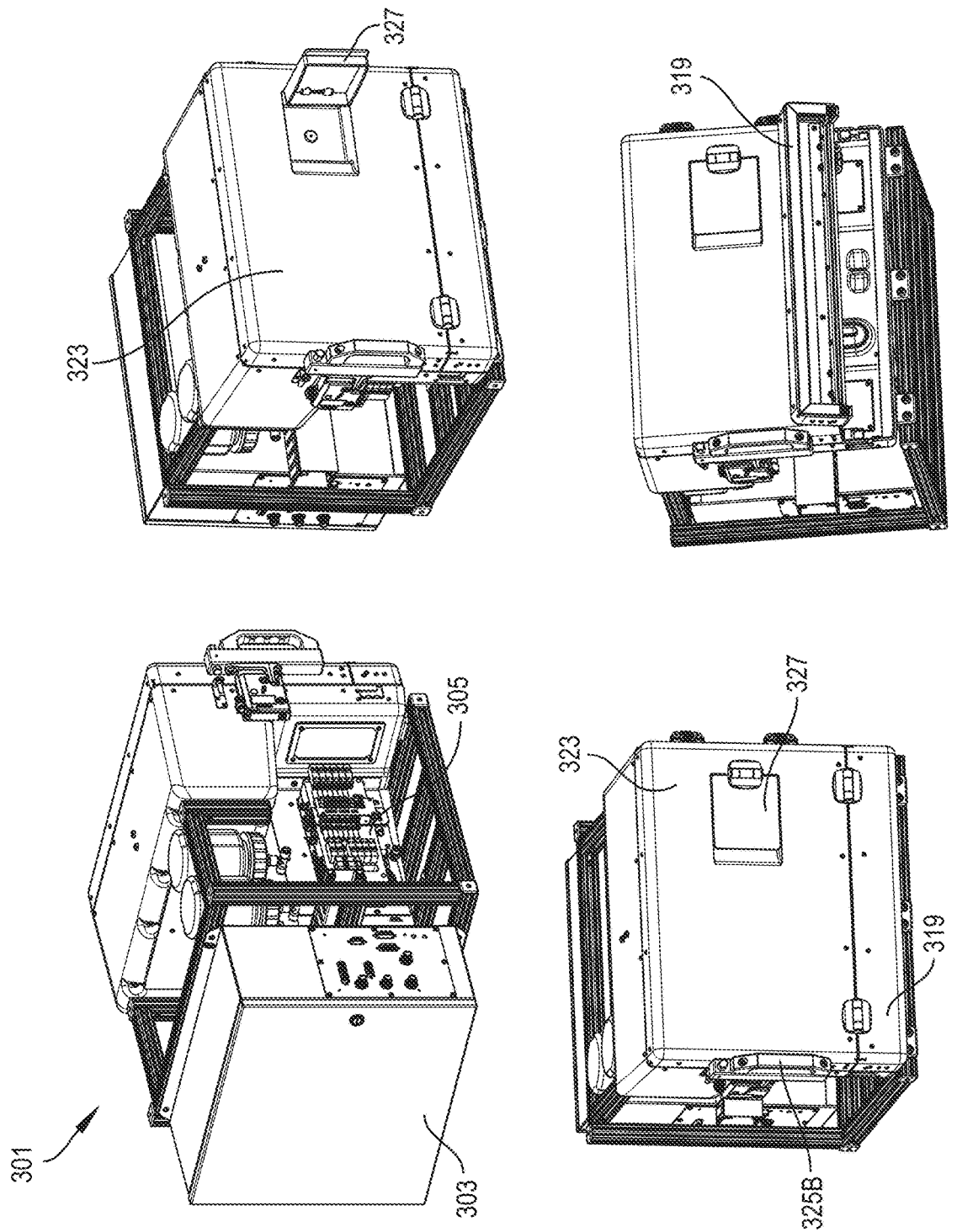

Referring now to FIGS. 14A-14C, system enclosure 301 can house the components of the present teachings including, but not limited to, fluid controls, bioreactor systems 118A (FIG. 1), and reservoir systems 116A (FIG. 1). System enclosure 301 can enable thermal control of the tissue and media, non-invasive sampling and waste removal, efficient cleaning and cassette access design, cassette bubble capture geometry, rack mountability, and compact footprint, among other features. Other features can include, but are not limited to including latches for safety, status lights, and access to user inputs. The thermal control enabled by system enclosure 301 can reduce or eliminate the generation of condensate. In the event of condensation or a leak, however, the surfaces of the areas in which components of the enclosure are mounted can be sealed and slightly inclined so that any fluid flows away from the electronics and towards a door. Thermal control can be enabled by the structure of the latch 3326, gaskets between front door 323/sample door 327/waste door 319 and the main body of system enclosure 301, and insulation of system enclosure 301. These features can limit the loss of heat to the external environment. The temperature of the media itself can be controlled by manifold heaters 1451 (FIG. 14I) in bioreactor and reservoir modules, and heating tray 3327 (FIG. 14G) in the reservoir module. Manifold heater 1451 (FIG. 14I) can include resistor 1453 (FIG. 14I) and thermal cutoff 1455 (FIG. 14I) that turns the heat off if the manifold exceeds a threshold temperature. In some configurations, multiple manifold heaters 1451 (FIG. 14I) can be included on opposite sides of the manifold, for example. The heating tray can be placed in the reservoir module at position 326A (FIG. 14G) and can include heating pads to warm or maintain the warmth of media before the media is circulated through the reservoir module and into the bioreactor. Uninsulated tubing connecting the various parts of the system can radiate energy from the fluid traversing the tubing as the fluid moves through the system. In some configurations, temperature control can, in part, be achieved by the radiated energy. In some configurations, the tubing can be insulated. Without opening front door 323, and therefore minimizing thermal modification and potential deviations from a thermal setpoint, and possibly raising power draw, sample door 327 can provide sample line access through which a sample from reservoir system 116A (FIG. 1) can be pumped under the control of fluid control components 2907 (FIG. 1) as described herein (see FIG. 5I). Again, without opening front door 323, module/waste line access door 319 can be opened to provide waste line access through which waste from reservoir system 116A (FIG. 1) and reservoir system 116A (FIG. 1) can be pumped as described herein (see FIG. 5G). In some configurations, module/waste line access door 319 can swing vertically to expose waste line. A vertical swing can reduce the space required to access waste line, and can reduce the sag/strain on its hinge. Further, a vertical swing can enable the insertion/removal of module and waste lines without the door hinge hindering the removal. Both module line and waste line can be operably coupled through tubing with disposable cassette 700 media inlet and waste outlet ports. In some configurations, disposable cassette 700 can include tubing attached to all cassette ports. In some configurations, the tubing can be welded or otherwise connected with aseptic fittings to the module and waste lines. In some configurations, sample line tubing can be fed through the sample line access hole and stored in the sample line access door. In some configurations, front door 323 can be moved by grasping door handle 325A that can include proud pull 325 (FIG. 14B) and a latch coupling. The latch coupling can operably couple with, for example, but not limited to, electronic rotary latch 3326 (FIG. 14A) that can include a door and latch status switch, such as, but not limited to, SOUTHCO® R4-EM-8 Series Electronic Rotary Latch. In some configurations, front door 323 can be moved by grasping flush door release 325B (FIG. 14C). To expose manifold pump side plate 30053 (FIG. 14B), side door 318 (FIG. 14A) has been removed in FIG. 14B. Accumulator jar(s) 304 (FIG. 14B) can be used to minimize deviations in pressure or vacuum supplied to the fluid management system by providing a reservoir of controlled gas to absorb the impact of any small pressure changes. Electronics that can power and enable data flow and control of the system can be located in electronics box 303.

Figure 14D:
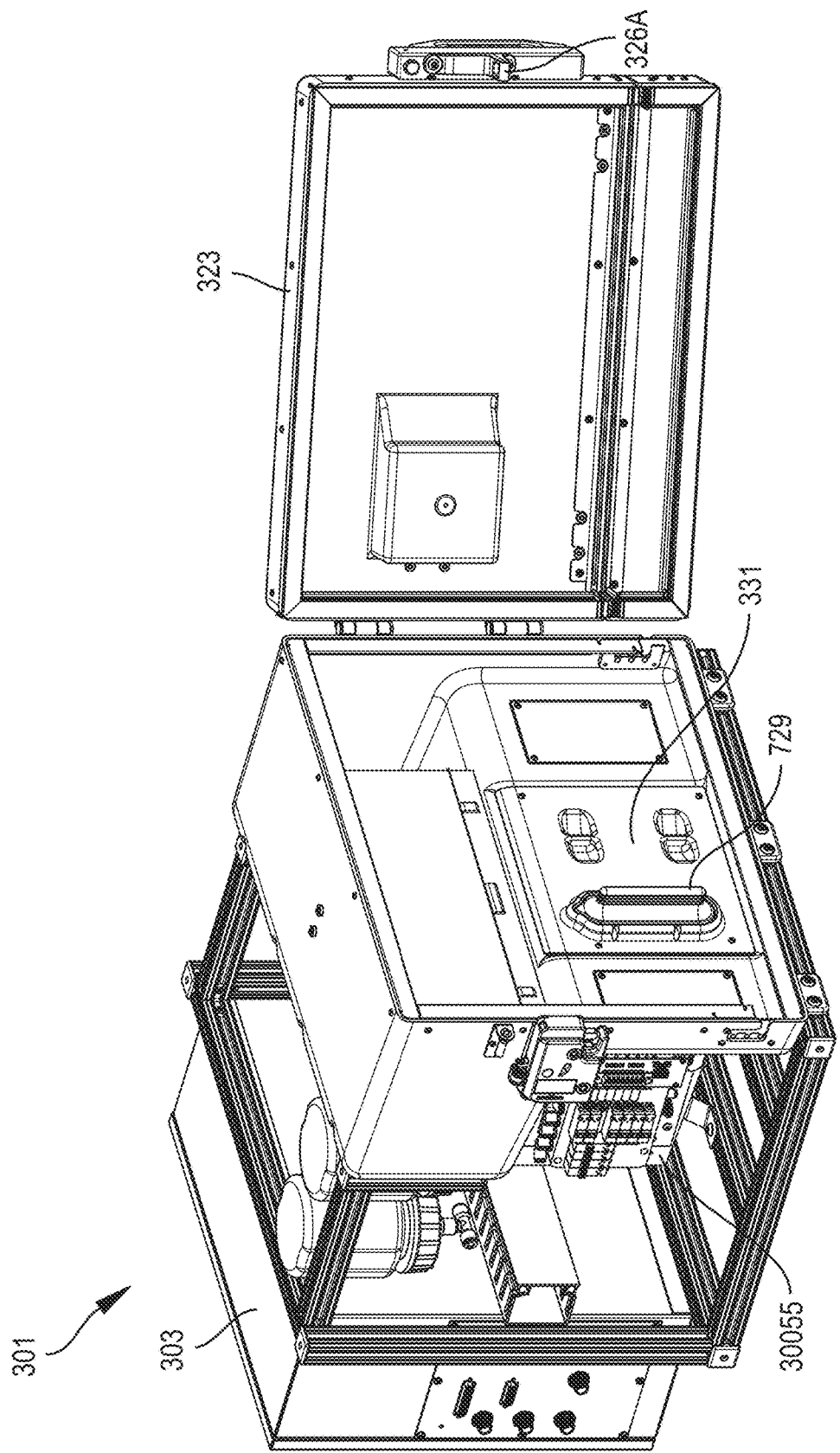
Figures 2, 14D:
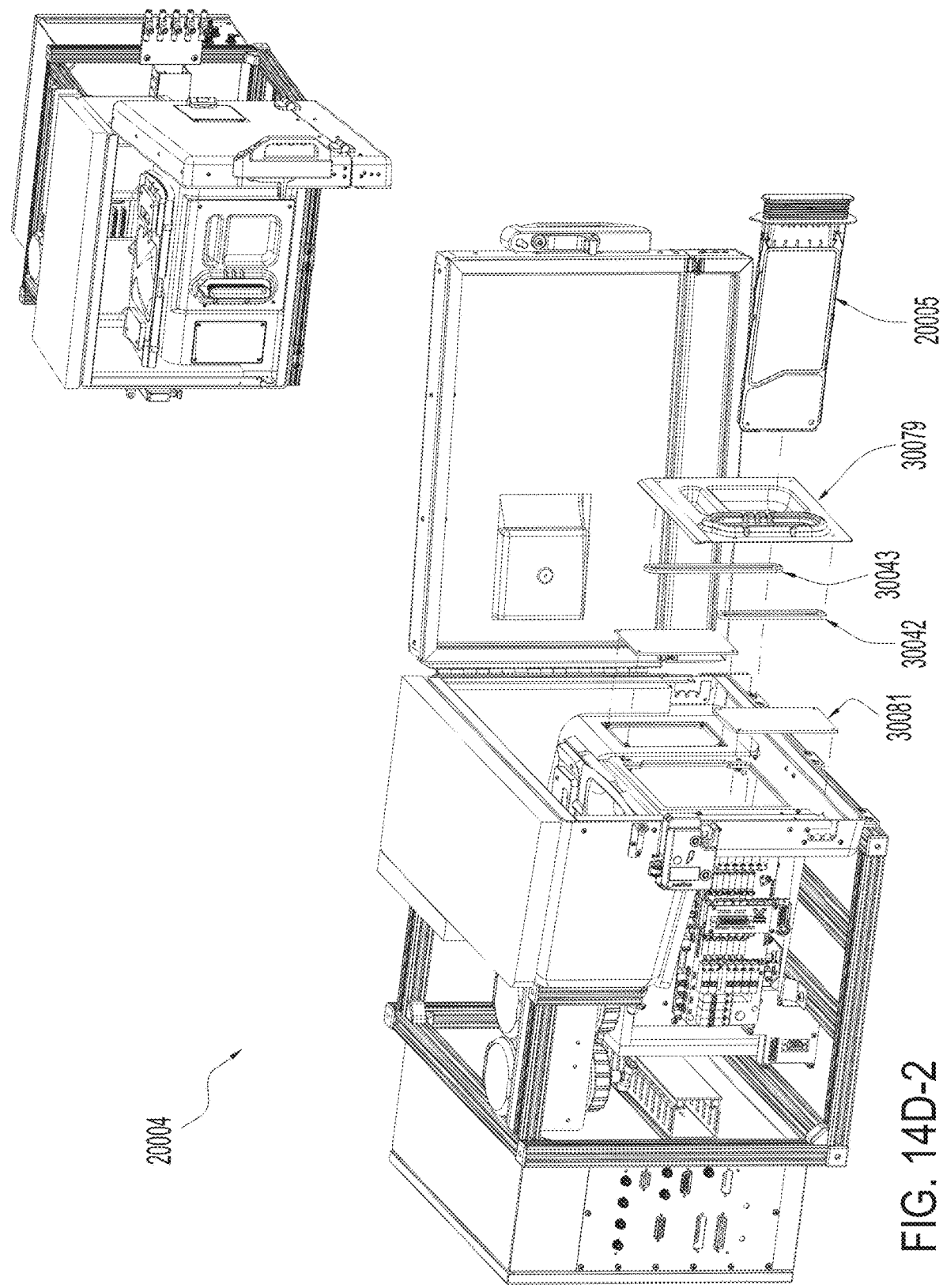
Figures 3, 14D:
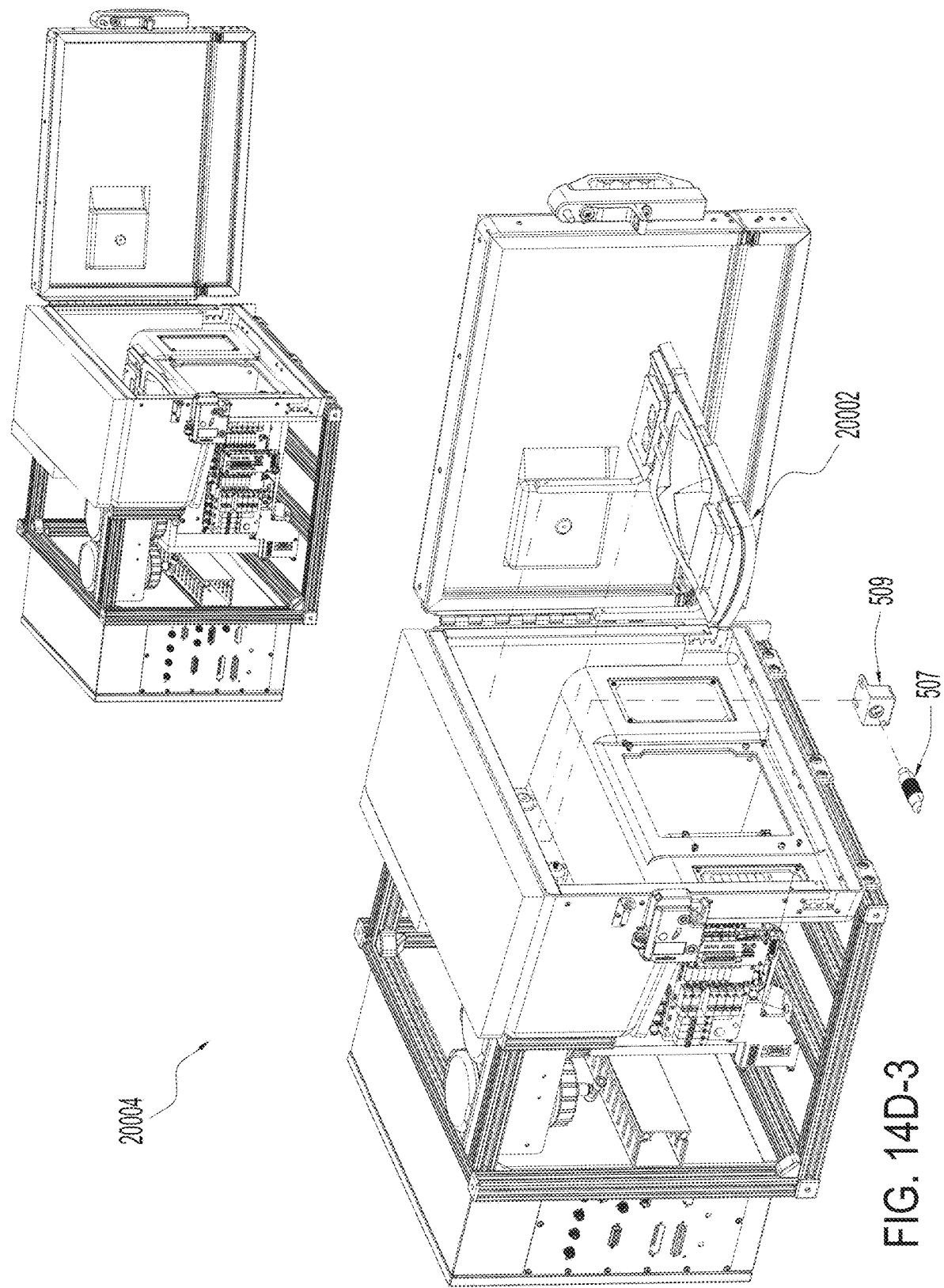
Figures 4, 14D:
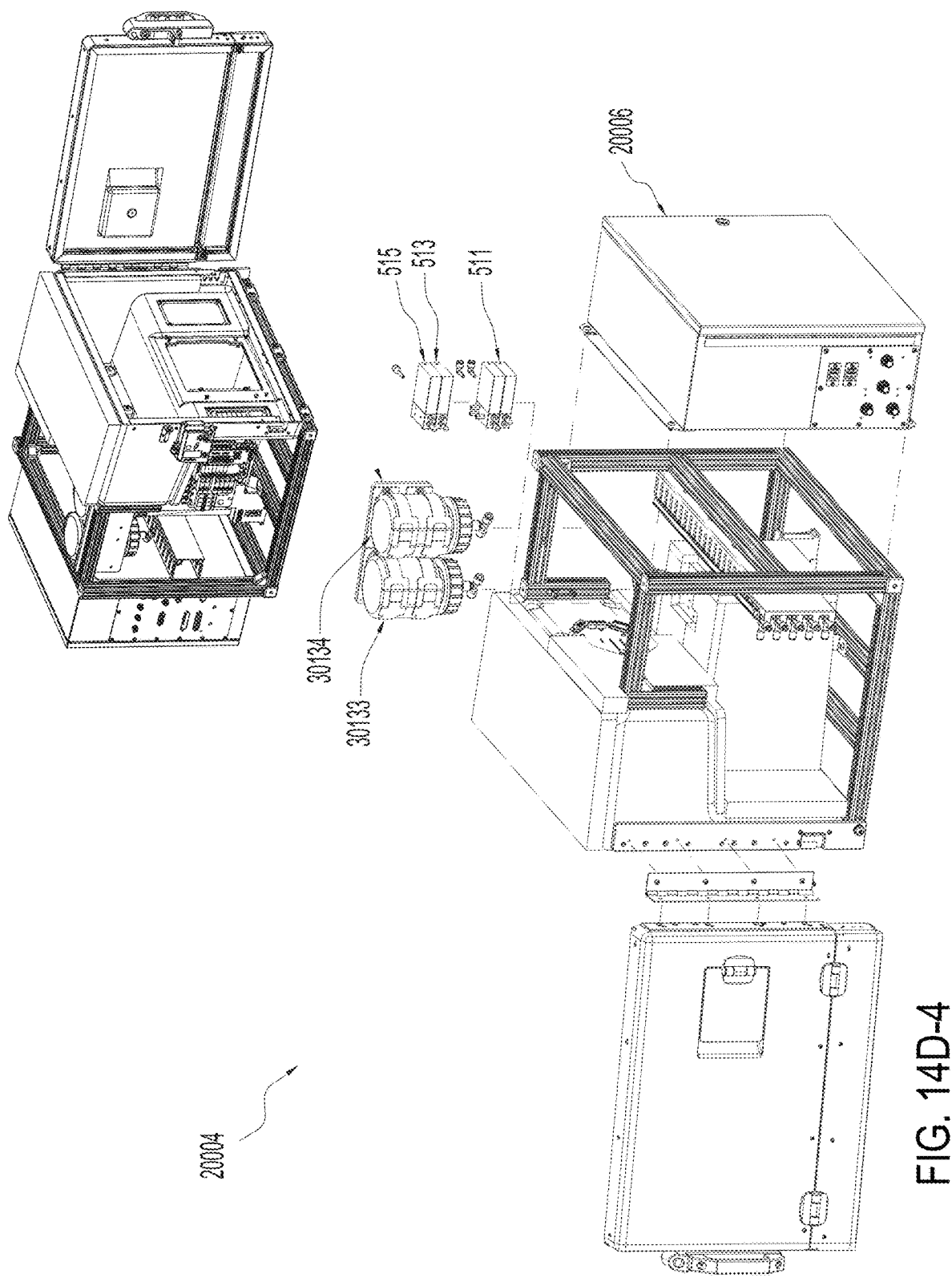
Figures 5, 14D:
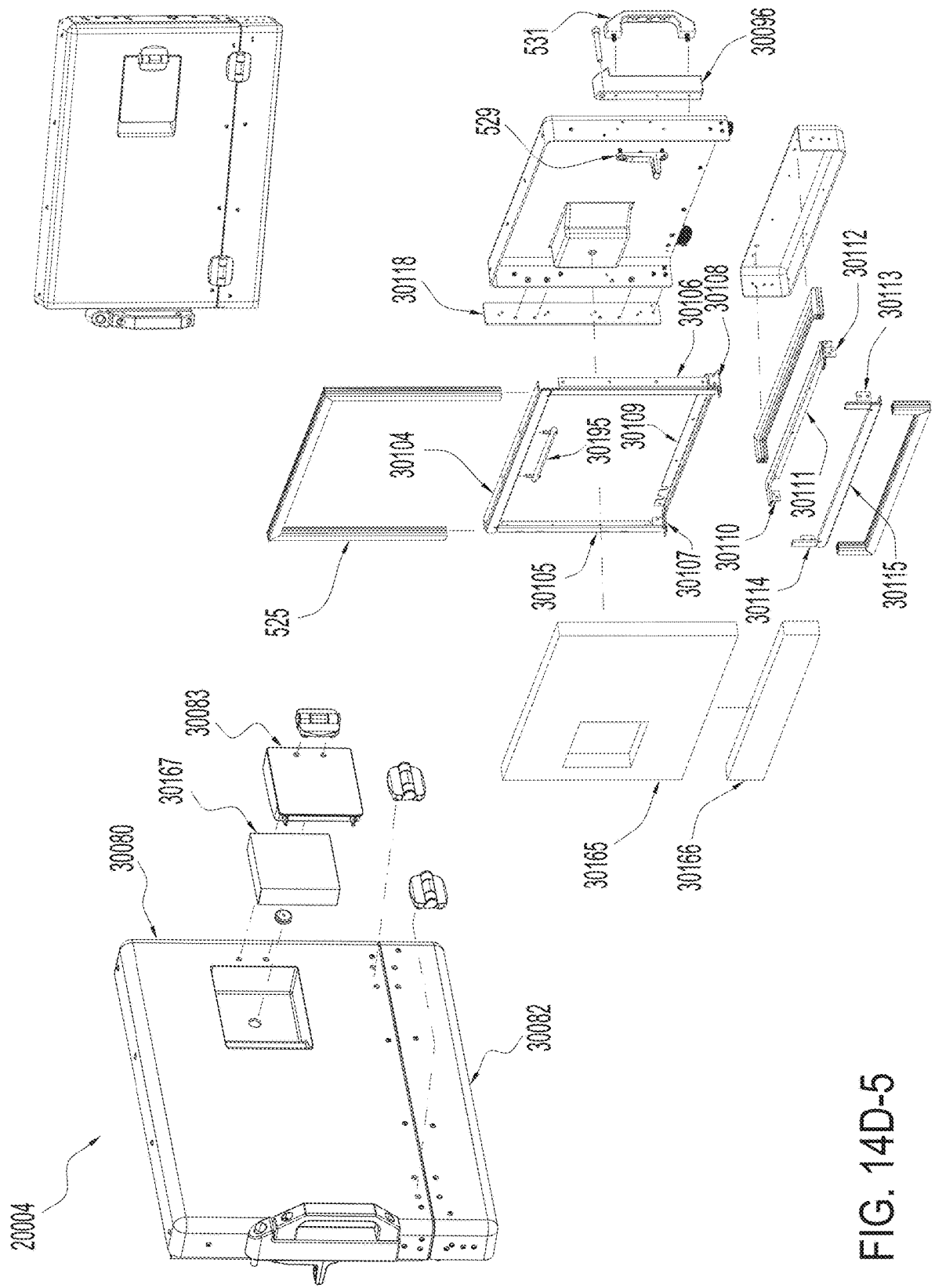
Figures 6, 14D:
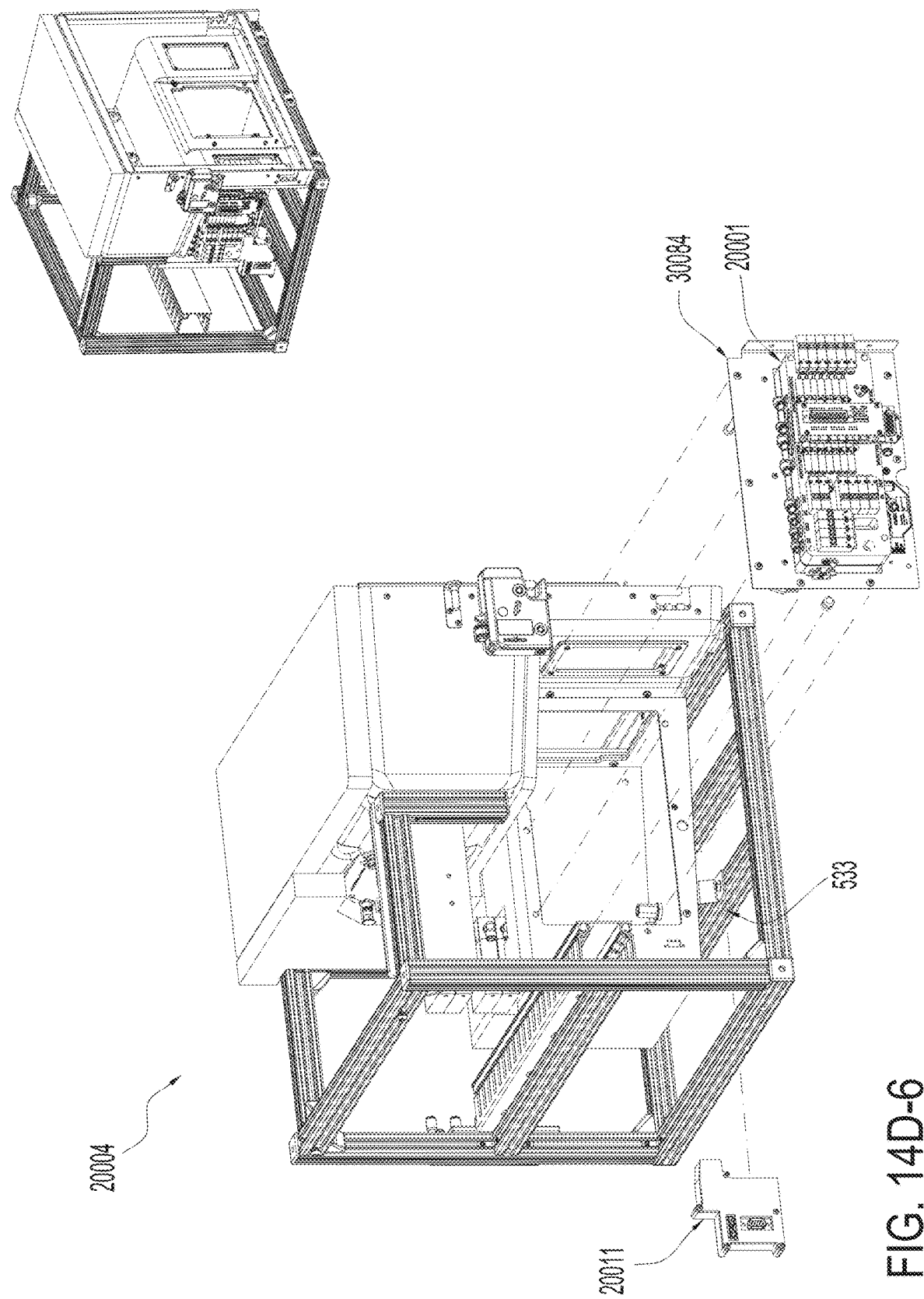
Figure 14D:
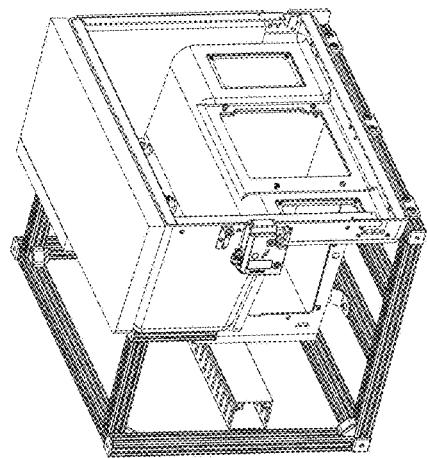
Figure 7:
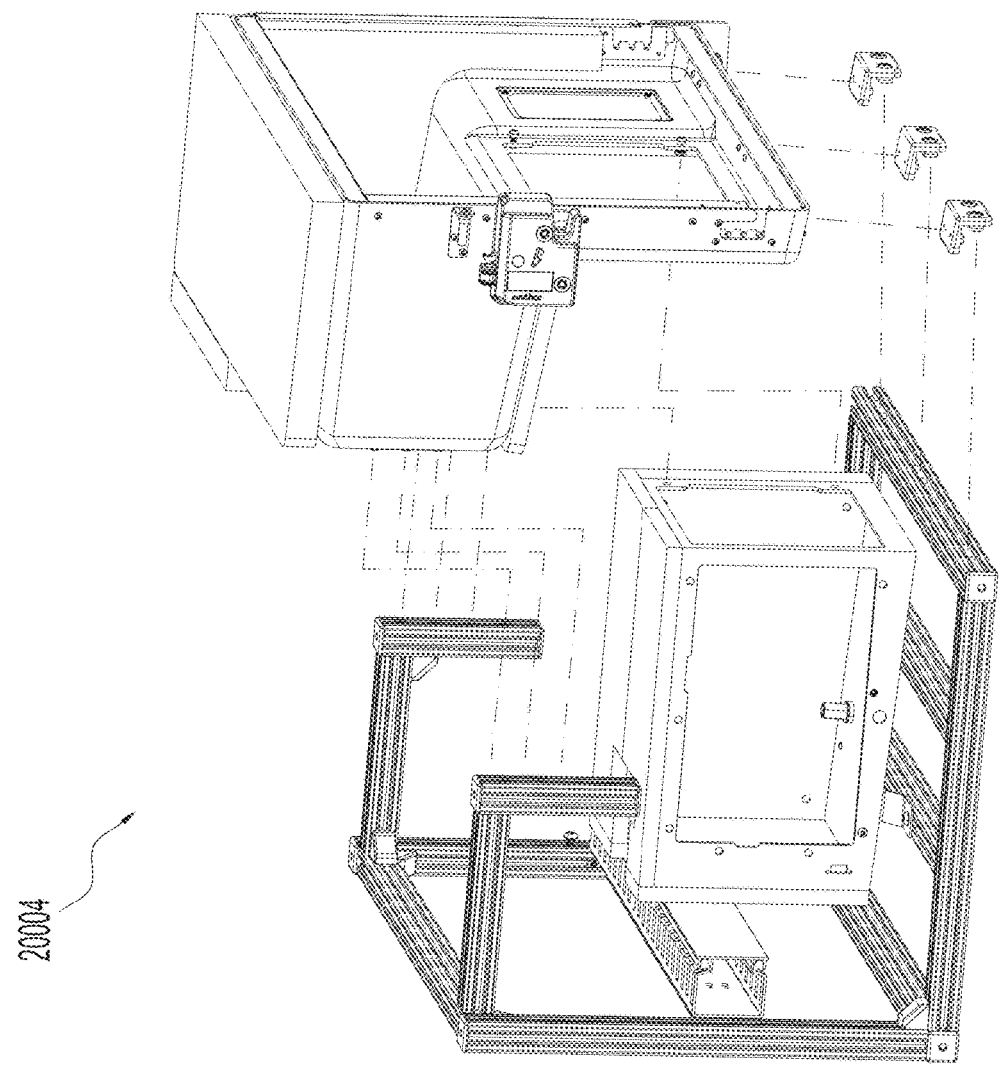
Figures 8, 14D:
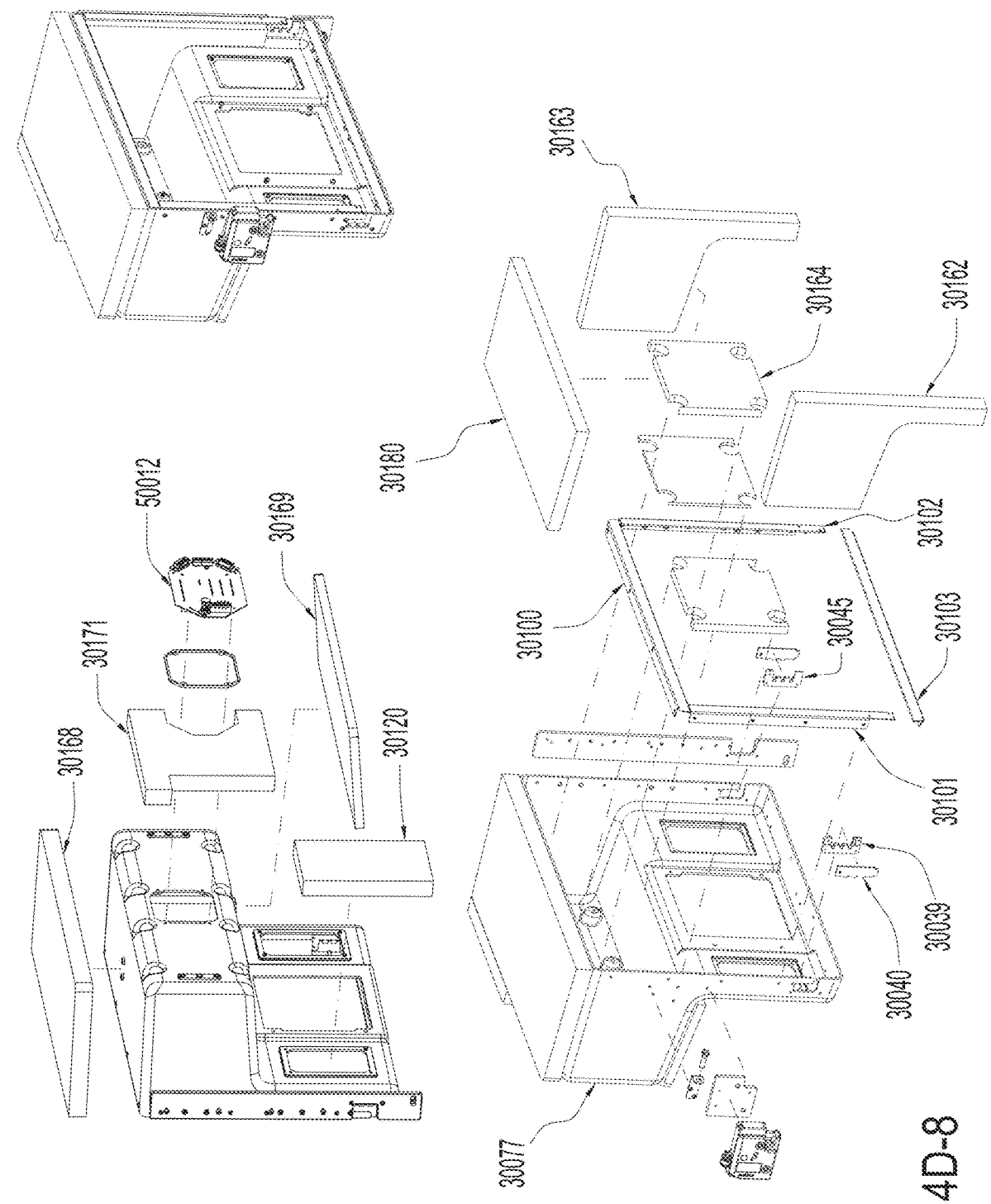
Figures 9, 14D:
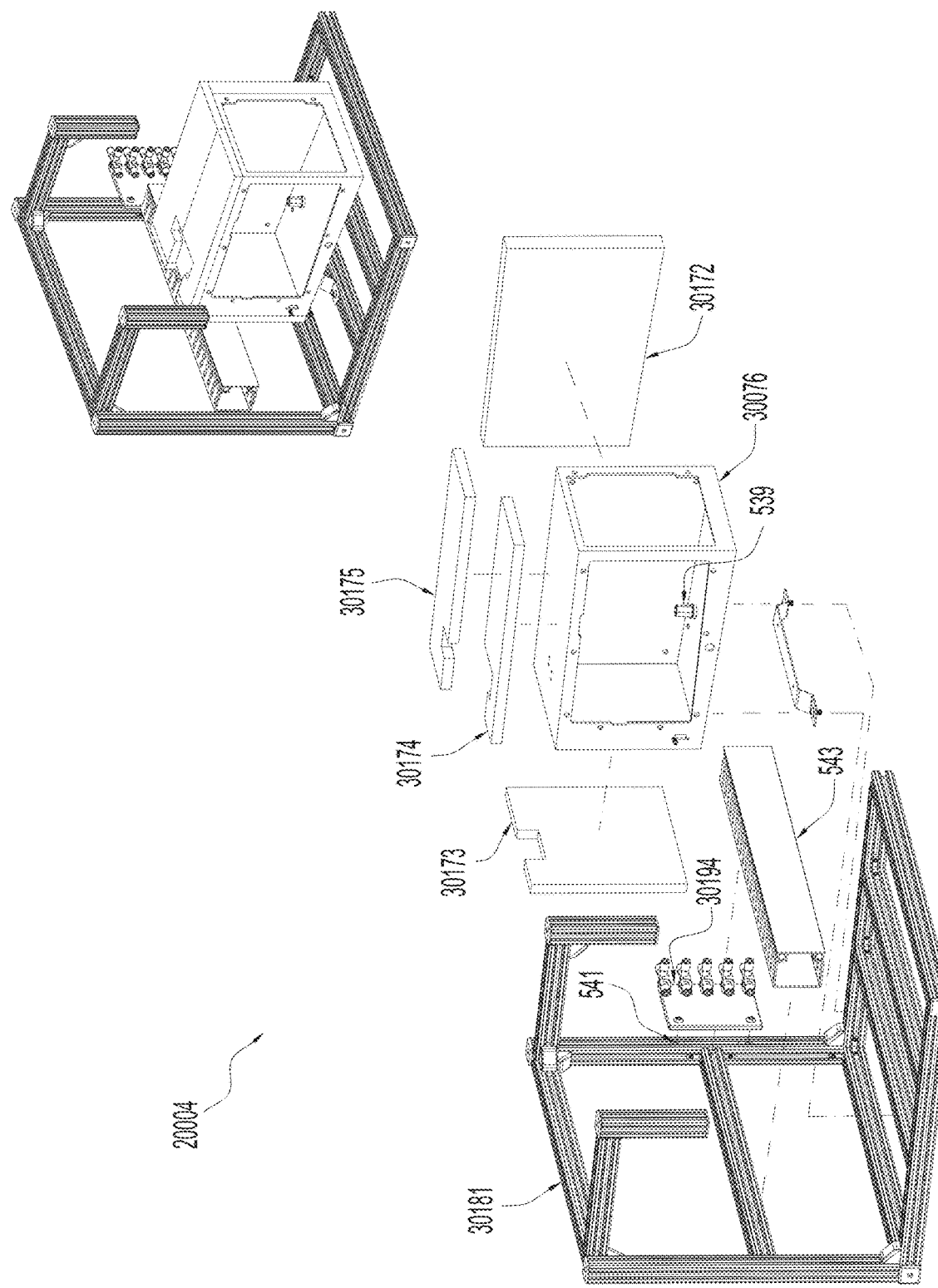
Figures 10, 14D:
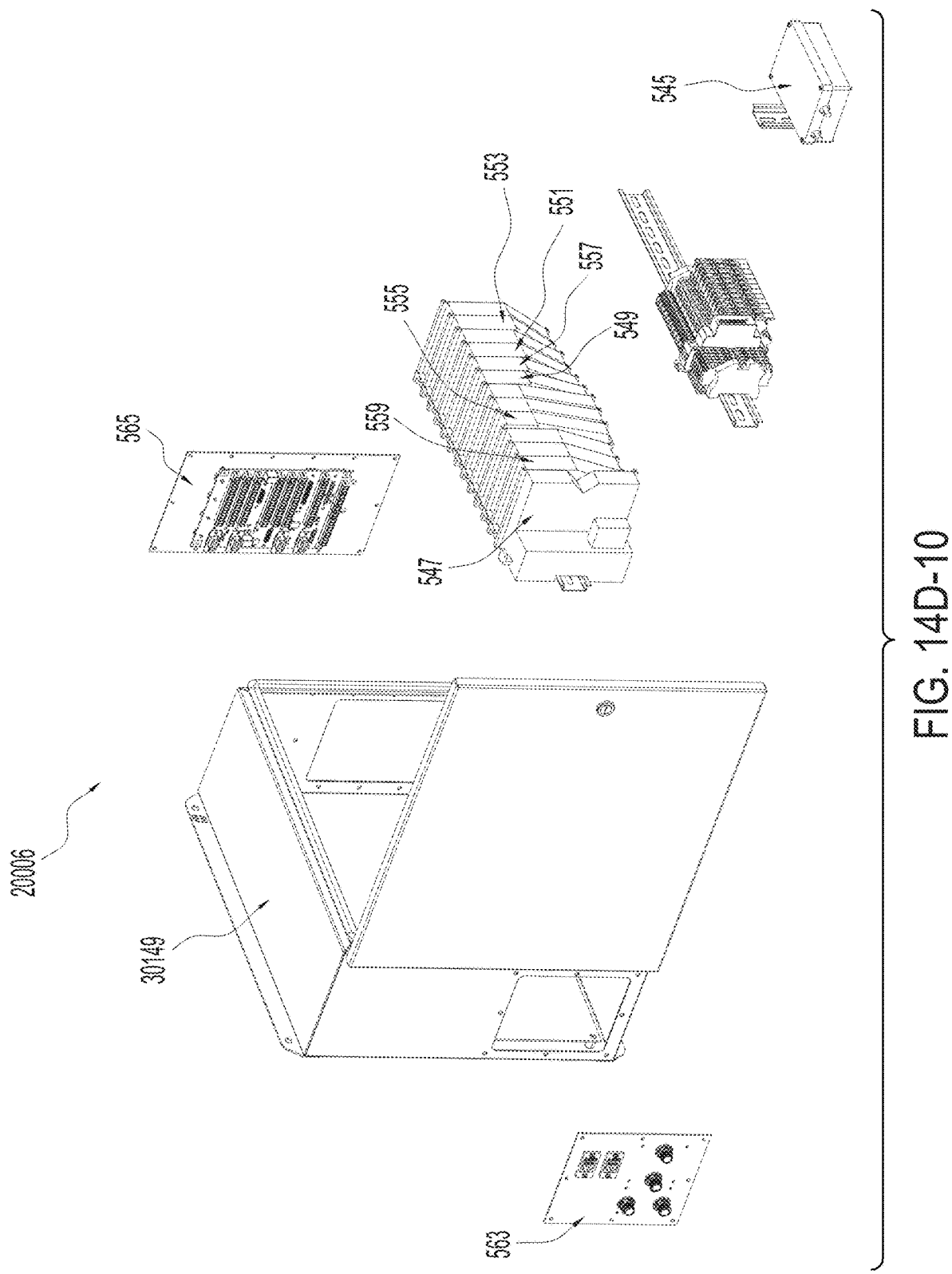
Figures 11, 14D:
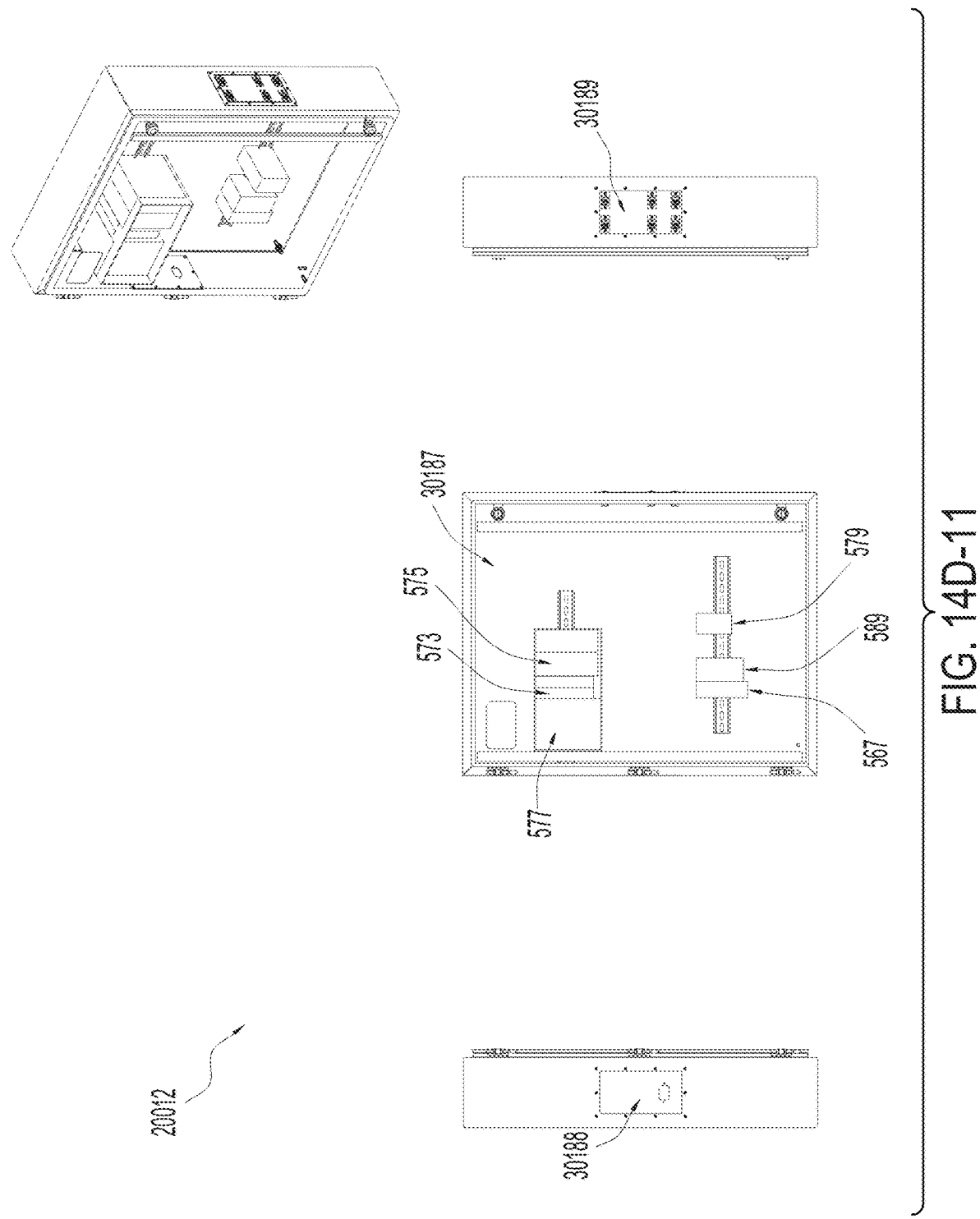
Figures 12, 14D:
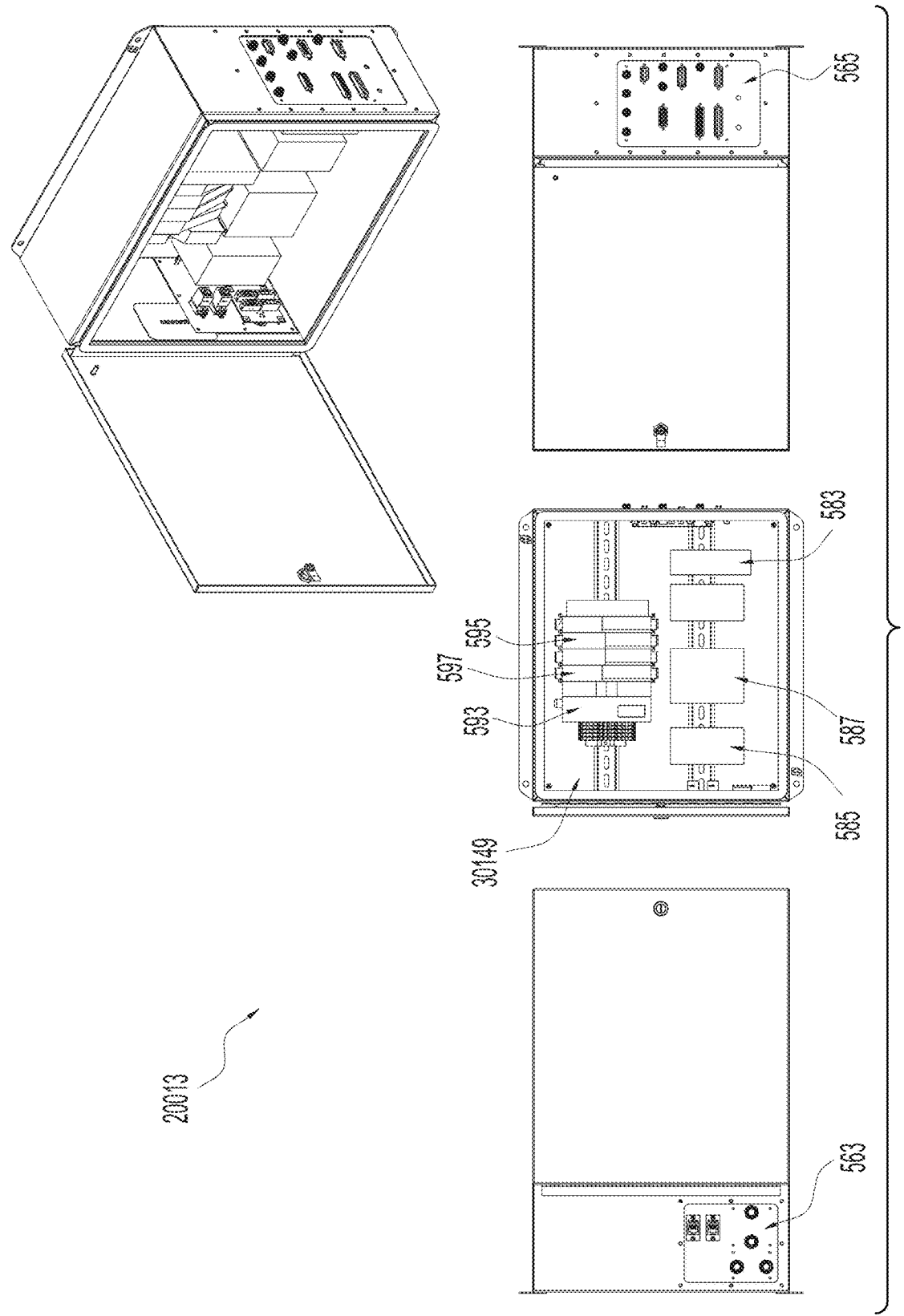
Figure 14E:
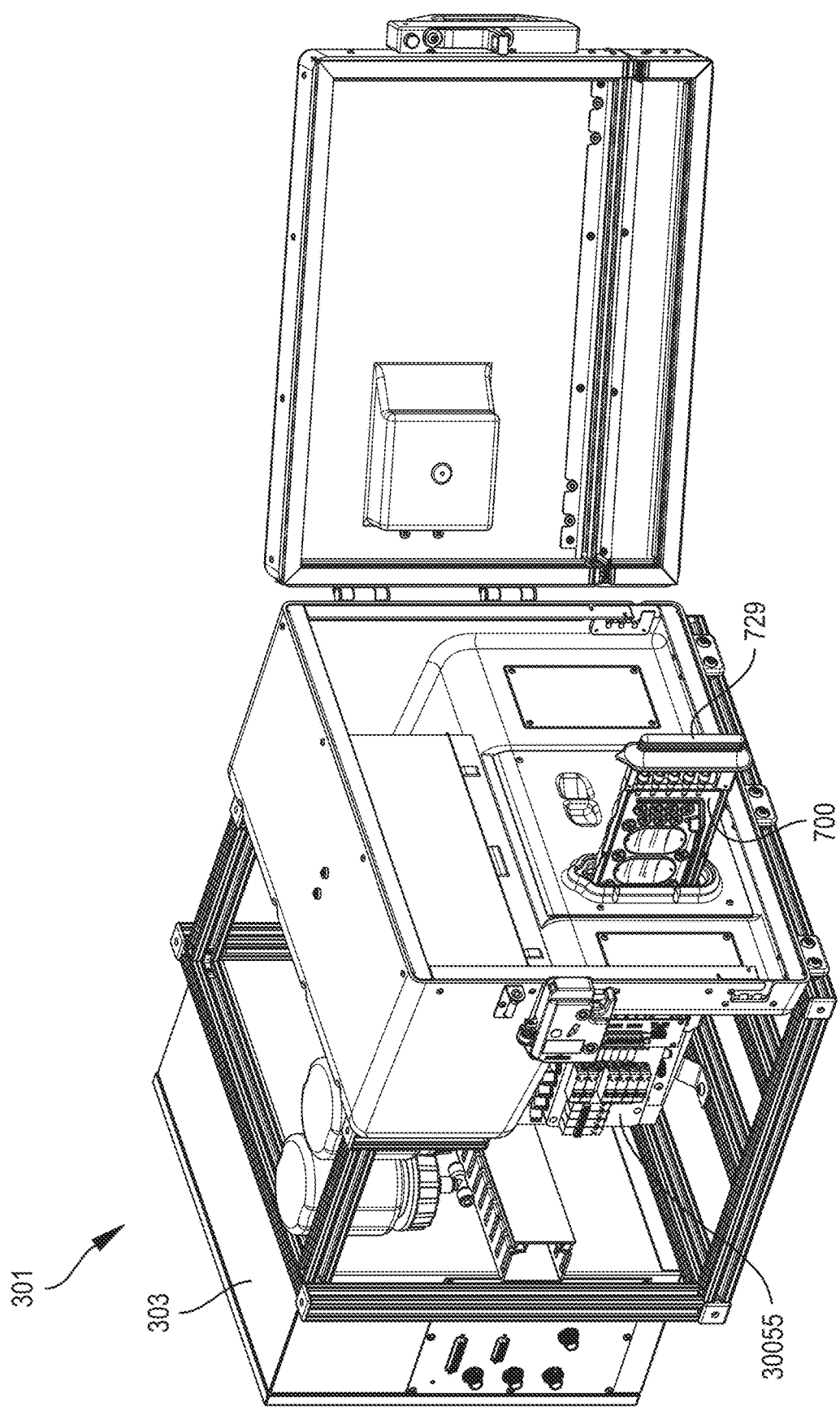
Figure 14F:
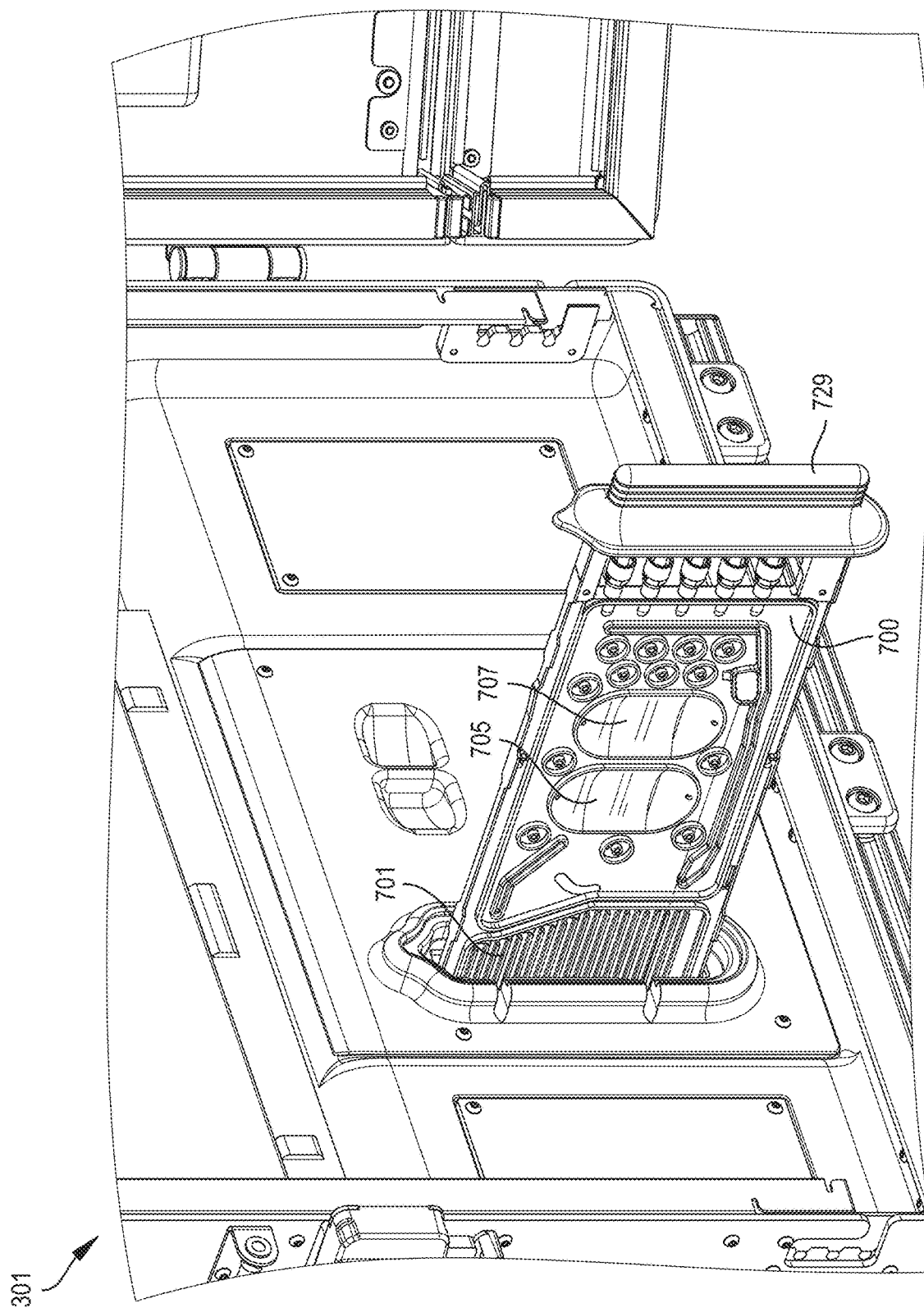
Figure 14G:
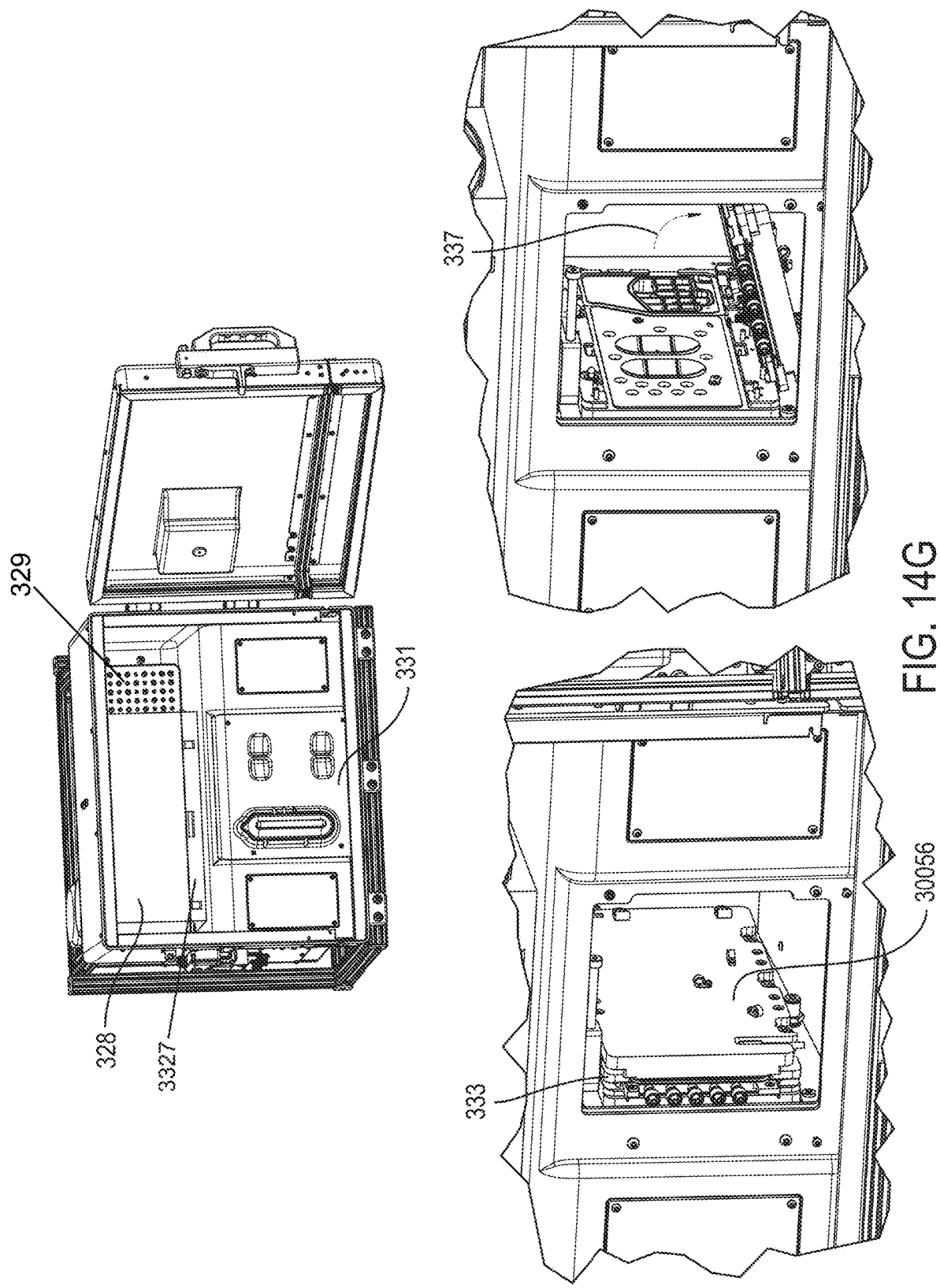

Referring now to FIGS. 14D-14G, behind first door 323 can be positioned removable cover 331. Removable cover 331 can allow maintenance access to an enclosure that can house cassette 700 (FIG. 14E) and associated components. Disposable cassette 700 can be inserted into system enclosure 301, surrounded by components of the manifold/cassette assembly 305 (FIG. 14I). The vertical orientation of cassette 700 can encourage air that is trapped in gas exchange area 701 or anywhere upstream of the pumping chamber outlet, for example, in pump chambers 705/707, to migrate to a position that can enable bubble detection and removal. Bubble detection can be performed in the pumping chamber outlet, and trapped air can be backpumped into the waste line. Detaching removable cover 331 can enable maintenance of internal components of the thermal enclosure, for example, but not limited to manifold pump side gasket 30066, manifold upper gas exchange gasket 30067, manifold channel side gasket 30068, manifold lower gas exchange gasket 30069 (FIG. 14K). Cassette 700 can be removed without removing cover 331. Latches 333 (FIG. 14G) can enable manifold backing plate 30056 (FIG. 14G) to be swung away 337 (FIG. 14G) for easy access to manifold pump side plate 30053 (FIG. 14K) pneumatic connections of manifold bladder 30072 (FIG. 14K), and manifold pump side gasket 30066, manifold channel side gasket 30068, manifold lower gas exchange gasket 30069 (FIG. 14K), and other components. Mounting plate 329 can support user-supplied device(s), user-supplied sensors, and user-supplied exercise hardware (collectively referred to as user-supplied equipment). In some configurations, mounting plate 329 may be composed of a grid of M4 and M6 threaded holes. In some configurations, the threaded holes may be spaced 5 cm apart. In some configurations, custom 3D printed or machined brackets may be used to transition between existing mounting features on user-supplied equipment and the mounting plate. In some configurations, user-supplied equipment may interface with the user interface board 50012 (FIG. 14D-8). User-supplied equipment connected to the user interface board 50012 may be monitored and controlled by the system software. The software required to monitor and control the user-supplied equipment may be custom to the user's process, or selected from previously prepared software. A user-supplied device can be mounted on mounting plate 329 (FIG. 14G), which is shown partially covered by placeholder block 328 (FIG. 14G). In some configurations, multiple mounting plates can be used for the user-supplied device as well as other devices such as, for example, but not limited to, exercise hardware.

Referring now to FIG. 14D-1, reservoir heater 20002 can include an insulated tray supported by brackets and including thermal elements maintaining the temperature of the contents of a reservoir. In some configurations, reservoir heater 20002 can maintain the temperature of holding tank 30122. Holding tank 30122 can rest upon holders 30142 and 30143, and can be secured by clamps 30144 and 30190. Secured holding tank 30122 can rest upon tray 30088. On the opposite side of tray 30088 are thermal elements 505. In some configurations, exemplary thermal elements 505 can include, but are not limited to including, MCMASTER-CARR® 7945T892 24 VDC heaters. Brackets 30089 and 30090 provide contoured surfaces on which the holding tank configuration can rest. The configuration can also include a thermal cutoff device (TCO) mounted by TCO mount 30094 and a resistance temperature detector (RTD) connected by RTD bracket 30093. Brackets 30089 and 30090 can be surrounded by foam insulation 30184 that can insulate thermal elements 505. The configuration can include thermostat 503. In some configurations, thermostat 503 can include DIGI-KEY® 60° B12A06005AEDA0GE thermostat.

Referring now to FIGS. 14D-2 through 14D-9, thermal envelope 20004 can house molded cassette assembly 20005 (FIG. 14D-2) that can slide into internal access panel 30079 (FIG. 14D-2). Internal access panel 30079 (FIG. 14D-2) can be secured into thermal envelop 20004 by front panel mounts 30042 (FIG. 14D-2) and 30043 (FIG. 14D-2). Thermal envelope 20004 can also include further barriers to various types of contamination, including, but not limited to, internal side panels 30081 (FIG. 14D-2). Thermal envelope 20004 can house thermal control for the content of a media reservoir enclosed in thermal envelope 20004. In some configurations, thermal control can include reservoir heater 20002 (FIG. 14D-3). Thermal envelope can also include a sensor that can detect the height of holding container 30122 (FIG. 14D-3) in order to insure that holding container 30122 (FIG. 14D-3) contains media. The height of the holding container correlates to its volume. Determining when the holding container is not at an appropriate height can ensure that there is always enough media or solution. In some configurations, the sensor can include proximity sensor 507 (FIG. 14D-3) such as, for example, but not limited to an ALLEN-BRADLEY® 873M-D18RA1300 ultrasonic sensor. Proximity sensor 507 (FIG. 14D-3) can be held in place by, for example, but not limited to, bracket 509 (FIG. 14D-3). Bracket 509 (FIG. 14D-3) can include, but is not limited to including, an ALLEN-BRADLEY® 871A-SCBP18 snap clamp bracket. Thermal envelope 20004 can house accumulator containers 30133 (FIG. 14D-4) that can be mounted to accumulator mounting plate 30134 (FIG. 14D-4). Proportional pressure control valve 511 (FIG. 14D-4) can be coupled with proportional pressure regulators 513/515 (FIG. 14D-4) to assess the contents of accumulator containers 30133 (FIG. 14D-4). Accumulator containers 30133 (FIG. 14D-4) provide consistent pressure/vacuum on the pump chambers by storing air between pressurizations and vents. Thermal envelope 20004 can include electronics box 20006 (FIG. 14D-4) that can house power and data controls for the system. Thermal envelope 20004 can include barriers such as thermal enclosure primary door 30080 (FIG. 14D-5), lower door 30082 (FIG. 14D-5), and sampling door 30083 (FIG. 14D-5). The primary and lower doors can include plates 30104-30106 (FIG. 14D-5) and 30110-30115 (FIG. 14D-5). Primary door 30080 (FIG. 14D-5) can include sealing faces 30107-30109 (FIG. 14D-5). Exemplary sealing faces 30107-30109 (FIG. 14D-5) (other sealing faces are shown but not labeled) can include magnetic gaskets 525 that can enable a seal on steel flanges 30104, 30105, 30106, for example. Each of primary, lower, and sample doors includes insulation 30165-30167 (FIG. 14D-5) respectively. A media bag can be suspended upon media bag rod 30195 (FIG. 14D-5). Media bag rod can compactly hang the media bag, which can enable draining of the media. Primary door 30080 can be fitted with sensor 529 (FIG. 14D-5) that can indicate the status of the door. Primary door 30080 (FIG. 14D-5) can include gasket 525 (FIG. 14D-5), and can be opened and shut with handle 531. Handle 531 to access the primary door is mounted to the primary door via handle mount 30096. Latch 529 engages with latch receiver 535 (FIG. 14D-8) to serve as a lock for the system. Adapter plates 30118 (FIG. 14D-5) and 30117 (FIG. 14D-8) are used to mount a hinge to thermal envelope 20004.]] Thermal envelope 20004 can include manifold mount plate 30084 (FIG. 14D-6) and thermal enclosure base 30077 (FIG. 14D-6) and thermal enclosure base 30077 (FIG. 14D-8) that can hold pump 20001 (FIG. 14D-6), and can be mounted within thermal enclosure 20004. Structural parts such as T-slotted extrusion 533 (FIG. 14D-6) can enable flexible placement of the components of the system within thermal envelope 20004. Thermal enclosure 20004 can house a glucose sensor that can be controlled by glucose board 20011 (FIG. 14D-8). The base can be insulated and sealed by components 30162-30180 (FIG. 14D-8) (insulation) and 30100-30103 (FIG. 14D-8) (sealing faces). Status of various components of thermal envelope 20004 can be provided by user interface 50012 (FIG. 14D-8), for example. Thermal envelope 20004 can include supply drain components 30039/30040/30045 (FIG. 14D-8). Thermal envelope 20004 can house manifold enclosure 30076 (FIG. 14D-9) that can be insulated on all sides by components 30172-30175 (FIG. 14D-9). Manifold enclosure 30076 can be mounted in manifold frame 30181 (FIG. 14D-9), and can include shock absorber 539 (FIG. 14D-9) that can serve as a soft stop for the manifold door to rest upon when fully opened. Gas, positive pressure, and vacuum lines (not shown) that run between systems can be routed through wire duct hinged cover 543 (FIG. 14D-9). No need to reference 30085 30194. Push-to-connect fittings retainer 30194 can be mounted onto the frame 541 to assist in securing push to connect fittings used to connect tubing in order to minimize leaks on fittings.

Referring now to FIGS. 14D-10, 14D-11, and 14D-12, electronics box 20006 electronics box PLC 20012 (FIG. 14D-11) and electronics box rack 20013 (FIG. 14D-12) can include enclosure 30149 and circuit boards for data management. Circuit boards can include, but are not limited to including, sensor board 545, data communications boards 547/559, analog input boards 549/551/553, and power boards 553/557. Connector panels 565 and 563 can enable data and communications cabling connections.

Referring now to FIGS. 14D-11 and 14D-12, electronics box 30187 (FIG. 14D-11) can include electronics box PLC 20012 (FIG. 14D-11) that can include components such as breakers 567 (FIG. 14D-11)/583 (FIG. 14D-12), power supplies 569/577 (FIG. 14D-11) and 585/587 (FIG. 14D-12), ethernet bridge, switch, and connections 573/579/30188/30189 (FIG. 14D-11), controller 575 (FIG. 14D-11), and control box 30149 (FIG. 14D-12). Control box 30149 (FIG. 14D-12) can include ethernet adapter 593 (FIG. 14D-12) and analog input modules 595/597 (FIG. 14D-12).

Referring now to FIGS. 14H-14P, manifold pump side plate 30053 can implement the structure laid out with respect to pneumatic block 2011 (FIG. 12A) that can enable pumping of the media through reservoir/bioreactor module cassettes 700. Applying positive or negative pressure to different regions on cassette 700 can close fluid valves and deliver fluid, or can open fluid valves and withdraw fluid, respectively. Positive pressure can inflate manifold bladder 30072 (FIG. 14K) that can press cassette 700 against manifold interface components, forming a seal during pumping. Exemplary manifold/cassette configuration 305 can include the structure, electronics, and valves that can pump fluid through system 3000 (FIG. 1A). The description herein refers to cassette 700 for exemplary purposes only. Any of cassettes 699/700 (FIGS. 6A-6D) and other similar cassettes can be accommodated by a version of manifold/cassette 305. In addition, a manifold side plate with similar characteristics to manifold pump side plate 30053 can accommodate cassettes 107/111 (FIGS. 2A/2B) and other similar cassettes.

Continuing to refer to FIGS. 14H-14P, manifold/cassette configuration 305 can include, but is not limited to including, manifold backing plate 30056 that can operably couple with manifold latch 30057. Manifold latch 30057 can span the components of manifold/cassette configuration 305 and can enable both retaining of the components in adjacency to each other as well as detachment of the components from each other to enable cleaning of the durable components and replacement of the disposable components. Cassette 700 can include optional handle 729 that can operably couple with cassette 700. Handle 729 can enable the withdrawal of cassette 700 from manifold/cassette configuration 305. When cassette 700 is withdrawn from manifold/cassette configuration 305, the components surrounding cassette 700 can be cleaned. In some configurations, handle 729 can include sliding features that can securely encase the sides of cassette 700. In some configurations, handle 729 can include any type of secure, possibly removable, attachment means such as, for example, but not limited to, glue, screws, and hook and eye, that can attach handle 729 to cassette 700. Cassette 700 can include keyed features that can enable correct placement of cassette 700 in manifold/cassette configuration 305. Keyed features can include, but are not limited to including, geometric features.

Figure 14H:
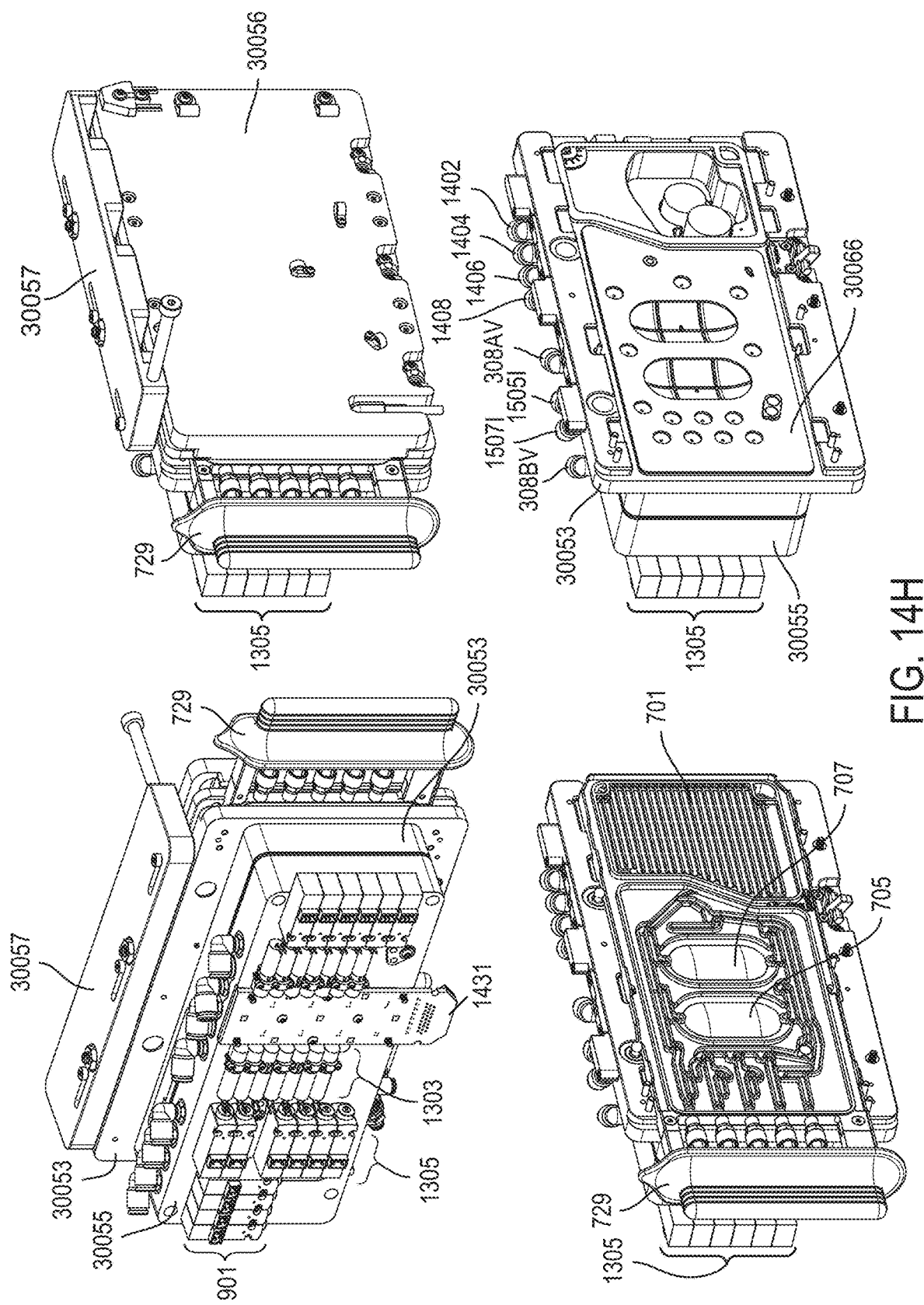
FIGS. 14H-14J are perspective diagrams of the manifold of the present teachings.
Figure 14I:
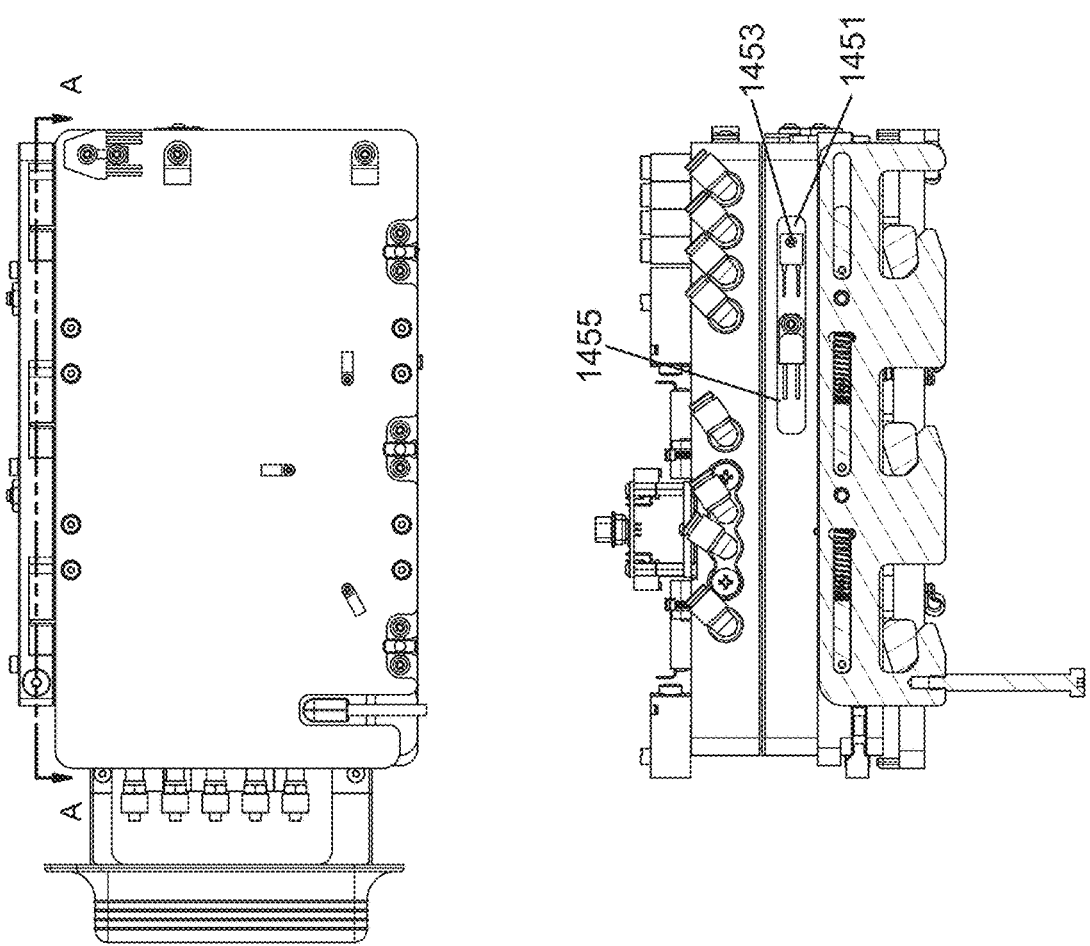
Figure 14I:
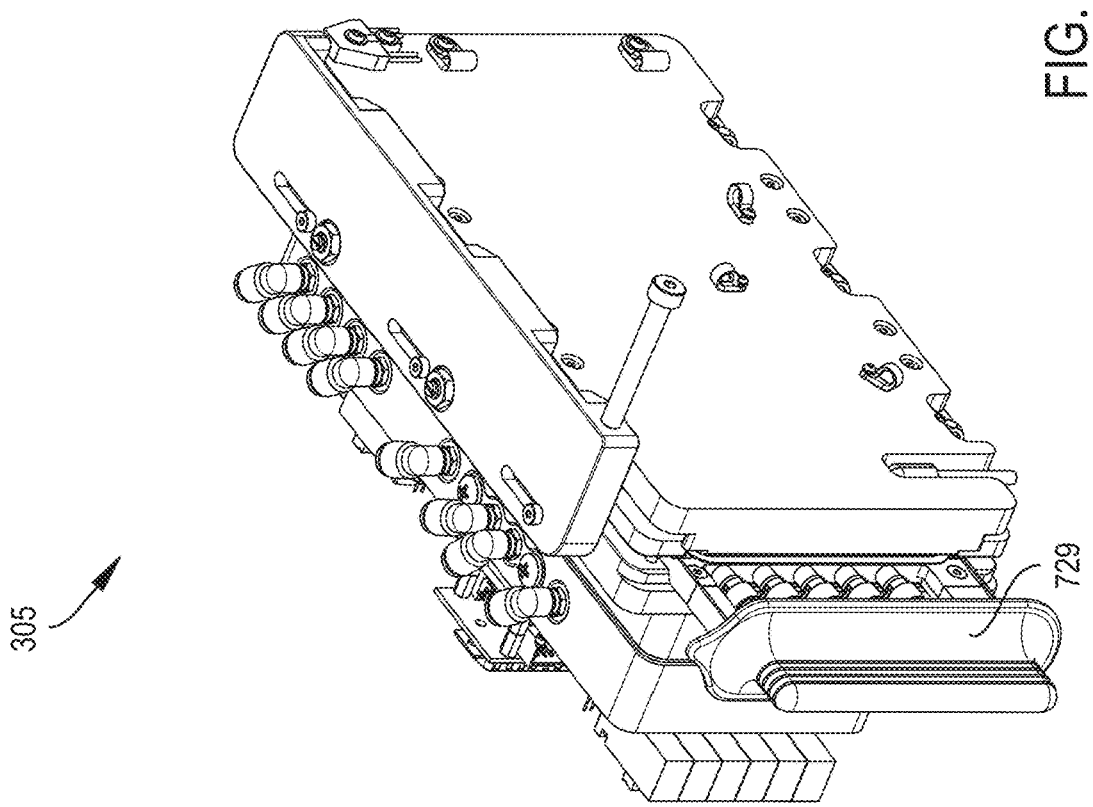
Figure 14J:
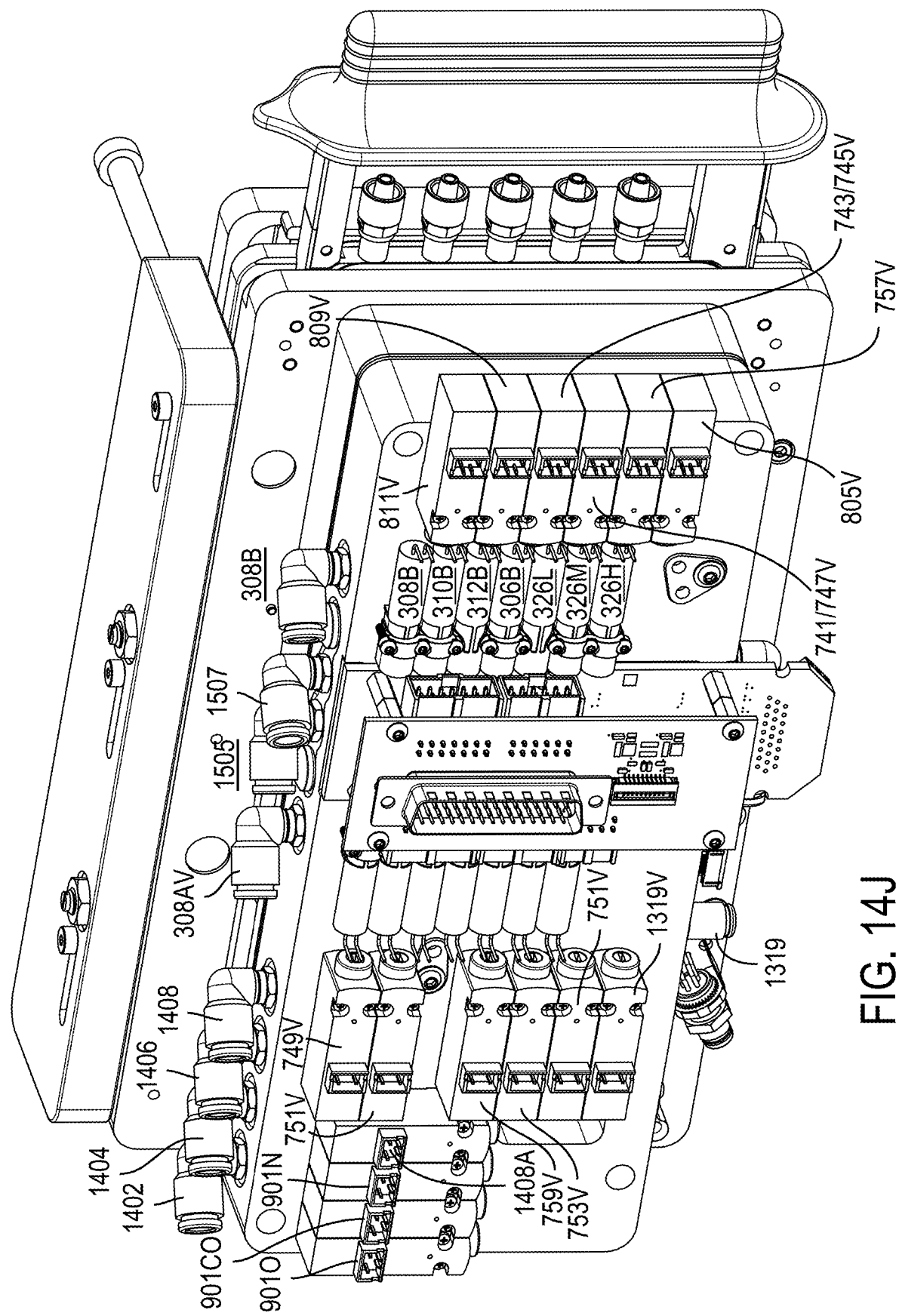
Figure 14K:
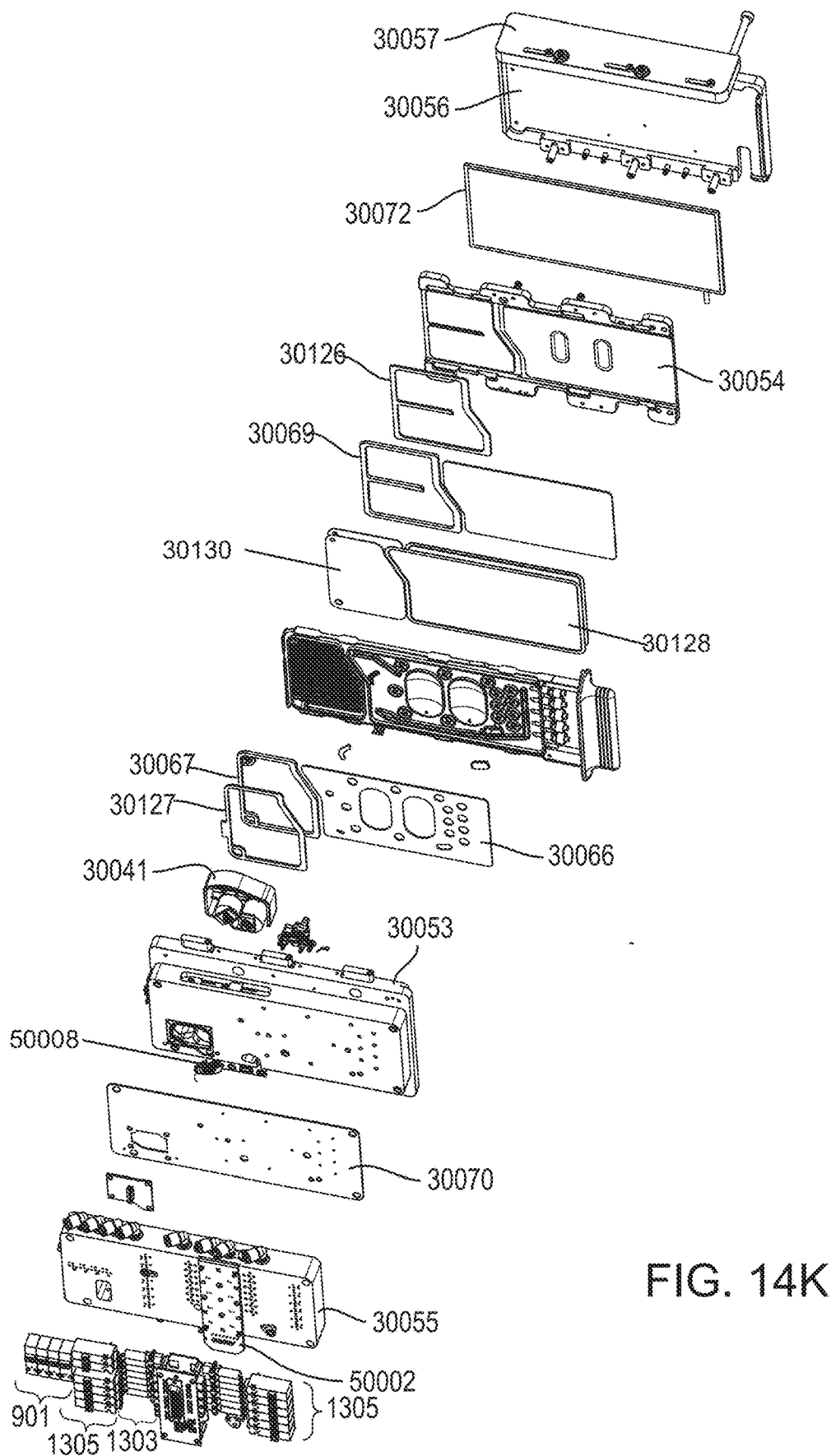
FIGS. 14K-14P are exploded perspective diagrams of the manifold of FIGS. 14H-14J.
Figure 14L:
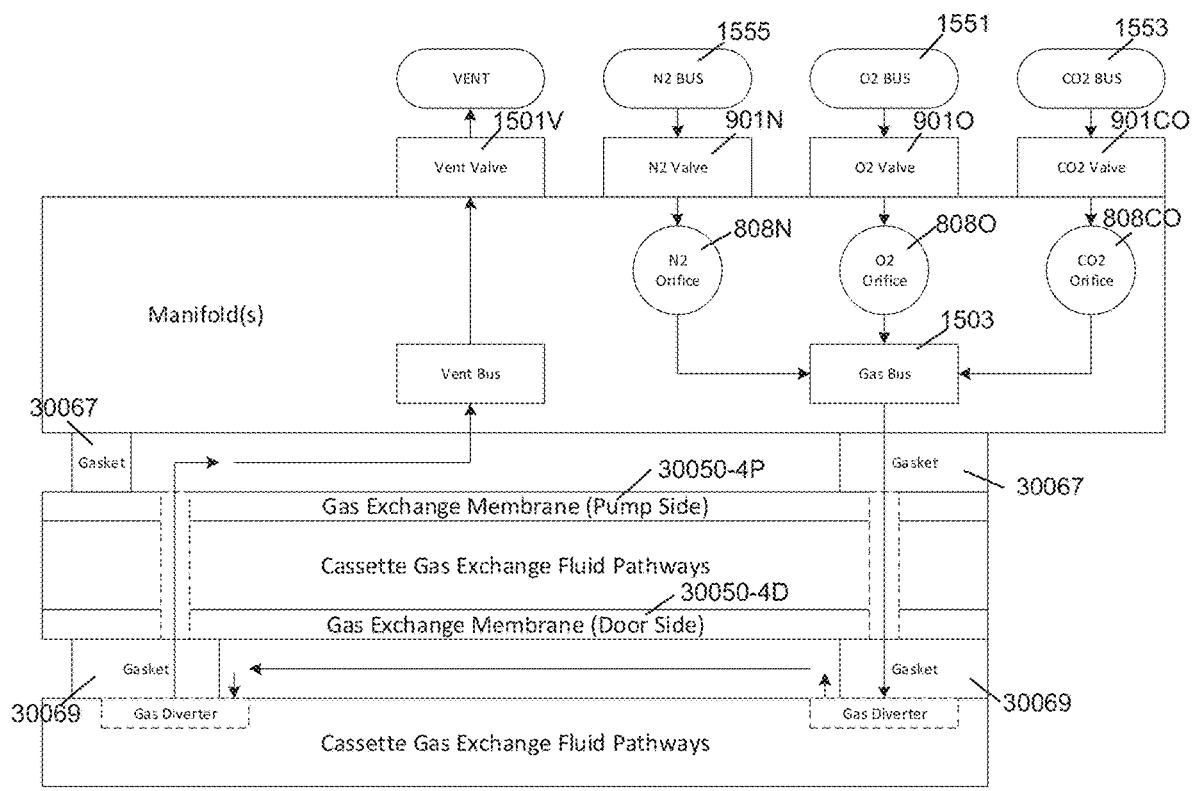

Continuing to refer to FIGS. 14H-14P, manifold/cassette configuration 305 can include manifold bladder 30072 (FIG. 14K) that can be inflated by compressed air 1505 (FIG. 12A) through compressed air inlet 15051 (FIG. 14J) to apply pressure upon cassette 700 through manifold channel side plate 30054 (FIG. 14K) and manifold channel side gasket 30068. Gas exchange membranes 30130/30131 (FIG. 14K) can enable gas exchange of the fluid traversing gas exchange area 701, while pumping membranes 30128/30129 (FIG. 14K) can discourage gas exchange of the fluid elsewhere on cassette 700. In some configurations, a gap between the two parts of fluid membrane 30128/30129 (FIG. 14K) might be present. This gap can take into account that there could be an overhang between the two sealing surfaces. Gas can be provided to surface of gas exchange membranes 30130/30131 (FIG. 14K) through first (or second) gas exchange corner 30054-1 (FIG. 14N), maintaining a flow of the desired gas(es) over the membrane and ultimately into the fluid. The sizes of corners 30054-1 (FIG. 14N) can be entirely arbitrary, relative to each other and relative to gas exchange membranes 30130/30131 (FIG. 14K), suiting the geometry of cassette 700. The mixed gases travel from a port in manifold pump side plate 30053 (FIG. 14K) through corners 30054-1 (FIG. 14K), over gas exchange membranes 30130/30131 (FIG. 14K), and out a vent port in manifold pump side plate 30053 (FIG. 14K). Lower/upper gas exchange gasket shims 30126/30127 (FIG. 14K) and manifold upper/lower gas exchange gaskets 30067/30069 (FIG. 14K) can decrease the probability of gas leaks during the exchange process. Gas exchange can adjust the properties of the fluid when sensors that are situated on cassette 700 detect that the fluid is in need of adjustment, as discussed herein. Sensors can include, but are not limited to including glucose, temperature, dissolved oxygen, and pH. Gasses that can be used to adjust properties of the fluid can include, but are not limited to including, oxygen, carbon dioxide, and nitrogen. These gasses can enter the manifold through oxygen inlet 1402 (FIG. 14H), carbon dioxide inlet 1404 (FIG. 14H), and nitrogen inlet 1406 (FIG. 14H). Valves 901O (FIG. 14L), 901CO (FIG. 14L), and 901N (FIG. 14L) can meter the introduction of the gasses according to the gas pressure required to adjust the fluid properties to desired values.

Continuing to refer to FIGS. 14H-14P, manifold/cassette configuration 305 can include manifold pump gasket 30066 (FIG. 14K) that can assist in sealing against the cassette fluid membrane pump side membrane 30128 (FIG. 14K). In particular, cassette fluid membrane 30128 (FIG. 14K) can enable pressure to be provided onto pumping chambers and valves on cassette 700 while maintaining the barrier between durable and disposable components. Manifold upper gas exchange gasket 30067 (FIG. 14K) and upper gas exchange gasket shim 30127 (FIG. 14K) are part of the gas exchange process as they enable a sealed situation so that gas can move from gas supplies to gas exchange membranes 30130/30131 (FIG. 14K) without leakage. In particular, manifold upper gas exchange gasket 30067 (FIG. 14K) can include gas exchange corners 30054-1 (FIG. 14N) that can provide for the movement of gas around cassette gas exchange area 701. Upper gas exchange gasket shim 30127 (FIG. 14K) can also include an insert into gas exchange corner 30054-1 (FIG. 14K) with a geometry matches that accommodates manifold upper gas exchange gasket 30067. Manifold/cassette configuration 305 can include manifold pump side plate 30053 (FIG. 14K) and manifold inner backer 30070 (FIG. 14K) that together can respond to selective pressure provided by the positive and negative air pressure entering manifold pump side plate 30053 (FIG. 14K). The positive and negative air pressure can be metered by the valves of manifold pump side plate 30053 (FIG. 14K). Manifold pump side plate 30053 (FIG. 14K) can include gas sensor cover 30041 (FIG. 14K) that itself can include, for example, but not limited to, an oxygen sensor carrier and a carbon dioxide sensor carrier. Manifold pump side plate 30053 (FIG. 14K) can include a glucose sensor adapter board and modules.

Continuing to refer to FIGS. 14H-14P, manifold/cassette configuration 305 can include manifold pump side plate 30053 (FIG. 14K) that can route incoming positive and negative pressure and gasses to cassette 700. Manifold pump side plate 30053 (FIG. 14K) can include reference chambers 911A/B (FIG. 14K), the function of which is described herein. Manifold pump side plate 30053 (FIG. 14K) can include positive inlet 15051 (FIG. 14J) that can admit compressed air to manifold pump side plate 30053 (FIG. 14K), and negative inlet 15071 (FIG. 14J) that can create negative air pressure on manifold pump side plate 30053 (FIG. 14K). Manifold pump side plate 30053 (FIG. 14K) can include reference chamber vents 308AV/BV (FIG. 14J). Pressure upon reference chambers 911A/B (FIG. 14K) results from air 15051 when diverted from the pumping chamber by valves 1303. Manifold pump side plate 30053 (FIG. 14K) can provide mounting points for, for example, but not limited to, various valves, octal pressure sensor board 50002 (FIG. 14M), a manifold interconnect board, and a gas sensor interconnect board. The valves can include, but are not limited to including, solenoid valves and 3/2 NC valves. In some configurations, solenoid valves can include, but are not limited to including, high flow capacity, low power, magnetically latched, 3-port solenoid valves designed to accommodate a small footprint and ultra-low heat. In some configurations, solenoid valves can include, but are not limited to including, 3/2 closed monostable solenoid valves having, for example, a 10 l/m flow capacity.

Continuing to refer to FIGS. 14H-14P, manifold pump side plate 30053 (FIG. 14K) can include valve control regions that can be defined in the control surface of manifold pump side plate 30053 (FIG. 14K) by, for example, but not limited to, scoring, groove, rib or other feature in or on the surface of the control surface, and can be arranged to move the fluid in cassette 700 in a direction generally, transverse to the plane of the sheet. By moving inwardly/outwardly, the valve control regions can move associated portions of the cassette membrane on cassette 700 so as to open and close respective fluid valve ports of cassette 700, and thus control flow in cassette 700. Pump control region 802 (FIG. 14H) can be pressurizable to move associated shaped portions of the cassette membrane. Pump control region 802 (FIG. 14H) can be shaped in a way to correspond to the shape of pump chambers 705/707 (FIG. 14H) when parts of pump control region 802 are extended into pump chambers 705/707 (FIG. 14H). Each of the pump areas and pump control region 802 (FIG. 14H) can include an associated vacuum or evacuation port that can be used to remove all or substantially all of any air or other fluid that may be present between the cassette membrane of cassette 700 (FIG. 14H) and the control surface. Negative and positive pressure delivery can control the delivery of desired volumes of fluid with pump operation and/or the open/closed state of the various valve ports. The pump areas and pump control region 802 (FIG. 14K) can be moved by controlling pneumatic pressure and/or volume on manifold pump side plate 30053 (FIG. 14K). In some configurations, pump control region 802 (FIG. 14H) can be moved by gravity-based systems, hydraulic systems, and/or mechanical systems such as, for example, but not limited to, by linear motors or other means, or by a combination of systems including pneumatic, hydraulic, gravity-based and mechanical systems.

Figure 14M:
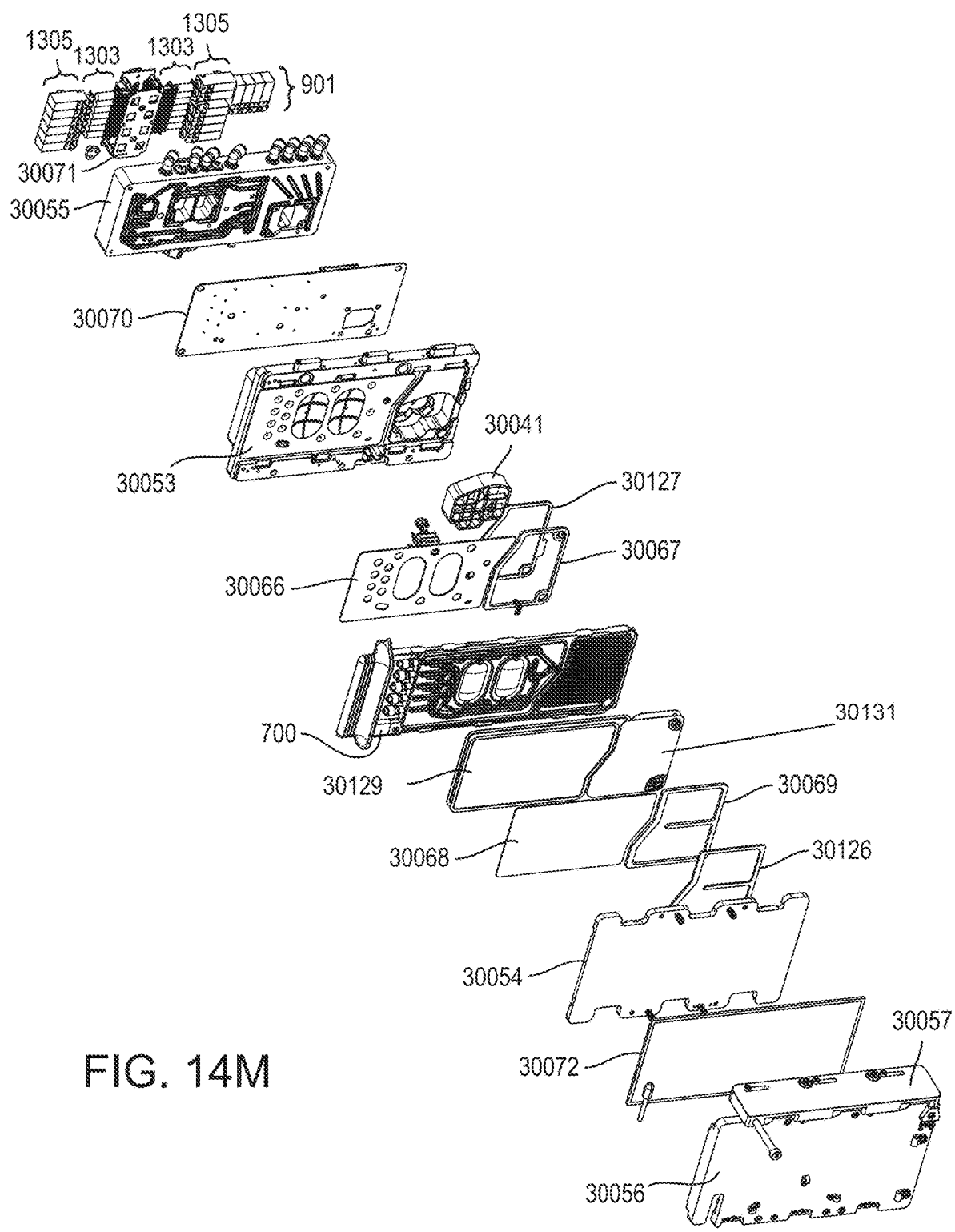
Figure 14N:
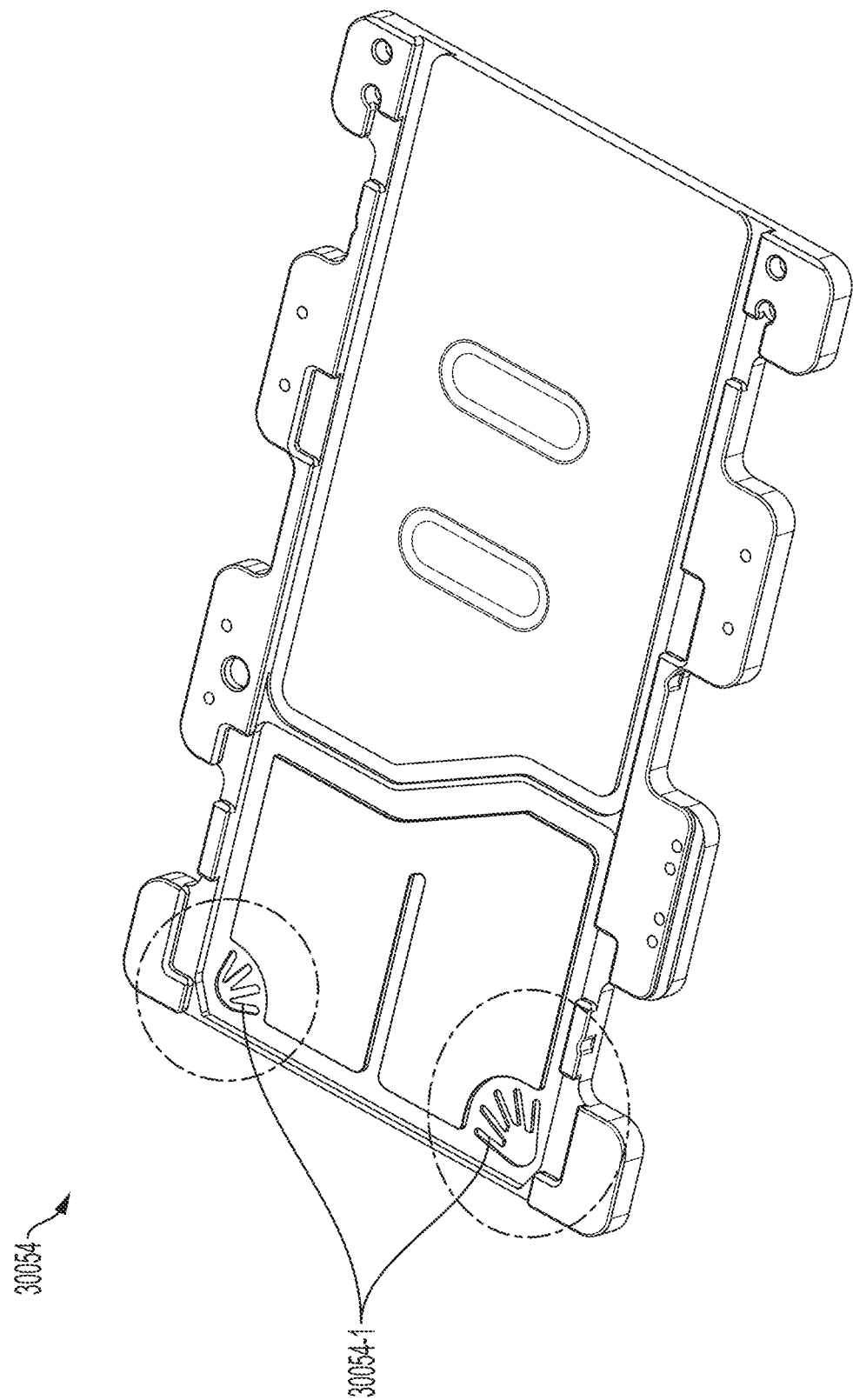
Figure 14O:
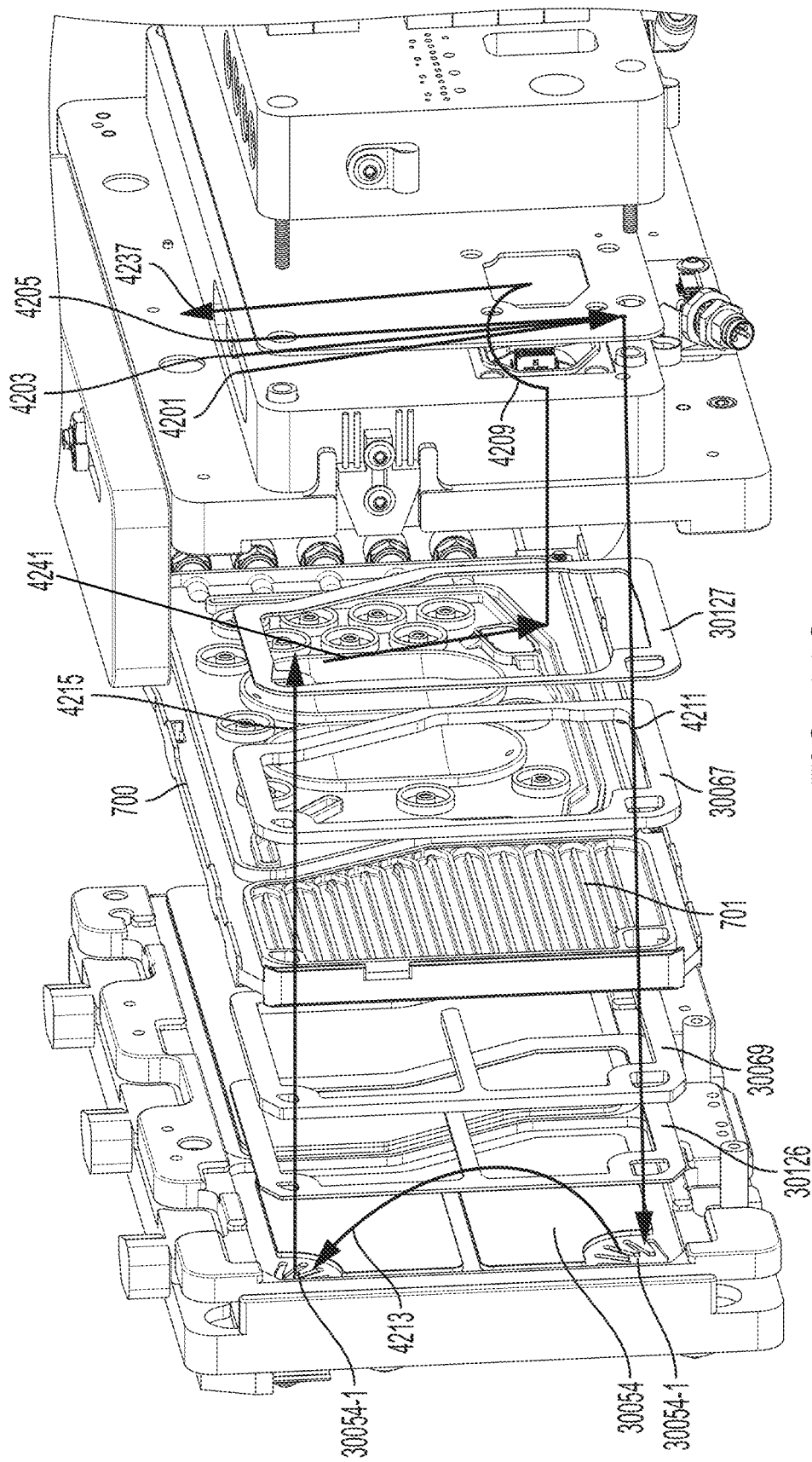
Figure 14P:
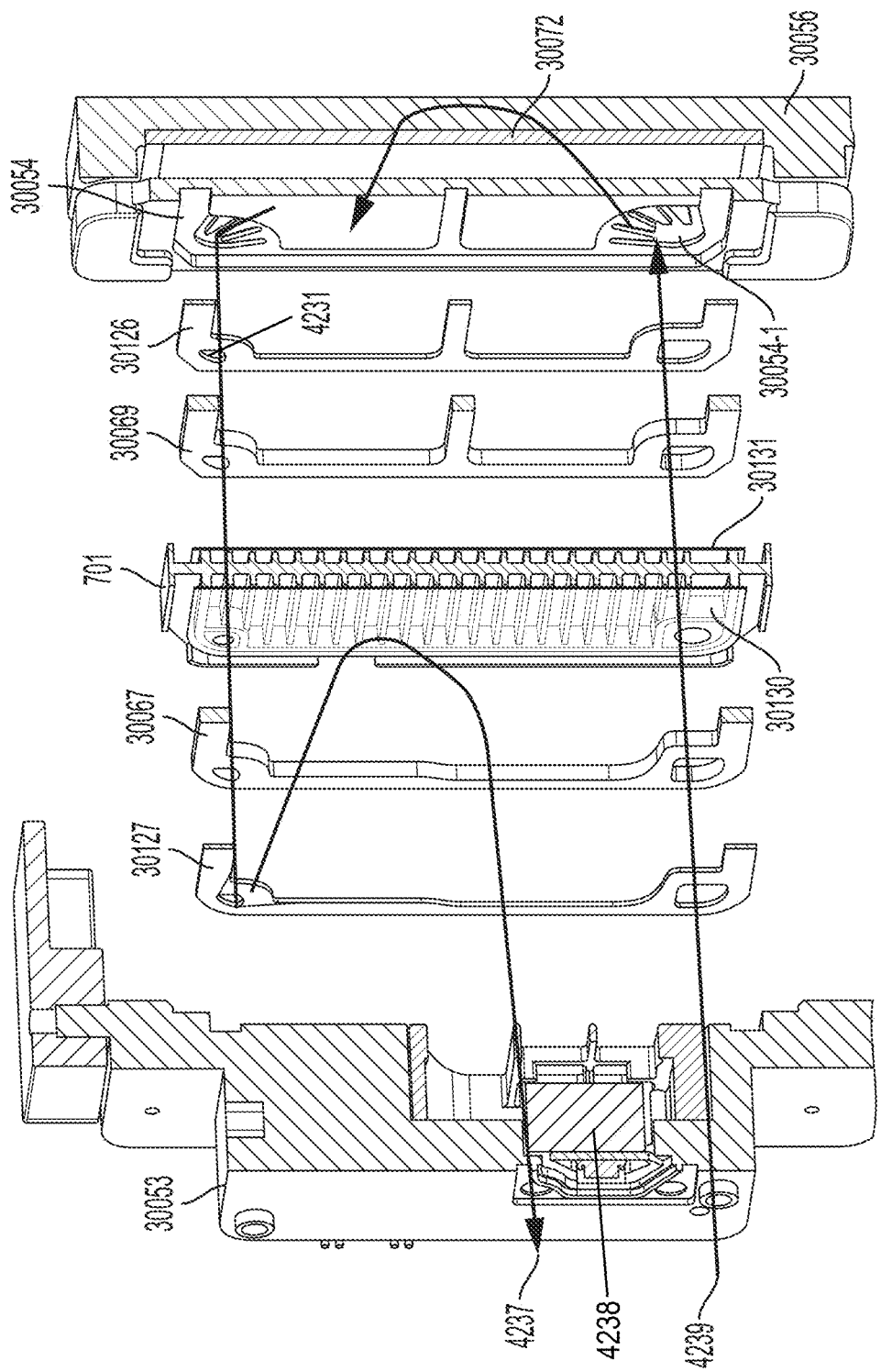

Referring now to FIGS. 14O-14P, the addition of gas into the system is metered by valves 901N, 901O, and 901CO (FIG. 14L) on manifold top plate 30055 (FIG. 14M). The gas passes from manifold top plate 30055 (FIG. 14M), through valves 901N/901O/901CO (FIG. 14J), back into manifold top plate 30055 (FIG. 14M), through manifold inner gasket 30070 (FIG. 14M), and into manifold pump side plate 30053 (FIG. 14P). As the gas exits manifold pump side plate 30053 (FIG. 14P), it is passed through isolated flow paths in the lower corners of gas exchange gasket shim 30127 (FIG. 14P), 30067 (FIG. 14P), 30130 (FIG. 14P), 700 (FIG. 14O), 30131 (FIG. 14P), 30069 (FIG. 14P), and 30126 (FIG. 14P) until it reaches manifold channel side plate 30054 (FIG. 14P). Channels in manifold channel side plate 30054 (FIG. 14P), combined with the shapes of lower gas exchange gasket shim 30126 (FIG. 14P) and lower gas exchange gasket 30069 (FIG. 14P), encourage the gas to disperse evenly across channel side gas exchange membrane 30131 (FIG. 14P), promoting gas diffusion with the fluid contained within cassette 700 (FIG. 14O) gas exchange area 701 (FIG. 14P). The gas returns to the pump side through an isolated flow path in the upper corners of 30126 (FIG. 14P), 30069 (FIG. 14P), 30131 (FIG. 14P), 700 (FIG. 14O), 30130 (FIG. 14P), 30067 (FIG. 14P), gas exchange gasket shim 30127 (FIG. 14P) until it reaches manifold pump side plate 30053 (FIG. 14P). Channels in manifold pump side plate 30053 (FIG. 14P), combined with the shapes of gas exchange gasket shim 30127 and 30067, can encourage the gas to disperse evenly across pump side gas exchange membrane 30130 (FIG. 14P), promoting gas diffusion with the fluid contained within cassette 700 (FIG. 14O) gas exchange area 701 (FIG. 14P). As the gas takes path 4237 (FIG. 14P), it passes by gaseous sensors in enclosure 4238 (FIG. 14P), providing feedback to improve the gas control system's ability to monitor and control the gas ratio. The gas then then exits through the manifold pump side plate 30053 (FIG. 14P) when vent valve 1501V (FIG. 14L) on manifold top plate 30055 (FIG. 14M) is opened.

Figure 15A:
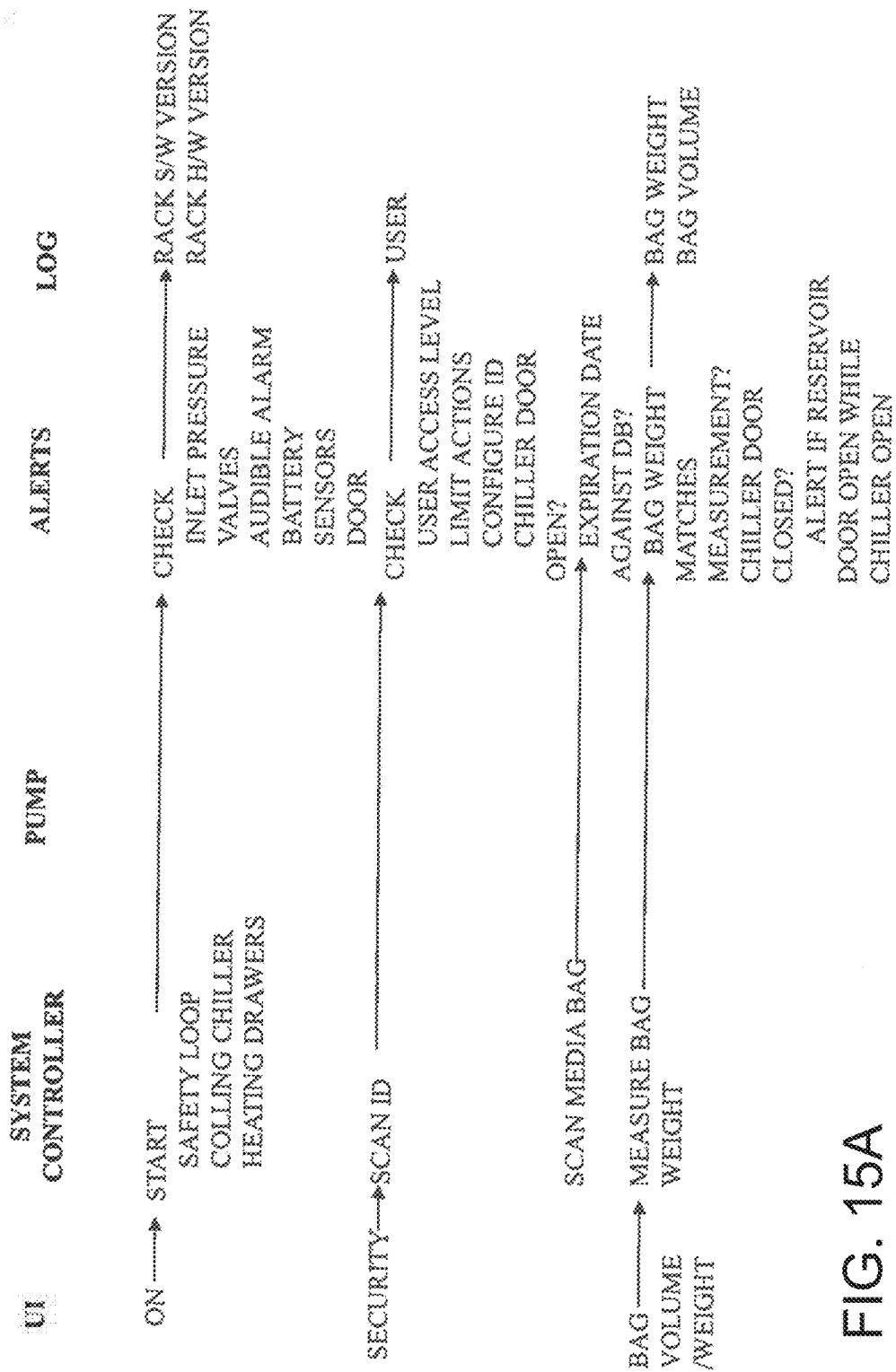
FIGS. 15A-15C are workflow diagrams of the use of the system of the present teachings.

Referring now to FIG. 15A, in some configurations, using the system of the present teachings can include following a workflow 2601 which can include, but is not limited to including, a series of steps that can occur automatically. For example, upon enabling the system of the present teachings, a safety loop can be performed, and temperature controls can be activated. During the safety loop, inlet pressure valves, an audible alarm, batteries, sensors, and the orientation of the enclosure door can be checked. The software and hardware versions can be logged. Following the safety loop, a security check can be performed automatically. The security check can include scanning the operator's identification and logging the operator's information. The security check can include checking the operator's access level, and setting the operator's allowed actions according to the access level. The security check can include checking if the chiller door is open, scanning the media source, and checking properties of the media source for validity. Properties of the media source can include type, contents, and expiration date. Workflow 2601 can include further checking of the properties of the media source, for example, but not limited to, the weight of the media source container and the volume of the media container, both of which can be logged. Workflow 2601 can include checking the orientation of the chiller door and raising an alert if the chiller door is open while the reservoir door is open.

Figure 15B:
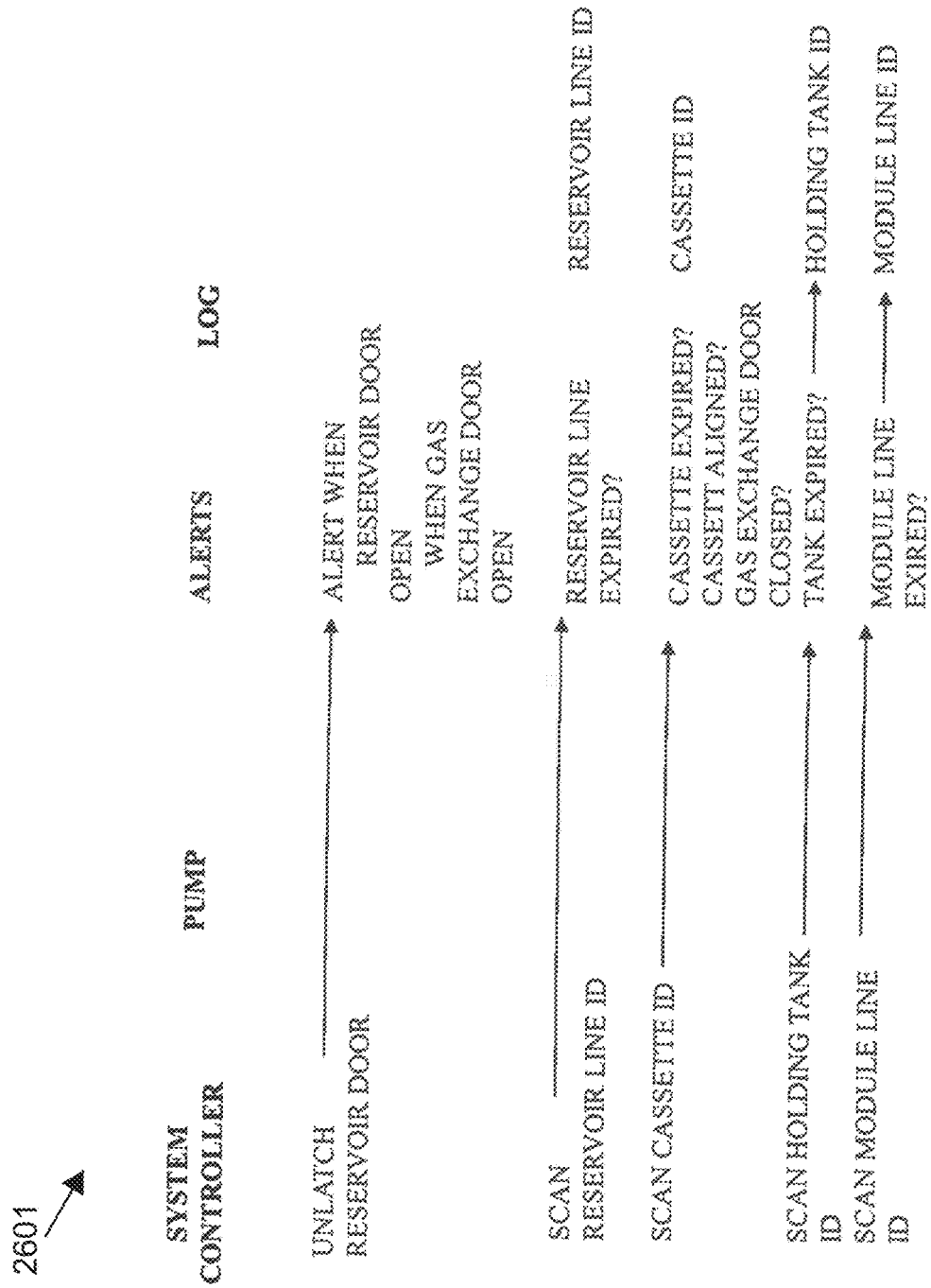

Referring now to FIG. 15B, in some configurations, workflow 2601 can include unlatching the reservoir door, raising an alert when the reservoir door is open or the gas exchange door is open. In some configurations, where the gas exchange area is integrated with the cassette, an alarm can be raised if the reservoir/bioreactor door is opening while the system is pumping. Workflow 2601 can include scanning and logging the reservoir line identification, and raising an alert if the expiration date of the reservoir line has been reached or passed. Workflow 2601 can include scanning and logging the cassette identification, and raising an alert if the cassette expiration date has been reached or has passed. Workflow 2601 can include raising an alert if the cassette is placed in the cassette holder incorrectly and if the gas exchange door is not closed. Workflow 2601 can include scanning and logging the holding tank identification, and raising an alert if the holding tank expiration date has been reached or has passed. Workflow 2601 can include scanning and logging the module line identification, and raising an alert if the module line expiration date has been reached or has passed.

Figure 15C:
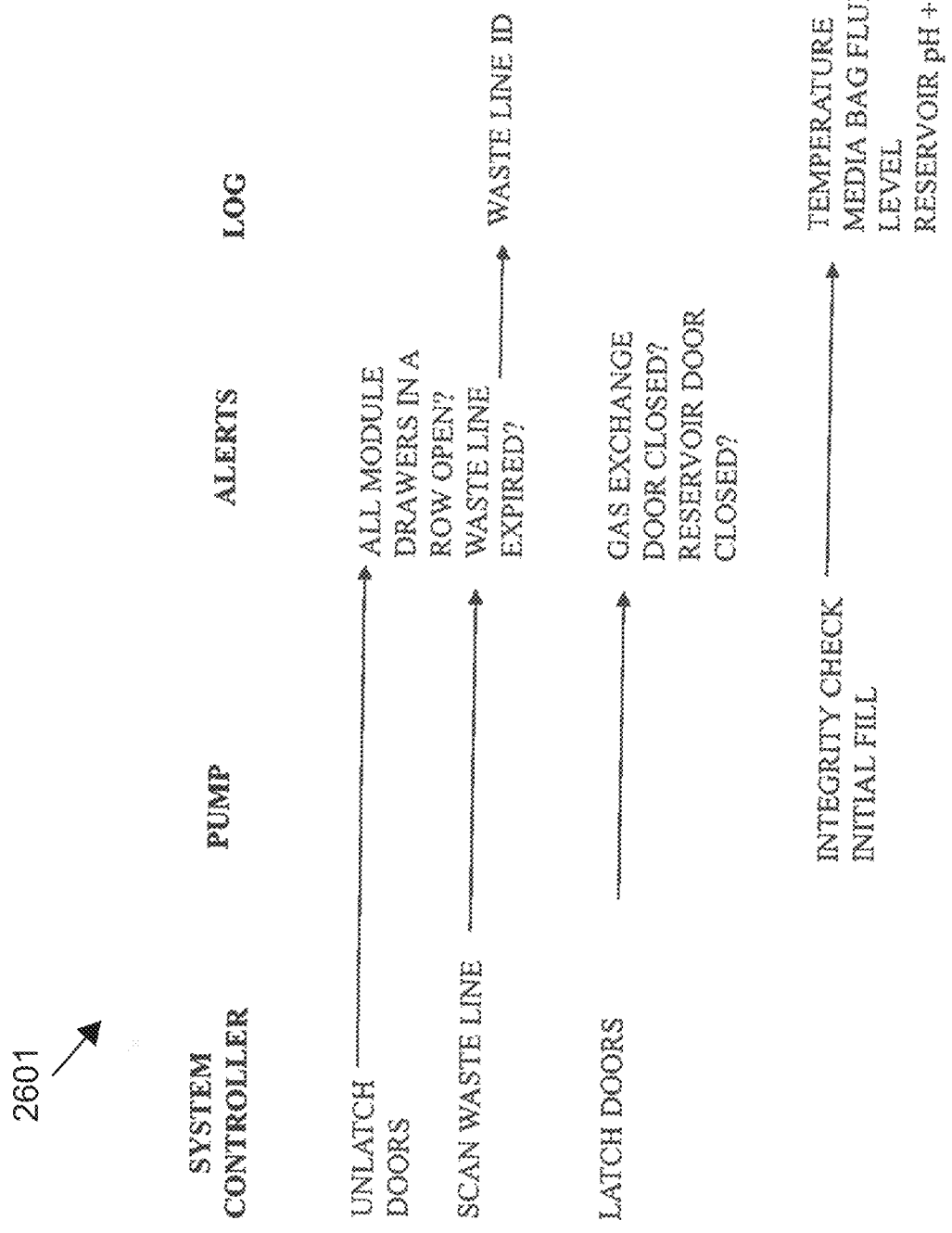

Referring now to FIG. 15C, workflow 2601 can include unlatching enclosure doors in a row and raising an alert when all enclosure doors in a row are unlatched. Workflow 2601 can include scanning and logging the waste line identification, and raising an alert if the waste line expiration date has been reached or has passed. Workflow 2601 can include latching enclosure doors, and raising an alert if the gas exchange door and the reservoir doors are open. Workflow 2601 can include performing an integrity check and initial fill using the system's pumps, and logging the temperature, the media source fluid level and the pH and dissolved oxygen in the reservoir fluid.

Various alternatives and modifications can be devised by those skilled in the art without departing from the disclosure. Accordingly, the present disclosure is intended to embrace all such alternatives, modifications and variances. Additionally, while several example configurations of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular configurations. And, those skilled in the art will envision other modifications within the scope and spirit of the claims appended hereto. Other elements, steps, methods and techniques that are insubstantially different from those described above and/or in the appended claims are also intended to be within the scope of the disclosure.

The drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the example configurations of the disclosure described herein are capable of operation in other sequences and/or arrangements than are described or illustrated herein.

The invention claimed is:

1. A method for automatic centralized fluid management and culture control comprising:
    (a) automatically, by a system controller, monitoring temperature, nutrient concentration, and dissolved gas concentrations of a cell or tissue culture media;
    (b) automatically, by the system controller, maintaining the temperature of the cell or tissue culture media in a media reservoir at a first pre-selected value;
    (c) automatically, by the system controller, adjusting the temperature, the nutrient concentration, and the dissolved gas concentrations of the cell or tissue culture media to second pre-selected values prior to delivery to a user-supplied device;
    (d) automatically, by the system controller, delivering the temperature, the nutrient concentration, and dissolved gas concentration-adjusted cell or tissue culture media to the user-supplied device;
    (e) automatically, by the system controller, recirculating the temperature, the nutrient concentration, and the dissolved gas concentration-adjusted cell or tissue culture media through a flow path including the media reservoir, a reservoir line, a reservoir module cassette, a holding container, a module line, and a bioreactor module cassette within the user-supplied device;
    (f) automatically, by the system controller, monitoring the temperature, the nutrient concentration, and the dissolved gas concentrations of the adjusted cell or tissue culture media to verify they remain at the second pre-selected values through the user-supplied device;
    (g) if the temperature, or the nutrient concentration, or the dissolved gas concentrations of the adjusted cell or tissue culture media meet the second pre-selected values, automatically, by the system controller, repeating steps (e)-(f); and
    (h) if the temperature, or the nutrient concentration, or the dissolved gas concentrations of the adjusted cell or tissue culture media do not meet the second pre-selected values, automatically, by the system controller, delivering the recirculated adjusted cell or tissue culture media to a waste vessel or a sample vessel.

2. The method as in claim 1 wherein the user-supplied device comprises a bioreactor.

3. The method as in claim 1 wherein the automatic delivering of the temperature, the nutrient concentration, and the dissolved gas concentration-adjusted cell or tissue culture media comprises delivering through a sterile flow path including disposable hardware.

4. The method as in claim 3 wherein the disposable hardware comprises sterilizable hardware.

5. The method as in claim 1 wherein the first pre-selected value comprises a range of 0-8° C.

6. The method as in claim 1 wherein the second pre-selected values comprise a range of 32-40° C.

7. The method as in claim 1 wherein the recirculating comprises using a sterile flow path including the media reservoir, the reservoir line, the reservoir module cassette, the holding container, the module line, the bioreactor module cassette, and the user-supplied device.

8. The method as in claim 1 wherein the monitoring comprises using disposable sensors and non-invasive sensors.

9. The method as in claim 8 wherein the disposable sensors are integrated into the bioreactor module cassette and the reservoir module cassette.

10. The method as in claim 1 wherein each of the adjusting comprises temperature control using the heating elements, gas diffusion through semi-permeable plastics, or replacement of the cell or tissue culture media.

* * * * *